(12) United States Patent
Betschart et al.

(10) Patent No.: US 7,452,886 B2
(45) Date of Patent: *Nov. 18, 2008

(54) PYRROLO PYRIMIDINES AS AGENTS FOR THE INHIBITION OF CYSTEIN PROTEASES

(75) Inventors: Claudia Betschart, Basel (CH); Kenji Hayakawa, Hyogo Pref. (JP); Osamu Irie, Ibaraki Pref. (JP); Junichi Sakaki, Ibaraki Pref. (JP); Genji Iwasaki, Ibaraki Pref. (JP); Rene Lattmann, Oberwil (CH); Martin Missbach, Gipf-Oberfrick (CH); Naoki Teno, Ibaraki Pref. (JP)

(73) Assignee: Novartis AG, Basel (CH)

( * ) Notice: Subject to any disclaimer, the term of this patent is extended or adjusted under 35 U.S.C. 154(b) by 406 days.

This patent is subject to a terminal disclaimer.

(21) Appl. No.: 10/487,760

(22) PCT Filed: Aug. 29, 2002

(86) PCT No.: PCT/EP02/09663

§ 371 (c)(1),
(2), (4) Date: Oct. 14, 2004

(87) PCT Pub. No.: WO03/020721

PCT Pub. Date: Mar. 13, 2003

(65) Prior Publication Data

US 2005/0054851 A1    Mar. 10, 2005

(30) Foreign Application Priority Data

Aug. 30, 2001  (GB) ................................. 0121033.5

(51) Int. Cl.
*A61K 31/497* (2006.01)
*A61K 31/519* (2006.01)
*A61P 9/10* (2006.01)
*C07D 403/06* (2006.01)
*C07D 487/04* (2006.01)
*C07D 473/00* (2006.01)
*A61K 31/52* (2006.01)
*A61K 31/527* (2006.01)

(52) U.S. Cl. ............................ 514/252.15; 514/252.16; 514/265.1; 514/263.1; 514/263.2; 514/263.22; 544/359; 544/280; 544/230; 544/231; 544/264; 544/276

(58) Field of Classification Search ................. 544/359, 544/280, 230, 231; 514/265.1, 252.16, 252.15
See application file for complete search history.

(56) References Cited

U.S. PATENT DOCUMENTS 4,220,770 A   9/1980   Gass
5,683,999 A   11/1997  Jadhav et al.

FOREIGN PATENT DOCUMENTS

CH    437 911    11/1967

OTHER PUBLICATIONS

Wang et. al.; International Journal fo Pharmaceutics; 2004; 277; 73-79.*
Caplus Abstract Accession No. 2001:816647 & WO 01/83460.
Caplus Abstract Accession No. 1999:710017 & Heterocycles vol. 51, No. 11, (1999), Yong-Goo Chang and Kyongtae Kim, "A Facile Synthesis of N-arylcyanoformamidoximes . . . ", pp. 2653-2666.
Caplus Abstract Accession No. 1999:504266 & Bioorg. Med Chem Lett. vol. 9, No. 14, 1999, G Caravatti et al, "Structure-Based Design of a Non-Peptidic Antagonist . . . ", pp. 1973-1978.
Caplus Abstract Accession No. 1996:628861 & Bioorg. Med. Chem. Lett. vol. 6, No. 19, 1996, T Besson et al., Antimicrobial Evaluation of 3,1-Benzoxazin-4-ones . . . pp. 2342-2348.
Caplus Abstract Accession No. 1990:515257 Nippon Kagaku Kaishi vol. 4, 1990, Y Mori et al, Syntheses and Reactions of Cyano-1,3,5-Triazines, pp. 396-4000.
Falgeuyret, J.P. et al, "Novel, Nonpetidic Cyanamides as Potent and Reversible Inhibitors of Human Cathepsins K and L", 2001, Journal of Medicinal Chemistry, vol. 44, pp. 94-104.

* cited by examiner

*Primary Examiner*—Brenda L. Coleman
*Assistant Examiner*—Susanna Moore
(74) *Attorney, Agent, or Firm*—Novartis; John B. Alexander

(57) ABSTRACT

The invention provides compounds of Formula I or a pharmaceutically acceptable salt or ester thereof wherein the symbols have meaning as defined, which are inhibitors of cathepsin K and find use pharmaceutically for treatment of diseases and medical conditions in which cathepsin K is implicated, e.g. various disorders including inflammation, rheumatoid arthritis, osteoarthritis, osteoporosis and tumors.

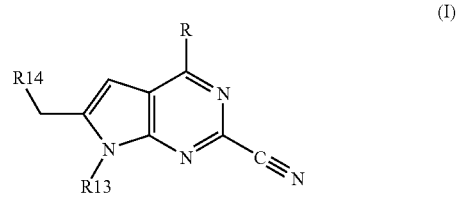

(I)

7 Claims, No Drawings

PYRROLO PYRIMIDINES AS AGENTS FOR THE INHIBITION OF CYSTEIN PROTEASES

This invention relates to inhibitors of cysteine proteases, in particular to pyrrolo pyrimidine nitrile cathepsin K inhibitors and to their pharmaceutical use for the treatment or prophylaxis of diseases or medical conditions in which cathepsin K is implicated.

Cathepsin K is a member of the family of lysosomal cysteine cathepsin enzymes, e.g. cathepsins B, K, L and S, which are implicated in various disorders including inflammation, rheumatoid arthritis, osteoarthritis, osteoporosis, tumors (especially tumor invasion and tumor metastasis), coronary disease, atherosclerosis (including atherosclerotic plaque rupture and destabilization), autoimmune diseases, respiratory diseases, infectious diseases and immunologically mediated diseases (including transplant rejection).

Accordingly the present invention provides a compound of formula I, or a pharmaceutically acceptable salt or ester thereof

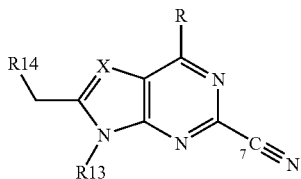

I wherein
R is H, —R2, —OR2 or NR1R2,
wherein R1 is H, lower alkyl or $C_3$ to $C_{10}$ cycloalkyl, and
R2 is lower alkyl or $C_3$ to $C_{10}$ cycloalkyl, and
wherein R1 and R2 are independently, optionally substituted by halo, hydroxy, lower alkoxy, CN, $NO_2$, or optionally mono- or di-lower alkyl substituted amino;
X is =N— or =C(Z)-,
wherein Z is H, —C(O)—NR3R4, —NH—C(O)—R3, —CH$_2$—NH—C(O)—R3, —C(O)—R3, —S(O)—R, —S(O)$_2$—R3, —CH$_3$—C(O)—R3, —CH$_2$—NR3R4, —R4, —C≡C—CH$_2$—R5, N-heterocyclyl, N-heterocyclyl-carbonyl, or —C(P)=C(Q)-R4 wherein
R13 is lower alkyl, $C_3$ to $C_{10}$ cycloalkyl or $C_3$-$C_{10}$cycloalkyl-lower alkyl, all of which are independently optionally substituted by halo, hydroxy, CN, $NO_2$ or optionally mono- or di-lower alkyl-substituted amino; and
R14 is H or optionally substituted (aryl, aryl-W—, aryl-lower alkyl-W—, $C_3$ to $C_{10}$ cycloalkyl, $C_3$ to $C_{10}$ cycloalkyl-W—, N-heterocyclyl or N-heterocyclyl-W— (wherein N-heterocyclyl is as defined above), phthalimide, hydantoin, oxazolidinone, or 2,6-dioxo-piperazine),
wherein —W— is —O—, —C(O)—, —NH(R6)-, —NH(R6)-C(O)—, —NH(R6)-C(O)—O—, (where R6 is as defined above), —S(O)—, —S(O)$_2$— or —S—,
wherein R14 is optionally substituted by R18 which represents from 1 to 10 substitutents selected from halo, hydroxy, CN, $NO_2$, oxo, amido, carbonyl, sulphonamido, lower-alkyldioxymethylene, or optionally substituted (lower-alkoxy, lower-alkyl, lower-alkenyl, lower alkynyl, lower alkoxy carbonyl, optionally mono- or di-lower alkyl substituted amino, aryl, aryl-lower alkyl, aryl-lower alkenyl, aryloxy, aroyl, lower-alkylsulphonyl, arylsulphonyl, N-heterocyclyl, N-heterocyclyl-lower alkyl (wherein N-heterocyclyl is as defined above), heterocyclyl or R14 comprising aryl has aryl fused with a hetero-atom containing ring, and wherein R18 is optionally substituted by R19 which represents from 1 to 4 substitutents selected from halo, hydroxy, CN, $NO_2$ or oxo, or optionally substituted (lower-alkoxy, lower-alkyl, lower-alkoxy-lower-alkyl, $C_3$-$C_{10}$cycloalkyl lower-alkoxy carbonyl, halo-lower alkyl, optionally mono- or di-lower alkyl substituted amino, aryl, aryloxy, aroyl (e.g. benzoyl), acyl (e.g. lower-alkyl carbonyl), lower-alkylsulphonyl, arylsulphonyl or N-heterocyclyl, or N-heterocyclyl-lower alkyl (wherein N-heterocyclyl is as defined above)), wherein R19 is optionally substituted by from 1 to 4 substitutents selected from halo, hydroxy, CN, $NO_2$, oxo, optionally mono- or di-lower alkyl substituted amino, lower-alkyl, or lower-alkoxy.

Above and elsewhere in the present description the following terms have the following meanings.

Halo or Halogen Denote I, Br, Cl or F.

The term "lower" referred to above and hereinafter in connection with organic radicals or compounds respectively defines such as branched or unbranched with up to and including 7, preferably up to and including 5 and advantageously one, two or three carbon atoms.

A lower alkyl group is branched or unbranched and contains 1 to 7 carbon atoms, preferably 1-5 carbon atoms. Lower alkyl represents; for example, methyl, ethyl, propyl butyl, isopropyl isobutyl, tertiary butyl or neopentyl (2,2-dimethylpropyl).

Halo-substituted lower alkyl is $C_1$-$C_7$lower alkyl substituted by up to 6 Halo Atoms.

A lower alkoxy group is branched or unbranched and contains 1 to 7 carbon atoms, preferably 1-4 carbon atoms. Lower alkoxy represents for example methoxy, ethoxy, propoxy, butoxy, isopropoxy, isobutoxy or tertiary butoxy.

A lower alkene, alkenyl or alkenyloxy group is branched or unbranched and contains 2 to 7 carbon atoms, preferably 2-4 carbon atoms and contains at least one carbon-carbon double bond. Lower alkene lower alkenyl or lower alkenyloxy represents for example vinyl, prop-1-enyl, alkyl, butenyl, isopropenyl or isobutenyl and the oxy equivalents thereof.

A lower alkyne, alkynyl or alkynyloxy group is branched or unbranched and contains 2 to 7 carbon atoms, preferably 2-4 carbon atoms and contains at least one carbon-carbon triple bond. Lower alkyne or alkynyl represents for example ethynyl, prop-1-ynyl, propargyl, butynyl, isopropynyl or isobutynyl and the oxy equivalents thereof.

In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-$C_2$-$C_3$-alkylene and other substituents, for instance as described in the examples; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2C_3$-alkylene-phenyl is 2,3-dihydrobenzofuran-5-yl.

Preferred as carbocyclic aryl is naphthyl, phenyl or phenyl optionally substituted, for instance, as described in the examples, e.g. mono- or disubstituted by lower alkoxy, phenyl, halogen, lower alkyl or trifluoromethyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted as defined above.

Preferably, heterocyclic aryl is pyridyl, indolyl, quinolinyl, pyrrolyl, thiazolyl, isoxazolyl, triazolyl, tetrazolyl, pyrazolyl, imidazolyl, thienyl, or any said radical substituted, especially mono- or di-substituted as defined above.

Cycloalkyl represents a saturated cyclic hydrocarbon optionally substituted by lower alkyl which contains 3 to 10 ring carbons and is advantageously cyclopropyl, cyclopentyl, cyclohexyl, cycloheptyl or cyclooctyl optionally substituted by lower alkyl.

N-heterocyclyl is as defined above. Preferred N-heterocyclic substituents are optionally substituted pyrrolidine, pyrrole, diazole, triazole, tetrazole, imidazole, oxazole, thiazole, pyridine, pyrimidine, triazine, piperidine, piperazine, morpholine, phthalimde, hydantoin, oxazolidinone or 2,6-dioxopiperazine and, for example, as hereinafter described in the examples.

Preferably R is H

Thus in a preferred embodiment the invention provides a compound of formula II or a pharmaceutically acceptable salt or ester thereof

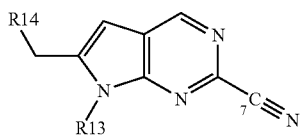

II wherein R13 and R14 are as defined above.

Preferably R13 is lower alkyl e.g. straight chain or more preferably branched-chain $C_1$-$C_6$ alkyl, e.g. especially 2-ethylbutyl, isobutyl, or 2,2-dimethylpropyl; or $C_3$-$C_6$cycloalkyl, especially cyclopropyl, cyclopentyl or cyclohexyl; or $C_3$-$C_6$cycloalkyl-lower alkyl, e.g. $C_3$-$C_6$cycloalkylmethyl.

Preferably R14 is optionally substituted (aryl, aryl-W—, aryl-lower alkyl-W—, $C_3$ to $C_{10}$ cycloalkyl, $C_3$ to $C_6$ cycloalkyl-W— or N-heterocyclyl or N-heterocyclyl-W— (wherein N-heterocyclyl is as defined above), phthalimide, hydantoin, oxazolidinone, or 2,6-dioxo-piperazine.

—W— is prefrably —O—, —NH(R27)-, (where R27 is H or lower alkyl), —S— or —S(O)$_2$—.

R14 as aryloxy is preferably optionally substituted (phenoxy, methylenedioxyphenoxy, 3,4(2-oxa-1,3-imidazo)phenoxy, 3,4(2-oxo-1-thio-3-dihydrofuran)phenoxy, pyridyloxy, pyrazinyloxy, benzopyrazinyloxy, quinazolinyloxy or pyrimidinyloxy).

R14 as aryloxy is preferably optionally substituted by halo, hydroxy, lower alkyl, N-heterocyclyl-lower alkyl, and trifluoromethyl.

Examples of R14 as aryloxy are pyridin-4-yloxy, 6-chloropyridin-3-yloxy, 6-methylpyridin-3-yloxy, 3-chloropyridin-4-yloxy, 2-chloropyridin-4-yloxy, pyridin-3-yloxy, 3-methylpyridin-4-yloxy, 2-hydroxypyridin-4-yloxy, 5-chloropyridin-3-yloxy, 4-imidazolmethyl-pyridn-3-yloxy, 6-hydroxypyridazin-3-yloxy, 6-methoxypyridazin-3-yloxy, 2-difluoromethylpyridin-4-yloxy, 2-trifluoromethylpyridin-4-yloxy, 3,4(2-oxa-1,3-imidazo)phenoxy, 3,4-methylenedioxy-phenoxy, 3-trifluoromethylphenoxy, 3,4(2-oxo-1-thio-3-dihydrofuran)phenoxy, 3-chloro-quinolin-6-yloxy, 4-(4-acetyl-piperazin-1-ylphenoxy, 4-(4-methyl-piperazin-1-ylmethyl)-phenoxy, 4,5-benzo-2-methyl-pyrimidin-4-yloxy, 6-chloro-pyrimidin-4-yloxy, 6-(4-methyl-piperazin-1-yl)-pyrimidin-4-yloxy and 6-morpholin-4-yl-pyrimidin-4-yloxy.

R14 as aryl-lower alkoxy is, for example, pyridinyl-lower alkyl, e.g. pyridin-4-ylmethoxy.

R14 as arylamine is preferably optionally substituted (phenylamino, pyridylamino or pyrimidinylamino).

R14 as arylamine is preferably optionally substituted by halo, lower alkyl or lower alkoxy.

R14 as N-hetrocyclyl-lower alkylamine is for example, piperidyl-lower alky, e.g. piperidylethylamino.

R14 as arylcarbonylamino is for example, benzamide, e.g. 4-fluorobenzamide.

Examples of R14 as arylamine, N-heterocyclyl-lower alkylamine and arylcarbonyl amino are: (4-chlorophenyl)-methyl-amino, 6-chloropyridin-3-ylamino, 6-methoxypyridin-3-ylamino, 5-methylpyridin-4-ylamino, piperidin-1-ylamino, 4-chloropyrimidin-2-ylamino or 4-fluorobenzamido.

R14 as arylsuphanyl is preferably optionally substituted (phenyl, pyridinyl, triazolyl or thioimidazolyl), e.g. pyridin-2-yl, pyridin-4-yl, triazol-3-yl or thioimidazol-2-yl.

R14 as cycloalkylsulphanyl is preferably optionally substituted $C_3$-$C_6$cycloalkyl, e.g. cyclopentylsulphanyl or cyclohexylsuphanyl.

R14 as cycloalkylsulphonyl is preferably optionally substituted $C_3$-$C_6$cycloalkyl, e.g. cyclopentylsulphonyl or cyclohexylsulphonyl.

R14 as N-heterocyclyl is preferably optionally substituted (aromatic N-heterocyclyl or aliphatic N-heterocyclyl) (wherein N-heterocyclyl is as defined above).

R14 as aromatic N-heterocyclyl is preferably optionally substituted (imidazolyl, benzimidazolyl, triazolyl, benztriazolyl, dihyrosulphonazolyl, benz-dihydroslphonazolyl or tetrazolyl).

R14 as aromatic N-heterocyclyl is preferably optionally substituted by from 1-3 substituents selected from halo, lower alkyl, cyano, nitro, aryl (e.g. phenyl, pyridinyl or pyrimidinyl), amino aryl (e.g. phenyl, pyridinyl or pyrimidinyl), aryl-lower alkyl (e.g. phenyl, pyridinyl or pyrimidinyl), carbonylamino, N-heterocyclyl-lower alkyl-carbonylamino, hydroxy-lower alkyl-aryl, haloaryl or N-heterocyclyl-lower alkyl-aryl.

Examples of R14 as aromatic N-heterocyclyl are: imidazol-1-yl, 4,5-dichloroimidazol-1-yl, 2-methylimidazol-1-yl, 4,5-dicyanoimidazol-1-yl, 2-ethylimidazol-1-yl, 2-phenylimidazol-1-yl, 2,4,5-trichloroimidazol-1-yl, 4,5-di(carbonylamino)imidazol-1-yl, 2-propylimidazol-1-yl, 4,5-dimethylimidazol-1-yl, 4,5-benzotriazol-1-yl, 3,4-benzo-2-dioxo-2S,1N-dihydrothiazolyl, 3-nitro-[1,2,4]triazol-1-yl, 3,5-dibromo-[1,2,4]triazol-1-yl, 3-nitro-5-bromo-[1,2,4]triazol-1-yl, 4-nitroimidazol-1-yl, [1,2,3]triazol-2-yl, [1,2,3]triazol-1-yl, 4-methyl-[1,2]imidazol-1-yl, 3-amino-[1,2,4]triazol-1-yl, 3-(2-piperidin-1-ylamido)-[1,2,4]triazol-1-yl, tetrazol-1-yl, tetrazol-2-yl, 5-pyrimidinyltetrazol-2-yl, 5-pyrimidinyltetrazol-1-yl, 5-(4-hydroxymethyl-phenyl)tetrazol-2-yl, 5-(3-fluorophenyl)tetrazol-2-yl, 5-3-fluorophenly)tetrazol-2-yl, 5-pyridin-4-yl-tetrazol-2-yl, 5-pyridin-3-yl-tetrazol-2-yl, 5-(pyridin-4-ylmethyl)-tetrazol-2-yl, 5-(piperidin-1-ylmethyl)-tetrazol-2-yl, 5-piperidin-1-yl-tetrazol-2-yl, 5-pyrrolidin-1-yl-tetrazol-2-yl, 5-(4-piperidin-1-ylphenyl)-tetrazol-2-yl, 5-(4-(4-methylpiperazin-1-yl)phenyl)-tetrazol-2-yl and 5-(4-[1,2,4]triazol-1-ylmethylphenyl)-tetrazol-2-yl.

R14 as aliphatic N-heterocyclyl is preferably optionally substituted (piperidin-yl [preferably piperidin-1-yl], partially unsaturated piperidinyl, e.g. piperid-3,4-en-1-yl, piperazinyl [preferably piperazin-1-yl] or morpholinyl, e.g. 1,1-dioxo-1$\lambda^6$-thiomorpholinyl).

R14 as aliphatic N-heterocyclyl is preferably optionally substituted by from 1-3 substituents selected from halo, hydroxy, nitro, cyano, amino, oxo $C_3$-$C_{10}$ cycloalkyl, $C_3$-$C_{10}$ cycloalkyl-amino, halo-lower alkyl, aryl, halo-aryl, nitro-aryl, lower-alkyl aryl, lower-alkoxy aryl, di-loweralkoxy-aryl, loweralkoxy, halo-aryl, hydroxy-loweralkoxy, halo-aryl, halo, nitro-aryl, lower-alkyl, nitro-aryl, halo-lower alkyl, nitro-aryl, lower alkyl, lower-alkoxy-lower alkyl, nitro-aryl, lower alkyl, halo-aryl, aryl-lower alkenyl, lower-alkyl-carbonyl aryl, lower-alkylcarbonyl, arylcarbonyl, lower-alkoxycarbonyl, (aryl-loweralkoxycarbamoyl)-lower alkyl, (loweralkoxycarbamoyl)-lower alkyl, carboxamidinyl, halo-aryl-lower alkyl, aryl-lower alkyl, lower-alkyl-sulphonamido-aryl, halo-lower-alkyl-sulphonamido-aryl, halo-lower-alkoxy-aryl, halo-loweralkyl-aryl, arylaminocarbonyl, amino-arylcarbonyl-N-heterocyclyl, N-heterocyclyl, lower-alkyl-N-heterocyclyl, N-heterocyclyl-lower-alkyl-amino, (wherein N-heterocyclyl is as defined above).

Examples of R14 as as aliphatic N-heterocyclyl are: 4-(2-methoxy-phenyl)-piperazin-1-yl, 4-(4-fluorophenyl)-piperazin-1-yl, 4-(2-chlorophenyl)-piperazin-1-yl, 4-(pyridin-2-yl)-piperazin-1-yl, 4-(pyrimidin-2-yl)-piperazin-1-yl, 4-(4-nitrophenyl)-piperazin-1-yl, 4-(3-prop-2,3-en-1-yl)-piperazin-1-yl, 4-(2-fluorophenyl)-piperazin-1-yl, 4-(2-methylphenyl)-piperazin-1-yl, 4-(3-chlorophenyl)-piperazin-1-yl, 4-(4-chlorophenyl)-piperazin-1-yl, 4-(2,3-dimethylphenyl)-piperazin-1-yl, 4-(2,4-difluorophenyl)-piperazin-1-yl, 4-(2-cyanophenyl)-piperazin-1-yl, 4-(4-methylphenyl)-piperazin-1-yl, 4-(2-pyrimidin-4-yl)-piperazin-1-yl, 4-(4-methylcarbonylphenyl)-piperazin-1-yl, 4-methyl-piperazin-1-yl, 4-ethyl-piperazin-1-yl, 4-methylcarbonyl-piperazin-1-yl, 4-pyridin-4-yl-piperazin-1-yl, 4-t.butoxycarbonyl-piperazin-1-yl, 4-benzoxycarbamoylmethyl-piperazin-1-yl, 4-thiazol-1-yl-piperazin-1-yl, 4-pyrazin-2-yl-piperazin-1-yl, 4-(3-chloropyrazin-2-yl)-piperazin-1-yl, 4-(2-fluoro-4-nitro-phenyl)-piperazin-1-yl, 4-(2-chloro-4-nitro-phenyl)-piperazin-1-yl, 4-(5-ethyl-pyrimidin-2-yl)-piperazin-1-yl, 4-(2-methyl-4-nitro-phenyl)-piperazin-1-yl, 4-(2-trifluoromethyl-4-nitro-phenyl)-piperazin-1-yl, 4-(6-fluoro-pyridin-3-yl)-piperazin-1-yl, piperazin-1-yl, 4-(2-fluoro-4-methyl-phenyl)-piperazin-1-yl, 4-(2-methyl-4-fluoro-phenyl)-piperazin-1-yl, 4-carboxamidino-piperazin-1-yl, 4-(4-fluorobenzyl)-piperazin-1-yl, 4-(2,4-difluorobenzyl)-piperazin-1-yl, 4-(2,4,5-trifluorobenzyl)-piperazin-1-yl, 4-butyryl-piperazin-1-yl, 4-propyryl-piperazin-1-yl, 4-imidazol-4-yl-piperazin-1-yl, 4-(4-methylsulphoamidophenyl)-piperazin-1-yl, 4-(4-ethylsulphoamidophenyl)-piperazin-1-yl, 4-(4-2,2,2-trifluoroethylsulphoamidophenyl)-piperazin-1-yl 4-(4-methylsulphoamido-2-methyl-phenyl)-piperazin-1-yl, 4-(4-methylsulphoamido-2-fluoro-phenyl)-piperazin-1-yl, 4-(4-methylsulphoamido-2-chloro-phenyl)-piperazin-1-yl, 4-(4-methylsulphoamido-2-trifluoromethyl-phenyl)-piperazin-1-yl, 4-(4-ethylsulphoamido-2-fluoro-phenyl)-piperazin-1-yl, 4-(4-trifluoromethoxyphenyl)-piperazin-1-yl, 4-(4-methoxyphenyl)-piperazin-1-yl, 4-(4-trifluoromethylphenyl)-piperazin-1-yl, 4-(2,4-dimethoxyphenyl)-piperazin-1-yl, 4-(3,4-dimethylphenyl)-piperazin-1-yl, 4-(2,6-dimethylphenyl)-piperazin-1-yl, 4-(4-ethoxyphenyl)-piperazin-1-yl, 4-(4-ethoxy-2-fluoro-phenyl)-piperazin-1-yl, 4-(4[2-hydroxy-ethoxy]-2-fluoro-phenyl)-piperazin-1-yl, 4-cyclopentyl-piperazin-1-yl, 4-ethoxyethyl-piperazin-1-yl, 4-methoxyethyl-piperazin-1-yl, 4-phenylpiperidin-1-yl, 4-oxo-piperidin-1-yl, 4-1,2-9,10 tetrahydro-isoquinolin-1-yl, 4-pyrrolidin-1-yl-piperidin-1-yl, 4-hydroxy-4(4-chlorophenyl)-piperidin-1-yl 4(4-chlorophenyl)-piperidin-1-yl, 4-(2,4-dimethoxy-phenyl)-piperidin-1-yl, 4-hydroximino-piperidin-1-yl, 4-amino-piperidin-1-yl, 4-(3-imidazol-1-yl-propylamino)-piperidin-1-yl 4-cyclopropylamino-piperidin-1-yl, 4-phenylamido-piperidin-1-yl triazol-2-yl amido-piperidin-1-yl, 4-(4-(3-amino)-imidazol-1-ylcarbonylpiperazidin-1-yl-piperidin-1-yl, 4-(4-methylpiperazidin-1-yl)-piperidin-1-yl, 4-pyrrolidin-1-yl-piperidin-1-yl or 1,1-dioxo-1$\lambda^6$thiomorpholin-4-yl.

R14 may be optionally substituted thiophenyl, e.g. thiophen-2-yl or thiophen-3-yl.

R14 as carbocyclic aryl is preferably optionally substituted (phenyl or naphthylenyl, preferably phenyl), R14 as carbocyclic aryl is preferably optionally substituted by from 1-4 substituents selected from halo, hydroxy, nitro, cyano, amino, oxo, lower-alkyl, halo-lower-alkyl, sulphonamido, lower-alkylsulphonamido, lower-alkenylsulphonamido, loweralkoxy-lower-alkylsulphonamido, halo-lower-alkylsulphonamido, arylsulphonamido, halo-arylsuphonamido, di-lower-alkylarylsulphonamido, hydroxy-lower alkyl, lower-alkoxy, lower-alkylcarbonylamino, carboxylower-alkylcarbonylamino, aryl-lower-alkylsuccinimido, lower-alkoxy-carbonylamino, di-lower alkylamino, di-lower alkylaminocarbonyl, di-lower alkylamino-lower alkyl, di-lower alkylamino-lower alkylamino-lower-alkyl, di-loweralkoxy-loweralkylamino-lower alkyl, $C_3$-$C_{10}$ cycloalkyl, methylene-1,2-dioxyethylene, N-heterocyclyl, N-heterocyclyl-carbonyl, N-heterocyclyl-lower alkyl, N-heterocyclyl-amino, hydroxy-lower-alkyl-N-heterocyclyl-lower alkyl, N-heterocyclyl-lower alkylamino-lower alkyl, lower-alkyl-N-hetrocyclyl, lower-alkyl-N-hetrocyclyl-lower alkyl, lower-alkoxy-N-hetrocyclyl (wherein N-heterocyclyl is as defined above).

Examples of R14 as carbocyclic aryl are: phenyl, naphthalene-2-yl, 4-(1,2-dioxyethylmethylene)-phen-1-yl 3,4-dioxyethylphen-1-yl, 4-chlorophenyl, 4-(4-methyl-piperazin-1-yl)-phenyl, 4-morpholin-1-yl-phenyl, 4-(4-isopropyl-piperazin-1-yl)-phenyl, 4-(4-(2-methoxyethyl)-piperazin-1-yl)-phenyl, 4-(4-methylcarbonyl-piperazin-1-yl)-phenyl, 4-(4-t.butoxycarbonylyl-piperazin-1-yl)-phenyl, 4-(4-ethyl-sulphonyl-piperazin-1-yl)-phenyl, 4-(4-methyl-piperazin-1-yl)-phenyl, 4-(4-methylTAB006?1-yl)-phenyl, 4-hydroxymethylphenyl, 4-bromomethylphenyl, 4-(diethylaminomethyl)-phenyl, 4-(2,2-dimethoxy)-ethylaminophenyl, 4-(4-methyl-piperazin-1-ylmethyl)-phenyl, 4-(morpholin-1-yl-methyl)-phenyl, 4-(4-(2-hydroxyethyl)-piperazin-1-yl)-methylphenyl, 4-(4-(2,2-diethylaminoethylamino)-piperazin-1-ylmethyl)-phenyl, 4-(4-ethyl-piperazin-1-yl)-phenyl, 4-(4-(1,1-ethyl-(2,2-diethylaminoethyl)-amino)-piperazin-1-yl)-methylphenyl, 4-methoxy-phenyl, 4-n-propyloxy-phenyl, 4-fluorophenyl, 4-trifluoromethylphenyl, 4-methylphenyl, 4-ethylphenyl, 4-n-butylphenyl, 4-(4-ethyl-piperazin-1-ylmethyl)-phenyl, 4-(4-morpholin-1-ylmethyl)-phenyl, 4-(4-methylcarbonyl-piperazin-1-ylmethyl)-phenyl, 4-(imidazol-1-ylmethyl)-phenyl, 4-[1,2,4]triazol-1-ylmethyl-phenyl, 4-(morpholine-4-carbonyl-phenyl, 4-dimethylaminocarbonylphenyl, 4-(4-methyl-piperazin-1-ylcarbonyl)-phenyl, 4-(morpholine-4-aminocarbonyl)-phenyl, 4-methylsulphonamido-phenyl, 4-t-butoxy-cabonylamino-phenyl, 4-dimethylaminophenyl, 4-aminophenyl, 4-pyrrol-1-ylphenyl, 4-n-butylsulphonamidophenyl, 4-isopropylsulphonamidophenyl, 4-(4-chlorophenylsulphonamido)-phenyl, 4-(1,2-dimethylimidazol-4-ylsulphonamido)-phenyl, 4-(dimethylaminosulphonamido)-phenyl, 4-ethylsulphonamidophenyl, 4-n-propylsulphonamidophenyl, 4-(prop-2-en-1-ylsulphonamido)-phenyl, 4-(2-methoxyethylsulphonamido)-phenyl, 4-(3-chloro-n-prop-1-ylsulphonamido)-phenyl, 4-(1-methlyimidazol-4-ylsulphonamido)-phenyl, 4-(amnosulphonamido)-phenyl, 4-(2,2,2-trifluoroeth-1-ylsulphonamido)-phenyl, 4-(N-methyl-methanesulphonamido)-phenyl, 4-(methylcarbonylamino)-phenyl, 4-(n-butylcarbonylamino)-phenyl, 4-(2-carboxyeth-1-ylcarbonylamino)-phenyl, 4-(4-benzylsuccinamo-1-yl)-phenyl, R14 as phthalimide, hydantoin, oxazolidinone or 2,6-dioxo-piperazine is preferably optionally substituted (isoindolyl, e.g. isoindol-2-yl, 2,6-dioxo-piperidin-1-yl, 3,4-benzo-2,6-dioxo-isopiperazin-1-yl, 2,5-dioxo-imidazolidin-1-yl, 2,5-dioxo-oxazolidin-1-yl, 1,3-dioxo-2,3-dihydro-1H-pyrrolo[3,4-c]pyridin-5-yl, 2,5-dioxo-thiazolidin-1-yl, 2,6-dioxo-4,5-dihydro-1H-pyrimidin-1-yl, 2-oxo-morpholino[5,6-?]pyridin-?-yl, 1,4-dioxo-3,4-dihydro-1H-phthalazinyl, 2,4,8,8-tetraoxo-1-oxa-8λ$^6$-thia-3-aza-spiro[4,5]dec-3-yl, 2,4-dioxo-1-oxa-3,8-diaza-spiro[4,5]dec-3-yl or 2,4-dioxo-1,3,8-triaza-spiro[4,5]dec-3-yl.

R14 as phthalimide, hydantoin, oxazolidinone or 2,6-dioxo-piperazine is preferably optionally substituted by from 1-8 substituents selected from halo, hydroxy, nitro, cyano, amino, oxo, lower-alkyl, lower-alkenyl, lower-alkynyl, $C_3$-$C_{10}$cycloalkyl, $C_3$-$C_{10}$cycloalkyl-lower-alkyl, lower-alkoxy, lower-alkoxy-lower-alkyl, lower-alkoxy-lower-alkoxy-lower-alkyl, halo-lower-alkyl, aryl, aryl-lower-alkyl, halo-aryl-lower-alkyl, halo-aryloxy-lower-alkyl-carbonyl, lower-alkyl-sulphonyl, lower-alkyl-carbonyl, lower-alkoxy-carbonyl, sulphonamido, lower-alkylsulphonamido, lower-alkenylsulphonamido, loweralkoxy-lower-alkylsulphonamido, halo-lower-alkylsulphonamido, arylsulphonamido, N-heterocyclyl-aryl-lower-alkyl or N-heterocyclyl-lower-alkyl (wherein N-heterocyclyl is as defined above).

Examples of R14 as phthalimide, hydantoin, oxazolidinone or 2,6-dioxo-piperazine are: 1,3-dioxo-1,3-dihydro-isoindol-2-yl, 2,6-dioxo-piperidin-1-yl, 2,5-dioxo-3-methyl-imidazol-1-yl, 2,5-dioxo-4,4-dimethyl-oxazol-1-yl, 6-nitro-1,3-dioxo-1,3-dihydro-isoindol-2-yl 2,5-dioxo-3N,4,4-trimethyl-imidazol-1-yl, 2,5-dioxo-imidazol-1-yl, 2,6-dioxo-4,5-dihydro-1H-pyrimidin-1-yl, 2,5-dioxo-thiazolidin-1-yl, 2,5-dioxo-oxazolidin-1-yl, 6-bromo-1,3-dioxo-1,3-dihydro-isoindol-2-yl, 4,4-diethyl-2,5-dioxo-oxazolidin-1-yl, 4,4-dimethyl-2,5-dioxo-oxazolidin-1-yl, 6-methylsulphonamido-1,3-dioxo-1,3-dihydro-isoindol-2-yl, 3-methyl-1,4-dioxo-3,4-dihydro-1H-phthalazin-2-yl, 3-(4-chlorobenzyl)-2,5-dioxo-imidazolidin-1-yl, 3-(4-chlorobenzyl)-2,5-dioxo-imidazolidin-1-yl, 3-(2-chlorobenzyl)-2,5-dioxo-imidazolidin-1-yl, 3-(2,4-dichlorobenzyl)-2,5-dioxo-imidazolidin-1-yl, 3-(3-fluoropyridin-4-ylmethyl)-2,5-dioxo-imidazolidin-1-yl, 3-(4-fluoropyridin-3-ylmethyl)-2,5-dioxo-imidazolidin-1-yl, 3-(2-fluorobenzyl)-2,5-dioxo-imidazolidin-1-yl, 3-(6-fluoropyridin-2-ylmethyl)-2,6-dioxo-4,5-dihydro-1H-pyrimidin-1-yl, 3-(2-pyrrolidin-1-ylethyl)-2,5-dioxo-imidazolidin-1-yl 3-(4-fluoropyridin-3-ylmethyl)-2,6-dioxo-4,5-dihydro-1H-pyrimidin-1-yl, 3-(2.4-difluorobenzyl)-2,5-dioxo-imidazolidin-1-yl 3-(2.4-difluorobenzyl)-2,6-dioxo-4,5-dihydro-1H-pyrimidin-1-yl, 3-pyrazin-2-yl-2,56-dioxo-imidazolidin-1-yl, 3-(4-chlorobenzyl)-2,6-dioxo-4,5-dihydro-1H-pyrimidin-1-yl, 3-(2-methoxyethyl)-2,6-dioxo-4,5-dihydro-1H-pyrimidin-1-yl, 3-(2-methoxyethyl-2,5-dioxo-imidazolidin-1-yl, 3-(4-chlorobenzyl)-4-isopropyl-2,5-dioxo-imidazolidin-1-yl, 3-(4-chlorobenzyl)-4-methyl-2,5-dioxo-imidazolidin-1-yl, 3-(4-(4-methylpiperazin-1-yl)benzyl)-2,5-dioxo-imidazolidin-1-yl, 3-(4-piperidin-1-ylbenzyl)-2,5-dioxo-imidazolidin-1-yl, 2,4,8,8-tetraoxo-1-oxa-8λ$^6$-thia-3-aza-spiro[4,5]dec-3-yl, 2,4-dioxo-1-oxa-3,8-diaza-spiro[4,5]dec-3-yl, 8-(4-chlorobenzyl)-2,4-dioxo-1-oxa-3,8-diaza-spiro[4,5]dec-3-yl, 8-(4-fluorobenzyl)-2,4-dioxo-1-oxa-3,8-diaza-spiro[4,5]dec-3-yl, 8-ethyl-2,4-dioxo-1-oxa-3,8-diaza-spiro[4,5]dec-3-yl, 8-n-propyl-2,4-dioxo-1-oxa-3,8-diaza-spiro[4,5]dec-3-yl, 8-(3,3,3-trifluoro-n-propyl)-2,4-dioxo-1-oxa-3,8-diaza-spiro[4,5]dec-3-yl, 8-isobutyl-2,4-dioxo-1-oxa-3,8-diaza-spiro[4,5]dec-3-yl, 8-cyclopropylmethyl-2,4-dioxo-1-oxa-3,8-diaza-spiro[4,5]dec-3-yl, 8-n-butyl-2,4-dioxo-1-oxa-3,8-diaza-spiro[4,5]dec-3-yl, 8-methylsulphonyl-2,4-dioxo-1-oxa-3,8-diaza-spiro[4,5]dec-3-yl, 8-methylcarbonyl-2,4-dioxo-1-oxa-3,8-diaza-spiro[4,5]dec-3-yl, 1-methyl-2,4-dioxo-1,3,8-triaza-spiro[4,5]dec-3-yl, 1-methyl-8-n-propyl-2,4-dioxo-1,3,8-triaza-spiro[4,5]dec-3-yl, 1-methyl-8-cyclopropylmethyl-2,4-dioxo-1,3,8-triaza-spiro[4,5]dec-3-yl, 1-methyl-8-cyclobutylmethyl-2,4-dioxo-1,3,8-triaza-spiro[4,5]dec-3-yl, 1-methyl-8-cyclohexylmethyl-2,4-dioxo-1,3,8-triaza-spiro[4,5]dec-3-yl, 1-methyl-8-prop-2-ynyl-2,4-dioxo-1,3,8-triaza-spiro[4,5]dec-3-yl, 1-methyl-8-(4-chlorobenzyl)-2,4-dioxo-1,3,8-triaza-spiro[4,5]dec-3-yl, 1-methyl-8-(2,4-difluorobenzyl)-2,4-dioxo-1,3,8-triaza-spiro[4,5]dec-3-yl, 1-methyl-8-(2-ethoxyethyl)-2,4-dioxo-1,3,8-triaza-spiro[4,5]dec-3-yl, 1-methyl-8-(2-(2-ethoxy)-ethoxymethyl)-2,4-dioxo-1,3,8-triaza-spiro[4,5]dec-3-yl, 1-methyl-8-(2-methoxyethyl)-2,4-dioxo-1,3,8-triaza-spiro[4,5]dec-3-yl, 1-methyl-8-(2-(2-methoxy)-ethoxyethyl)-2,4-dioxo-1,3,8-triaza-spiro[4,5]dec-3-yl, 1-methyl-8-butylsulphonyl-2,4-dioxo-1,3,8-triaza-spiro[4,5]dec-3-yl, 1-methyl-8-butylcarbonyl-2,4-dioxo-1,3,8-triaza-spiro[4,5]dec-3-yl, 8-n-propyl-2,4-dioxo-1,3,8-triaza-spiro[4,5]dec-3-yl, 8-(4-fluorobenzyl)-2,4-dioxo-1,3,8-triaza-spiro[4,5]dec-3-yl, 8-n-butyl-2,4-dioxo-1,3,8-triaza-spiro[4,5]dec-3-yl, 8-(3,3,3-trifluoropropyl)-2,4-dioxo-1,3,8-triaza-spiro[4,5]dec-3-yl 8-isobutyl-2,4-dioxo-1,3,8-triaza-spiro[4,5]dec-3-yl, 8-pyrimidin-2-yl-2,4-dioxo-1,3,8-triaza-spiro[4,5]dec-3-yl, 4-t-butoxycarbonyl-2,6-dioxo-piperazin-1-yl, 4-phenylsulphanyl-2,6-dioxo-piperazin-1-yl 4-(4-fluorobenzyl)-2,6-dioxo-piperazin-1-yl, 4-(2-ethoxyethyl)-2,6-dioxo-piperazin-1-yl 4-(2-methoxyethyl)-2,6-dioxo-piperazin-1-yl, 4-propargyl-2,6-dioxo-piperazin-1-yl 4-(butane-1-sulphonyl)-2,6-dioxo-piperazin-1-yl 4-methylsulphonyl-2,6-dioxo-piperazin-1-yl 4-(4-chlorophenoxymethylcarbonyl)-2,6-dioxo-piperazin-1-yl and 4-(4-fluorophenyl)-2,6-dioxo-piperazin-1-yl.

Particularly preferred compounds of the invention are the compounds of the examples Compounds of formula V' or a pharmaceutically acceptable salts or esters thereof

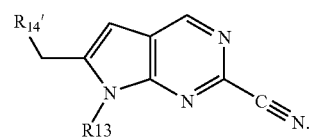

V' wherein R13 is as defined above and R14' is as defined above for R14, except that R14' is not optionally substituted carbocyclic aryl, may be prepared by coupling of a halo precursor of formula XI

XI

R13 is as defined above and Halo is preferably bromo, with an R14' precursor.

Compounds of formula V''' or a pharmaceutically acceptable salts or esters thereof

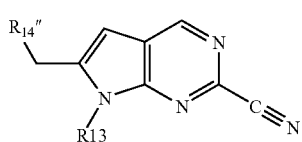

wherein R13 is as defined above and R14" is optionally substituted (carbocylic aryl or azole) may be prepared by cyclising a corresponding carbocyclic arly-1-prop-2-yne, or azole-1-prop-2-yne of formula XII with a 5-halo-pyrimidine-2-carbonitrile precursor of formula XIII

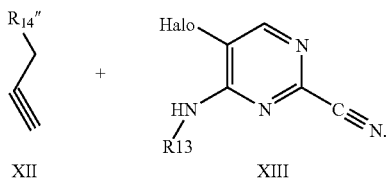

wherein Halo is preferably Br, and R13 and R14" are as defined above.

The above coupling and cyclisation reactions may be carried out under various conditions and in the presence of solvents and other reagents as required, including catalysts and co-factors as known in the art and for instance, as hereinafter described in the examples.

The starting materials may be prepared and the coupled and cyclised products may be converted into other compounds of formula V and salts and esters thereof using methods and procedures known in the art, and as hereinafter described in the examples.

Accordingly the present invention further provides processes for the preparation of compounds of Formula I

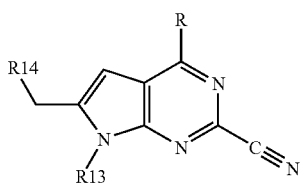

as hereinbefore defined, comprising
i) for the preparation of compounds of formula V' or a pharmaceutically acceptable salts or esters thereof

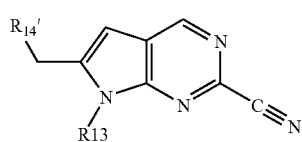

wherein R13 is as defined above and R14' is as defined above for R14, except that R14' is not optionally substituted carbocyclic aryl, coupling of a halo precursor of formula XI

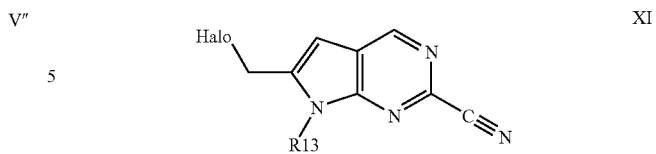

wherein R13 is as defined above and Halo is preferably bromo, with an R14' precursor;

ii) for the prearation of compounds of formula V" or a pharmaceutically acceptable salts or esters thereof

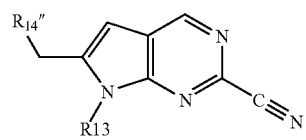

wherein R13 is as defined above and R14" is optionally substituted (carbocylic aryl or azole), cyclising a corresponding carbocyclic arly-1-prop-2-yne, or azole-1-prop-2-yne of formula XII with a 5-halo-pyrimidine-2-carbonitrile precursor of formula XIII

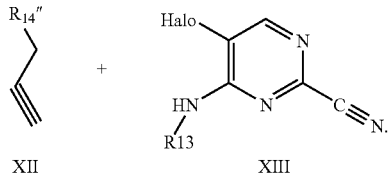

wherein Halo is preferably Br, and R13 and R14" are as defined above; and thereafter, if desired, converting the product obtained into a further compound of formula I, or into a salt or ester thereof.

Compounds of the invention are either obtained in the free form, or as a salt thereof if salt forming groups are present.

Compounds of the Invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$-$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$-$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The compounds of the invention exhibit valuable pharmacological properties in mammals and are particularly useful as inhibitors of cathepsin K.

The cathepsin K inhibitory effects of the compound of the invention can be demonstrated in vitro by measuring the inhibition of e.g. recombinant human cathepsin K.

The In Vitro assay is Carried out as Follows:

For Cathepsin K:

The assay is performed in 96 well microtiter plates at ambient temperature using recombinant human cathepsin K. Inhibition of cathepsin K is assayed at a constant enzyme (0.16 nM) and substrate concentration (54 mM Z-Phe-Arg-AMCA—Peptide Institute Inc. Osaka, Japan) in 100 mM sodium phosphate buffer, pH 7.0, containing 2 mM dithiothreitol 20 mM Tween 80 and 1 mM EDTA. Cathepsin K is preincubated with the inhibitors for 30 min, and the reaction is initiated by the addition of substrate. After 30 min incubation the reaction is stopped by the addition of E-64 (2 mM), and fluorescence intensity is read on a multi-well plate reader at excitation and emission wavelengths of 360 and 460 nm, respectively. Compounds of the Invention typically have $IC_{50}$s for inhibition of human cathepsin K of less than about 100 nM down to about 1 nM or less, preferably of about 5 nM or less, e.g. about 0.5 nM. Thus for example, the compounds of Examples 6-15 and 7-45 have $IC_{50}$s for inhibition of human cathepsin K of 1 nM and 0.6 nM respectively.

In view of their activity as inhibitors of cathepsin K, Compounds of the Invention are particularly useful in mammals as agents for treatment and prophylaxis of diseases and medical conditions involving elevated levels of cathepsin K. Such diseases include diseases involving infection by organisms such as *pneumocystis carinii, trypsanoma cruzi, trypsanoma brucei, crithidia fusiculata*, as well as parasitic diseases such as schistosomiasis and malaria, tumours (tumour invasion and tumour metastasis), and other diseases such as metachromatic leukodystrophy, muscular dystrophy, amytrophy and similar diseases.

Cathepsin K, has been implicated in diseases of excessive bone loss, and thus the Compounds of the Invention may be used for treatment and prophylaxis of such diseases, including osteoporosis, gingival diseases such as gingivitis and periodontitis, Paget's disease, hypercalcemia of malignancy, e.g. tumour-induced hypercalcemia and metabolic bone disease. Also the Compounds of the Invention may be use for treatment or prophylaxis of diseases of excessive cartilage or matrix degradation, including osteoarthritis and rheumatoid arthritis as well as certain neoplastic diseases involving expression of high levels of proteolytic enzymes and matrix degradation.

Compounds of the Invention, are also indicated for preventing or treating coronary disease, atherosclerosis (including atherosclerotic plaque rupture and destabilization), autoimmune diseases, respiratory diseases and immunologically mediated diseases (including transplant rejection).

Compounds of the Invention are particularly indicated for preventing or treating osteoporosis of various genesis (e.g. juvenile, menopausal, post-menopausal, post-traumatic, caused by old age or by cortico-steroid therapy or inactivity).

Beneficial effects are evaluated in in vitro and in vivo pharmacological tests generally known in the art, and as illustrated herein.

The above cited properties are demonstrable in in vitro and in vivo tests, using advantageously mammals, e.g. rats, mice, dogs, rabbits, monkeys or isolated organs and tissues, as well as mammalian enzyme preparations, either natural or prepared by e.g. recombinant technology. Compounds of the Invention can be applied in vitro in the form of solutions, e.g. preferably aqueous solutions or suspensions, and in vivo either enterally or parenterally, advantageously orally, e.g. as a suspension or in aqueous solution, or as a solid capsule or tablet formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the Compounds of the Invention for the treatment of rheumatoid arthritis can be determined using models such as or similar to the rat model of adjuvant arthritis, as described previously (R. E. Esser, et. al. J. Rheumatology, 1993, 20, 1176.)

The efficacy of the compounds of the invention for the treatment of osteoarthritis can be determined using models such as or similar to the rabbit partial lateral meniscectomy model, as described previously (Colombo et al. Arth. Rheum. 1993 26, 875-886). The efficacy of the compounds in the model can be quantified using histological scoring methods, as described previously (O'Byrne et al. Inflamm Res 1995, 44, S117-S118).

The efficacy of the compounds of the invention for the treatment of osteoporosis can be determined using an animal model such as the ovariectomised rat or other similar species, e.g. rabbit or monkey, in which test compounds are administered to the animal and the presence of markers of bone resorption are measured in urine or serum (e.g. as described in Osteoporos Int (1997) 7:539-543).

Accordingly in further aspects the invention provides:

A Compound of the Invention for use as a pharmaceutical;

a pharmaceutical composition comprising a Compound of the Invention as an active ingredient;

a method of treating a patient suffering from or susceptible to a disease or medical condition in which cathepsin K is implicated, comprising administering an effective amount of a Compound of the Invention to the patient, and the use of a Compound of the Invention for the preparation of a medicament for therapeutic or prophylactic treatment of a disease or medical condition in which cathepsin K is implicated.

The present invention relates to methods of using Compounds of the Invention and their pharmaceutically acceptable salts, or pharmaceutical compositions thereof, in mammals for inhibiting cathepsin K, and for the treatment of cathepsin K dependent conditions, such as the cathepsin K dependent conditions, described herein, e.g. inflammation, osteoporosis, rheumatoid arthritis and osteoarthritis.

Particularly the present invention relates to a method of selectively inhibiting cathepsin K activity in a mammal which comprises administering to a mammal in need thereof an effective cathepsin K inhibiting amount of a Compound of the Invention.

More specifically such relates to a method of treating osteoporosis, rheumatoid arthritis, osteoarthritis, and inflammation (and other diseases as identified above) in mammals comprises administering to a mammal in need thereof a correspondingly effective amount of a Compound of the Invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20-133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLES

Example 1 describes the preparation of 6-bromomethyl-7H-pyrrolo[2,3-d]pyrimidine-2-carbonitrile derivatives which are key intermediates for the preparation of compounds of Formula V.

Example 1-1

6-Bromomethyl-7-neopentyl-7H-pyrrolo[2,3-d]pyrimidine-2-carbonitrile

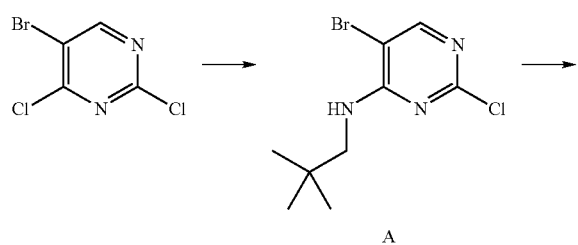

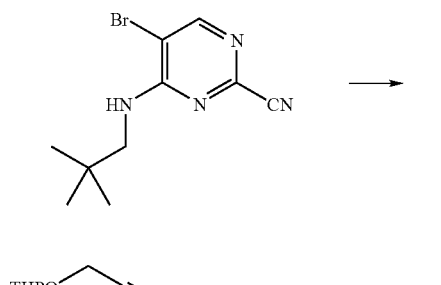

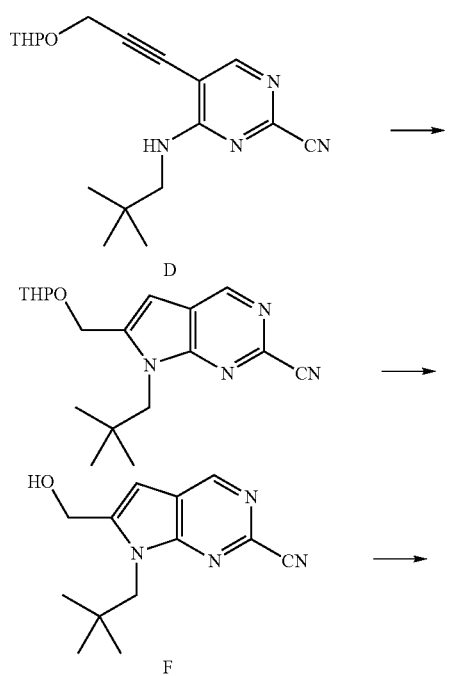

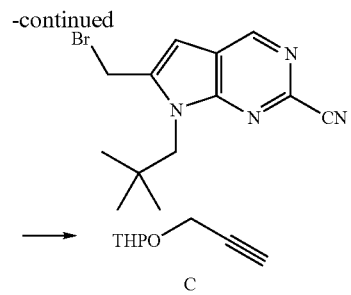

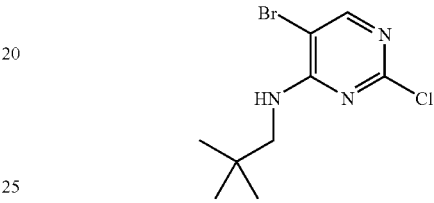

A) 5-Bromo-2-chloro-4-(neopentyl)aminopyrimidine (A)

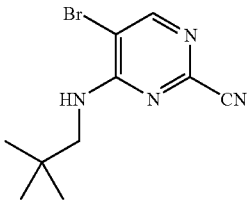

Neopentylamine (30 ml, 0.255 mol) is added dropwise at 0° C. over 20 min to a soln. of 5-bromo-2,4-dichloropyrimidine (29.17 g, 0.128 mol) in MeOH (230 ml). After stirring for 20 min at 0° C., the mixture is warmed to room temperature, stirred for 3 h, and evaporated. The residue is suspended in 300 ml of EtOAc, washed with sat. aq. NaHCO$_3$ soln. (80 ml) and brine (80 ml), dried (MgSO$_4$), and evaporated. The residue is chromagraphed on silica gel column (800 g of silica gel; hexane/EtOAc 5:1) to give the product (A) (32.64 g, 92%). White crystals. $^1$H-NMR (400 MHz, CDCl$_3$) δ 1.00 (s), 3.36 (d, J=8.0), 5.52-5.61 (br. s), 8.12 (s). Rf 0.48 (hexane/EtOAc 5:1).

B) 5-Bromo-2-cyano-4-(neopentyl)aminopyrimidine (B)

At room temperature, to an aqueous soln. (26 ml) of NaCN (8.610 g, 0.176 mol) is added successively DMSO (33 ml), DABCO (4.395 g, 39.2 mmol), and a soln. of A (32.59 g, 0.117 mol) in DMSO (200 ml). The mixture is stirred for 2 h at 60° C., poured into an ice water (ca. 750 ml), extracted (2×200 ml of EtOAc, and 2×200 ml of Et$_2$O), and dried (MgSO$_4$). The organic layer is treated with SiO$_2$ (90 g), evaporated, and the residue is chromatographed on a silica gel column. (850 g of silica gel; hexane/EtOAc 4:1) to give the product (B) (28.95 g, 92%). Light yellow solid.

$^1$H-NMR (400 MHz, CDCl$_3$) δ 1.00 (s), 3.38 (d, J=8.0), 5.14-5.29 (br. s), 8.30 (s). Rf 0.43 (hexane/EtOAc 4:1).

C) Propargyl (tetrahydro-2H-pyran-2-yl) ether (C)

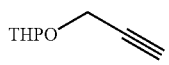

At 0° C., 3,4-dihydro-2H-pyran (173 ml, 1.90 mol) is added dropwise over 10 min to a soln. of propargyl alcohol (88.49 g, 1.58 mol) and TsOH.H$_2$O (16.08 g, 84.53 mmol) in CH$_2$Cl$_2$ (880 ml). After stirring for 80 min at 0° C., the mixture is warmed to room temperature, stirred for 3 h, treated with Et$_3$N (12 ml), and evaporated. A vacuum distillation (20 mmHg, 80° C.) gives C (224 g, quant.). Colourless oil. $^1$H-NMR (400 MHz, CDCl$_3$) δ 1.46-1.70 (m, 4 H), 1.70-1.91 (n, 2 H), 2.41 (t, J=2.2), 3.49-3.58 (m, 1 H), 3.81-3.88 (m, 1 H), 3.49-3.58 (m, 1 H), 4.23 (dd, J=15, 2.2), 4.30 (dd, J=15, 2.2), 4.83 (t, J=3.0).

D) 2-Cyano-4-(neopentyl)amino-5-[3-(tetrahydro-2H-pyran-2-yloxy)-prop-1-ynyl]-pyrimidine (D)

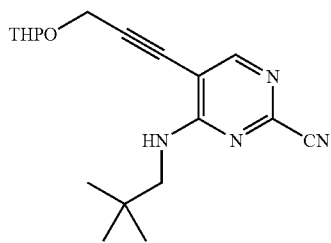

At room temperature, a soln. of B (42.50 g, 0.158 mol) and C (44 ml, 0.313 mol) in dry DMF (420 ml) is treated with Et$_3$N (66 ml, 0.473 mol), CuI (3.1 g, 16.3 mmol), and (Ph$_3$P)$_2$PdCl$_2$ (5.0 g, 7.1 mmol). The mixture is stirred for 2 h at 80° C., poured into an ice water (ca. 3000 ml), extracted (2×400 ml of EtOAc, and 3×300 ml of Et$_2$O), washed with 2% aq. Na$_2$EDTA soln. (2×350 ml), and dried (MgSO$_4$). The organic layer is treated with SiO$_2$ (120 g), evaporated, and the residue is cheomatographed on a silica gel column (1800 g of silica gel; hexane/EtOAc 2:1) to give the product (D) (47.14 g, 92%). Orange solid. $^1$H-NMR (400 MHz, CDCl$_3$) δ 1.47-1.70 (m, 4 H), 1.70-1.92 (m, 2 H), 3.31-3.43 (m, 2 H), 3.52-3.61 (m, 1 H), 3.84-3.92 (m, 1 H), 4.53 (AB q, J=7.0), 4.86 (t, J=3.0), 5.89-5.97 (br. s), 8.21 (s). Rf 0.44 (hexane/EtOAc 2:1).

E) 7-Neopentyl-6-(tetrahydro-2H-pyran-2-yloxy)methyl-7H-pyrrolo[2,3-d]pyrimi-dine-2-carbonitrile (E)

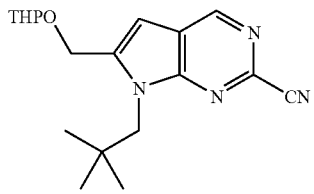

At room temperature, a soln. of D (43.94 g, 0.134 mol) in dry DMF (350 ml) is treated with DBU (7.1 ml, 47.5 mmol), stirred for 2 h at 100° C., poured into an ice water (ca 2500 11l), extracted (2×500 ml of EtOAc, and 2×500 ml of Et$_2$O), washed with H$_2$O (2×300 ml), dried (MgSO$_4$), and evaporated. A soln. of the residue in CH$_2$Cl$_2$/MeOH 1:1 (1000 ml) is treated with activated charcoal (10 g), stirred at 40° C. for 30 min, and filtered. An evaporation of the filtrate gives the product (E) (40.86 g, 93%). Brown solid. $^1$H-NMR (400 MHz, CDCl$_3$) δ 1.10 (s), 1.51-1.70 (m, 4 H), 1.70-1.90 (m, 2 H), 3.53-3.63 (m, 1 H), 3.83-3.94 (m, 1 H), 4.22 (s), 4.67 (t, J=3.0), 4.75 (d, J=13.0), 5.04 (d, J=13.0), 6.58 (s), 8.93 (s). Rf 0.38 (hexane/EtOAc 2:1).

F) 6-Hydroxymethyl-7-neopentyl-7H-pyrrolo[2,3-d]pyrimidine-2-carbonitrile (F)

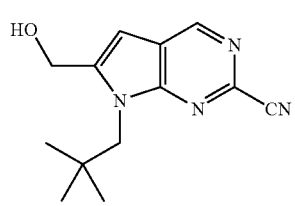

At room temperature, a soln. of E (40.86 g, 0.124 mol) in THF (300 ml) is treated with MeOH (600 ml) and TsOH.H$_2$O (2.30 g, 12.1 mmol), stirred for 3 h, treated with Et$_3$N (1.75 ml), and evaporated. The residue is suspended in 30 ml of EtOAc, and filtered. Washing the cake with EtOAc (100 ml) gives the product (F) (20.76 g, batch 1). The filtrate is evaporated, dissolved in 500 ml of CH$_2$Cl$_2$, washed with H$_2$O (100 ml) and brine (100 ml), and evaporated. The residue is suspended in 10 ml of EtOAc, and filtered. Washing the cake with EtOAc (30 ml) gives further the product (F) (2.65 g, batch 2). The filtrate is treated with SiO$_2$ (30 g), evaporated, and the residue is chromatographed on a silica gel column (300 g of silica gel; CH$_2$Cl$_2$/EtOAc 3:2) to give another F (2.58 g, batch 3). Combining the batches 1-3 gives F (25.99 g, 87%). Yellow solid. $^1$H-NMR (400 MH, CDCl$_3$) δ 1.10 (s), 1.90 (t, J=6.0), 4.23 (s), 4.98 (d, J=6.0), 6.68 (s), 8.92 (s). Rf 0.46 (CHCl$_3$/EtOAc 3:2).

G) 6-Bromomethyl-7-neopentyl-7H-pyrrolo[2,3-d]pyrimidine-2-carbonitrile

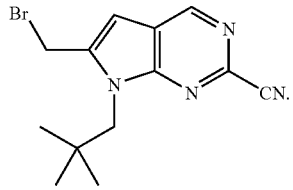

At 0° C., a soln. of CBr$_4$ (56.1 g, 0.17 mol) in dry CH$_2$Cl$_2$ (150 ml) is added dropwise over 15 min to a soln. of F (20.65 g, 84.5 mmol) and Ph$_3$P (44.2 g, 0.17 mol) in dry CH$_2$Cl$_2$ (150 ml). After stirring for 30 min at 0° C., the mixture is warmed to room temperature, stirred for 3 h. The mixture is diluted with CH$_2$Cl$_2$ (300 ml), washed with sat. aq. NaHCO$_3$ soln. (150 ml) and brine (150 ml), and dried (MgSO$_4$). The org. layer is treated with SiO$_2$ (70 g), evaporated, and the residue is loaded on a silica gel column. FC (800 g of silica gel; hexane/EtOAc 7:4) gives the title compound (20.36 g, 78%). Yellow solid. $^1$H-NMR (400 MHz, CDCl$_3$) δ 1.12 (s), 4.27 (s), 4.72 (s), 4.84 (s), 6.75 (s), 8.95 (s). Rf 0.44 (hexane/EtOAc 7:4).

Example 2 Describes the Preparation of 6-Aryloxy-7H-pyrrolo[2,3-d]pyrimidine-2-carboxamide Derivatives

Example 2-1

6-(6-Chloro-pyridin-3-yloxymethyl)-7-(2,2-dimethyl-propyl)-7H-pyrrolo[2,3-d]pyrimidine-2-carbonitrile

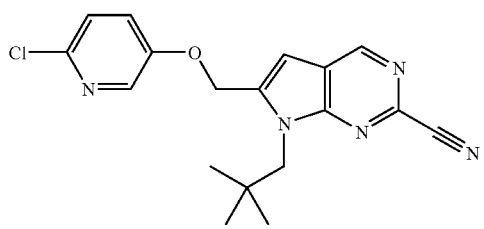

6-Bromomethyl-7-(2,2-dimethyl-propyl)-7H-pyrrolo[2,3-d]pyrimidine-2-carbonitrile (1.3 mmol) is dissolved in DMSO (or DMF) (4 ml). To the solution, 2-chloro-5-hydroxypyridine (1.56 mmol) and $K_2CO_3$ (1.69 mmol) are added. The mixture is stirred at room temperature under nitrogen atomosphere for 11 h. The reaction mixture is diluted with water and extracted with AcOEt (twice) and $Et_2O$ (twice). The combined organic layer is washed with water and brine, dried over $MgSO_4$, and concentrated in vacuo. The residue is purified by silica gel column chromatography (n-hexane:AcOEt=1:1) to give the product in 99% yield.

By repeating the procedures described above using appropriate starting materials and conditions the following compounds of formula 2-1 are obtained as identified below in Table 2-1.

TABLE 2-1

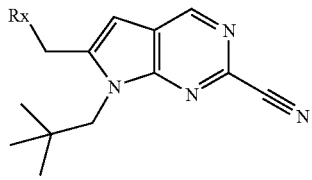

| Expl. No. | Rx | Yield(%) | Rf(solvent) | NMR(400 MHz, δ) |
|---|---|---|---|---|
| 2-1 | Cl-pyridine-O- (6-Cl, 3-O) | 99 | 0.34 (n-hexane:AcOEt = 1:1) | (DMSO-$d_6$) 0.97(s, 9H), 4.25(s, 2H), 5.56(s, 2H), 7.03(s, 1H), 7.49(d, 1H), 7.67(dd, 1H), 8.28(d, 1H), 9.18(d, 1H) |
| 2-2 | $CH_3$-pyridine-O- | 55 | 0.24 (n-hexane:AcOEt = 1:1) | (CDCl$_3$) 1.03(s, 9H), 2.53(s, 3H), 4.25(s, 2H), 5.33(s, 1H), 6.77(s, 1H), 7.11(d, 1H), 7.17(dd, 1H), 8.26(d, 1H), 8.97(s, 1H) |
| 2-3 | 2-Cl-4-OMe-pyridine | 75 | 0.27 (n-hexane:AcOEt = 1:1) | (CDCl$_3$) 1.04(s, 9H), 4.22(s, 2H), 5.35(s, 1H), 6.81(s, 1H), 6.84(dd, 1H), 6.94(d, 1H), 8.28(d, 1H), 9.01(s, 1H) |
| 2-4 | 4-OMe-pyridine | 66 | 0.25 ($CH_2Cl_2$:MeOH = 9:1) | (CDCl$_3$) 1.07(s, 9H), 4.10(s, 2H), 5.22(s, 2H), 6.41(s, 1H), 6.45(d, 2H), 7.30(d, 2H), 8.96(s, 1H) |
| 2-5 | 3-OMe-pyridine | 57 | 0.26(AcOEt) | (CDCl$_3$) 1.04(s, 9H), 4.26(s, 2H), 5.36(s, 2H), 6.79(s, 1H), 7.28–7.27(m, 2H), 8.33–8.31(m, 1H), 8.40(brs, 1H), 8.98(s, 1H) |
| 2-6 | pyridine-4-CH$_2$-O- | 35 | 0.47 (n-hexane:AcOEt = 1:2) | (CDCl$_3$)1.00(s, 9H), 4.22(s, 2H), 4.57(s, 2H), 4.84(s, 2H), 6.70(s, 1H), 7.25–7.26(m, 2H), 8.61–8.62(m, 2H), 8.96(s, 1H). |
| 2-7 | 2-Me-4-OMe-pyridine | 28 | 0.20 (n-hexane:AcOEt = 1:1) | (CDCl$_3$): 8.99(s, 1H), 8.39(d, 1H), 6.79(s, 1H), 6.75(d, 1H), 6.71(dd, 1H), 5.33(s, 2H), 4.23(s, 2H), 2.55(s, 3H), 1.03(s, 9H) |

TABLE 2-1-continued

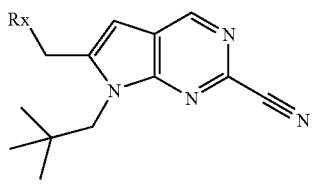

| Expl. No. | Rx | Yield(%) | Rf(solvent) | NMR(400 MHz, δ) |
|---|---|---|---|---|
| 2-8 | | 27 | 0.43 (CH$_2$Cl$_2$:MeOH = 9:1) | (DMSO): 0.96(s, 9H), 4.22(s, 2H), 5.41(s, 2H), 5.95(dd, 1H), 5.98(d, 1H), 7.01(s, 1H), 7.29(d, 1H), 9.19(s, 1H), 11.18(s, 1H) |
| 2-9 | | 26 | 0.29 (n-hexane:AcOEt = 2:1) | (CDCl$_3$) 1.04(s, 9H), 4.24(s, 2H), 5.35(s, 2H), 6.80(s, 1H), 7.30(t, 1H), 8.29–8.28(m, 2H), 9.00(s, 1H) |
| 2-10 | | 11 | 0.22 (CH$_2$Cl$_2$:MeOH = 9:1) | (DMSO): 0.95(s, 9H), 4.23(s, 2H), 5.21(s, 2H), 5.51(s, 2H), 6.87(s, 1H), 7.00(s, 1H), 7.15(s, 1H), 7.21(d, 1H), 7.55(dd, 1H), 7.70(s, 1H), 8.37(d, 1H), 9.15(s, 1H) |
| 2-11 | | 64 | 0.14 (AcOEt) | (DMSO-d$_6$) 0.97(s, 9H), 4.24(s, 2H), 5.50(s, 2H), 6.93(d, 1H), 7.00(s, 1H), 7.26(d, 1H), 9.18(s, 1H), 12.28(s, 1H) |
| 2-12 | | 74 | 0.4 (CHCl$_3$:acetone = 9:1) | (CDCl$_3$) 1.04(s, 9H), 4.24(s, 2H), 5.41(s, 2H), 6.82(s, 1H), 7.03–7.08(m, 1H), 7.27–7.31(m, 1H), 8.60–8.65(m, 1H), 9.01(s, 1H) |
| 2-13 | | 77 | 0.56 (n-hexane:AcOEt = 1:1) | (CDCl$_3$) 1.05(s, 9H), 4.25(s, 2H), 5.39(s, 2H), 6.87(s, 1H), 7.03(s, 1H), 7.12–7.17(m, 1H), 7.78–7.82(m, 1H), 9.02(s, 1H) |
| 2-14 | | 90 | 0.24 (n-hexane:AcOEt = 3:1) | (CDCl$_3$) 1.02(s, 9H), 4.25(s, 2H), 5.22(s, 2H), 5.94(s, 2H), 6.36–6.40(m, 1H), 6.52–6.54(m, 1H), 6.70–6.75(m, 2H), 8.96(s, 1H) |
| 2-15 | | 18 | 0.25 (n-hexane:AcOEt = 3:1) | (CDCl$_3$) 1.04(s, 9H), 4.26(s, 2H), 5.34(s, 2H), 6.79(s, 1H), 7.12–7.16(m, 1H), 7.21(brs, 1H), 7.29–7.33(m, 1H), 7.42–7.48(m, 1H), 8.98(s, 1H) |
| 2-16 | | 3 | 0.49 (n-hexane:AcOEt = 1:1) | (CDCl$_3$) 1.03(s, 9H), 4.25(s, 2H), 5.32(s, 2H), 6.79(s, 1H), 6.87–6.92(m, 1H), 6.95–6.98(m, 1H), 7.31–7.34(m, 1H), 8.98(s, 1H) |

TABLE 2-1-continued

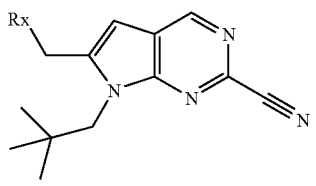

2-1

| Expl. No. | Rx | Yield(%) | Rf(solvent) | NMR(400 MHz, δ) |
|---|---|---|---|---|
| 2-17 | (7-chloro-4-methoxyquinoline) | 14 | 0.56 (CH$_2$Cl$_2$:MeOH = 9:1) | (CDCl$_3$+DMSO-d$_6$) 1.04(s, 9H), 4.29(s, 2H), 5.55(s, 2H), 6.85–6.89(m, 1H), 6.90(s, 1H), 7.45–7.50(m, 1H), 8.05–8.12(s, 2H), 8.78–8.83(m, 1H), 9.03(s, 1H) |
| 2-18 | (4-(4-methoxyphenyl)-piperazinyl acetyl) | 9 | 0.34 (CHCl$_3$:acetone = 4:1) | (CDCl$_3$) 1.02(s, 9H), 2.14(s, 3H), 3.02–3.12(m, 4H), 3.59–3.65(m, 2H), 3.74–3.80(m, 2H), 4.26(s, 2H), 5.25(s, 2H), 6.74(s, 1H), 6.90(s, 4H), 8.95(s, 1H) |
| 2-19 | (2-methyl-4-methoxyquinazoline) | 57 | 0.53 (n-hexane:AcOEt = 1:3) | (CDCl$_3$) 1.07(, 9H), 2.75(s, 3H), 4.35(s, 2H), 5.90(s, 2H), 6.87(s, 1H), 7.48–7.54(m, 1H), 7.79–7.91(m, 2H), 8.07–8.12(m, 1H), 8.97(s, 1H) |

2-20

7-(2,2-Dimethyl-propyl)-6-(pyridin-4-yloxymethyl)-7H-pyrrolo[2,3-d]pyrimidine-2-carbonitrile hydrochloride

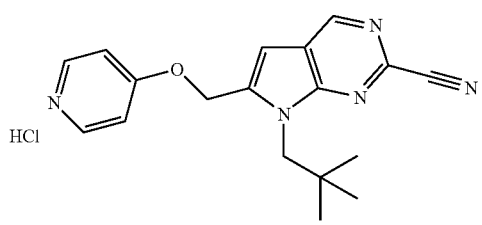

To a solution of 7-(2,2-dimethyl-propyl)-6-(pyridin-4-yloxymethyl)-7H-pyrrolo[2,3-d]pyrimidine-2-carbonitrile (0.31 mmol) obtained above in acetonitrile (3 ml) and CH$_2$Cl$_2$ (5 ml) is added 4N hydrogen chloride in dioxane (2 ml) at room temperature. The solvent is evaporated to give the product in 94% yield. $^1$H NMR(400 MHz, DMSO-d$_6$) δ 1.0(s, 9H), 4.27(s, 2H), 6.02(s, 2H), 6.55(s, 1H), 7.38-7.46(m, 2H), 8.71-8.78(m, 2H), 9.13(s, 1H).

2-21

6-(2-Difluoromethyl-pyridin-4-yloxymethyl)-7-(2,2-dimethyl-propyl)-7H-pyrrolo[2,3-d]pyrimidine-2-carbonitrile Preparation of 2-difluoromethyl-pyridin-4-ol A mixture of (E)-4-methoxy-but-3-en-2-one (20 mmol) and ethyl difluoroacetate (24 mmol) is added dropwise to a mixture of potassium tert-butoxide (26 mmol) and diethyl ether (50 ml) under nitrogen atmosphere at −15° C. over 30 min. The mixture is allowed to warm up to room temperature slowly over 3 h. After cooling to 0° C., acetic acid (26 mmol) and H$_2$O (10 ml) are successively added dropwise to the reaction mixture. The organic layer is separated, washed with sat. aq. NaHCO$_3$, dried over MgSO$_4$, and evaporated in vacuo. The residue is dissolved in i-propanol (30 ml). To the solution, conc. HCl (2 ml) is added and the mixture is refluxed for 3 h. After cooling, the reaction mixture is neutralised with sat. aq. NaHCO$_3$ and extracted with CH$_2$Cl$_2$. The organic layer is dried over MgSO$_4$ and evaporated in vacuo. The residue is dissolved in i-propanol (20 ml). To the solution, 28% aq. NH$_3$ (50 mmol) is added and the mixture is refluxed for 20 h. After cooling, the reaction mixture is diluted with H$_2$O and extracted with AcOEt. The organic layer is dried over MgSO$_4$ and evaporated in vacuo. The residue is purified by silica gel column chromatography (n-hexane:AcOEt=1:1) to give 2-difluoromethyl-pyridin-4-ol in 32% yield.

2-Difluoromethyl-pyridin-4-ol (1.18 mmol) obtained above is dissolved in CH$_3$CN (5 ml). To the solution, 6-bromomethyl-7-(2,2-dimethyl-propyl)-7.H.-pyrrolo[2,3-.d.]pyrimidine-2-carbonitrile (0.98 mmol) and potassium carbonate (2.25 mmol) are added. The mixture is allowed to stir at room temperature under nitrogen atmosphere overnight. The reaction mixture is diluted with H₂O and extracted with ethyl acetate. The organic layer is dried over MgSO₄ and evaporated in vacuo. The residue is purified by silica gel column chromatography (n-hexane:AcOEt=1:1) to give 6-(2-difluoromethyl-pyridin-4-yloxymethyl)-7-(2,2-dimethyl-propyl)-7H-pyrrolo[2,3-d]pyrimidine-2-carbonitrile in 76% yield. Rf=0.28 (n-hexane:AcOEt=1:1). ¹H NMR (400 MHz, CDCl₃) δ: 1.04(s, 9H), 4.24(s, 2H), 5.41(s, 2H), 6.62(t, 1H), 6.82(s, 1H), 6.98(dd, 1H), 7.24(d, 1H), 8.54(d, 1H), 9.01(s, 1H).

2-22

7-(22-Dimethyl-propyl)-6-(6-methoxy-pyridazin-3-yloxymethyl)-7H-pyrrolo[2,3-d]pyrimidine-2-carbonitrile

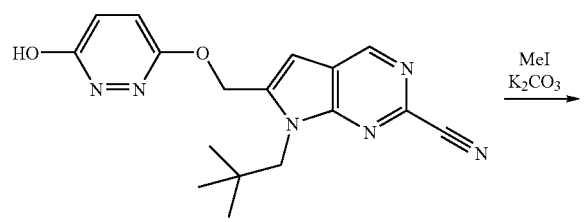

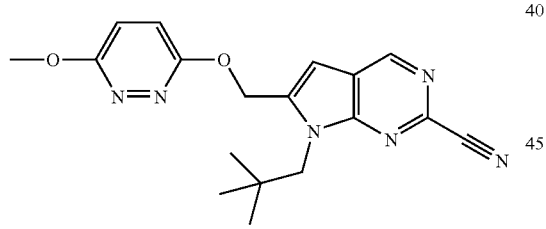

7-(2,2-Dimethyl-propyl)-6-(6-hydroxy-pyridazin-3-yloxymethyl)-7H-pyrrolo[2,3-d]pyrimidine-2-carbonitrile (0.296 mmol) obtained above is dissolved in DMSO (1 ml). To the solution, K₂CO₃ (0.385 mmol) and MeI (0.354 mmol) are added successively. The mixture is stirred at room temperature under nitrogen atmosphere for 4 h. After removal of precipitates by filtration, the filtrate is purified by HPLC (water-0.1% TFA:acetonitrile-0.1% TFA). Fractions are collected, basified with 5% NaHCO₃ aq., and extracted with AcOEt. The organic layer is washed with brine, dried over MgSO₄ and concentrated to give the product in 19% yield. Rf (CH₂Cl₂:MeOH=9:1). ¹H NMR(400 MHz, DMSO-d₆) δ 1.04(s, 9H), 3.67(s, 3H), 4.23(s, 2H), 5.44(s, 2H), 6.78(s, 1H), 6.96(s, 2H), 8.98(s, 1H).

2-23

7-Cyclohexyl-6-[4-(4-methyl-piperazin-1-ylmethyl)-phenoxymethyl]-7H-Pyrrolo[2,3-d]pyrimidine-2-carbonitrile

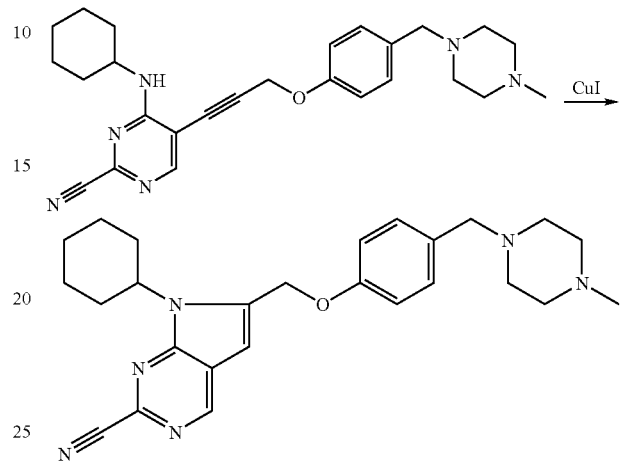

A mixture of compound 12-4 (see below) (1.1 mol), i-Pr₂NEt (12 ml), and CuI (0.11 mmol) and dry DMF (6 ml) is heated at 80° C. under nitrogen atmosphere for 4 days. After cooling, the reaction mixture is diluted with water and extracted with AcOEt. The organic layer is washed with brine, dried over sodium sulfate, and concentrated in vacuo. The crude product is purified by silica gel column chromatography to give the product in 9% yield. Rf=0.60 (CH₂Cl₂:MeOH=1:5). ¹H-NMR (400 MHz, CDCl₃). 1.31-1.46 (m, 3H), 1.68-1.78 (m, 1H), 1.87-1.98 (m 4H), 2.29 (s, 3H), 2.46 (brs, 8H), 2.57-2.70 (m, 2H), 3.47 (s, 2H), 4.36 (tt, 1H), 5.22 (s, 2H), 6.68 (s, 1H), 6.94 (d, 2H), 7.27 (d, 2H), 8.93 (s, 1H).

2-24

7-(2,2-Dimethyl-propyl)-6-[4-(4-methyl-piperazin-ylmethyl)-phenoxymethyl]-7H-pyrrolo[2,3-d]pyrimidine-2-carbonitrile

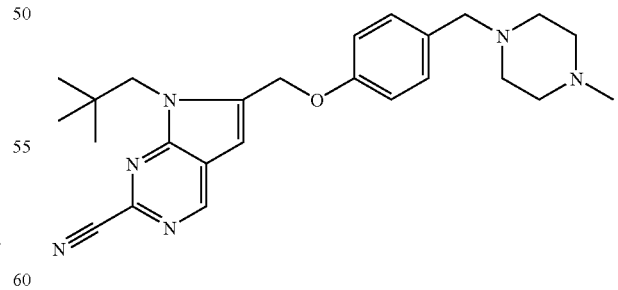

Following by the procedure described above, compound 12-7 (see below) is converted to the title.

Yield 12%. Rf=0.57 (CH₂Cl₂:MeOH=1:5). ¹H-NMR (400 MHz, CDCl₃) δ 1.03 (s, 9H), 2.28 (s, 3H), 2.46 (brs, 8H), 3.47 (s, 2H), 4.26 (s, 1H), 5.29 (s, 2H), 6.76 (s, 1H), 6.94 (d, 2H), 7.27 (d, 2H), 8.96 (s, 1H).

2-25

6-(6-Chloro-pyrimidin-4-yloxymethyl)-7-(2,2-dimethyl-propyl)-7H-pyrrolo[2,3-d]pyrimidine-2-carbonitrile

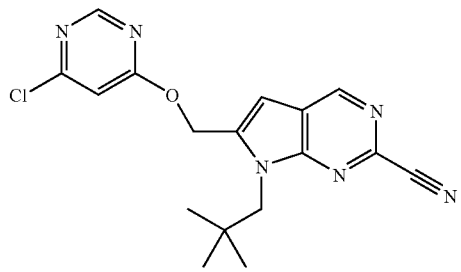

To a solution of 7-(2,2-dimethyl-propyl)-6-hydroxymethyl-7H-pyrrolo[2,3-d]pyrimidine-2-carbonitrile (1.0 mmol) in THF (10 ml) is added NaH (1.2 mmol) at room temperature under nitrogen atmosphere. After 15 min stirring, 4,6-dichloropyrimidine (1.1 mmol) is added and the mixture is stirred at room temperature for 1 h. The reaction mixture is diluted with $H_2O$ and extracted with AcOEt. The organic extracts are dried over Na2SO4 and concentrated. The residue obtained is purified by column chromatography on silica gel to give the product in 92% yield. Rf=0.49 (AcOEt:n-hexane=1:2). $^1$H NMR(400 MHz, CDCl$_3$) δ 1.05 (s, 9H), 4.26(s, 2H), 5.74(s, 2H), 6.83(s, 1H), 6.86(s, 1H), 8.62(s, 1H), 8.97(s, 1H).

2-26

7-(2,2-Dimethyl-propyl)-6-[6-(4-methyl-piperazin-1-yl)-pyrimidin-4-yloxymethyl]-7H-pyrrolo[2,3-d]pyrimidine-2-carbonitrile

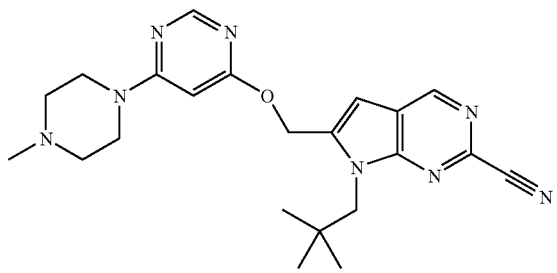

A mixture of 2-25 (0.3 mmol) obtained above, 4-methylpiperazine (0.36 mmol), and triethylamine (0.9 mmol) in DMF (5 ml) is heated at 80° C. under nitrogen atmosphere for 3 h. After cooling to room temperature, the mixture is diluted with H2O and extracted with ether. The organic extracts are dried over Na2SO4 and concentrated in vacuo. The residue obtained is purified by column chromatography on silica gel to give the product in 93% yield. Rf=15 (AcOEt:n-hexane=1:2). $^1$NMR(400 MHz, CDCl$_3$) δ 1.03 (s, 9H), 2.33(s, 3H), 2.44-2.47 (m, 4H), 3.59-3.62(m, 4H), 4.24(s, 2H), 5.64(s, 2H), 5.85(s, 1H), 6.76(s, 1H), 8.30(s, 1H), 8.94(s, 1H).

2-27

7-(2,2-Dimethyl-propyl)-6-(6-morpholin-4-yl-pyrimidin-4-yloxymethyl)-7H-pyrrolo[2,3-d]pyrimidine-2-carbonitrile

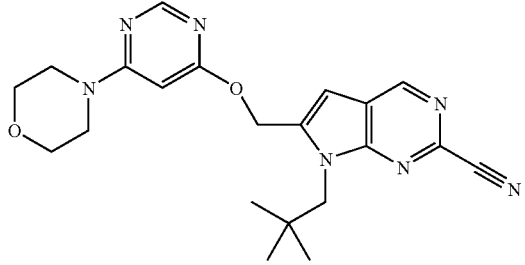

A mixture of 2-25 (0.32 mmol), morpholine (0.38 mmol), and triethylamine (0.96 mmol) in DMF (5 ml) is heated at 60° C. under nitrogen atmosphere for 17 h. After cooling to room temperature, the mixture is diluted with H2O and extracted with ether. The organic extracts are dried over $Na_2SO_4$ and concentrated in vacuo. The residue obtained is purified by column chromatography on silica gel to give the product in 97% yield. Rf=0.17 (AcOEt:n-hexane=1:2). $^1$NMR(400 MHz, CDCl$_3$) δ 1.03 (s, 9H), 3.57(t, 4H), 3.77 (t, 4H), 4.24(s, 2H), 5.65(s, 2H), 5.85(s, 1H), 6.76(s, 1H), 8.31(s, 1H), 8.94(s, 1H).

Example 3 Describes the Preparation of 6-arylamino-7H-pyrrolo-[2,3-d]pyrimidine-2-carbonitrile Derivatives

Example 3-1

6-{[(4-chloro-phenyl)-methyl-amino]-methyl}-7-(2,2-dimethyl-propyl)-7H-pyrrolo[2,3-d]pyrimidine-2-carbonitrile

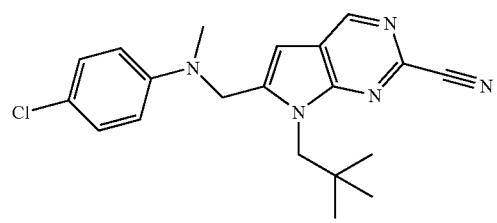

To a solution of 6-bromomethyl-7-(2,2-dimethyl-propyl)-7H-pyrrolo[2,3-d]pyrimidine-2-carbonitrile (1 mmol) in DMF (or DMSO) (5 ml) are added 4-chloro-N-methylaniline (1.2 mmol) and potassium carbonate (2.4 mmol). The mixture is heated at 50° C. for 13 h. The reaction mixture is diluted with AcOEt, washed with water and brine, dried over sodium sulfate and concentrated. The crude product is purified by HPLC (n-hexane:AcOEt) to give the product in 27% yield. Rf=0.69(n-hexane:AcOEt=1:1). $^1$H NMR(400 MHz, CDCl$_3$) δ 1.06(s, 9H), 3.03(s, 3H), 4.13(s, 2H), 4.71(s, 2H), 6.40(s, 1H), 6.62-6.69(m, 2H), 7.17-7.23(m, 2H), 8.84(s, 1H).

By repeating the procedures described above using appropriate starting materials and conditions (room temperature, purification by silica gel column chromatography) the following compounds of formula 3-1 are obtained as identified below in Table 3-1.

TABLE 3-1

3-1

[Structure: pyrrolo[2,3-d]pyrimidine-2-carbonitrile core with N-neopentyl group and Rx-CH2- substituent]

| Example No. | Rx | Yield(%) | Rf(solvent) | NMR(400 MHz, δ) |
|---|---|---|---|---|
| 3-2 | [6-chloro-pyridin-3-yl-NH-] | 41 | 0.26 (n-hexane:AcOEt = 2:1) | (CDCl$_3$) 1.00(s, 9H), 4.23(s, 2H), 4.66(d, 2H), 6.71(s, 1H), 6.82(t, 1H), 7.07(dd, 1H), 7.18(d, 1H), 7.80(d, 1H), 9.07(s, 1H) |
| 3-3 | [6-methoxy-pyridin-3-yl-NH-] | 14 | 0.24 (n-hexane:AcOEt = 1:1) | (CDCl$_3$) 1.04(s, 9H), 3.73(br, 1H), 3.87(s, 3H), 4.20(d, 2H), 4.56(d, 2H), 6.65(s, 1H), 6.66(d, 1H), 7.01(dd, 1H), 7.59(d, 1H), 8.90(d, 1H) |
| 3-4 | [2-methyl-pyridin-4-yl-NH-] | 4 | 0.26 (n-hexane:AcOEt = 1:1) | (CDCl$_3$) 1.02(s, 9H), 2.51(s, 3H), 4.20(s, 2H), 5.48(s, 2H), 6.77(s, 1H), 7.15(d, 1H), 7.26(d, 1H), 7.42(bs, 1H), 8.35(d, 1H), 8.95(s, 1H) |
| 3-5 | [2-(piperidin-1-yl)ethyl-N(Me)-] | 78 | 0.14(MeOH) | (CDCl$_3$) 1.00(s, 9H), 1.41–1.49(m, 2H), 1.52–1.60(m, 4H), 1.61(brs, 1H), 2.35(brs, 4H), 2.45(t, 2H), 2.72 (t, 2H), 4.06(s, 2H), 4.22(s, 2H), 6.61(s, 1H), 8.83(s, 1H) |

3-6

6-[(4-Chloro-pyrimidin-2-ylamino)-methyl]-7-(2,2-dimethyl-propyl)-7H-pyrrolo[2,3-d]pyrimidine-2-carbonitrile

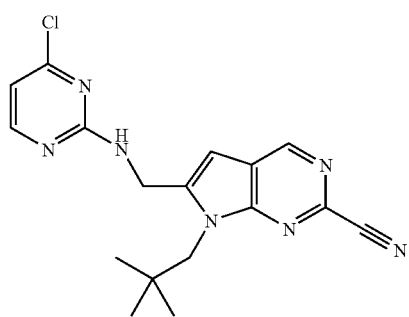

C

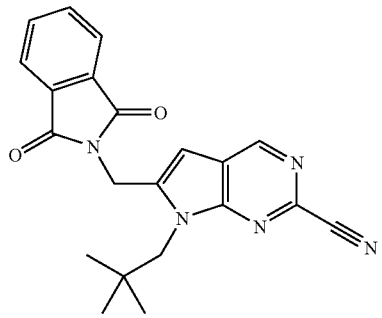

A

Preparation of 6-aminomethyl-7-(2,2-dimethyl-propyl)-7H-pyrrolo[2,3-d]pyrimidine-2-carbonitrile A To a solution of 7-(2,2-dimethyl-propyl)-6-(1,3-dioxo-1,3-dihydro-isoindol-2-ylmethyl)-7H-pyrrolo[2,3-d]pyrimidine-2-carbonitrile (B) (15.0 mmol) in MeOH (150 ml) is added hydrazine monohydrate (30.0 mmol) at room temperature. The mixture is refluxed for 4 h. After cooling down to room temperature, the reaction mixture is diluted with H2O and extracted with ethyl acetate. The organic extracts are dried over sodium sulfate and concentrated. The residue obtained is purified by column chromatography on silica gel to give the product in 55% yield. Rf=0.21 (CH2Cl2:MeOH=20:1). $^1$H NMR(400 MHz, CDCl$_3$) δ 1.01 (s, 9H), 4.15(s, 2H), 4.16(d, 2H), 6.65(s, 1H), 8.90(s, 11).

6-Aminomethyl-7-(2,2-dimethyl-propyl)-7H-pyrrolo[2,3-d]pyrimidine-2-carbonitrile (A) (1.0 mmol) obtained

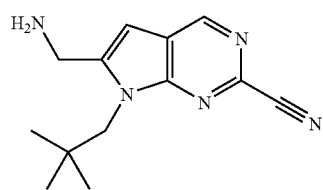

B above and 2,4-dichloropyrimidine (1.2 mmol) are dissolved in toluene (15 ml). To the solution are added Pd(OAc)2 (0.05 mmol), (t-Bu)2P(o-biphenyl) (0.1 mmol), and CsCO3 (1.5 mmol) at room teperature. The suspension is refluxed under nitrogen atmosphere for 20 h. After cooling down to room temperature, the reaction mixture is diluted with H2O and extracted with ether. The organic extracts are dried over sodium sulfate and concentrated in vacuo. The residue obtained is purified by column chromatography on silica gel to give the product in 14% yield. Rf=0.40 (AcOEt:n-hexane=2:1). $^1$H NMR(400 MHz, CDCl$_3$) δ 1.06 (s, 9H), 4.21(s, 2H), 4.93(d, 2H), 5.58(s, 1H), 6.61(s, 1H), 6.68(d, 1H), 8.18 (d, 1H), 8.89(s, 1H).

3-7

N.-[2-Cyano-7-(2,2-dimethyl-propyl)-7H-pyrrolo[2,3-d]pyrimidin-6-ylmethyl]-4-fluoro-benzamide

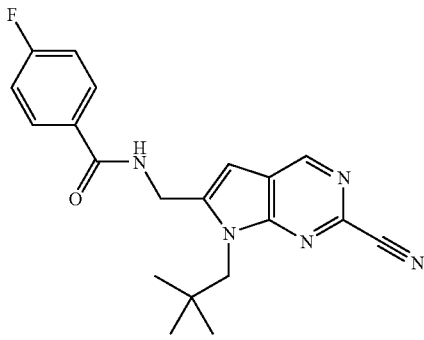

To a solution of 4-fluorobenzoic acid (0.75 mmol) in toluene (5 ml) are added dropwise oxalylchloride(1.125 mmol) and one drop of DMF at room temperature. The mixture is heated at 70 ° C. for 30 min. The reaction mixture is concentrated to remove oxalylchloride and the solvent. The residue is dissolved in THF (5 ml) and 6-aminomethyl-7-(2,2-dimethyl-propyl)-7H-pyrrolo[2,3-d]pyrimidine-2-carbonitrile (0. 5 mmol) obtained above is added. After stirring at room temperature for 1 h, the reaction mixture is diluted with sat.NaHCO3 aq. and extracted with ether. The organic extracts are dried over sodium sulfate and concentrated in vacuo. The residue obtained is purified by column chromatography on silica gel to give the product in 96% yield. Rf=0.26 (AcOEt:n-hexane=1:1). $^1$H NMR(400 MHz, CDCl$_3$) δ 1.04 (s, 9H), 4.20(s, 2H), 4.94(d, 2H), 6.60(s, 1H), 6.64(s, 1H), 7.15(t, 2H), 7.83-7.86(m, 2H), 8.84(s, 1H).

Example 4 Describes the Preparation of 6-arylsulfanyl-7H-pyrrolo-[2,3-d]pyrimidine-2-carbonitrile Derivatives Example 4-1

7-(2,2-Dimethyl-propyl)-6-(pyridin-2-ylsulfanylmethyl)-7H-pyrrolo[2,3d]pyrimidine-2-carbonitrile To a solution of 6-bromomethyl-7-(2,2-dimethyl-propyl)-7H-pyrrolo[2,3-d]pyrimidine-2-carbonitrile (0.65 mmol) in DMF (10 ml), 2-mercaptopyridine (0.78 mmol) is added. The solution is stirred at room temperature for 2 h, and poured into aqueous sodium hydrogen carbonate. The organic layer is extracted with AcOEt, washed with water, dried over magnesium sulfate, and concentrated. The crude product is purified by silica gel column chromatography to give the product in 81% yield.

By repeating the procedures described above using appropriate starting materials (K$_2$CO$_3$ is used as a base for examples 4-4, 4-6 and 4-7) and conditions (purification by aluminum oxide column chromatography for examples 4-4 and 4-5), the following compounds of formula 4-1 are obtained as identified below in Table 4-1.

TABLE 4-1

4-1

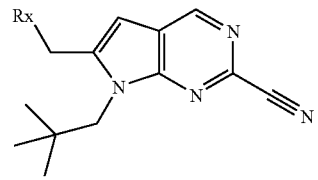

| Expl. No. | Rx | Yield(%) | Rf(solvent) | $^1$H NMR(400 MHz, CDCl$_3$) δ |
|---|---|---|---|---|
| 4-1 | (2-pyridyl-S–) | 81 | 0.54 (n-hexane:AcOEt = 1:1) | 1.05(s, 9H), 4.25(s, 2H), 4.75(s, 2H), 6.68(s, 1H), 7.03(m, 1H), 7.16(d, 1H), 7.51(ddd, 1H), 8.45(m, 1H), 8.84(s, 1H). |
| 4-2 | (1H-1,2,4-triazol-3-yl-S–) | 72 | 0.21 (n-hexane:AcOEt = 1:1) | 1.03(s, 9H), 4.25(s, 2H), 4.65(s, 2H), 6.68(s, 1H), 8.20(s, 1H), 8.86(s, 1H). |
| 4-3 | (4-pyridyl-S–) | 78 | 0.29 (n-hexane:AcOEt = 1:1) | 1.04(s, 9H), 4.24(s, 2H), 4.43(s, 2H), 6.66(s, 1H), 7.12(d, 2H), 8.45(d, 2H), 8.90(s, 1H). |
| 4-4 | (phenyl-S–) | 83 | 0.64 (n-hexane:AcOEt = 1:1) | 1.00(s, 9H), 4.21(s, 2H), 4.29(s, 2H), 6.37(s, 1H), 7.26(m, 5H), 8.82(s, 1H). |

TABLE 4-1-continued

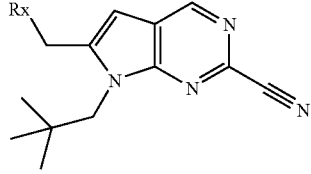

4-1

| Expl. No. | Rx | Yield(%) | Rf(solvent) | $^1$H NMR(400 MHz, CDCl$_3$) δ |
|---|---|---|---|---|
| 4-5 | 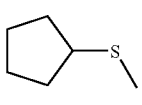 | 51 | 0.57 (n-hexane:AcOEt = 1:1) | 1.03(s, 9H), 4.23(s, 2H), 4.74(s, 2H), 6.64(s, 1H), 7.27(m, 1H), 7.73(d, 1H), 8.87(s, 1H). |
| 4-6 | 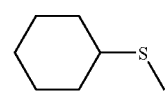 | 59 | 0.61 (n-hexane:AcOEt = 1:1) | 1.01(s, 9H), 1.45–1.60(m, 4H), 1.73(m, 2H), 1.94(m, 2H), 2.95(m, 1H), 3.98(s, 2H), 4.26(s, 2H), 6.58(s, 1H), 8.89(s, 1H). |
| 4-7 | 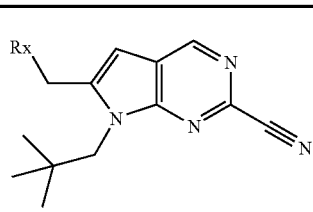 | 93 | 0.68 (n-hexane:AcOEt = 1:1) | 1.01(s, 9H), 1.22–1.41(m, 5H), 1.61(m, 1H), 1.74(m, 2H), 1.91(m, 2H), 2.55(m, 1H), 3.97(s, 2H), 4.25(s, 2H), 6.58(s, 1H), 8.89(s, 1H). |

4-8

6-Cyclopentanesulfonylmethyl-7-(2,2-dimethyl-propyl)-7H-pyrrolo[2,3-d]pyrimidine-2-carbonitrile To a solution of the sulfide of example 4-4 (0.25 mmol) obtained above in dichloromethane (20 ml), sodium hydrogen carbonate (0.89 mmol) and m-chloroperbenzoic acid (0.62 mmol) are added. The suspension is stirred at room temperature for 1 h, and poured into sodium sulfite aq. The organic layer is extracted with AcOEt, washed with water, dried over magnesium sulfate, and concentrated to give the product in 39% yield.

4-9

6-Cyclon-hexanesulfonylmethyl-7-(2,2-dimethyl-propyl)-7H-pyrrolo[2,3-d]pyrimidine-2-carbonitrile This compound is obtained from the compound of example 4-7 (0.44 mmol) in the similar way described in Example for 4-8. Purification of resulting solids by washing with methanol gives the product in 59% yield.

Compounds of formula 4-2 as identified in Table 4-2 are prepared as described above

TABLE 4-2

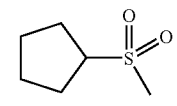

4-2

| Example No. | Rx | Yield(%) | Rf(solvent) | $^1$H NMR(400 MHz, CDCl$_3$ δ) |
|---|---|---|---|---|
| 4-8 | 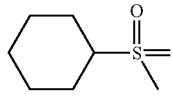 | 39 | 0.24 (n-hexane:AcOEt = 1:1) | 0.99(s, 9H), 1.68(m, 2H), 1.85(m, 2H), 1.95–2.18(m, 4H), 3.44(m, 1H), 4.36(s, 2H), 4.56(s, 2H), 6.84(s, 1H), 8.99(s, 1H). |
| 4-9 | | 59 | 0.31 (n-hexane:AcOEt = 1:1) | 1.00(s, 9H), 1.30(m, 3H), 1.61(m, 2H), 1.77(m, 1H), 1.99(m, 2H), 2.20(d, 2H), 2.97(m, 1H), 4.35(s, 2H), 4.53(s, 2H), 6.68(s, 1H), 9.00(s, 1H). |

Example 5 Describes the Preparation of 6-azole-7H-pyrrolo-[2,3-d]pyrimidine-2-carbonitrile Derivatives

Example 5-1

7-(2,2-Dimethyl-propyl)-6-imidazol-1-ylmethyl-7H-pyrrolo[2,3-d]pyrimidine-2-carbonitrile

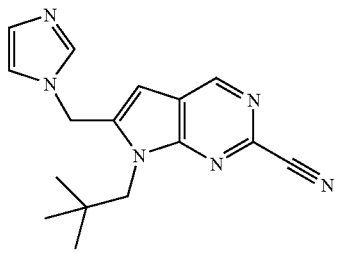

1-Prop-2-ynyl-1H-imidazole (15 mmol) is dissolved in DMF at room temperature under nitrogen atmosphere. To the solution, 5-bromo-4-(2,2-dimethyl-propylamino)-pyrimidine-2-carbonitrile (8 mmol), triethylamine (24 mmol), copper(I) iodide (0.8 mmol), and dichlorobis(triphenylphosphine)palladium (II) (0.4 mmol) are added successively. The mixture is heated at 80° C. under nitrogen atmosphere for 3 h. After cooling at room temperature, the mixture is diluted with $H_2O$ and AcOEt and filtered with celite. The organic layer is taken, dried over $MgSO_4$ and evaporated in vacuo. The residue is purified by silica gel column chromatography (AcOEt:MeOH=20:1) to give 7-(2,2-dimethyl-propyl)-6-imidazol-1-ylmethyl-7H-pyrrolo[2,3-d]pyrimidine-2-carbonitrile in 64% yield.

By repeating the procedure described above using appropriate starting materials and conditions, the following compounds of formula 5-1 are obtained as identified below in Table 5-1.

TABLE 5-1

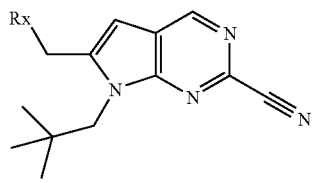

5-1

| Example No | Rx | Yield(%) | Rf(solvent) | $^1$H NMR(400 MHz, δ) |
|---|---|---|---|---|
| 5-1 | | 64 | 0.13(AcOEt) | ($CDCl_3$): 1.06(s, 9H), 4.06(s, 2H), 5.42(s, 2H), 6.36(s, 1H), 6.92(s, 1H), 7.17(s, 1H), 7.58(s, 1H), 8.93(s, 1H) |
| 5-2 | | 45 | 0.42(AcOEt) | ($CDCl_3$): 1.08(s, 9H), 4.14(s, 2H), 5.36(s, 2H), 6.29(s, 1H), 7.43(s, 1H), 8.95(s, 1H) |
| 5-3 | | 49 | 0.40 (AcOEt:MeOH = 4:1) | ($CDCl_3$): 1.08(s, 9H), 2.38(s, 3H), 3.94(s, 2H), 4.95(s, 2H), 6.09(s, 1H), 6.83(d, 1H), 6.97(s, 1H), 9.12(s, 1H) |
| 5-4 | | 10 | 0.15 (nhexane:AcOEt = 1:1) | ($CDCl_3$): 1.08(s, 9H), 3.98(s, 2H), 5.30(s, 2H), 6.22(s, 1H), 7.75(s, 1H), 8.78(s, 1H) |
| 5-5 | | 11 | 0.25 (n-hexane:AcOE = 1:1) | ($CDCl_3$): 1.08(s, 9H), 1.34(t, 3H), 2.65(dd, 2H), 4.11(s, 2H), 5.30(s, 2H), 6.09(s, 1H), 6.82(s, 1H), 7.08(s, 1H), 8.88(s, 1H) |

TABLE 5-1-continued

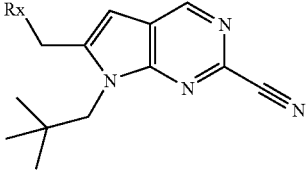

| Example No | Rx | Yield(%) | Rf(solvent) | ¹H NMR(400 MHz, δ) |
|---|---|---|---|---|
| 5-6 | 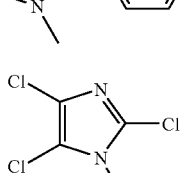 | 11 | 0.35(AcOEt) | (CDCl₃): 0.87(s, 9H), 3.88(s, 3H), 5.44(s, 2H), 6.42(s, 1H), 6.95(s, 1H), 7.23(s, 1H), 7.42–7.47(m, 2H), 7.53–7.57(m, 2H), 8.93(s, 1H) |
| 5-7 | 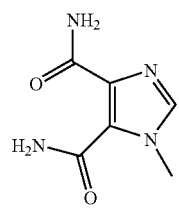 | 97 | 0.15 (n-hexane:AcOEt = 5:1) | (CDCl₃): 1.10(s, 9H), 4.21(s, 2H), 5.37(d, 2H), 6.10(t, 1H), 8.92(s, 1H) |
| 5-8 | 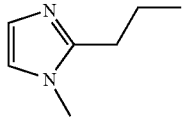 | 80 | 0.15 (n-hexane:AcOEt = 3:1) | (DMSO): 1.02(s, 9H), 4.28(s, 2H), 6.02(s, 2H), 6.04(s, 1H), 7.55(s, 1H), 7.91(s, 1H), 8.10(s, 1H), 8.21(s, 1H), 9.01(s, 1H), 10.7(s, 1H) |
| 5-9 | 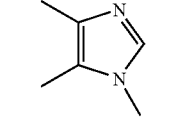 | 33 | 0.48 (AcOEt:MeOH = 4:1) | (CDCl₃): 0.97(t, 3H), 1.08(s, 9H), 1.78(dd, 2H), 2.60(t, 2H), 4.11(s, 2H), 5.30(s, 2H), 6.08(s, 1H), 6.80(s, 1H), 7.07(s, 1H), 8.88(s, 1H) |
| 5-10 | 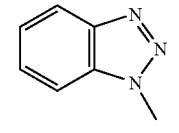 | 30 | 0.40 (AcOEt:MeOH = 4:1) | (CDCl₃): 1.09(s, 9H), 2.06(s, 3H), 2.21(s, 3H), 4.13(s, 2H), 5.25(s, 2H), 6.05(s, 1H), 7.44(s, 1H), 8.86(s, 1H) |
| 5-11 | 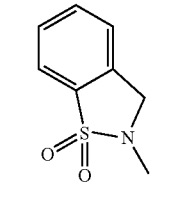 | 90 | 0.35 (n-hexane:AcOEt = 1:1) | (CDCl₃): 1.12(s, 9H), 4.23(s, 2H), 6.15(s, 2H), 6.48(s, 1H), 7.51–7.38(m, 3H), 8.12(d, 1H), 8.91(s, 1H) |
| 5-12 | 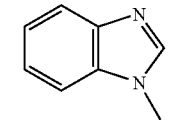 | 45 | 0.45 (n-hexane:AcOEt = 1:1) | (CDCl₃): 1.06(s, 9H), 4.20(s, 2H), 4.32(s, 2H), 4.73(s, 2H), 6.80(s, 1H), 7.33(d, 1H), 7.57–7.63(m, 2H), 7.86(d, 1H), 8.97(s, 1H) |
| 5-13 | 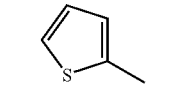 | 40 | 0.47 (n-hexane:AcOEt = 1:1) | (CDCl₃): 0.77(s, 9H), 3.24(d, 2H), 5.29(s, 2H), 5.46(brs, 1H), 8.23(s, 1H), 7.35–7.39(m, 2H), 7.52–7.53(m, 1H), 7.85–7.87(m, 1H), 8.02(brs, 1H) |
| 5-14 | | 92 | 0.50 (n-hexane:AcOEt = 5:1) | (CDCl₃): 1.04(s, 9H)4.10(s, 2H), 4.43(s, 2H), 6.44(s, 1H), 6.85–6.86(m, 1H), 6.97–6.99(m, 1H), 7.23–7.25(m, 1H), 8.87(s, 1H) |

TABLE 5-1-continued

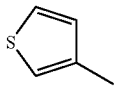

| Example No | Rx | Yield(%) | Rf(solvent) | $^1$H NMR(400 MHz, δ) |
|---|---|---|---|---|
| 5-15 | 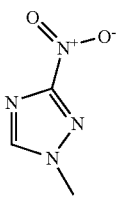 | 23 | 0.20 (n-hexane:AcOEt = 5:1) | (CDCl$_3$): 1.04(s, 9H), 4.08(s, 2H), 4.24(s, 2H), 6.32(s, 1H), 6.91–6.92(m, 1H), 7.00–7.02(m, 1H), 7.34–7.36(m, 1H), 8.84(s, 1H) |

5-16

7-(2,2-Dimethyl-propyl)-6-(3-nitro-[1,2,4]triazol-1-ylmethyl-7H-pyrrolo[2,3d]pyrimidine-2-carbonitrile

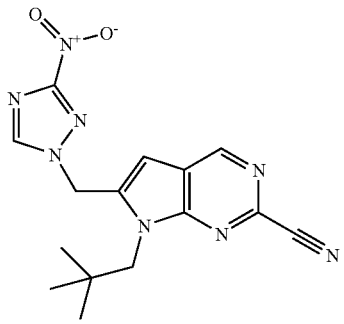

6-Bromomethyl-7-(2,2-dimethyl-propyl)-7H-pyrrolo[2,3-d]pyrimidine-2-carbonitrile (3 mmol) and 3-nitro-[1,2,4]triazole (3 mmol) are dissolved in DMSO (20 ml). Potassium carbonate (6 mmol) is added to the solution. The mixture is allowed to stir at room temperature overnight. The reaction mixture is diluted with H$_2$O and extracted with AcOEt. The organic layer is dried over MgSO$_4$ and evaporated in vacuo. The residue is purified by silica gel column chromatography (n-hexane:AcOEt=1:5) to give 7-(2,2-dimethyl-propyl)-6-(3-nitro-[1,2,4]triazol-1-ylmethyl)-7H-pyrrolo[2,3-d]pyrimidine-2-carbonitrile in 41% yield.

By repeating the procedure described above using appropriate starting materials and conditions, the following compound of formula 5-2 are obtained as identified below in Table 5-2.

TABLE 5-2

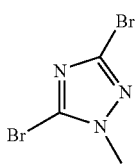

| Example No | Rx | Yield(%) | Rf(solvent) | $^1$H NMR(400 MHz, δ) |
|---|---|---|---|---|
| 5-6 | (3-nitro-1,2,4-triazol-1-yl) | 41 | 0.25 (n-hexane:AcOEt = 1:5) | (CDCl$_3$): 1.06(s, 9H), 4.22(s, 2H), 5.77(s, 2H), 6.67(s, 1H), 8.18(s, 1H), 9.02(s, 1H) |
| 5-7 | (3,5-dibromo-1,2,4-triazol-1-yl) | 41 | 0.40 (n-hexane:AcOEt = 1:1) | (CDCl$_3$): 1.06(s, 9H), 4.29(s, 2H), 5.61(s, 2H), 6.58(s, 1H), 8.97(s, 1H) |

TABLE 5-2-continued
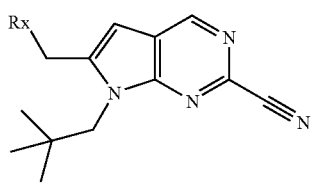
5-2
| Example No | Rx | Yield(%) | Rf(solvent) | $^1$H NMR(400 MHz, δ) |
|---|---|---|---|---|
| 5-18 | | 85 | 0.24 (AcOEt:MeOH = 10:1) | (CDCl$_3$): 1.05(s, 9H), 4.15(brs, 2H), 4.20(s, 2H), 5.43(s, 2H), 6.55(s, 1H), 7.75(s, 1H), 8.94(s, 1H) |
| 5-19 | | 74 | 0.48 (n-hexane:AcOEt = 1:5) | (CDCl$_3$): 1.09(s, 9H), 4.11(s, 2H), 5.52(s, 2H), 6.49(s, 1H), 7.56(d, 1H), 7.78(d, 1H), 8.98(s, 1H) |
| 5-20 | | 16 | 0.23 (n-hexane:AcOEt = 1:4) | (CDCl$_3$): 1.06(s, 9H), 4.21(s, 2H), 5.91(s, 2H), 6.64(s, 1H), 7.66(s, 2H), 8.94(s, 1H). |
| 5-21 | | 59 | 0.51 (n-hexane:AcOEt = 1:2) | (CDCl$_3$): 1.06(s, 9H), 4.14(s, 2H), 5.90(s, 2H), 6.59(s, 1H), 7.55(s, 1H), 7.77(s, 1H), 8.96(s, 1H). |
| 5-22 | | 38 | 0.34 (n-hexane:AcOEt = 1:1) | 1.04(s, 9H), 2.07(s, 3H), 4.10(s, 2H), 5.53(s, 2H), 6.46(s, 1H), 7.14(s, 1H), 7.37(s, 1H), 8.91(s, 1H). |

5-23

6-(3-Amino-[1,2,4]triazol-1-ylmethyl-7-(2,2-dimethyl-propyl)-7H-pyrrolo[2,3-d]pyrimidin-2-carbonitrile

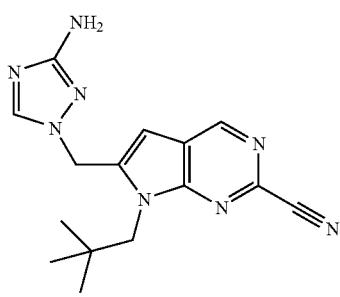

To a solution of the nitrotriazole (0.49 mmol) obtained above in MeOH is added PtO$_2$ (25 mg). The mixture is stirred at room temperature under hydrogen atmosphere overnight. The catalyst was removed by filtration. The filtrate is concentrated in vacuo and the residue is purified by silica gel column chromatography (AcOEt:MeOH=20:1) to give 6-(3-Amino-[1,2,4]triazol-1-ylmethyl)-7-(2,2-dimethyl-propyl)-7H-pyrrolo[2,3-d]pyrimidine-2-carbonitrile in 85% yield. Rf=0.24 (AcOEt:MeOH=10:1) $^1$H NMR (400 MHz, CDCl$_3$) δ: 1.05(s, 9H), 4.15(brs, 2H), 4.20(s, 2H), 5.43(s, 2H), 6.55(s, 1H), 7.75(s, 1H), 8.94(s, 1H).

5-24

N.-{1-[2-Cyano-7-(2,2-dimethyl-propyl)-7H-pyrrolo[2,3-d]pyrimidin-6-ylmethyl]-1H-[1,2,4]triazol-3-yl}-2-piperidin-yl-acetamide

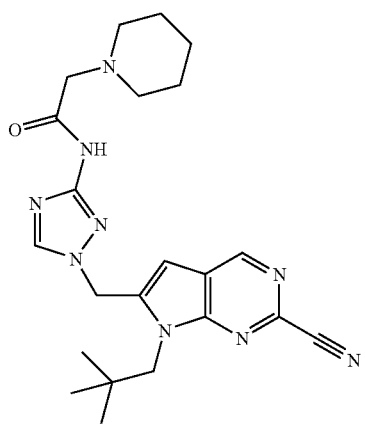

The amono-triazole (5-23) (1.61 mmol) obtained above is dissolved in CH$_2$Cl$_2$ (40 ml). To the solution, pyridine (2.09 mmol) and chloroacetyl chloride (1.93 mmol) are added successively and the mixture is stirred at room temperature under nitrogen atmosphere for 2 h. The reaction mixture is wshed with H$_2$O, dried over MgSO$_4$, and evaporated in vacuo. The residue is purified by silica gel column chromatography (AcOEt:MeOH=10:1) to give 2-chloro-.N.-{1-[2-cyano-7-(2,2-dimethyl-propyl)-7.H.-pyrrolo[2,3-.d.]pyrimidin-6-ylmethyl]-1.H.-[1,2,4]triazol-3-yl}-acetamide as an intermediate in 88% yield. The intermediate (0.52 mmol) is dissolved in DMF (10 ml) at room temperature under nitrogen atmosphere. To the solution, potassium carbonate (1.55 mmol) and piperidine (0.78 mmol) are added successively. The mixture is stirred at room temperature under nitrogen atmosphere for 5 h. The reaction mixture is diluted with H$_2$O and extracted with AcOEt. The organic layer is dried over MgSO$_4$ and evaporated in vacuo. The residue is purified by silica gel column chromatography (AcOEt:MeOH=10:3) to give N.-{1-[2-Cyano-7-(2,2-dimethyl-propyl)-7H-pyrrolo[2,3-d]pyrimidin-6-ylmethyl]-1H-[1,2,4]triazol-3-yl}-2-piperidin-1-yl-acetamide in 62% yield. Rf=0.27 (n-hexane:AcOEt=1:1). $^1$H NMR (400Mz, CDCl$_3$) δ: 1.05(s, 9H), 1.48-1.47(brm, 2H), 1.67-1.61(brm, 4H), 2.54(brs, 4H), 3.12(s, 2H), 4.20(s, 2H), 5.62(s, 2H), 6.56(s, 1H), 7.93(brs, 1H), 8.95(s, 1H), 9.78(brs, 1H).

5-25

7-(2,2-Dimethyl-propyl)-6-tetrazol-2-ylmethyl-7H-pyrrolo[2,3-d]pyrimidine-2-carbonitrile

5-26

7-(2,2-Dimethyl-propyl)-6-tetrazol-1-ylmethyl-7H-pyrrolo[2,3-d]pyrimidine-2-carbonitrile

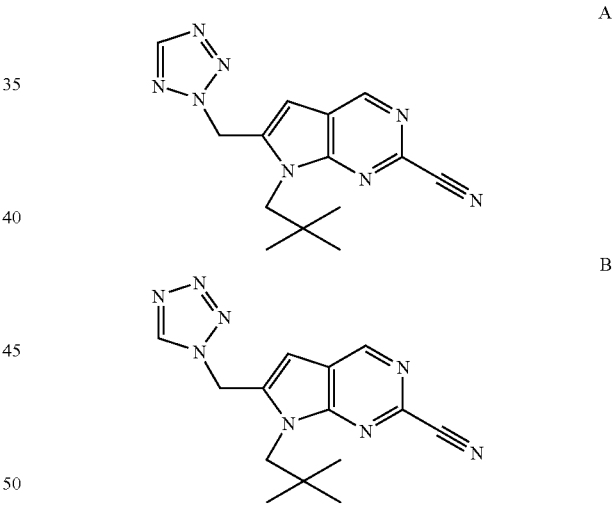

6-Bromomethyl-7-(2,2-dimethyl-propyl)-7H-pyrrolo[2,3-d]pyrimidine-2-carbonitrile (0.33 mmol) and 1H-tetrazole (0.65 mmol) are dissolved in DMF (3 ml). To the solution, K$_2$CO$_3$ (0.98 mmol) is added and the mixture is stirred at room temperature under nitrogen atmosphere for 23 h. The reaction mixture is diluted with water and extracted with AcOEt. The organic layer is washed with brine, dried over sodium sulfate, and concentrated. The crude product is purified by silica gel column chromatography to give A in 45% yield and B in 48% yield in the order of elution.

By repeating the procedure described above using appropriate starting materials and conditions, the following compounds formula 5-3 and 5-4 are obtained as identified in the Table 3 and Table 4.

TABLE 5-3

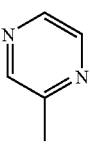

| Example No | R | Yield(%) | Rf(solvent) | $^1$H NMR(400 MHz, CDCl3) δ |
|---|---|---|---|---|
| 5-25 | H | 45 | 0.74 (AcOEt:n-hexane = 2:1) | 1.08(s, 9H), 4.28(s, 2H), 6.12(s, 2H), 6.76(s, 1H), 8.55(s, 1H), 8.98(s, 1H) |
| 5-27 | ![pyrazinyl] | 14 | 0.60 (AcOEt:n-hexane = 2:1) | 1.09(s, 9H), 4.33(s, 2H), 6.21(s, 2H), 6.85(s, 1H), 8.71(d, 1H), 8.74(d 1H), 9.46(s, 1H) |

TABLE 5-4

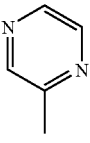

| Example No | R | Yield(%) | Rf(solvent) | $^1$H NMR(400 MHz, CDCl3) δ |
|---|---|---|---|---|
| 5-26 | H | 48 | 0.34 (AcOEt:n-hexane = 2:1) | 1.07(s, 9H), 4.20(s, 2H), 5.94(s, 2H), 6.60(s, 1H), 8.63(s, 1H), 8.98(s, 1H) |
| 5-27 | ![pyrazinyl] | 28 | 0.63 (AcOEt:n-hexane = 2:1) | 1.09(s, 9H), 4.40(s, 2H), 6.33(s, 1H), 6.48(s, 2H), 8.64(d, 1H), 8.79(d, 1H) 9.46(s, 1H) |

5-28

7-(2,2-Dimethylpropyl)-6-[5-(4-hydroxymethyl-phenyl)-tetrazol-2-ylmethyl]-7H-pyrrolo[2,3-d]pyrimidine-2-carbonitrile -continued

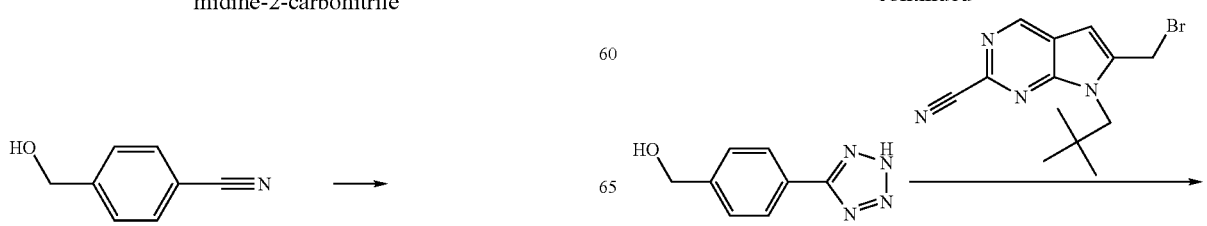

-continued

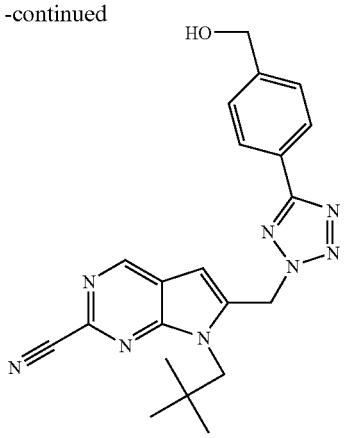

Preparation of [4-(2H-tetrazol-5-yl)-phenyl]-methanol
4-Hydroxymethyl-benzonitrile (7.5 mol) is dissolved in dry DMF (20 ml). To the solution are added sodium azide (8.3 mmol) and ammonium chloride (1.9 mmol at room temperature. The mixture is heated at 110° C. under nitrogen atmosphere for 24 h. After cooling, the reaction mixture is concentrated in vacuo. MeOH is added to the residue and filtered. The filtrate is concentrated to give the crude product in 57% yield.

[4-(2.H.-Tetrazol-5-yl)-phenyl]-methanol (3.5 mmol) and 6-bromomethyl-7-(2,2-dimethyl-propyl)-7H-pyrrolo[2,3-d] pyrimidine-2-carbonitrile (1,2 mmol) are dissolved in DMF (5 ml). K$_2$CO$_3$ (3.5 mmol) is added to the solution and the mixture is stirred at room temperature under nitrogen atmosphere for 4 h. The reaction mixture is diluted with water and extracted with AcOEt. The organic layer is washed with brine, dried over sodium sulfate, and concentrated. The crude product is purified by silica gel column chromatography to give the product in 98% yield.

By repeating the procedure described above using appropriate starting materials and conditions, the following compounds of formula 5-5 are obtained as identified below in Table 5-5.

TABLE 5-5

5-5

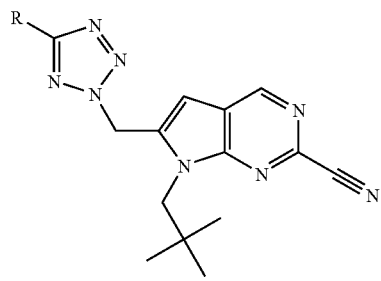

| Example No | R | Yield(%) | Rf(solvent) | $^1$H NMR(400 MHz, CDCl3) δ |
|---|---|---|---|---|
| 5-29 | | 98 | 0.23 (AcOEt:n-hexane = 1:1) | 1.09(s, 9H), 1.93(br, 1H), 4.32(s, 2H), 4.76(s, 2H), 6.12(s, 2H), 6.79(s, 1H), 7.48(d, 2H), 8.09(d, 2H), 8.97(s, 1H) |
| 5-30 | | 33 | 0.27 (AcOEt:n-hexane = 1:2) | 1.09(s, 9H), 4.32(s, 2H), 6.12(s, 2H), 6.79(s, 1H), 7.18(dt, 1H), 7.45(q, 1H), 7.80(dd, 1H), 7.91(d, 1H), 8.98(s, 1H) |
| 5-31 | | 30 | 0.16 (AcOEt:n-hexane = 1:1) | 1.10(s, 9H), 4.32(s, 2H), 6.16(s, 2H), 6.81(s, 1H), 7.98(d, 2H), 8.77(d, 2H), 8.99(s, 1H) |
| 5-32 | | 16 | 0.12 (AcOEt:n-hexane = 1:1) | 1.10(s, 9H), 4.33(s, 2H), 6.15(s, 2H), 6.81(s, 2H), 7.43(t, 2H), 8.39(d, 2H), 8.73(brs, 1H), 8.99(s, 1H), 9.34(brs, 1H) |

TABLE 5-5-continued

5-5
| Example No | R | Yield(%) | Rf(solvent) | $^1$H NMR(400 MHz, CDCl3) δ |
|---|---|---|---|---|
| 5-33 |  | 45 | 0.12 (AcOEt:n-hexane = 1:1) | 1.10(s, 9H), 4.41(s, 2H), 6.37(s, 2H), 6.55(s, 2H), 7.48(t, 1H), 7.94(t, 1H), 8.42(d, 1H), 8.66(d, 1H), 8.83(s, 1H) |
| 5-34 | 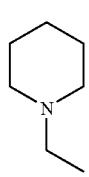 | 16 | 0.25 (AcOEt:n-hexane = 1:2) | 1.06(s, 9H), 4.23(s, 2H), 4.26(s, 2H), 6.04(s, 2H), 6.78(s, 1H), 7.22(d, 2H), 8.54(d 2H), 8.93(s, 1H) |
| 5-35 |  | 5 | 0.50 (MeOH:CH$_2$Cl$_2$ = 1:4) | 1.07(s, 9H), 1.38–1.45(m, 2H), 1.60(pent, 4H), 2.49(brt, 4H), 3.81(s, 2H), 4.30(s, 2H), 6.08(s, 2H), 6.69(s, 1H), 8.98(s, 1H) |
| 5-36 | 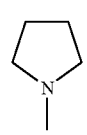 | 70 | 0.60 (AcOEt:n-hexane = 1:1) | 1.06(s, 9H), 1.61(brs, 6H), 3.43(brt, 4H), 4.27(s, 2H), 5.85(s, 2H), 6.71(s, 1H), 8.96(s, 1H) |
| 5-37 |  | 72 | 0.36 (AcOEt:n-hexane = 1:1) | 1.06(s, 9H), 1.96(t, 4H), 3.45(t, 4H), 4.80(s, 2H), 5.86(s, 2H), 6.72(s, 1H), 8.95(s, 1H) |

5-38

7-(2,2-Dimethyl-propyl)-6-[5-(4-piperidin-1-ylm-
ethyl-phenyl)-tetrazol-2-ylmethyl]-7H-pyrrolo[2,3-d]
pyrimidine-2-carbonitrile

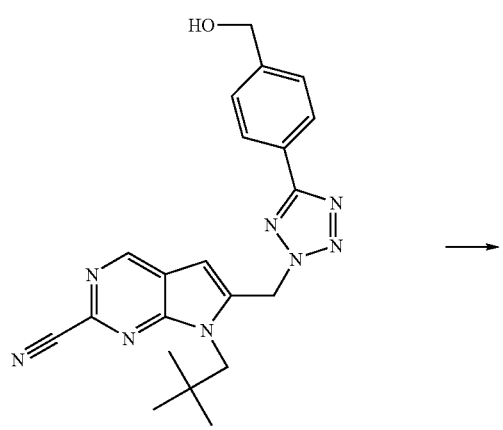

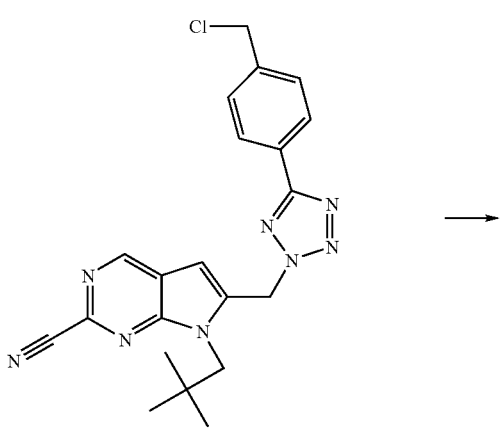

Preparation of 6-[5-(4-chloroethyl-phenyl)-tetrazol-2-yl-
methyl]-7-(2,2-diethyl-propyl)-7H-pyrrolo[2,3-d]pyrimi-
dine-2-carbonitrile 5-28 (1.1 mmol) obtained above and i-Pr$_2$NEt (3.4 mmol) are dissolved in CH$_2$Cl$_2$ (5 ml). To the solution is added methansulfonyl chloride (2.3 mmol) at 0° C. The mixture is stirred at room temperature under nitrogen atmosphere overnight. The reaction mixture is washed with water, dried over sodium sulfate, and concentrated. The crude product is purified by silica gel column chromatography to give the product in 94% yield.

6-[5-(4-Chloromethyl-phenyl)-tetrazol-2-ylmethyl]-7-(2,2-dimethyl-propyl)-7H-pyrrolo[2,3-d]pyrimidine-2-carbonitrile (0.23 mmol) obtained above is dissolved in DMF (5 ml). To the solution is added piperidine (0.69 mmol) at room temperature. The mixture is allowed to stir at room temperature under nitrogen atmosphere overnight. The reaction mixture is diluted with water and extracted with AcOEt. The organic layer is washed with brine, dried over sodium sulfate, and concentrated. The crude product is purified by silica gel column chromatography to give the product in 100% yield.

By repeating the procedure described above using appropriate starting materials and conditions, the following compounds of formula 5-6 are obtained as identified below in Table 5-6.

TABLE 5-6
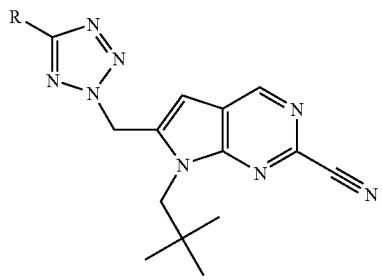
5-6
| Example No | R | Yield(%) | Rf(solvent) | $^1$H NMR(400 MHz, CDCl3) δ |
|---|---|---|---|---|
| 5-38 | (4-methylbenzyl)piperidine | 100 | 0.29 (AcOEt:MeOH = 9:1) | 1.09(s, 9H), 1.38–1.46(m, 2H), 1.59–1.54(m, 4H), 2.37(brs, 4H), 3.51(s, 2H), 4.32(s, 2H), 6.11(s, 2H), 6.77(s, 1H), 7.43(d, 2H), 8.04(d, 2H), 8.97(s, 1H) |
| 5-39 | 1-(4-methylbenzyl)-4-methylpiperazine | 87 | 0.22 (MeOH) | 1.09(s, 9H), 2.28(s, 3H), 2.47(brs, 8H), 3.55(s, 2H), 4.32(s, 2H), 6.11(s, 2H), 6.77(s, 1H), 7.44(d, 2H), 8.05(d, 2H), 8.97(s, 1H) |
| 5-40 | 1-(4-methylbenzyl)-1,2,4-triazole | 37 | 0.47 (AcOEt:MeOH = 9:1) | 1.09(s, 9H), 4.31(s, 2H), 5.40(s, 2H), 6.12(s, 2H), 6.78(s, 1H), 7.36(d, 2H), 7.99(s, 1H), 8.11(d, 2H), 8.97(s, 1H) |

Example 6 Describes the Preparation of 6-piperazinyl-7H-pyrrolo[2,3-d]pyrimidine-2-carbonitrile

Example 6-1

7-(2,2-Dimethyl-propyl)-6-[4-(2-methoxy-phenyl)-piperazin-1-ylmethyl]-7H-pyrrolo[2,3-d]pyrimidine-2-carbonitrile

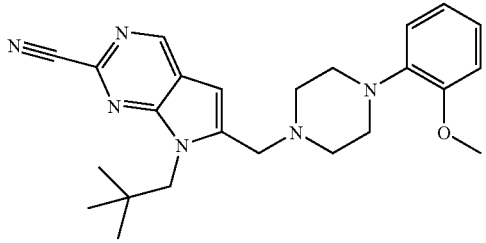

To a suspension of NaH (0.91 mmol) in DMF (10 ml), 1-(2-methoxyphenyl)piperazine (1.04 mmol) and 18-crown-6 (0.003 mmol) are successively added at 0° C. To the mixture, 6-bromomethyl-7-(2,2-dimethyl-propyl)-7H-pyrrolo[2,3-d]pyrimidine-2-carbonitrile (0.65 mmol) is added at 0° C. and the mixture is stirred for 2 h at ambient temperature. The reaction mixture is quenched with ice-water and extracted with AcOEt. The combined extracts are washed with $H_2O$, brine and dried over magnesium sulfate. Chromatography on silica gel (eluent; n-hexane:AcOEt=1:1) give 227 mg of desired 7-(2,2-Dimethyl-propyl)-6-[4-(2-methoxy-phenyl)-piperazin-1-ylmethyl]-7H-pyrrolo[2,3-d]pyrimidine-2-carbonitrile in 83% yield.

By repeating the procedures described above using appropriate starting materials and conditions the following compounds of formula 6-1 are obtained as identified below in Table 61.

TABLE 6-1

6-1

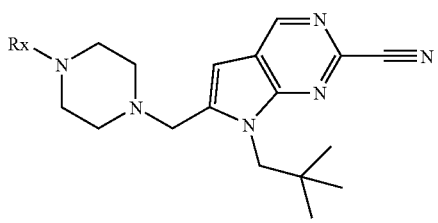

| Expl. No. | Rx | Yield(%) | Rf(Solvent) | NMR(400 MHz, δ) |
|---|---|---|---|---|
| 6-1 | ![o-methoxyphenyl] | 83 | 0.40 (n-hexane:AcOEt = 1:1) | (CDCl₃): 1.02(s, 9H), 2.60-2.72(m, 4H), 3.02-3.15(m, 4H), 3.86(s, 5H), 4.39(s, 2H), 6.60(s, 1H), 6.85-7.05(m, 4H), 8.90(s, 1H) |
| 6-2 | ![p-fluorophenyl] | 59 | 0.54 (n-hexane:AcOEt = 1:1) | (CDCl₃): 1.02(s, 9H), 2.52-2.65(m, 4H), 3.05-3.15(m, 4H), 3.84(s, 2H), 4.37(s, 2H), 6.61(s, 1H), 6.82-6.90(m, 2H), 6.93-7.00(m, 2H), 8.91(s, 1H) |
| 6-3 | ![o-chlorophenyl] | 57 | 0.66 (n-hexane:AcOEt = 1:1) | (CDCl₃): 1.03(s, 9H), 2.60-2.70(m, 4H), 3.02-3.12(m, 4H), 3.87(s, 2H, s), 4.39(s, 2H), 6.61(s, 1H), 6.95-7.07(m, 2H), 7.18-7.26(m, 1H), 7.35(dd, 1H), 8.91(s, 1H) |
| 6-4 | ![2-pyridyl] | 43 | 0.34 (n-hexane:AcOEt = 1:1) | (CDCl₃): 1.02(s, 9H), 2.52-2.62(m, 4H), 3.50-3.60(m, 4H), 3.83(s, 2H), 4.38(s, 2H), 6.58-6.70(m, 3H), 7.46-7.50(m, 1H), 8.18-8.20(m, 1H), 8.91(s, 1H) |
| 6-5 | ![2-pyrimidyl] | 56 | 0.30 (n-hexane:AcOEt = 1:1) | (CDCl₃): 1.02(s, 9H), 2.45-2.55(m, 4H), 3.75-3.85(m, 4H), 4.38(s, 2H), 6.50(t, 1H), 6.61(s, 1H), 8.30(d, 2H), 8.91(s, 1H) |

TABLE 6-1-continued

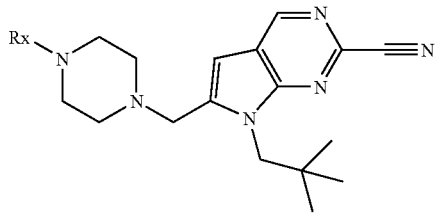

6-1

| Expl. No. | Rx | Yield(%) | Rf(Solvent) | NMR(400 MHz, δ) |
|---|---|---|---|---|
| 6-6 | O₂N–C₆H₄– (4-nitrophenyl) | 48 | 0.34 (n-hexane:AcOEt = 1:1) | (CDCl₃): 1.02(s, 9H), 2.60-2.65(m, 4H), 3.40-3.48(m, 4H), 3.86(s, 2H), 4.36(s, 2H), 6.62(s, 1H), 6.82(d, 2H), 8.12(d, 2H), 8.92(s, H) |
| 6-7 | PhCH=CHCH₂– (cinnamyl) | 73 | 0.22 (n-hexane:AcOEt = 1:1) | (CDCl₃): 1.00(s, 9H), 2.51(brs, 8H), 3.16(d, 2H), 3.79(s, 2H), 4.35(s, 2H), 6.20-6.30(m, 1H), 6.51(d, 1H), 6.57(s, 1H), 7.20-7.40(m, 5H), 8.88(s, 1H) |
| 6-8 | 2-F-C₆H₄– | 59 | 0.60 (n-hexane:AcOEt = 1:1) | (CDCl₃): 1.02(s, 9H), 2.60-2.70(m, 4H), 3.05-3.15(m, 4H), 3.85(s, 2H), 4.38(s, 2H), 6.61(s, 1H), 6.91-7.10(m, 4H), 8.91(s, 1H) |
| 6-9 | 2-Me-C₆H₄– | 55 | 0.66 (n-hexane:AcOEt = 1:1) | (CDCl₃): 1.03(s, 9H), 2.29(s, 3H), 2.55-2.65(m, 4H), 2.85-2.95(m, 4H), 3.86(s, 2H), 4.40(s, 2H), 6.61(s, 1H), 6.95-7.05(m, 2H), 7.15-7.20(m, 2H), 8.91(s, 1H) |
| 6-10 | 3-Cl-C₆H₄– | 50 | 0.34 (n-hexane:AcOEt = 1:1) | (CDCl₃): 1.02(s, 9H), 2.55-2.65(m, 4H), 3.15-3.25(m, 4H), 3.84(s, 2H), 4.36(s, 2H), 6.61(s, 1H), 6.70-6.90(m, 3H), 7.16(dd, 1H), 8.91(s, 1H) |
| 6-11 | 4-Cl-C₆H₄– | 45 | 0.72 (AcOEt) | (CDCl₃): 1.02(s, 9H), 2.61(t, 4H), 3.16(t, 4H), 3.84(s, 2H), 4.36(s, 2H), 6.61(s, 1H), 6.82(d, 2H), 7.20(d, 2H), 8.91(s, 1H) |
| 6-12 | 2,3-diMe-C₆H₃– | 48 | 0.68 (n-hexane:AcOEt = 1:1) | (CDCl₃): 1.03(s, 9H), 2.21(s, 3H), 2.26(s, 3H), 2.55-2.70(m, 4H), 2.85-2.95(m, 4H), 3.86(s, 2H), 4.40(s, 2H), 6.61(s, 1H), 6.90(m, 1H), 7.71(dd, 1H), 8.90(s, 1H) |
| 6-13 | 2,4-diF-C₆H₃– | 34 | 0.56 (n-hexane:AcOEt = 1:1) | (CDCl₃): 1.02(s, 9H), 2.55-2.70(m, 4H), 3.00-3.10(m, 4H), 3.85(s, 2H), 4.37(s, 2H), 6.61(s, 1H), 6.75-6.95(m, 3H, m), 8.90(s, 1H) |
| 6-14 | 2-CN-C₆H₄– | 54 | 0.46 (n-hexane:AcOEt = 1:1) | (CDCl₃): 1.02(s, 9H), 2.65-2.75(m, 4H), 3.17-3.27(m, 4H), 3.87(s, 2H), 4.37(s, 2H), 6.62(s, 1H), 6.95-7.05(m, 2H), 7.45-7.51(m, 1H), 7.56(dd, 1H), 8.91(s, 1H) |

TABLE 6-1-continued

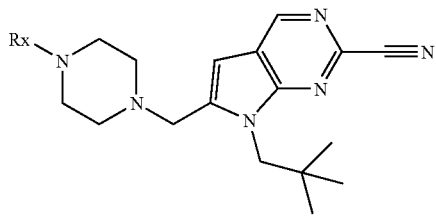

6-1

| Expl. No. | Rx | Yield(%) | Rf(Solvent) | NMR(400 MHz, δ) |
|---|---|---|---|---|
| 6-15 | (p-xylyl group) | 65 | 0.46 (n-hexane:AcOEt = 1:1) | (CDCl$_3$): 1.02(s, 9H), 2.27(s, 3H), 2.55-2.65(m, 4H), 3.10-3.20(m, 4H), 3.84(s, 2H), 4.37(s, 2H), 6.60(s, 1H), 6.82(d, 2H), 7.07(d, 2H), 8.90(s, 1H) |
| 6-16 | (5-pyrimidinyl) | 74 | 0.30 (AcOEt:EtOH = 10:1) | (CDCl$_3$): 1.02(s, 9H), 2.60-2.70(m, 4H), 3.25-3.35(m, 4H), 3.86(s, 2H), 4.36(s, 2H), 6.62(s, 1H), 8.36(s, 2H), 8.71(s, 1H), 8.92(s, 1H) |

6-17

6-[4-(4-Acetyl-phenyl)-piperazin-1-ylmethyl]-7-(2,2-dimethyl-propyl)-7H-pyrrolo[2,3-d]pyrimidine-2-carbonitrile

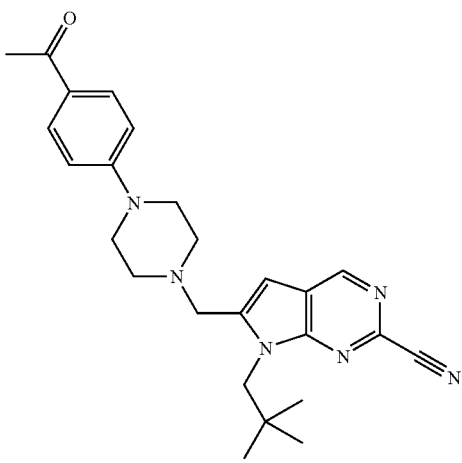

6-Bromomethyl-7-(2,2-dimethyl-propyl)-7H-pyrrolo[2,3-d]pyrimidine-2-carbonitrile (0.33 mmol) and 1-(4-piperazin-1-yl)-ethanone (0.39 mmol) are dissolved in DMF (3 ml) and potassium carbonate (0.78 mmol) is added to the solution. The reaction mixture is heated at 50° C. for 3 h. After the mixture is extracted whit AcOEt, the organic layer is washed with brine, dried over magnesium sulfate and filtrated. AcOEt is evaporated and the residue is purified by column chromatography on silica gel using n-hexane:AcOEt=1:1 (v/v). The product is obtained in 51.8% yield.

Rf=0.68 (n-hexane:AcOEt=1:5).

By repeating the procedures described above using appropriate starting materials and conditions the following compounds of formula 6-2 are obtained as identified below in Table 6-2.

TABLE 6-2

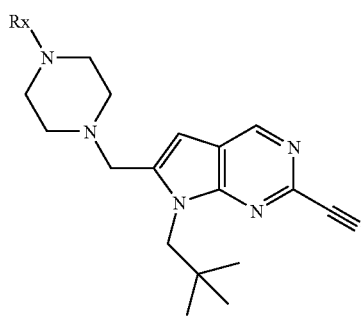

| Expl. No. | Rx | Yield(%) | Rf(Solvent) | $^1$H-NMR(400 MHz, δ) |
|---|---|---|---|---|
| 6-17 | 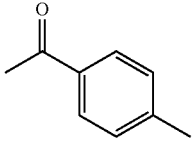 | 52 | 0.50 (n-hexane:AcOEt = 1:5) | (CDCl$_3$): 1.02(s, 9H), 2.52(s, 3H), 2.60-2.62(m, 4H), 3.35-3.37(m, 4H), 3.85(s, 2H), 4.36(s, 2H), 6.61(s, 1H), 6.86(d, 2H), 7.87(d, 2H), 8.91(s, 1H), |
| 6-18 | 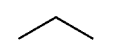 | 67 | 0.35 (CH$_2$Cl$_2$:MeOH = 9:1) | (CDCl$_3$): 1.01(s, 9H), 2.29(s, 3H), 2.48(br, 8H), 3.78(s, 2H), 4.35(s, 2H), 6.57(s, 1H), 8.88(s, 1H), |
| 6-19 |  | 49 | 0.37 (CH$_2$Cl$_2$:MeOH = 9:1) | (CDCl$_3$): 1.00(s, 9H), 1.06(t, 3H), 2.40-2.50(br, 10H), 3.78(s, 2H), 4.36(s, 2H), 6.57(s, 1H), 8.88(s, 1H), |
| 6-20 | 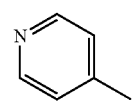 | 62 | 0.58 (CH$_2$Cl$_2$:MeOH = 9:1) | (CDCl$_3$): 1.01(s, 9H), 2.09(s, 3H), 2.43-2.45(m, 4H), 3.45-3.47(m, 2H), 3.62-3.64(br, 2H), 3.80(s, 2H), 4.33(s, 2H), 6.59(s, 1H), 8.89(s, 1H), |
| 6-21 | 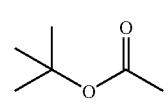 | 44 | 0.28 (CH$_2$Cl$_2$:MeOH = 9:1) | (CDCl$_3$): 1.02(s, 9H), 2.58-2.60(m, 4H), 3.33-3.35(m, 4H), 3.84(s, 2H), 4.36(s, 2H), 6.61(s, 1H), 6.64-6.65(m, 2H), 8.28-8.29(m, 2H), 8.92(s, 1H), |
| 6-22 | 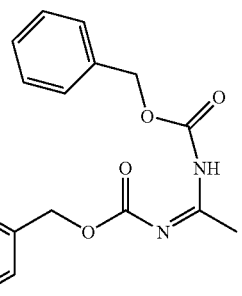 | 91 | 0.60 (n-hexane:AcOEt = 1:5) | (CDCl$_3$): 1.01(s, 9H), 1.45(s, 9H), 2.40(br, 4H), 3.43(br, 4H), 3.78(s, 2H), 4.34(s, 2H), 6.58(s, 1H), 8.90(s, 1H), |
| 6-23 |  | 60 | 0.36 (n-hexane:AcOEt = 1:1) | (CDCl$_3$): 1.00(s, 9H), 2.42(brs, 4H), 3.51(brs, 4H), 3.78(s, 2H), 4.32(s, 2H), 5.13(s, 2H), 5.21(s, 2H), 6.57(s, 1H), 7.30-7.41(m, 11H), 8.89(s, 1H). |
| 6-24 |  | 47 | 0.30 (n-hexane:AcOEt = 1:1) | (CDCl$_3$): 1.02(s, 9H), 2.59(m, 4H), 3.51(m, 4H), 3.84(s, 2H), 4.35(s, 2H), 6.59(d, 1H), 6.61(s, 1H), 7.20(d, 1H), 7.20(d, 1H), 8.91(s, 1H). |

TABLE 6-2-continued

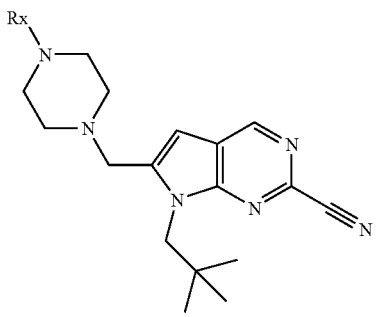

6-2

| Expl. No. | Rx | Yield(%) | Rf(Solvent) | ¹H-NMR(400 MHz, δ) |
|---|---|---|---|---|
| 6-25 | pyrazine with methyl | 55 | 0.20 (n-hexane:AcOEt = 1:1) | (CDCl$_3$): 1.03(s, 9H), 2.58(m, 4H), 3.61(m, 4H), 3.84(s, 2H), 4.37(s, 2H), 6.62(s, 1H), 7.87(d, 1H), 8.07(dd, 1H), 8.13(d, 1H), 8.92(s, 1H). |
| 6-26 | 3-chloro-6-methylpyridazine | 75 | 0.37 (n-hexane:AcOEt = 1:1) | (CDCl$_3$): 1.02(s, 9H), 2.59(m, 4H), 3.65(m, 4H), 3.84(s, 2H), 4.36(s, 2H), 6.61(s, 1H), 6.88(d, 1H), 7.21(d, 1H), 8.92(s, 1H). |
| 6-27 | 2-chloro-3-methylpyrazine | 68 | 0.25 (n-hexane:AcOEt = 1:1) | (CDCl$_3$): 1.02(s, 9H), 2.63(m, 4H), 3.47(m, 4H), 3.86(s, 2H), 4.38(s, 2H), 6.61(s, 1H), 7.89(d, 1H), 8.10(d, 1H), 8.91(s, 1H). |
| 6-28 | 3-fluoro-4-methyl-nitrobenzene | 79 | 0.40 (n-hexane:AcOEt = 1:1) | (CDCl$_3$): 1.03(s, 9H), 2.64(m, 4H), 3.30(m, 4H), 3.87(s, 2H), 4.35(s, 2H), 6.61(s, 1H), 6.90(dd, 1H), 7.91(dd, 1H), 7.98(dd, 1H), 8.92(s, 1H). |
| 6-29 | 3-chloro-4-methyl-nitrobenzene | 83 | 0.41 (n-hexane:AcOEt = 1:1) | (CDCl$_3$): 1.03(s, 9H), 2.63-2.71(m, 4H), 3.18-3.26(m, 4H), 3.88(s, 2H), 4.37(s, 2H), 6.62(s, 1H), 7.02(d, 1H), 8.08(dd, 1H), 8.26(d, 1H), 8.92(s, 1H) |

6-30

7-(2,2-Dimethyl-propyl)-6-[4-(5-ethyl-pyrimidin-2-yl)-piperazin-1-ylmethyl]-7H-pyrrolo[2,3-d]pyrimidine-2-carbonitrile

B. 5-Ethyl-2-piperazin-1-yl-pyrimidine

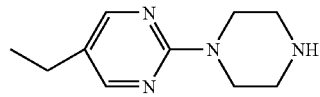

To 4-(5-ethyl-pyrimidin-2-yl)-piperazine-1-carboxylic acid .tert.-butyl ester (1.881 mmol) in $CH_2Cl_2$ (5.5 ml), trifluoroacetic acid (5.5 ml) is added at 0° C. The mixture is stirred at room temperature for 1 h and saturated sodium bicarbonate at 0° C. The aqueous layer is extracted with $CH_2Cl_2$ and the organic layer is dried over magnesium sulfate and concentrated to give the product in 89% yield. The crude product is used for the next step without purification.

Rf=0.33 ($CH_2Cl_2$:MeOH=9:1) $^1$H NMR(400 MHz, $CDCl_3$) δ 1.21 (t, 3H), 2.51 (q, 2H), 3.21 (dd, 4H), 4.10 (dd, 4-H), 8.22 (s, 2H)

C. 7-(2,2-Dimethyl-propyl)-6-[4-(5-ethyl-pyrimidin-2-yl)-piperazin-1-ylmethyl]-7H-pyrrolo[2,3-d]pyrimidine-2-carbonitrile

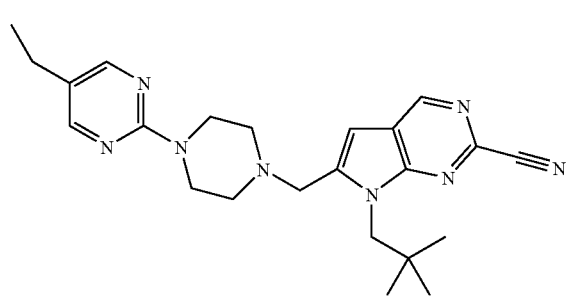

A. 4-(5-Ethyl-pyrimidin-2-yl)-piperazine-1-carboxylic acid tert-butyl ester

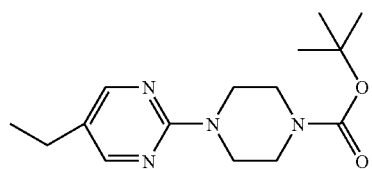

To piperazine-1-carboxylic acid .tert.-butyl ester (3.543 mmol) in EtOH (13 ml), triethylamine (1.5 ml) and 2-chloro-5-ethyl-pyrimidine (3.540 mmol) are added. The mixture is refluxed with stirring for 6 h. After cooling at room temperature, the reaction mixture is quenched with an ice water and extracted with AcOEt. The organic layer is washed with brine, dried over magnesium sulfate and concentrated to give the product in 41% yield. Rf=0.45 (n-hexane:AcOEt=10:1) $^1$H NMR(400 MHz, $CDCl_3$) δ 1.19 (t, 3H), 1.49 (s, 9H), 2.47 (q, 2H), 3.49 (dd, 4H), 3.76 (dd, 4H), 8.18 (s, 2H)

To sodium hydride (0.978 mmol) and 18-crown-6 (0.041 mmoles) in DMF (2.5 ml) suspension, 5-ethyl-2-piperazin-1-yl-pyrimidine (1.058 mmol) is added at room temperature. After 10 minutes, 7-(2,2-dimethyl-propyl)-6-(1-methyl-2,4-dioxo-1,3,8-triaza-spiro[4.5]dec-3-ylmethyl)-7H-pyrrolo[2,3-d]pyrimidine-2-carbonitrile (0.814 mmol) is added at 0° C. The mixture is stirred at room temperature for 5 h and quenched with an ice water. The mixture is extracted with AcOEt. The organic layer is washed with brine and dried over magnesium sulfate and concentrated. The crude product is purified by silica gel column chromatography to give the product in 60% yield.

Rf=0.28 (n-hexane:AcOEt=1:1) $^1$H NMR(400 MHz, $CDCl_3$) δ 1.02 (s, 9H), 1.19 (s, 3H), 2.43-2.55 (m, 4H), 3.77-3.84 (m, 6H), 4.38 (s, 2H), 6.60(s, 1H), 8.17 (s, 2H), 8.91 (s, 1H)

6-31

7-(2,2-Dimethyl-propyl)-6-[4-(2-methyl-4-nitro-phenyl)-piperazin-1-ylmethyl]-7H-pyrrolo[2,3-d]pyrimidine-2-carbonitrile

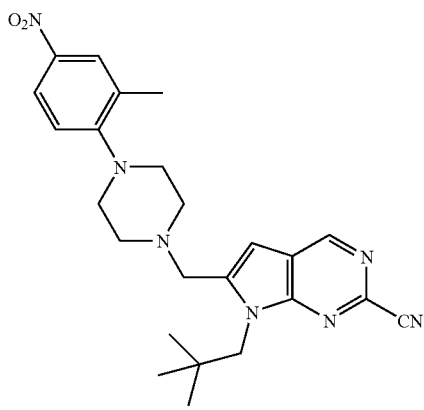

A. 1-(2-Methyl-4-nitro-phenyl)-piperazine

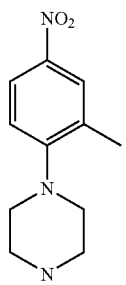

A suspension of piperazine (3.0 mmol), N,N-diisopropyl-ethylamine (6.0 mmol), and 2-fluoro-5-nitrotoluene (7.5 mmol) in acetonitrile are stirred at 50° C. for 3 h and then 100° C. for 9.5 h, and poured into water. The mixture is extracted with AcOEt. The organic layer is washed with water, dried over magnesium sulfate, and concentrated. The crude product is purified by silica gel column chromatography to give the product in 85% yield.

By repeating the procedures described above using appropriate starting materials and conditions the following compounds of formula 6-3 are obtained as identified below in Table 6-3.

TABLE 6-3

6-3

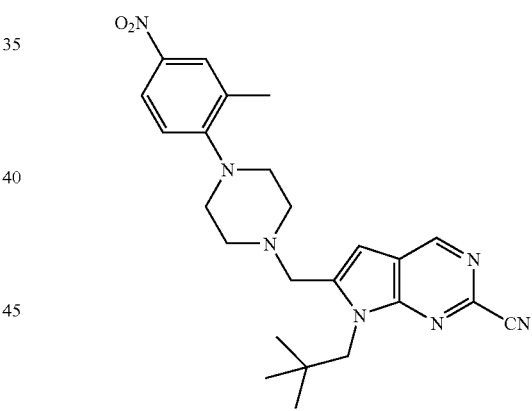

| Expl No. | Rx | Rf(Solvent) | $^1$H-NMR(400 MHz, δ) |
|---|---|---|---|
| 6-32 | — | 0.47 (MeOH:CH$_2$Cl$_2$ = 1:4) | (CDCl$_3$): 2.37(s, 3H), 2.99(m, 4H), 3.05(m, 4H), 6.98(d, 1H), 8.04(m, 1H), 8.05(s, 1H). |
| 6-33 | F-C(F)(F)- (CF$_3$C(CH$_3$)$_2$-) | 0.15 (n-hexane:AcOEt = 1:1) | (CDCl$_3$): 3.00-3.05(m, 4H), 3.05-3.13(m, 4H), 7.27(m, 1H), 8.31(dd, 1H), 8.51(d, 1H). |

B. 7-(2,2-Dimethyl-propyl)-6-[4-(2-methyl-4-nitro-phenyl)-piperazin-1-ylmethyl]-7H-pyrrolo[2,3-d]pyrimidine-2-carbonitrile To a solution of 1.1 (0.83 mmol) in DMF, 1-(2-methyl-4-nitro-phenyl)-piperazine (1.0 mmol) and potassium carbonate (1.0 mmol) are added. The suspension is stirred at room temperature. After 14 h, the resulting yellow suspension is poured into water. The mixture is extracted with AcOEt. The organic layer is washed with water, dried over magnesium sulfate, and concentrated. The crude product is purified by silica gel column chromatography to give the product in 79% yield.

By repeating the procedures described above using appropriate starting materials and conditions the following compounds of formula 6-3 are obtained as identified below in Table 6-4.

TABLE 6-4

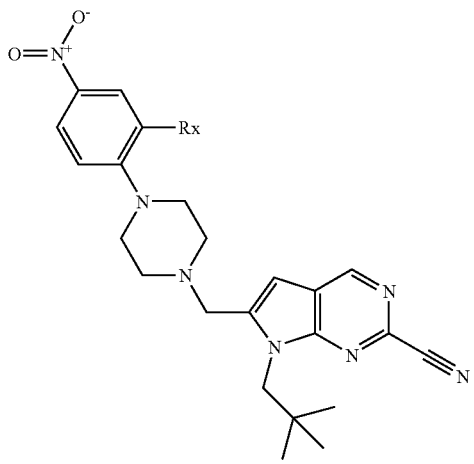

6-4

| Example Nos. | Rx | Yield(%) | Rf(Solvent) | ¹H-NMR(400 mHz, δ) |
|---|---|---|---|---|
| 6-34 | — | 79 | 0.45 (n-hexane:AcOEt = 1:1) | (CDCl₃): 1.03(s, 9H), 2.35(s, 3H), 2.65(m, 4H), 3.04(m, 4H), 3.48(s, 2H), 4.48(s, 2H), 6.62(s, 1H), 6.99(d, 1H), 8.03(m, 1H), 8.04(s, 1H), 8.91(s, 1H). |
| 6-35 | 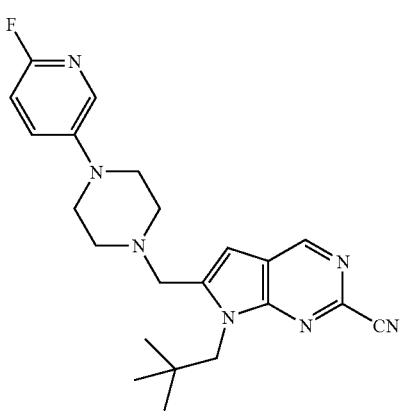 | 73 | 0.46 (n-hexane:AcOEt = 1:1) | (CDCl₃): 1.08(s, 9H), 2.57-2.68(s, 4H), 3.07-3.16(m 4H), 3.87(s, 2H), 4.37(s, 2H), 6.62(s, 1H), 7.29(d, 1H), 8.72(dd, 1H), 8.52(d, 1H), 8.91(s, 1H). |

6-36

7-(2,2-Dimethyl-propyl)-6-[4-(6-fluoro-pyridin-3-yl)-piperazin-1-ylmethyl]-7H-pyrrolo[2,3-d]pyrimidine-2-carbonitrile A. 4-(6-Fluoro-pyridin-3-yl)-piperazine-1-carboxylic acid tert-butyl ester

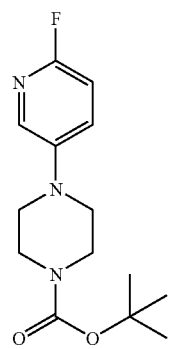

A suspension of piperazine-1-carboxylic acid tert-butyl ester hydrochloride (0.75 mmol), 5-bromo-2-fluoropyridine (0.90 mmol), (R)-2,2'-bis(diphenylphosphino)-1, 1'-binaphthyl (0.038 mmol), palladium acetate (0.038 mmol) and cesium carbonate (1.8 mmol) in toluene is stirred at 80° C. for 7 h and then 100° C. for 4 h, and poured into water. The mixture is extracted with AcOEt. The organic layer is washed with water, dried over magnesium sulfate, and concentrated. The crude product is purified by silica gel column chromatography to give the product in 43% yield. Rf=0.61 (n-hexane:AcOEt=1:1)

¹H NMR(400 MHz, CDCl₃) δ 1.48 (s, 9H), 3.08 (m, 4H), 3.59 (m, 4H), 6.83 (dd, 1H), 7.36 (m, 1H), 7.80 (d, 1H).

B. 7-(2,2-Dimethyl-propyl)-6-[4-(6-fluoro-pyridin-3-yl)-piperazin-1-ylmethyl]-7H-pyrrolo[2,3-d]pyrimidine-2-carbonitrile

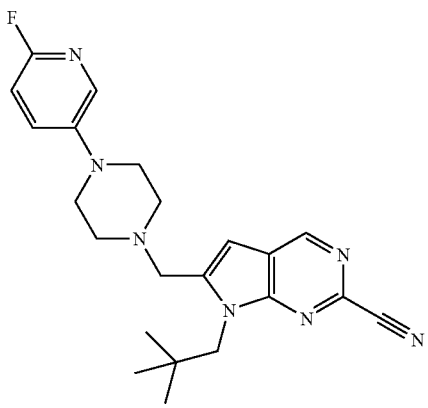

To a solution of 4-(6-fluoro-pyridin-3-yl)-piperazine-1-carboxylic acid tert-butyl ester (0.32 mmol) in CH$_2$Cl$_2$, trifluoroacetic acid (3.2 mmol) is added at 0° C., and the solution is stirred at room temperature. After 2 h, the solution is cooled again to 0° C. To the solution, DMF, potassium carbonate (1.9 mmol) and 1.1 (0.28 mmol) are added. The resulting suspension is stirred at room temperature for 2.5 h and poured into water. The mixture is extracted with AcOEt. The organic layer is washed with water, dried over magnesium sulfate, and concentrated. Purification by silica gel column chromatography, followed by washing of the resulting solids with MeOH gives the product in 63% yield. Rf=0.32 (n-hexane:AcOEt=1:1)

$^1$H NMR(400 MHz, CDCl$_3$) δ 1.02 (s, 9H), 2.63 (m, 4), 3.16 (m, 4H), 3.85 (s, 2H), 4.36 (s, 2H), 6.61 (s, 1H), 6.83 (dd, 1H), 7.33 (m, 1H), 7.78 (br.s, 1H), 8.91 (s, 1H).

6-37

7-(2,2-Dimethyl-propyl)-6-piperazin-1-ylmethyl-7H-pyrrolo[2,3-d]pyrimidine-2-carbonitrile

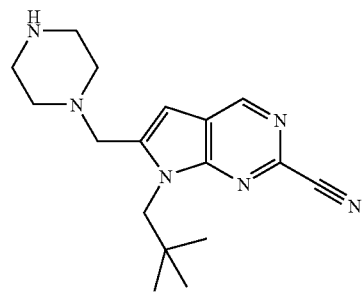

4N HCl/dioxane is added to 4-[2-cyano-7-(2,2-dimethyl-propyl)-7H-pyrrolo[2,3-d]pyrimidin-6-ylmethyl]-piperazine-1-carboxylic acid .tert.-butyl ester at 0° C. and stirred at 25° C. for 90 min. Ether is added to the residue to afford a precipitate, which is collected by filtration. The crude product is dissolved in MeOH and purified by reverse phase HPLC. The fractions (fraction Nos. 23-25) are collected and evaporated. The residue is extracted with ethyl acetate. The organic layer is washed with saturated sodium bicarbonate and brine, and dried over magnesium sulfate and filtrated. The solvent is removed by evaporation and dried in vacuo to afford the title compound. yield 58.1%, Rf=0.30 (CH$_2$Cl$_2$:MeOH=8:2).

$^1$H-NMR (400 MHz, CDCl$_3$) δ 1.01(s, 9H), 2.43(br, 4H), 2.90(br, 4H), 3.76(s, 2H), 4.36(s, 2H), 6.57(s, 1H), 8.89(s, 1H), 6-38

7-(2,2-Dimethyl-propyl-6-[4-(2-fluoro-4-methyl-phenyl)-piperazin-1-ylmethyl]-7H-pyrrolo[2,3-d]pyrimidine-2-carbonitrile

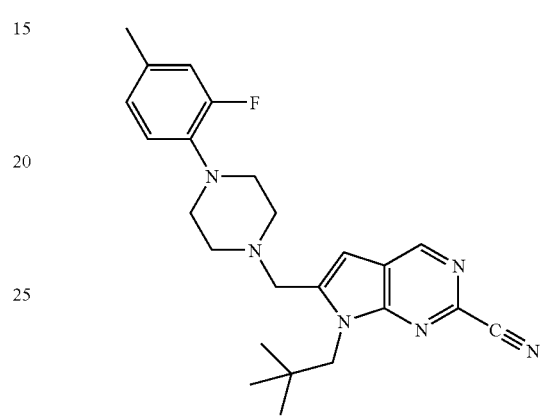

A suspension of 7-(2,2-dimethyl-propyl)-6-piperazin-1-ylmethyl-7H-pyrrolo[2,3-d]pyrimidine-2-carbonitrile (0.32 mmol), 4-bromo-3-fluorotoluene (3.84 mmol), biphenyl-2-yl-di-tert-butyl-phosphane (0.064 mmol), palladium acetate (0.064 mmol), cesium carbonate (0.45 mmol) in 1,4-dioxane is stirred at 100° C. for 24 h and poured into water. The mixture is extracted with AcOEt. The organic layer is washed with water, dried over magnesium sulfate, and concentrated. Purification by silica gel column chromatography gives the product in 18% yield. R-0.56 (n-hexane:AcOEt=1:1)

$^1$H NMR(400 MHz, CDCl$_3$) δ 1.02 (s, 9H), 2.28 (s, 3H), 2.63 (m, 4H), 3.05 (m, 4H), 3.84 (s, 2H), 4.49 (s, 2H), 6.59 (s, 1H), 6.77-6.87 (m, 3H), 8.90 (s, 1H).

6-39

7-(2,2-Dimethyl-propyl)-6-[4-(4-fluoro-2-methyl-phenyl-piperazin-1-ylmethyl]-7H-pyrrolo[2,3d]pyrimidine-2-carbonitrile

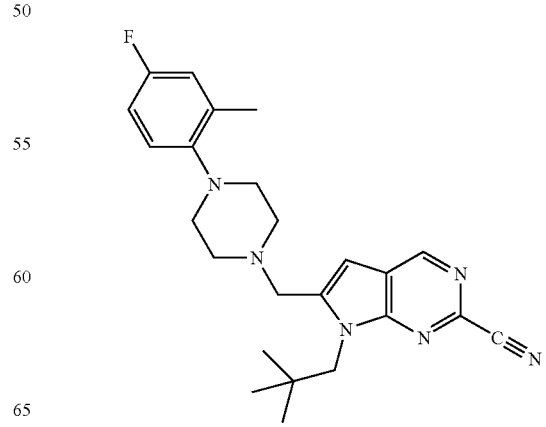

A suspension of 7-(2,2-dimethyl-propyl)-6-piperazin-1-ylmethyl-7H-pyrrolo[2,3-d]pyrimidine-2-carbonitrile (0.20 mmol), 2-bromo-5-fluorotoluene (2.0 mmol), (R)-2,2'-bis(diphenylphosphino)-1, 1'-binaphthyl (0.039 mmol), palladium acetate (0.039 mmol) and cesium carbonate (0.28 mmol) in toluene is stirred at 110° C. for 24 h, and poured into water. The mixture is extracted with AcOEt. The organic layer is washed with water, dried over magnesium sulfate, and concentrated. The crude product is purified by silica gel column chromatography to give the product in 24% yield. Rf=0.56 (n-hexane:AcOEt=1:1)

$^1$H NMR(400 MHz, CDCl$_3$) δ 1.03 (s, 9H), 2.28 (s, 3H), 2.59 (m, 4H), 2.88 (m, 4H), 3.86 (s, 2H), 4.49 (s, 2H), 6.60 (s, 1H), 6.78-6.91 (m, 2H), 6.95 (dd, 1H), 8.90 (s, 1H).

6-40

4-[2-Cyano-7-(2,2-dimethyl-propyl)-7H-pyrrolo[2,3-d]pyrimidin-6-ylmethyl]-piperazine-1-carboxamidine

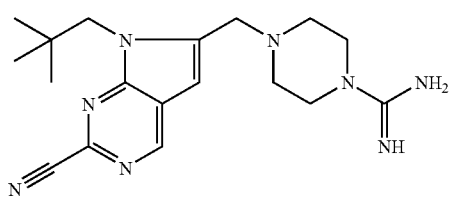

A. (tert.-Butoxcarbonylimino-{4-[2-cyano-7-(2,2-dimethyl-propyl)-7H-pyrrolo[2,3-d]pyrimidin-6-ylmethyl]-piperazin-1-yl}-methyl)-carbamic acid tert-butyl ester

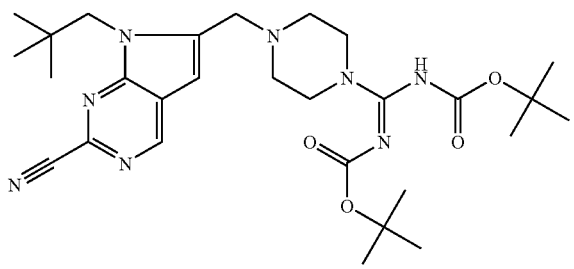

(tert.-Butoxycarbonylimino-piperazin-1-yl-methyl)-carbamic acid .tert.-butyl ester (1.3 mmol) and 6-bromomethyl-7-(2,2-dimethyl-propyl)-7H-pyrrolo[2,3-d]pyrimidine-2-carbonitrile (0.86 mmol) are dissolved in DMF (10 ml) and potassium carbonate (2.6 mmol) is added at room temperature. The mixture is stirred for overnight. Water and AcOEt are added and the organic layer is washed with brine, dried over sodium sulfate and concentrated. The crude product is purified by silica gel column chromatography to give the product in 75% yield. Rf=0.50 (n-hexane:AcOEt=1:2). $^1$H-NMR (400 MHz, CDCl$_3$) δ 1.01 (s, 9H), 1.52 (brs, 18H), 2.52 (t, 4H), 3.59 (brs, 4H), 3.81 (s, 2H), 4.33 (s, 2H), 6.59 (s, 1H), 8.91 (s, 1H).

B. 4-[2-Cyano-7-(2,2-dimethyl-propyl)-7H-pyrrolo[2,3-d]pyrimidin-6-ylmethyl]-piperazine-1-carboxamidine

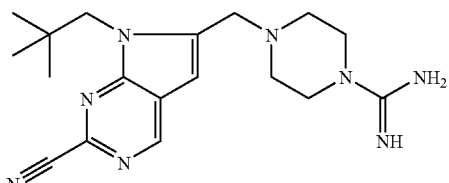

(tert-Butoxycarbonylimino-{4-[2cyano-7-(2,2-dimethyl-propyl)-7H-pyrrolo[2,3-d]pyrimidin-6ylmethyl]-piperazin-1-yl}-methyl)-carbamic acid .tert.-butyl ester (0.48 mmol) is dissolved in dioxane (10 ml) and 4N HCl in dioxane (5 ml) is added at 0° C. The mixture is stirred for overnight at room temperature. Water and AcOEt are added and the organic layer is washed with brine, dried over sodium sulfate and concentrated. The crude product is purified by silica gel column chromatography to give the product in 3% yield. Rf=0.26 (CH$_2$Cl$_2$:MeOH=1:4). $^1$H-NMR (400 MHz, CD$_3$OD) δ 1.09 (s, 9H), 2.59 (t, 4H), 3.49 (t, 4H), 3.93 (s, 2H), 4.40 (s, 2H), 6.89 (s, 1H), 8.98 (s, 1H).

6-41

7-(2,2-Dimethyl-propyl)-6-[4-(4-fluoro-benzyl)-piperazin-1-ylmethyl]-7H-pyrrolo[2,3-d]pyrimidine-2-carbonitrile

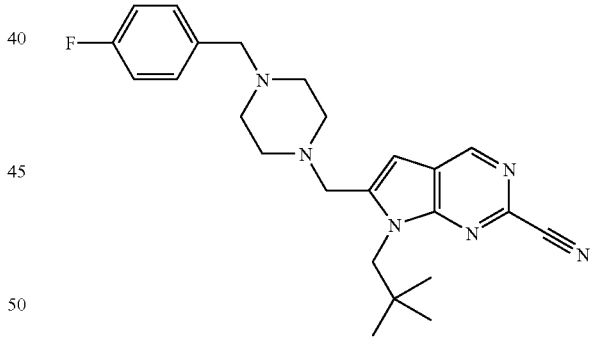

7-(2,2-Dimethyl-propyl)-6-piperazin-1-ylmethyl-7H-pyrrolo[2,3-d]pyrimidine-2-carbonitrile (0.4 mmol) and 1-bromomethyl-4-fluoro-benzene (0.6 mmol) is dissolved in DMF (5 ml) and potassium carbonate (0.6 mmol) is added to the solution. The reaction mixture is heated at 50° C. for 3 h. After the mixture is diluted with AcOEt, the organic layer is washed with brine, dried over magnesium sulfate and filtrated. AcOEt is evaporated and the residue is purified by reverse phase HPLC. The product is obtained in 90.5% yield. Rf=0.32 (n-hexane:AcOEt=1:5).

By repeating the procedures described above using appropriate starting materials and conditions the following compounds of formula 6-5 are obtained as identified below in Table 6-5.

TABLE 6-5

6-5

[Structure: Rx-CH2-piperazine-CH2-pyrrolopyrimidine-CN with N-neopentyl group]

| Expl. Nos. | Rx | Yield(%) | Rf(Solvent) | ¹H-NMR(400 mHz, δ) |
|---|---|---|---|---|
| 6-42 | 4-fluorophenyl | 30 | 0.32 (n-hexane:AcOEt = 1:5) | (CDCl$_3$): 1.00(s, 9H), 2.46(br, 8H), 3.46(s, 2H), 3.77(s, 2H), 4.35(s, 2H), 6.57(s, 1H), 6.97(t, 2H), 7.20-7.24(m, 2H), 8.88(s, 1H), |
| 6-43 | 2,4-difluorophenyl | 34 | 0.38 (n-hexane:AcOEt = 1:5) | (CDCl$_3$): 1.00(s, 9H), 2.47(br, 8H), 3.54(s, 2H), 3.77(s, 2H), 4.33(s, 2H), 6.57(s, 1H), 6.76-6.86(m, 2H), 7.28-7.34(m, 1H), 8.87(s, 1H) |
| 6-44 | 2,4,5-trifluorophenyl | 66 | 0.55 (n-hexane:AcOEt = 1:5) | (CDCl$_3$): 1.00(s, 9H), 2.48(br, 8H), 3.54(s, 2H), 3.77(s, 2H), 4.33(s, 2H), 6.57(s, 1H), 6.87-6.92(m, 1H), 7.19-7.26(m, 1H), 8.88(s, 1H), |

6-45

6-(4-Butyryl-piperazin-1-ylmethyl)-7-(2,2-dimethyl-propyl)-7H-pyrrolo[2,3-d]pyrimidine-2-carbonitrile

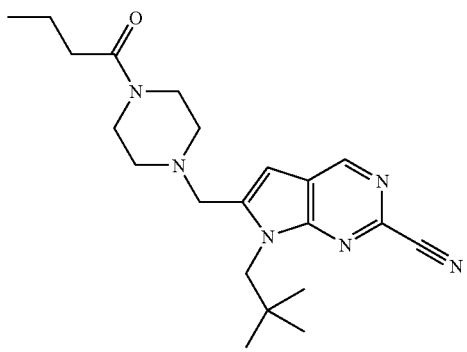

Butyric acid (0.35 mmol) and 7-(2,2-dimethyl-propyl)-6-piperazin-1-ylmethyl-7H-pyrrolo[2,3-d]pyrimidine-2-carbonitrile (0.29 mmol) are dissolved in DMF (10 ml) and cooled with ice. HOBt (0.42 mmol) and WSCD.HCl (0.42 mmol) are added to the cold solution, and the reaction mixture is stirred at 4° C.-25° C. overnight. After saturated ammonium chloride is added to the reaction mixture, the mixture is extracted with AcOEt. The organic layer is washed with saturated ammonium chloride and brine, dried over magnesium sulfate and evaporated down. The crude product is applied to silica gel column chromatography, which is eluted with following solvents: n-hexane:AcOEt=1:1 (v/v), n-hexane:AcOEt=1:4 (v/v) and n-hexane:AcOEt=1:9 (v/v). The solvent of the latter effluent is removed by evaporation and dried in vacuo to afford the title compound. yield 43.2%, Rf=0.19 (n-hexane:AcOEt=1:5).

By repeating the procedures described above using appropriate starting materials and conditions the following compounds of formula 6-6 are obtained as identified below in Table 6-6.

TABLE 6-6

6-6

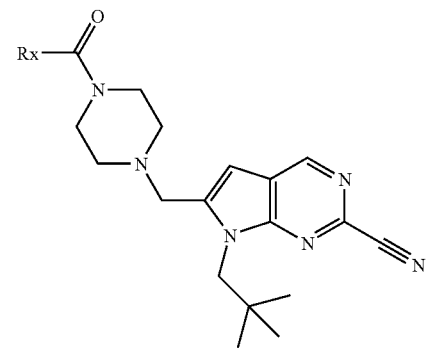

| Expl. No. | Rx | Yield(%) | Rf(Solvent) | $^1$H-NMR(400 mHz, δ) |
|---|---|---|---|---|
| 6-46 | ∼∼∼ | 43 | 0.19 (n-hexane:AcOEt = 1:5) | (CDCl$_3$): 0.96(t, 3H), 1.01(s, 9H), 2.09(s, 3H), 1.61-1.70(m, 2H), 2.91(t, 2H), 2.41-2.46(m, 4H), 3.45-3.48(m, 2H), 3.62-3.64(br, 2H), 3.80(s, 2H), 4.33(s, 2H), 6.59(s, 1H), 8.91(s, 1H), |
| 6-47 | (4-methylimidazole) | 35 | 0.31 (CH$_2$Cl$_2$:MeOH = 9:1) | (CDCl$_3$): 1.02(s, 9H), 2.09(s, 3H), 2.53-2.55(m, 4H), 3.50-4.3(br, 4H), 3.82(s, 2H), 4.35(s, 2H), 6.60(s, 1H), 7.52-7.63(m, 2H), 8.91(s, 1H), 9.6-10.6(br, 1H), |

6-48

N-(4-{4-[2-Cyano-7-(2,2-dimethyl-propyl)-7H-pyrrolo[2,3-d]pyrimidin-6-ylmethyl]-piperazin-1-yl}-phenyl)-methanesulfonamide

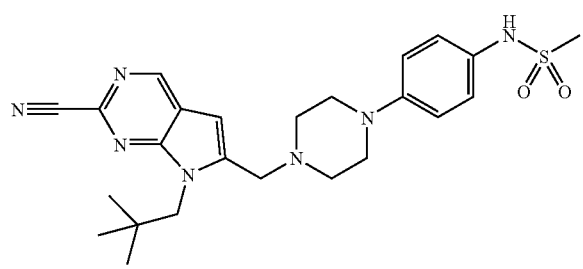

To a suspension of catalytic amount of PtO$_2$ in MeOH (20 ml) and AcOEt (20 ml), 7-(2,2-dimethyl-propyl)-6-[4-(5-nitro-pyrimidin-2-yl)-piperazin-1-ylmethyl]-7H-pyrrolo[2,3-d]pyrimidine-2-carbonitrile (1.15 mmol) is added and the mixture is stirred under H$_2$ atmosphere. After being stirred for 3 h, the reaction mixture is filtered through celite and concentrated under reduced pressure to give crude amine. To a solution of the crude amine in pyridine (10 ml), methanesulfonyl chloride (1.99 mmol) is added at 0° C. and the mixture is allowed to warm to ambient temperature and stirred for 2 h. The reaction mixture is poured into ice water and extracted with AcOEt. The combined extracts are washed with brine, dried over magnesium sulfate and concentrated under reduced pressure. The residue is purified by silica gel column chromatography (eluent; n-hexane:AcOEt=1:1) to give 296 mg of desired N-(4-{4-[2-cyano-7-(2,2-dimethyl-propyl)-7H-pyrrolo[2,3-d]pyrimidin-6-ylmethyl]-piperazin-1-yl}-phenyl)-methanesulfonamide in 49% yield. Rf=0.52 (AcOEt only). $^1$H NMR (400 MHz, CDCl$_3$) δ 1.02 (s, 9H), 2.55-2.65 (m, 4H), 2.94 (s, 3H), 3.15-3.25 (m, 4H), 3.85 (s, 2H), 4.37 (s, 2H), 6.17 (brs, 1H), 6.61 (s, 1H), 6.88 (d, 2H), 7.15 (d, 2H), 8.91 (s, 1H)

By repeating the procedures described above using appropriate starting materials and conditions the following compounds of formula 6-7 are obtained as identified below in Table 6-7.

TABLE 6-7

6-7

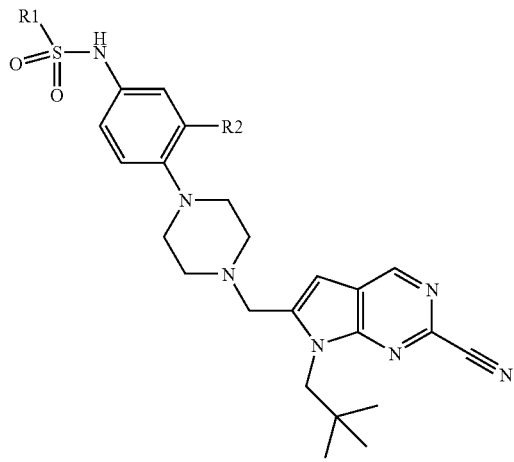

| Expl. No. | R1 | R2 | Yield(%) | Rf(Solvent) | $^1$H-NMR(400 MHz, δ) |
|---|---|---|---|---|---|
| 6-49 | ╲ | H | 49 | 0.52 (AcOEt only) | (CDCl$_3$): 1.02(s, 9H), 2.55-2.65(m, 4H), 2.94(s, 3H), 3.15-3.25(m, 4H), 3.85(s, 2H), 4.37(s, 2H), 6.17(brs, 1H), 6.61(s, 1H), 6.88(d, 2H), 7.15(d, 2H), 8.91(s, 1H) |
| 6-50 | ╱╲ | H | 64.7 | 0.47 (n-hexane:AcOEt = 1:5) | (CDCl$_3$): 1.02(s, 9H), 1.39(t, 3H), 1.61-1.70(m, 2H), 2.60-2.62(m, 4H), 3.04(q, 2H), 3.16-3.18(m, 4H), 3.84(s, 2H), 4.36(s, 2H), 6.07(s, 1H), 6.61(s, 1H), 6.86(d, 2H), 7.14(d, 2H), 8.91(s, 1H), |

TABLE 6-7-continued 6-7

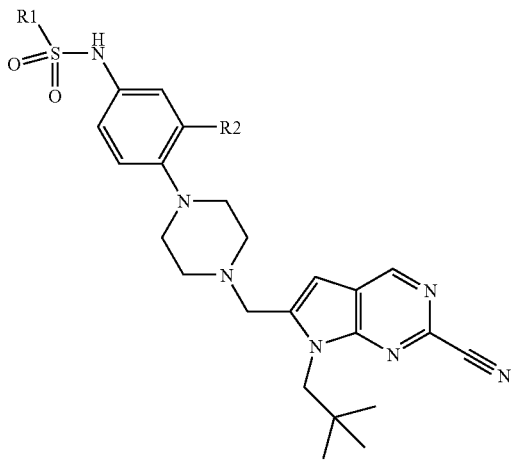

| Expl. No. | R1 | R2 | Yield(%) | Rf(Solvent) | $^1$H-NMR(400 MHz, δ) |
|---|---|---|---|---|---|
| 6-51 | F$_3$C-CH$_2$- | H | 36.9 | 0.62 (n-hexane:AcOEt = 1:5) | (CDCl$_3$): 1.02(s, 9H), 2.60-2.65(m, 4H), 3.19-3.21(m, 4H), 3.77(q, 2H), 3.85(s, 2H), 4.36(s, 2H), 6.40(s, 1H), 6.61(s, 1H), 6.86(d, 2H), 7.17(d, 2H), 8.91(s, 1H), |
| 6-52 | Me | — | 59 | 0.17 (n-hexane:AcOEt = 1:1) | (CDCl$_3$): 1.03(s, 9H), 2.29(s, 3H), 2.55-2.64(m, 4H), 2.85-2.92(m, 4H), 2.97(s, 3H), 3.86(s, 2H), 4.39(s, 2H), 6.13(s, 1H), 6.61(s, 1H), 6.98(d, 1H), 7.00-7.06(m, 2H), 8.90(s, 1H) |
| 6-53 | Me | —F | 26 | 0.19 (n-hexane:AcOEt = 1:1) | (CDCl$_3$): 1.02(s, 9H), 2.60-2.68(m, 4H), 2.98(s, 3H), 3.03-3.12(m, 4H), 3.85(s, 2H), 4.37(s, 2H), 6.20(s, 1H), 6.61(s, 1H), 6.86-6.94(m, 2H), 7.01(d, 1H), 8.91(s, 1H) |
| 6-54 | Me | —Cl | 76 | 0.18 (n-hexane:AcOEt = 1:1) | (CDCl$_3$): 1.02(s, 9H), 2.59-2.69(m, 4H), 3.00(s, 3H), 3.00-3.11(m, 4H), 3.86(s, 2H), 4.38(s, 2H), 6.30(s, 1H), 6.61(s, 1H), 7.01(d, 1H), 7.11(dd, 1H), 7.28(d, 1H), 8.91(s, 1H) |
| 6-55 | Me | —CF$_3$ | 57 | 0.28 (n-hexane:AcOEt = 1:1) | (CDCl$_3$): 1.03(s, 9H), 2.56-2.62(m, 4H), 2.87-2.94(m, 4H), 3.04(s, 3H), 3.85(s, 2H), 4.39(s, 2H), 6.40(s, 1H), 6.61(s, 1H), 7.37(d, 1H), 7.41-7.46(m, 2H), 8.90(s, 1H) |
| 6-56 | Et | —F | 49 | 0.23 (n-hexane:AcOEt = 1:1) | (CDCl$_3$): 1.02(s, 9H), 1.38(t, 3H), 2.58-2.68(m, 4H), 3.05-3.14(m, 4H), 3.85(s, 2H), 4.37(s, 2H), 6.18(s, 1H), 6.61(s, 1H), 6.87-6.90(m, 2H), 6.98-7.03(m, 1H), 8.91(s, 1H). |

The Following Compounds 6-51 to 6-62 are Similarly Prepared

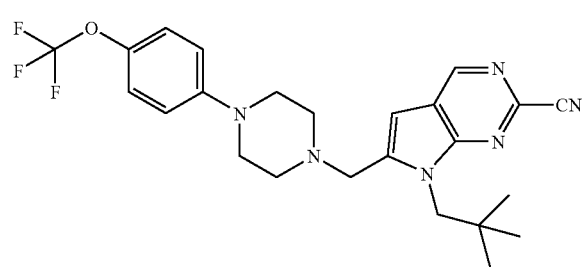

6-57

7(2,2-Dimethyl-propyl)-6-[4-(4-trifluoromethoxy-phenyl)-piperazin-1-ylmethyl]-7H-pyrrolo[2,3-d]pyrimidine-2-carbonitrile 1H-NMR (CDCl$_3$): 1.03 (s, 9H); 2.63 (m, 2H); 3.19 (m, 2H); 3.84 (s, 2H); 4.37 (s, 2H); 6.61 (s, 1H); 6.87 (d, 2H); 7.10 (d, 2H); 8.89 (s, 1H). MH+: 473

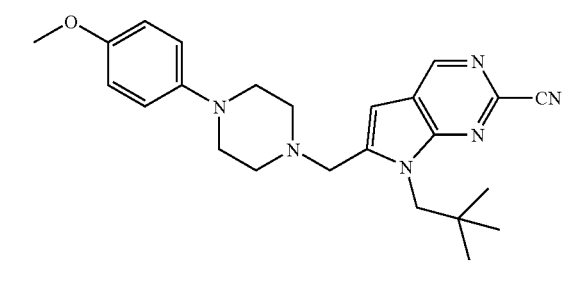

6-58

7-(2,2-Dimethyl-propyl)-6-[4-(4-methoxy-phenyl)-piperazin-1-ylmethyl]-7H-pyrrolo[2,3-d]pyrimidine-2-carbonitrile 1H-NMR (CDCl$_3$): 1.03 (s, 9H); 2.62 (m, 4H); 3.08 (m, 4H); 3.75 (s, 3H); 3.84 (s, 2H); 4.37 (s, 2H), 6.62 (s, 1H); 6.8-6.95 (m, 4H); 8.91 (s, 1H). MH+: 419

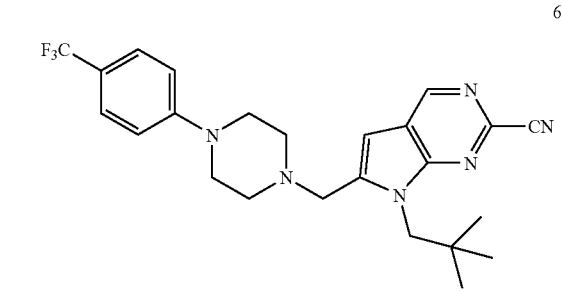

6-59

7-(2,2-Dimethyl-propyl)-6-[4-(4-trifluoromethyl-phenyl)-piperazin-1-ylmethyl]-7H-pyrrolo[2,3-d]pyrimidine-2-carbonitrile 1H-NMR (CDCl$_3$): 1.03 (s, 9H); 2.62 (m, 4H); 3.28 (m, 4H), 3.84 (s, 2H); 4.34 (s, 2H); 6.62 (s, 1H); 6.92 (d, 2H); 7.47 (d, 2H); 8.91 (s, 1H). MH+ 457

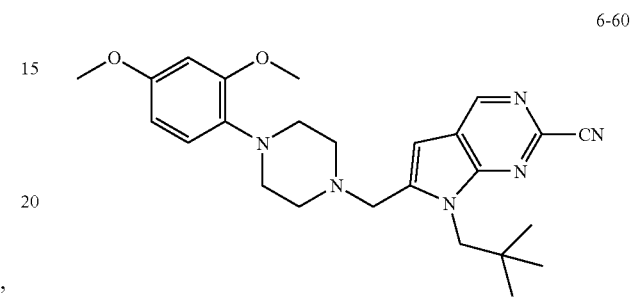

6-60

6-[4-(2,4-Dimethoxy-phenyl)-piperazin-1-ylmethyl]-7-(2,2-methyl-propyl)-7H-pyrrolo[2,3-d]pyrimidine-2-carbonitrile 1H-NMR (CDCl$_3$): 1.03 (s, 9H); 2.64 (m, 4H); 2.9-3.1 (bs, 4H); 3.76 (s, 3H); 3.83 (s, 3H); 3.84 (s, 2H); 4.38 (s, 2H) 6.4-6.5 (m, 2H); 6.51 (s, 1H); 6.84 (d, 1H); 8.89 (s, 1H). MH+ 449

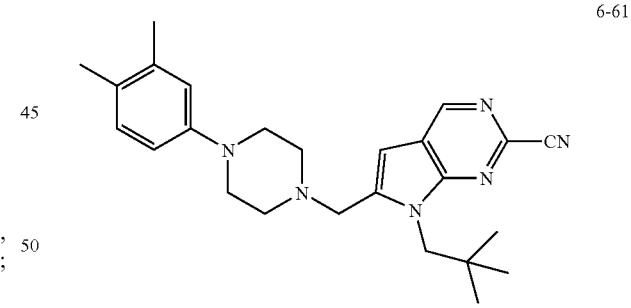

6-61

6-[4-(3,4-Dimethyl-phenyl)-piperazin-1-ylmethyl]-7-(2,2-dimethyl-propyl)-7H-pyrrolo[2,3-d]pyrimidine-2-carbonitrile 1H-NMR (CDCl$_3$): 1.03 (s, 9H); 2.18 (s, 3H); 2.24 (s, 3H); 2.60 (m, 4H); 3.13 (m, 4H); 3.84 (s, 2H); 4.37 (s, 2H); 6.62 (s, 1H); 6.67 (m, 1H); 6.73 (s, 1H); 7.01 (d, 1H); 8.91 (s, 1H). MH+: 417

6-62

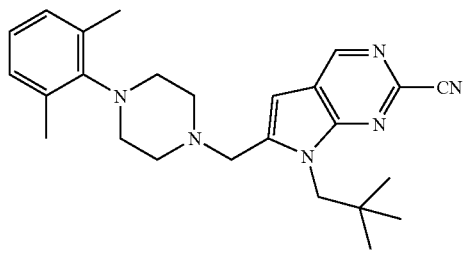

6-[4-(2,6-Dimethyl-phenyl)-piperazin-1-ylmethyl]-7-(2,2-dimethyl-propyl)-7H-pyrrolo[2,3-d]pyrimidine-2-carbonitrile 1H-NMR (CDCl$_3$): 1.03 (s, 9H); 2.16 (s, 6H); 2.55 (m, 4H); 3.10 (m, 4H); 3.82 (s, 2H); 4.41 (s, 2H); 6.62 (s, 1H); 6.97 (m, 3H); 8.91 (s, 1H). MH+: 417

6-63

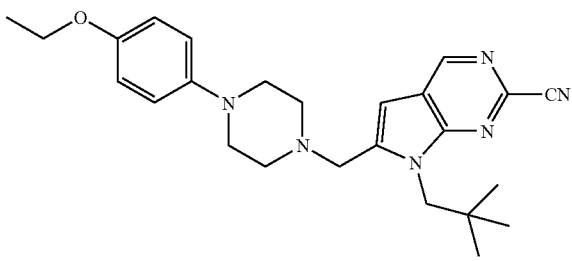

7-(2,2-Dimethyl-propyl)-6-[4-(4-ethoxy-phenyl)-piperazin-1-ylmethyl]-7H-pyrrolo[2,3-d]pyrimidine-2-carbonitrile 1H-NMR (CDCl$_3$): 1.03 (s, 9H); 1.38 (t, 3H); 2.61 (m, 4H); 3.08 (m, 4H); 3.83 (s, 2H); 3.98 (q, 2H); 4.35 (s, 2H), 6.60 (s, 1H); 6.8-6.95 (m, 4H); 8.91 (s, 1H). MH+: 433

6-64

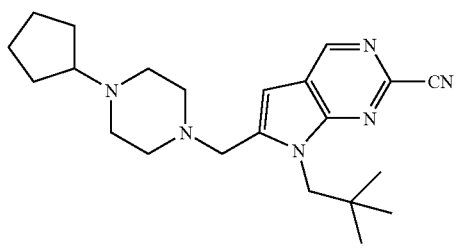

6-(4-Cyclopentyl-piperazin-1-ylmethyl)-7-(2,2-dimethyl-propyl)-7H-pyrrolo[2,3-d]pyrimidine-2-carbonitrile 1H-NMR (CDCl$_3$): 1.00 (s, 9H); 1.3-1.9 (m, 8H); 2.1-2.8 (bm, 9H); 3.76 (s, 2H); 4.34 (s, 2H); 6.56 (s, 1H); 8.81 (s, 1H). MH+: 381

6-65

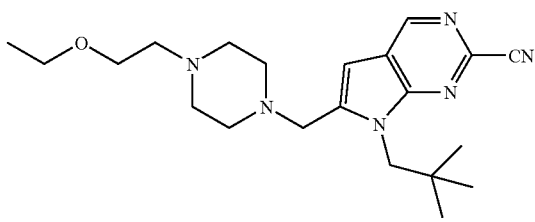

7-(2,2-Dimethyl-propyl)-6-[4-(2-ethoxy-ethyl)-piperazin-1-ylmethyl]-7H-pyrrolo[2,3-d]pyrimidine-2-carbonitrile 1H-NMR (CDCl$_3$): 1.00 (s, 9H); 1.18 (t, 3H); 2,3-2.7 (bm, 8H); 2.58 (t, 2H); 3.59 (q, 2H); 3.54 (t, 2H); 3.78 (s, 2H); 4.34 (s, 2H), 6.56 (s, 1H); 8.89 (s, 1H). MH+: 385

6-66

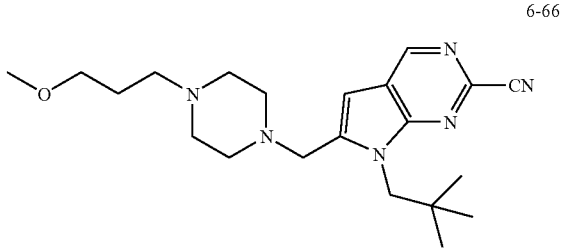

7-(2,2-Dimethyl-propyl)-6-[4-(3-methoxy-propyl)-piperazin-1-ylmethyl]-7H-pyrrolo[2,3-d]pyrimidine-2-carbonitrile 1H-NMR (CDCl$_3$): 0.98 (s, 9H); 1.73 (m, 2H); 2,3-2.6 (m, 10H); 3.30 (s, 3H); 3.40 (t, 2H); 3.76 (s, 2H); 4.33 (s, 2H), 6.55 (s, 1H); 8.87 (s, 1H). MH+: 385

6-67

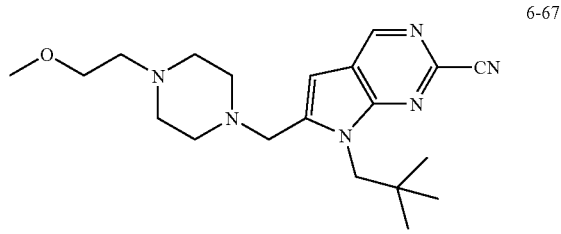

7-(2,2-Dimethyl-propyl)-6-[4-(2-methoxy-ethyl)-piperazin-1-ylmethyl]-7H-pyrrolo[2,3-d]pyrimidine-2-carbonitrile 1H-NMR (CDCl₃): 1.00 (s, 9H); 2.4-2.7 (bm, 8H); 2.58 (t, 2H); 3.35 (s, 3H); 3.50 (t, 2H); 3.54 (t, 2H); 3.78 (s, 2H); 4.34 (s, 2H), 6.56 (s, 1H); 8.88 (s, 1H). MH+: 371

6-68

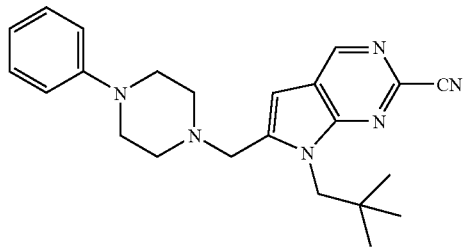

7-(2,2-Dimethyl-propyl)-6-(4-phenyl-piperidin-1-ylmethyl)-7H-pyrrolo[2,3-d]pyrimidine-2-carbonitrile 1H-NMR (CDCl₃, 2 rotamers): 1.03 (s, 9H); 1.6-1.9 (m, 3H); 2.17 (bt, 1H); 2.51 (m, 1H); 2.93 (bd, 1H); 3.80 (s, 1H); 4.26 (s, 1H); 4.38 (s, 1H); 4.71 (s, 0.5 H); 4.84 (s, 0.5H); 6.59 (s, 0.5H); 6.76 (s, 0.5H); 7.1-7.4 (m, 3H); 8.81 (s, 0.5H); 8.96 (bs, 0.5H). MH+: 388

6-69

7-(2,2-Dimethyl-propyl-6-[4-(4-ethoxy-2-fluoro-phenyl)-piperazin-1-ylmethyl]-7.H.-pyrrolo[2,3-.d.]pyrimidine-2-carbonitrile

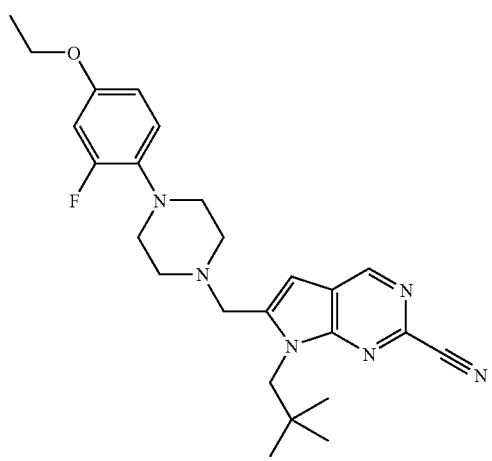

A. 4-(2-Fluoro-4-formyl-phenyl)-piperazine-1-carboxylic acid .tert.-butyl ester

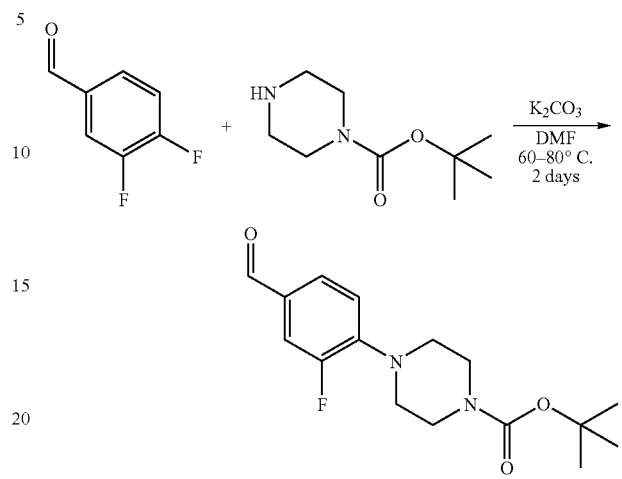

3,4-Difluoro-benzaldehyde (281 mmol) and piperazine-1-carboxylic acid, tert.-butyl ester (366 mmol) are dissolved in DMF (400 ml) and potassium carbonate (422 mmol) is added to the solution. The reaction mixture is heated at 100° C. for 24 h. After the mixture is extracted with AcOEt, the organic layer is washed with brine, dried over magnesium sulfate and filtered. The solvent is evaporated and the residue is purified by column chromatography on silica gel using n-hexane:AcOEt=3:1 (v/v).

Rf=0.23 (n-hexane:AcOEt=3:1). ¹H-NMR (400 MHz, CDCl₃) δ: 1.49 (s, 9H), 3.20-3.23 (m, 4H), 3.59-3.62 (m, 4H), 6.98 (t, 1H), 7.52-7.60 (m, 2H), 9.84 (s, 1H).

B. 4-(2-Fluoro-4-hydroxy-phenyl)-piperazine-1-carboxylic acid .tert.-butyl ester

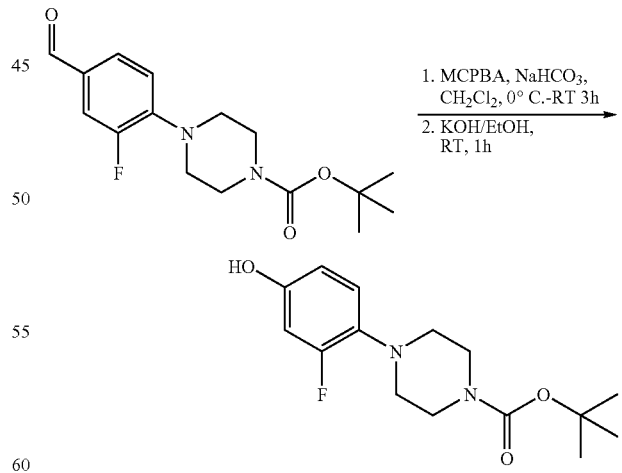

To a solution of 4-(2-fluoro-4-formyl-phenyl)-piperazine-1-carboxylic acid, tert.-butyl ester (97 mmol) in CH₂Cl₂ (600 ml), m-chloroperbenzoic acid (194 mmol) is added at 0° C. for 5 min and NaHCO₃ (243 mmol) is added at 0° C. The mixture is stirred at 0° C. for 20 min and at room temperature for 1 h. To the mixture, m-chloroperbenzoic acid (48.5 mmol) is added at 0° C. The reaction mixture is stirred at room temperature for 1 h, slowly quenched with saturated NaHCO$_3$ at 0° C. and extracted with AcOEt. The combined extracts are washed with saturated NaHCO$_3$, brine and dried over magnesium sulfate. The solvent is evaporated. To the residue, 10% KOH/EtOH is added at 0° C. and the reaction mixture is stirred at room temperature for 1 h. After the mixture is extracted with AcOEt, the organic layer is washed with brine, dried over magnesium sulfate and filtered. The solvent is evaporated and the residue is chromatographed on silica gel (eluent; n-hexane, n-hexane:AcOEt=5:1, n-hexane:AcOEt=4:1, n-hexane:AcOEt=3:1) to give 8.5 g of desired 4-(2-fluoro-4-hydroxy-phenyl)-piperazine-1-carboxylic acid, tert.-butyl ester.

Rf=0.47 (n-hexane:AcOEt=1:1). $^1$H-NMR (400 MHz, CDCl$_3$) δ: 1.48 (s, 9H), 1.50-2.00 (br, 1H), 2.91-2.94 (m, 4H), 3.57-3.59 (m, 4H), 6.53-6.62 (m, 2H), 6.83 (t, 1H).

C. 4-(4-Ethoxy-2-fluoro-phenyl)-piperazine-1-carboxylic acid .tert.-butyl ester

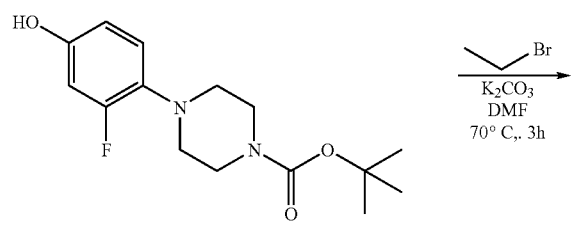

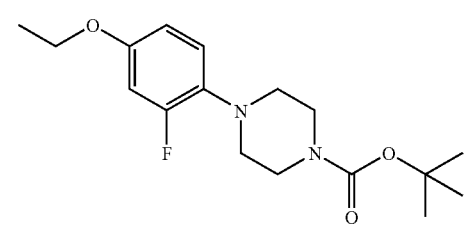

4-(2-Fluoro-4-hydroxy-phenyl)-piperazine-1carboxylic acid, tert.-butyl ester (17 mmol) and ethyl bromide (21 mmol) are dissolved in DMF (50 ml) and potassium carbonate (21 mmol) is added to the mixture. The reaction mixture is heated at 70° C. for 3 h. After the mixture is extracted with AcOEt, the organic layer is washed with brine, dried over magnesium sulfate and filtered. The solvent is evaporated and the residue is purified by column chromatography on silica gel using n-hexane, n-hexane:AcOEt=4:1 (v/v).

Rf=0.68 (n-hexane:AcOEt=4:1). $^1$H-NMR (400 MHz, CDCl$_3$) δ: 1.39 (t, 3H), 1.48 (s, 9H), 2.92-2.95 (m, 4H), 3.57-3.59 (m, 4H), 3.97 (q, 2H), 6.59-6.66 (m, 2H), 6.87 (t, 1H).

D. 7-(2,2-Dimethyl-propyl)-6-[4-(4-ethoxy-2-fluoro-phenyl)-piperazin-1-ylmethyl]-7.H.-pyrrolo[2,3-.d.]pyrimidine-2-carbonitrile

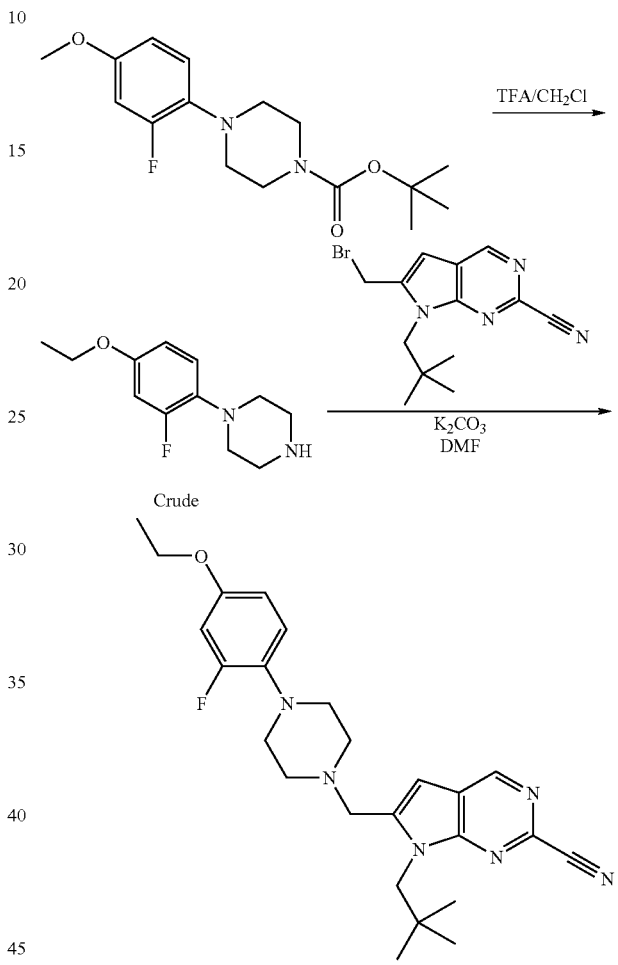

To a solution of 4-(4-Ethoxy-2-fluoro-phenyl)-piperazine-1-carboxylic acid, tert.-butyl ester (12 mmol) in CH$_2$Cl$_2$ (150 ml), TFA (29 ml) is added at 0° C. The reaction mixture is stirred at room temperature for 1 h. The solvent is removed by evaporation and dried to give crude product, 1-(4-ethoxy-2-fluoro-phenyl)-piperazine. To the crude product in DMF (50 ml), potassium carbonate (30 mmol) is successively added at 0° C. The mixture is stirred at 0° C. for 15 min. 6-Bromomethyl-7-(2,2-dimethyl-propyl)-7.H.-pyrrolo[2,3-.d.]pyrimidine-2-carbonitrile (12 mmol) is added to the mixture at 0° C. The reaction mixture is stirred at room temperature for 3 h and quenched with saturated ammonium chloride. The mixture is extracted with AcOEt. The combined extracts are washed with H$_2$O, brine and dried over magnesium sulfate. The solvent is evaporated and the residue is purified by column chromatography on silica gel using n-hexane:AcOEt=2:1 (v/v).

Rf=0.26 (n-hexane:AcOEt=2:1). $^1$H-NMR (400 MHz, CDCl$_3$) δ: 1.02 (s, 9H), 1.38 (t, 3H), 2.62-2.64 (m, 4H), 3.00-3.02 (m, 4H), 3.84 (s, 2H), 3.96 (q, 2H), 4.38(s, 2H), 6.58-6.65 (m, 2H), 6.87 (t, 1H), 8.90 (s, 1H).

6-70

7-(2,2-Dimethyl-propyl)-6-{4-[2-fluoro-4-(2-hydroxy-ethoxy)-phenyl]-piperazin-1-ylmethyl}-7.H.-pyrrolo[2,3-.d.]pyrimidine-2-carbonitrile

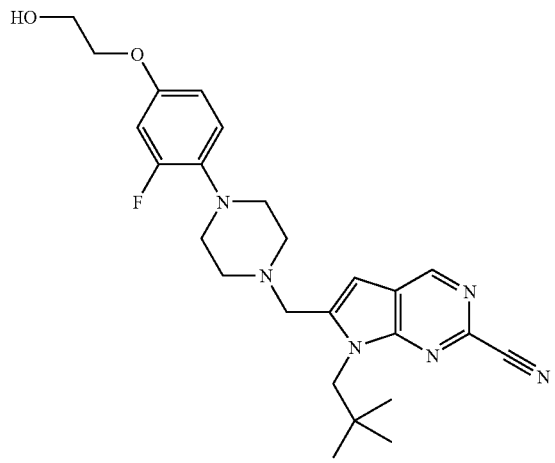

A. 4-(2-Fluoro-4-formyl-phenyl)-piperazine-1-carboxylic acid, tert.-butyl ester

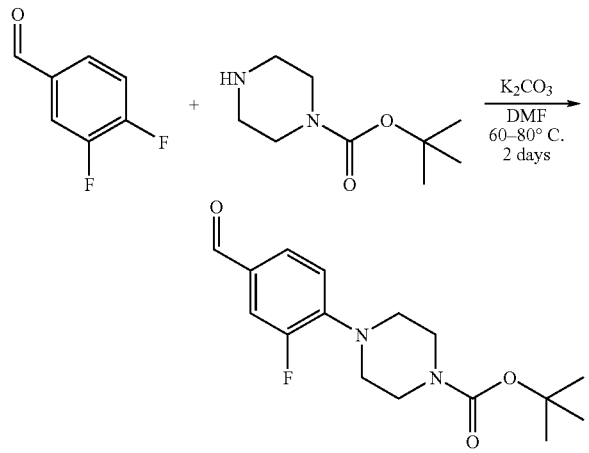

3,4-Difluoro-benzaldehyde (281 mmol) and piperazine-1-carboxylic acid, tert.-butyl ester (366 mmol) are dissolved in DMF (400 ml) and potassium carbonate (422 mmol) is added to the solution. The reaction mixture is heated at 100° C. for 24 h. After the mixture is extracted with AcOEt, the organic layer is washed with brine, dried over magnesium sulfate and filtrated. The solvent is evaporated and the residue is purified by column chromatography on silica gel using n-hexane:AcOEt=3:1 (v/v).

Rf=0.23 (n-hexane:AcOEt=3:1). $^1$H-NMR (400 MHz, CDCl$_3$) δ: 1.49 (s, 9H), 3.20-3.23 (m, 4H), 3.59-3.62 (m, 4H), 6.98 (t, 1H), 7.52-7.60 (m, 2H), 9.84 (s, 1H).

B. 4-(2-Fluoro-4-hydroxy-phenyl)-piperazine-1-carboxylic acid, tert.-butyl ester

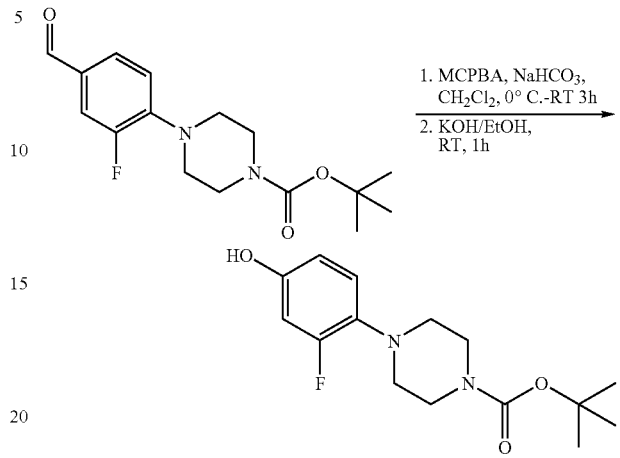

To the solution of 4-(2-fluoro-4-formyl-phenyl)-piperazine-1-carboxylic acid, tert.-butyl ester (97 mmol) in CH$_2$Cl$_2$ (600 ml), m-chloroperbenzoic acid (194 mmol) is added at 0° C. for 5 min and NaHCO$_3$ (243 mmol) is added at 0° C. The mixture is stirred at 0° C. for 20 min and at room temperature for 1 h. To the mixture, m-chloroperbenzoic acid (48.5 mmol) is added at 0° C. The reaction mixture is stirred at room temperature for 1 h, slowly quenched with saturated NaHCO$_3$ at 0° C. and extracted with AcOEt. The combined extracts are washed with saturated NaHCO$_3$, brine and dried over magnesium sulfate. The solvent is evaporated. To the residue, 10% KOH/EtOH is added at 0° C. and the reaction mixture is stirred at room temperature for 1 h. After the mixture is extracted with AcOEt, the organic layer is washed with brine, dried over magnesium sulfate and filtered. The solvent is evaporated and the residue is chromatographed on silica gel using n-hexane, n-hexane:AcOEt=5:1, n-hexane:AcOEt=4:1, n-hexane AcOEt=3:1 to give the desired 4-(2-fluoro-4-hydroxy-phenyl)-piperazine-1-carboxylic acid, tert-butyl ester.

Rf=0.47 (n-hexane:AcOEt=1:1). $^1$H-NMR (400 MHz, CDCl$_3$) δ: 1.48 (s, 9H), 1.50-2.00 (br, 1H), 2.91-2.94 (m, 4H), 3.57-3.59 (m, 4H), 6.53-6.62 (m, 2H), 6.83 (t, 1H).

C. 4-{2-Fluoro-4-[2-(tetrahydro-pyran-2-yloxy)-ethoxy]-phenyl}-piperazine-1-carboxylic acid .tert.-butyl ester

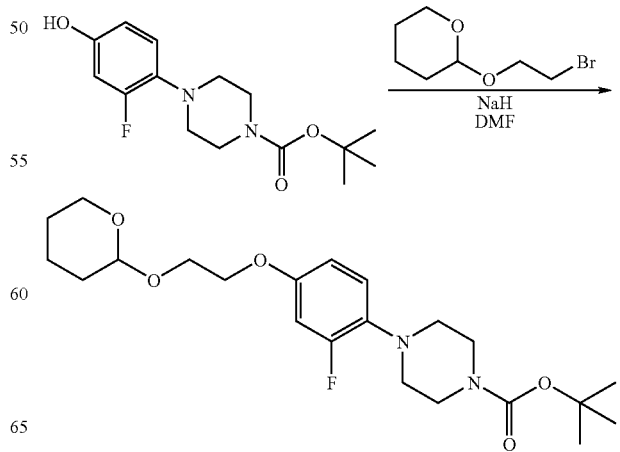

To a suspension of NaH (21.3 mmol) in DMF (50 ml), 4-(2-fluoro-4-hydroxy-phenyl)-piperazine-1-carboxylic acid, tert.-butyl ester (17.8 mmol) is successively added at 0° C. To the mixture, 2-(2-bromoethoxy)-tetrahydro-2H-pyrane (24.9 mmol) is added at 0° C. and the mixture is stirred for 2 h at ambient temperature. The reaction mixture is quenched with ice-water and extracted with AcOEt. The combined extracts are washed with H₂O, brine and dried over magnesium sulfate. Chromatography on silica gel using n-hexane, n-hexane:AcOEt=6:1, n-hexane:AcOEt=4:1 gives the desired 4-{2-fluoro-4-[2-(tetrahydro-pyran-2-yloxy)-ethoxy]-phenyl}-piperazine-1-carboxylic acid, tert-butyl ester.

Rf=0.53 (n-hexane:AcOEt=1:1). ¹H-NMR (400 MHz, CDCl₃) δ: 1.48 (s, 9H), 1.51-1.85 (m, 7H), 2.92-2.95 (m, 4H), 3.50-3.59 (m, 5H), 3.76-3.81 (m, 1H), 3.86-3.91 (m, 1H), 4.00-4.05 (m, 1H), 4.08-4.15 (m, 1H), 4.69 (t, 1H), 6.64-6.72 (m, 2H), 6.87 (t, 1H).

D. 7-(2,2-Dimethyl-propyl)-6-{4-[2-fluoro-4-(2-hydroxy-ethoxy)-phenyl]-piperazin-1-ylmethyl}-7.H.-pyrrolo[2,3-.d.]pyrimidine-2-carbonitrile

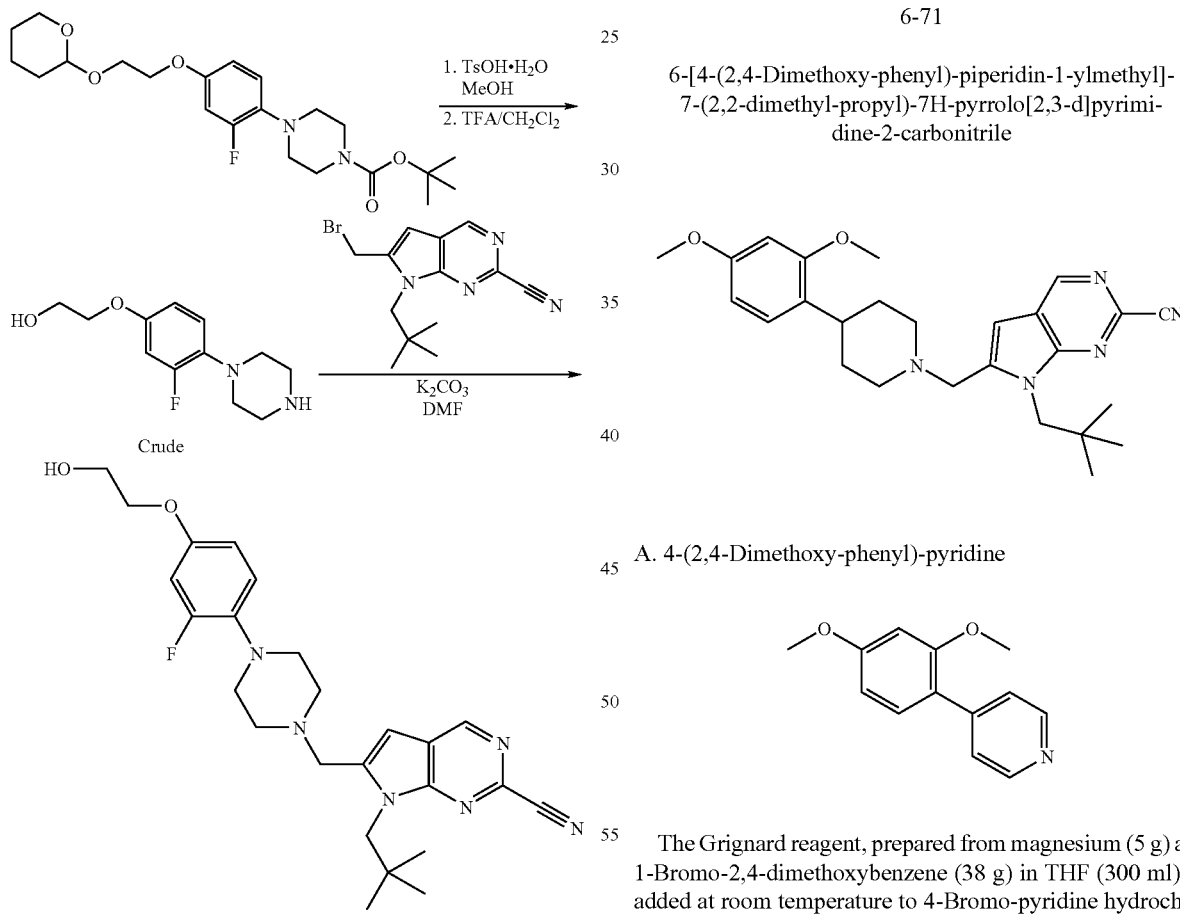

p-Toluenesulfonic acid monohydrate (45.2 mmol) is added to 4-{2-fluoro-4-[2-(tetrahydro-pyran-2-yloxy)-ethoxy]-phenyl}-piperazine-1-carboxylic acid, tert.-butyl ester (22.6 mmol) in MeOH (50 ml) at room temperature. The reaction mixture is stirred at room temperature for 1.5 h. After the mixture is extracted with AcOEt, the organic layer is washed with brine, dried over magnesium sulfate and filtered. The solvent is evaporated. To the residue in CH₂Cl₂ (9 ml), TFA (17.5 ml) is added at 0° C. The reaction mixture is stirred at room temperature for 1 h. The solvent is removed by evaporation and dried to give brown crude oily product, 2-(3-fluoro-4-piperazin-1-yl-phenoxy)-ethanol. To the crude product in DMF (100 ml), potassium carbonate (113 mmol) is successively added at 0° C. The mixture is stirred at 0° C. for 15 min. 6-Bromomethyl-7-(2,2-dimethyl-propyl)-7.H.-pyrrolo[2,3-.d.]pyrimidine-2-carbonitrile (22.6 mmol) is added to the mixture at 0° C. The reaction mixture is stirred at room temperature for 3 h and quenched with saturated ammonium chloride. The mixture is extracted with AcOEt. The combined extracts are washed with H₂O, brine and dried over magnesium sulfate. The solvent is evaporated and the residue is purified by column chromatography on silica gel using n-hexane:AcOEt=3:2 (v/v).

Rf=0.42 (n-hexane:AcOEt=1:5). ¹H-NMR (400 MHz, CDCl₃) δ: 1.02 (s, 9H), 1.94 (t, 1H), 2.62-2.64 (m, 4H), 3.01-3.03 (m, 4H), 3.85 (s, 2H), 3.92-3.96 (m, 2H), 4.01-4.04 (m, 2H), 4.38 (s, 2H), 6.61 (s, 1H), 6.62-6.69 (m, 2H), 8.90 (s, 1H).

6-71

6-[4-(2,4-Dimethoxy-phenyl)-piperidin-1-ylmethyl]-7-(2,2-dimethyl-propyl)-7H-pyrrolo[2,3-d]pyrimidine-2-carbonitrile

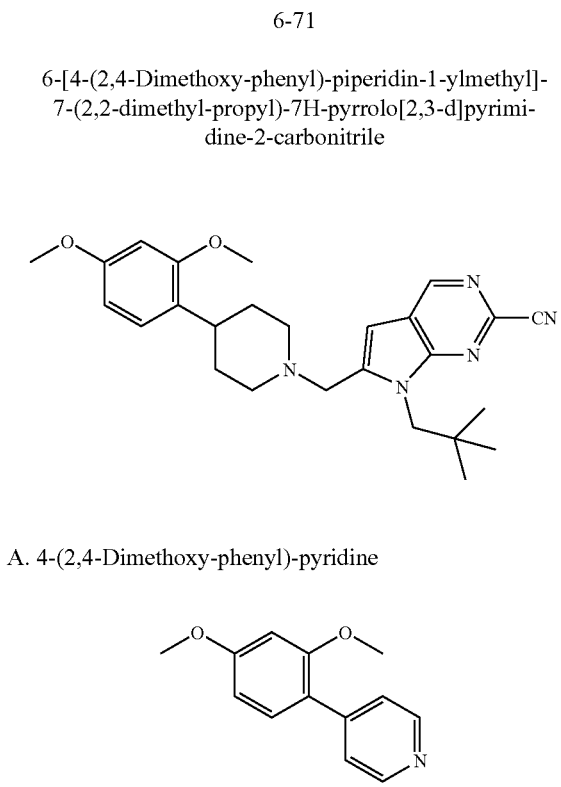

A. 4-(2,4-Dimethoxy-phenyl)-pyridine

The Grignard reagent, prepared from magnesium (5 g) and 1-Bromo-2,4-dimethoxybenzene (38 g) in THF (300 ml), is added at room temperature to 4-Bromo-pyridine hydrochloride salt in THF (10 ml). The mixture is heated under reflux for 2 hours and then evaporated to dryness. The residue is taken up in ethyl acetate and extracted with 1N hydrochloric acid. The aqueous phase is neutralised with 4M sodium hydroxide solution and extracted with ethyl acetate. The organic phase is dried with magnesium sulfate, evaporated and the residue is purified by column chromatography on silica gel using n-hexane:AcOEt=1:1 (v/v). MS-APCI⁺ (M+H)⁺=216

B. 4-(2,4-Dimethoxy-phenyl)-piperidine

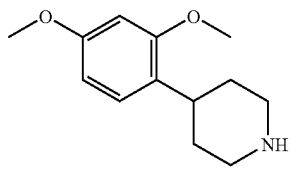

4-(2,4-Dimethoxy-phenyl)-pyridine (6.9 g) is dissolved in a mixture of Ethanol (140 ml) and conc hydrochloric acid (3.5 ml). PtO2 (0.7 g) is added and the mixture is stirred under hydrogen atmosphere for 8 hours. The catalyst is filtered off and the solution is evaporated to dryness. MS-APCI+ (M+H)+ =222

C. 6-[4-(2,4-Dimethoxy-phenyl)-piperidin-1-ylmethyl]-7-(2,2-dimethyl-propyl)-7H-pyrrolo[2,3-d]pyrimidine-2-carbonitrile

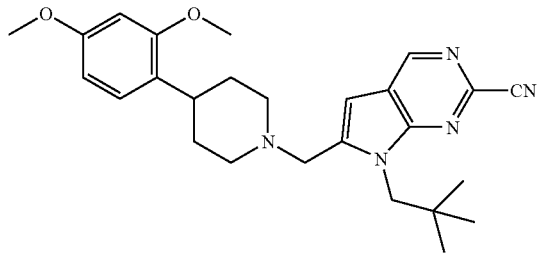

6-Bromomethyl-7-(2,2-dimethyl-propyl)-7H-pyrrolo[2,3-d]pyrimidine-2-carbonitrile (2.2 g) and 4-(2,4-Dimethoxy-phenyl)-piperidine (2.0 g) are dissolved in Acetone (30 ml) and potassium carbonate (3.6 g) is added to the solution. The reaction mixture is stirred for 6 h at room temperature. The mixture is diluted with ethyl acetate, washed with brine, dried over magnesium sulfate and filtrated. Ethyl acetate is evaporated and the residue is purified by column chromatography on silica gel using n-hexane:AcOEt=1:1 (v/v).

mp: 60-63° C. 1H-NMR (CDCl3): 1.02 (s, 9H); 1.5-1.9 (m, 4H); 2.19 (bt, 2H); 2.8-3.0 (m, 3H); 3.7-3.9 (m, 8H); 4.39 (s, 2H); 6.4-6.5 (m, 2H); 6.58 (bs, 1H); 7.08 (d, 1H); 8.88 (s, 1H). MS-APCI+ (M+H)+=448

6-72

6-{4-[4-(2-dimethylamino-ethoxy)-phenyl]-piperidin-1-ylmethyl}-7-(2,2-dimethyl-propyl)-7H-pyrrolo[2,3-d]pyrimidine-2-carbonitrile

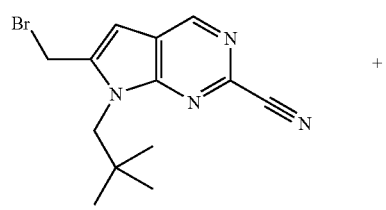 +

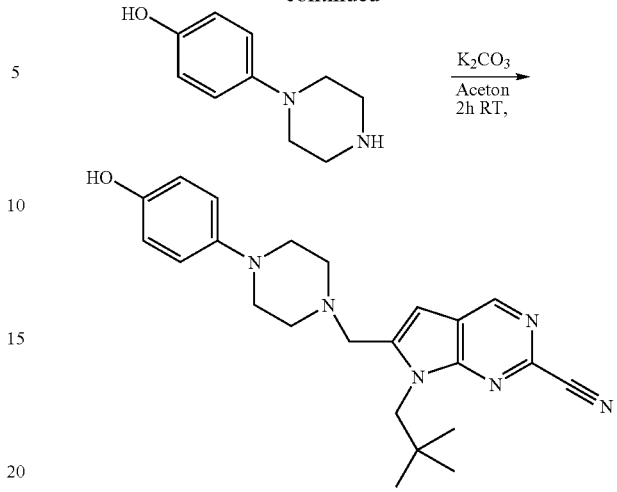

0.5 g of 6-bromomethyl-7-(2,2-dimethyl-propyl)-7H-pyrrolo[2,3-d]pyrimidine-2-carbonitrile, 0.7 g of 4-piperazin-1-yl-phenol and 1.1 g of potassium carbonate were stirred in 5 ml acetone at 25° C. for 2 hours. The mixture was extracted with ethyl acetate/water, dried over sodium sulfate and evaporated to driness. After trituration with dichloromethane 7-(2,2-dimethyl-propyl)-6-[4-(4-hydroxy-phenyl)-piperazin-1-ylmethyl]-7H-pyrrolo[2,3-d]pyrimidine-2-carbonitrile was obtained as yellow solid.

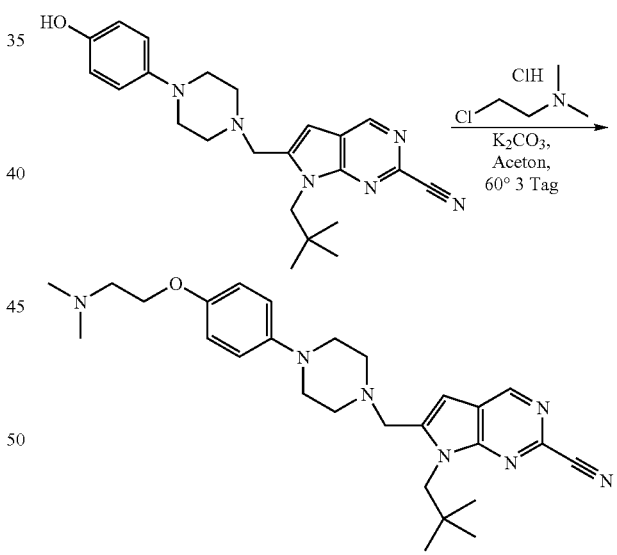

0.24 g 7-(2,2-dimethyl-propyl)-6-[4-(4-hydroxy-phenyl)-piperazin-1-ylmethyl]-7H-pyrrolo[2,3-d]pyrimidine-2-carbonitrile and 0.128 g dimethylaminoethane.HCl were stirred in 2 ml of acetone in the presence of 0.41 g of potassium carbonate. After 18 hours the mixture was extracted with ethyl acetate/water, dried over Magnesium sulfate and evaporated. The residue was chromatographed on silicagel using CH2Cl2/MeOH yielding 6-{4-[4-(2-dimethylamino-ethoxy)-phenyl]-piperazin-1-ylmethyl}-7-(2,2-dimethyl-propyl)-7H-pyrrolo[2,3-d]pyrimidine-2-carbonitrile as colorless wax.

By repeating the procedures described above using appropriate starting materials and conditions the following compounds of formula 6-8 are obtained as identified below in Table 6-8.

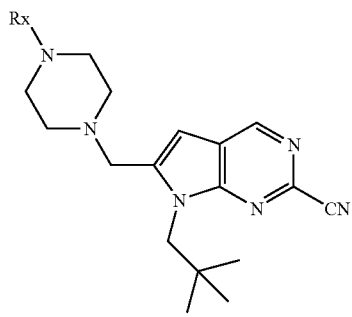

6-8

| | Rx | Name | NMR |
|---|---|---|---|
| 6-73 | 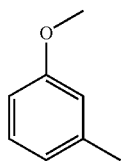 | 7-(2,2-Dimethyl-propyl)-6-[4-(3-methoxy-phenyl)-piperazin-1-ylmethyl]-7H-pyrrolo[2,3-d]pyrimidine-2-carbonitrile | CDCl$_3$, 300 MHz: 1.02(s, 9H), 2.62(m, 4H), 3.20(m, 4H), 3.78(s, 3H), 3.84(m, 2H), 4.36(s, 2H), 6.4-6.55 (m, 4H), 7.18(m, 1H), 8.91(s, 1H). MH$^+$: 419. |
| 6-74 | 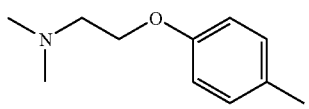 | 6-{4-[4-(2-Dimethylamino-ethoxy)-phenyl]-piperazin-1-ylmethyl}-7-(2,2-dimethyl-propyl)-7H-pyrrolo[2,3-d]pyrimidine-2-carbonitrile | CDCl$_3$, 300 MHz: 1.01(s, 9H), 2.37 (s, 6H), 2.61(m, 4H), 2.76(m, 2H), 3.08(m, 4H), 3.83(s, 2H), 4.03(t, 2H), 4.36(s, 2H), 6.59(s,1H), 6.84 (m, 4H), 8.87(s, 1H). MH$^+$: 476 |
| 6-75 | 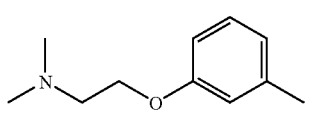 | 6-{4-[3-(2-Dimethylamino-ethoxy)-phenyl]-piperazin-1-ylmethyl}-7-(2,2-dimethyl-propyl)-7H-pyrrolo[2,3-d]pyrimidine-2-carbonitrile | CDCl$_3$, 300 MHz: 1.02(s, 9H), 2.40 (s, 6H), 2.59(m, 4H), 2.82(m, 2H), 3.17(m, 4H), 3.82(s, 2H), 4.07(t, 2H), 4.35(s, 2H), 6.35-6.55(m, 3H), 6.58(s, 1H), 7.13(t, 1H), 8.87(s, 1H). MH$^+$: 476 |
| 6-76 | 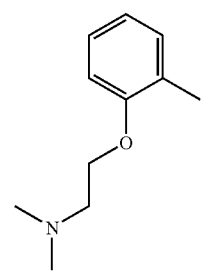 | 6-{4-[2-(2-Dimethylamino-ethoxy)-phenyl]-piperazin-1-ylmethyl}-7-(2,2-dimethyl-propyl)-7H-pyrrolo[2,3-d]pyrimidine-2-carbonitrile | CDCl$_3$, 300 MHz: 1.01(s, 9H), 2.37 (s, 6H), 2.63(m, 4H), 2.80(m, 2H), 3.08(m, 4H), 3.82(s, 2H), 4.10(m, 2H), 4.37(s, 2H), 6.58(s, 1H),6.8-7.0 (m, 4H), 8.85(s, 1H). MH$^+$: 476 |
| 6-77 | 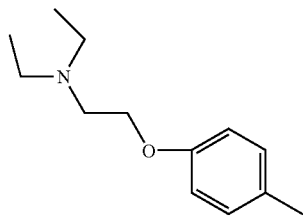 | 6-{4-[4-(2-Diethylamino-ethoxy)-phenyl]-piperazin-1-ylmethyl}-7-(2,2-dimethyl-propyl)-7H-pyrrolo[2,3-d]pyrimidine-2-carbonitrile | CDCl$_3$, 300 MHz: 1.02(s, 9H), 1.10 (t, 6H), 2.61(m, 4H), 2.71(q, 4H), 2.92(t, 2H), 3.08(m, 4H), 3.68(s, 2H), 4.03(t, 2H), 4.37(s, 2H), 6.60(s, 1H), 6.84(m, 4H),8.89(s, 1H). MH$^+$: 504. |
| 6-78 | 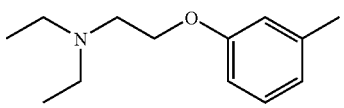 | 6-{4-[3-(2-Diethylamino-ethoxy)-phenyl]-piperazin-1-ylmethyl}-7-(2,2-dimethyl-propyl)-7H-pyrrolo[2,3-d]pyrimidine-2-carbonitrile | CDCl$_3$, 300 MHz: 1.02(s, 9H), 1.10 (t, 6H), 2.60(m, 4H), 2.68(q, 4H), 2.91(t, 2H), 3.18(m, 4H), 3.83(s, 2H), 4.05(t, 2H), 4.24(s, 2H), 6.35-6.55(m, 3H), 6.61(s, 1H),7.15(t, 1H), 8.89(s, 1H). MH$^+$: 504 |

-continued

| | | | 6-8 |
|---|---|---|---|

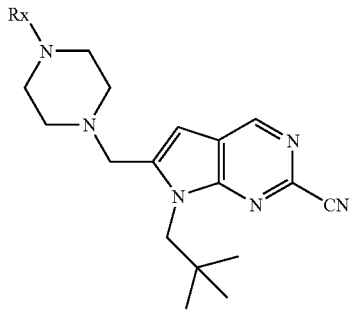

| 6-79 | 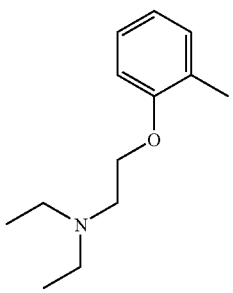 | 6-{4-[2-(2-Diethylamino-ethoxy)-phenyl]-piperazin-1-ylmethyl}-7-(2,2-dimethyl-propyl)-7H-pyrrolo[2,3-d]pyrimidine-2-carbonitrile | CDCl$_3$, 300 MHz: 1.02(s, 9H), 1.08 (t, 6H), 2.5-2.8(m, 8H), 2.93(t, 2H), 3.09(m, 4H), 3.84(s, 2H), 4.09(m, 2H), 4.24(s, 2H), 6.60(s, 1H), 6.8-7.05(m, 4H), 8.88(s, 1H).MH$^+$: 504 |
| 6-80 | 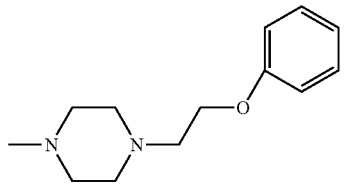 | 7-(2,2-Dimethyl-propyl)-6-(4-{4-[2-(4-methyl-piperazin-1-yl)-ethoxy]-phenyl}-piperazin-1-ylmethyl)-7H-pyrrolo[2,3-d]pyrimidine-2-carbonitrile | CDCl$_3$, 300 MHz: 1.01(s, 9H), 2.43 (s, 3H), 2.5-3.0(m, 16H), 3.08(m, 2H), 3.84(s, 2H), 4.06(t, 2H), 4.36(s, 2H), 6.60(s, 1H), 6.84(m, 4H), 8.89 (s, 1H).MH$^+$: 531. |
| 6-81 | 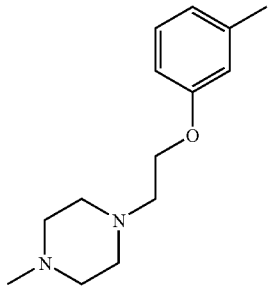 | 7-(2,2-Dimethyl-propyl)-6-(4-{3-[2-(4-methyl-piperazin-1-yl)-ethoxy]-phenyl}-piperazin-1-ylmethyl)-7H-pyrrolo[2,3-d]pyrimidine-2-carbonitrile | CDCl$_3$, 300 MHz: 1.02((s, 9H); 2.33 ((s, 3H), 2.3-2.8((m, 12H), 2.60((t, 2H), 3.18((m, 4H), 3.83((s, 2H), 4.08 ((t, 2H), 4.36((s, 2H), 6.4-6.6((m, 3H), 6.60((s, 1H),(7.14(t, 1H), 8.89 ((s, 1H). MH$^+$:: 531 |
| 6-82 | 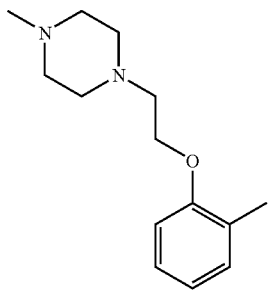 | 7-(2,2-Dimethyl-propyl)-6-(4-{2-[2-(4-methyl-piperazin-1-yl)-ethoxy]-phenyl}-piperazin-1-ylmethyl)-7H-pyrrolo[2,3-d]pyrimidine-2-carbonitrile | CDCl$_3$, 300 MHz: 1.01(s, 9H), 2.34 (s, 3H), 2.4-2.9(m, 12H), 2.84(t, 2H), 3.08(m, 4H), 3.83(s, 2H), 4.10(t, 2H), 4.35(s, 2H), 6.87(s, 1H), 6.8-7.0 (m, 4H),8.89(s, 1H). MH$^+$: 531 |
| 6-83 | 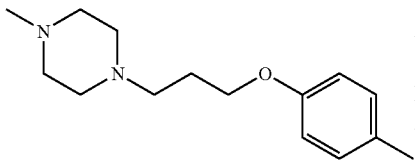 | 7-(2,2-Dimethyl-propyl)-6-(4-{4-[3-(4-methyl-piperazin-1-yl)-propoxy]-phenyl}-piperazin-1-ylmethyl)-7H-pyrrolo[2,3-d]pyrimidine-2-carbonitrile | CDCl$_3$, 300 MHz: 1.01(s, 9H), 1.95 (m, 2H), 2.29(s, 3H), 2.3-2.7(m, 14H), 3.07(m, 4H), 3.84(s, 2H), 3.95 (m, 2H), 4.36(s, 2H), 6.71(s, 1H), 6.84(m, 4H), 8.89(s, 1H).MH$^+$: 545. |

-continued

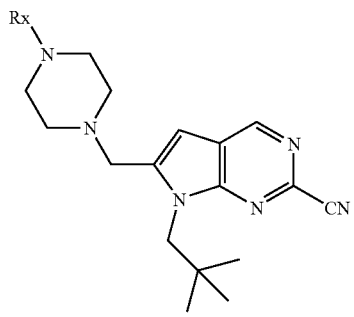

6-8

| | | | |
|---|---|---|---|
| 6-84 | 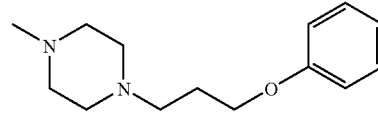 | 7-(2,2-Dimethyl-propyl)-6-(4-{3-[3-(4-methyl-piperazin-1-yl)-propoxy]-phenyl}-piperazin-1-ylmethyl)-7H-pyrrolo[2,3-d]pyrimidine-2-carbonitrile | CDCl$_3$, 300 MHz: 1.03(s, 9H), 1.95 (m, 2H), 2.30(s, 3H), 2.4-2.7(m, 14H), 3.18(m, 4H), 3.83(s, 2H), 3.99 (t, 2H), 4.37(s, 2H), 6.35-6.55(m, 3H), 6.61(s, 1H), 7.15(t, 1H), 8.90(s, 1H). MH$^+$: 545 |
| 6-85 | 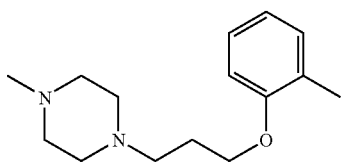 | 7-(2,2-Dimethyl-propyl)-6-(4-{2-[3-(4-methyl-piperazin-1-yl)-propoxy]-phenyl}-piperazin-1-ylmethyl)-7H-pyrrolo[2,3-d]pyrimidine-2-carbonitrile | CDCl$_3$, 300 MHz: 1.02(s, 9H), 2.03 (m, 2H), 2.31(s, 3H), 2.4-2.7(m, 14H), 3.08(m, 4H), 3.83(s, 2H), 4.03 (t, 2H), 4.35(s, 2H), 6.61(s, 1H), 6.8-7.0(m, 4H), 8.89(s, 1H).MH$^+$: 545 |
| 6-86 | 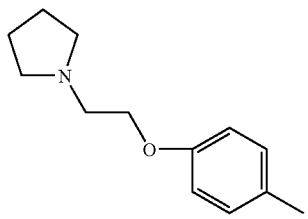 | 7-(2,2-Dimethyl-propyl)-6-{4-[4-(2-pyrrolidin-1-yl-ethoxy)-phenyl]-piperazin-1-ylmethyl}-7H-pyrrolo[2,3-d]pyrimidine-2-carbonitrile | CDCl$_3$, 300 MHz: 1.02(s, 9H), 1.7-1.9(m, 4H), 2.62(m, 4H), 2.72(m, 4H), 2.95(t, 2H), 3.08(m, 4H), 3.84 (s, 2H), 4.09(t, 2H), 4.37(s, 2H), 6.60 (s, 1H), 6.84(m, 4H), 8.89(s, 1H). MH$^+$: 502. |
| 6-87 | 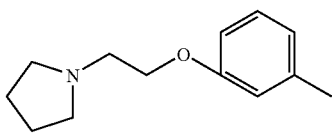 | 7-(2,2-Dimethyl-propyl)-6-{4-[3-(2-pyrrolidin-1-yl-ethoxy)-phenyl]-piperazin-1-ylmethyl}-7H-pyrrolo[2,3-d]pyrimidine-2-carbonitrile | CDCl$_3$, 300 MHz: 1.01(s, 9H), 1.82 (m, 4H), 2.5-2.75(m, 8H), 2.91(t, 2H), 3.17(m, 4H), 3.82(s, 2H), 4.10 (t, 2H), 4.36(s, 2H), 6.4-6.55(m, 3H), 6.60(s, 1H), 7.14(t, 1H), 8.89(s, 1H), MH$^+$: 502 |
| 6-88 | 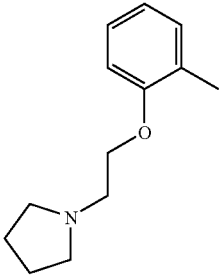 | 7-(2,2-Dimethyl-propyl)-6-{4-[2-(2-pyrrolidin-1-yl-ethoxy)-phenyl]-piperazin-1-ylmethyl}-7H-pyrrolo[2,3-d]pyrimidine-2-carbonitrile | CDCl$_3$, 300 MHz: 1.02(s, 9H), 1.82 (m, 4H), 2.4-2.8(m, 8H), 2.95(t, 2H), 3.08(m, 4H), 3.85(s, 2H), 4.01(t, 2H), 4.38(s, 2H), 7.05(s, 1H), 6.8-7.05(m, 4H), 8.89(s, 1H).MH$^+$: 502 |
| 6-89 | 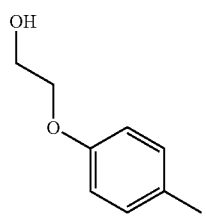 | 7-(2,2-Dimethyl-propyl)-6-{4-[4-(2-hydroxy-ethoxy)-phenyl]-piperazin-1-ylmethyl}-7H-pyrrolo[2,3-d]pyrimidine-2-carbonitrile | CD$_3$OD, 300 MHz: Hydrochloride 0.99(s, 9H), 3.30(m, 4H), 3.38(m, 4H), 3.79(m, 2H), 4.07(m, 2H), 4.48 (s, 2H), 4.63(s, 2H), 7.01(m, 2H), 7.20m, 3H), 9.16(s, 1H). MH$^+$: 449 |

-continued

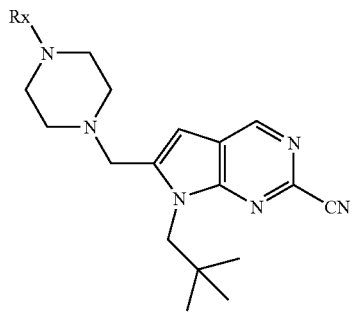

6-8

| 6-90 | 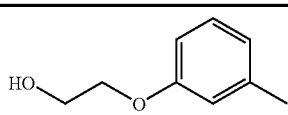 | 7-(2,2-Dimethyl-propyl)-6-{4-[3-(2-hydroxy-ethoxy)-phenyl]-piperazin-1-ylmethyl}-7H-pyrrolo[2,3-d]pyrimidine-2-carbonitrile | CDCl$_3$, 300 MHz: 1.01(sm9H), 2.61 (m, 4H), 3.18(m, 4H), 3.70(m, 2H), 3.80(m, 2H), 4.05(m, 2H), 4.36(s, 2H), 6.4-6.7(m, 4H), 7.14(t, 1H), 8.89(s, 1H). MH$^+$: 449. |
|---|---|---|---|
| 6-91 | 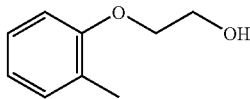 | 7-(2,2-Dimethyl-propyl)-6-{4-[2-(2-hydroxy-ethoxy)-phenyl]-piperazin-1-ylmethyl}-7H-pyrrolo[2,3-d]pyrimidine-2-carbonitrile | CDCl$_3$, 300 MHz: 1.01((s, 9H), 2.80 ((m, 4H), 3.18((m, 4H), 3.69((m, 2H), 3.99((s, 2H), 4.17((m2H), 4.47 ((s2H), 6.68((s, 1H), 6.95-7.15((m, 4H), 8.91((s, 1H). MH$^+$: 449 |
| 6-92 | 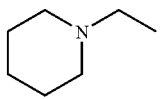 | 7-(2,2-Dimethyl-propyl)-6-[4-(2-piperidin-1-yl-ethyl)-piperazin-1-ylmethyl]-7H-pyrrolo[2,3-d]pyrimidine-2-carbonitrile | CDCl$_3$, 300 MHz: 1.00(s, 9H), 1.44 (m, 2H), 1.59(m, 4H), 2.3-2.9(m, 16H), 3.76(s, 2H), 4.34(s, 2H), 6.55 (s, 1H), 8.87(s, 1H). MH$^+$: 424. |
| 6-93 | 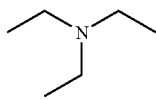 | 6-[4-(2-Diethylamino-ethyl)-piperazin-1-ylmethyl]-7-(2,2-dimethyl-propyl)-7H-pyrrolo[2,3-d]pyrimidine-2-carbonitrile | CDCl$_3$, 300 MHz: 0.99(s, 9H), 1.04 (t, 6H), 2.4-2.7(m, 16H), 3.76(s, 2H), 4.33(s, 2H), 6.55(s, 1H), 8.86(s, 1H). MH$^+$: 412. |
| 6-94 | 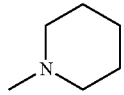 | 7-(2,2-Dimethyl-propyl)-6-[4-(1-methyl-piperidin-4-yl)-piperazin-1-ylmethyl]-7H-pyrrolo[2,3-d]pyrimidine-2-carbonitrile | CDCl$_3$, 300 MHz: 0.99(s, 9H), 1.5-1.9(m, 4H), 1.04(m, 2H), 2.28(m, 1H), 2.32(s, 3H), 2.52(m, 8H), 2.98 (m, 2H), 3.76(s, 2H), 4.23(s, 2H), 6.56(s, 1H), 8.87(s, 1H). MH$^+$: 410. |

By repeating the procedures described above using appropriate starting materials and conditions the following compounds of formula 6-9 are obtained as identified below in Table 6-9

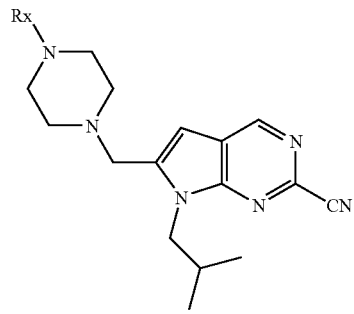

6-9

| Expl No | Rx | Name | $^1$H NMR(400 MHz, δ) |
|---|---|---|---|
| 6-95 | (4-methoxyphenyl) | 7-Isobutyl-6-[4-(4-methoxy-phenyl)-piperazin-1-yl-methyl]-7H-pyrrolo[2,3-d]pyrimidine-2-carbonitrile | CDCl$_3$, 300 MHz: 0.92(d, 6H), 2.36 (m, 1H), 2.77 (m, 4H), 3.09(m, 4H), 3.77(m, 5H), 4.26(d, 2H), 6.58(s, 1H), 6.86(m, 4H), 8.89(s, 1H). MH$^+$: 405. |
| 6-96 | (3-methoxyphenyl) | 7-Isobutyl-6-[4-(3-methoxy-phenyl)-piperazin-1-yl-methyl]-7H-pyrrolo[2,3-d]pyrimidine-2-carbonitrile | CDCl$_3$, 300 MHz: 0.92(d, 6H), 2.36 (m, 1H), 2.66(m, 4H), 3.20(m, 4H), 3.76(m, 2H), 3.79(s, 3H). 4.27(d, 2H), 8.4-8.6(m, 4H), 7.18(m, 1H), 8.90(s, 1H).MH$^+$: 405 |
| 6-97 | (4-ethoxyphenyl) | 6-[4-(4-Ethoxy-phenyl)-piperazin-1-yl-methyl]-7-isobutyl-7H-pyrrolo[2,3-d]pyrimidine-2-carbonitrile | CDCl$_3$, 300 MHz: 0.92(d, 6H), 1.38 (t, 3H), 2.36(m, 1H), 2.68(m, 4H), 3.10(m, 4H), 3.77(s, 2H), 3.97(q, 2H), 4.26(d, 2H), 6.58(s, 1H), 6.84 (m, 4H),8.88(s, 1H). MH$^+$: 419 |

-continued

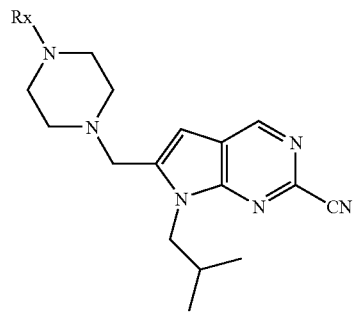

6-9

| Expl No | Rx | | ¹H NMR(400 MHz, δ) |
|---|---|---|---|
| 6-98 | (2,4-dimethoxyphenyl)piperazine structure | 6-[4-(2,4-Dimethoxy-phenyl)-piperazin-1-ylmethyl]-7-isobutyl-7H-pyrrolo[2,3-d]pyrimidine-2-carbonitrile | CDCl₃, 300 MHz: 0.92((d, 6H), 2.36((m, 1H), 2.71((m, 4H), 3.01 ((m, 4H), 3.78((s, 5H), 3.83((s, 3H), 4.28((d, 2H), 6.39-6.47((m, 2H), 6.58 ((s, 1H),6.86((m, 1H), 8.88((s, 1H). MH⁺:: 435 |
| 6-99 | 3-(2-diethylamino-ethoxy)phenyl piperazine structure | 6-{4-[3-(2-Diethylamino-ethoxy)-phenyl]-piperazin-1-ylmethyl}-7-isobutyl-7H-pyrrolo[2,3-d]pyrimidine-2-carbonitrile | CDCl₃, 300 MHz: 0.92(d, 6H), 1.11 (t, 6H), 2.36(m, 1H), 2.6-2.8(m, 8H), 2.93(t, 2H), 3.18(m, 4H), 3.76 (s, 2H), 4.08(t, 2H), 4.25(d,2H), 6.4-6.55(m, 3H), 6.57(s, 1H), 7.14 (t, 1H), 8.89(s, 1H). MH⁺: |
| 6-100 | 4-[2-(4-methylpiperazin-1-yl)ethoxy]phenyl piperazine structure | 7-Isobutyl-6-(4-{4-[2-(4-methyl-piperazin-1-yl)-ethoxy]-phenyl}-piperazin-1-yl-methyl)-7H-pyrrolo[2,3-d]pyrimidine-2-carbonitrile | CDCl₃, 300 MHz: 0.93((d, 6H), 2.37((m, 1H), 2.49((bs, 3H), 2.6-2.9((m, 14H), 3.09(m, 4H), 3.78(s, 2H),4.08(m, 2H), 4.27(s, 2H), 6.58 (s, 1H), 6.86(m, 4H), 8.90(s, 1H). MH⁺: 517 |
| 6-101 | 3-[2-(4-methylpiperazin-1-yl)ethoxy]phenyl piperazine structure | 7-Isobutyl-6-(4-{3-[2-(4-methyl-piperazin-1-yl)-ethoxy]-phenyl}-piperazin-1-yl-methyl)-7H-pyrrolo[2,3-d]pyrimidine-2-carbonitrile | CDCl₃, 300 MHz: 0.91(d, 6H), 2.2-2.4(m, 4H), 2.4-2.8(m, 12H), 2.82 (t, 2H), 3.17(m, 4H), 3.75(s, 2H), 4.08(m, 2H), 4.25(d, 2H), 6.35-6.55(m, 3H), 6.56(s, 1H), 7.15(t, 1H), 8.89(s, 1H). MH⁺: 517 |

-continued
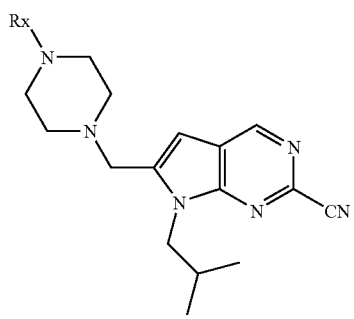
6-9
| Expl No | Rx | | ¹H NMR(400 MHz, δ) |
|---|---|---|---|
| 6-102 | 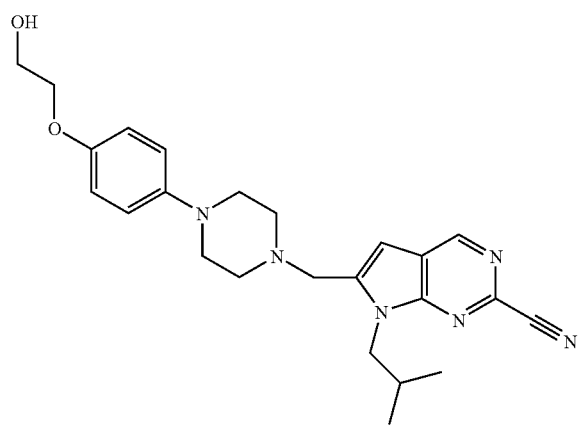 | 7-Isobutyl-6-(4-{2-[2-(4-methyl-piperazin-1-yl)-ethoxy]-phenyl}-piperazin-1-yl-methyl)-7H-pyrrolo[2,3-d]pyrimidine-2-carbonitrile | CDCl₃, 300 MHz: 0.92(d, 6H), 2.33 (s, 3H), 2.35-2.8(m, 13H), 2.83(t, 2H), 3.08(m, 4H), 3.76(s, 2H), 4.11 (m, 2H), 4.26(d, 2H), 6.58(s, 1H), 6.8-7.0(m, 4H), 8.88(s, 1H). MH⁺: 517 |
| 6-103 | | 6-{4-[4-(2-Hydroxy-ethoxy)-phenyl]-piperazin-1-ylmethyl}-7-isobutyl-7H-pyrrolo[2,3-d]pyrimidine-2-carbonitrile | CDCl₃, 300 MHz: 0.92((d, 6H), 2.34((m, 1H), 2.72((bs, 4H), 3.13 ((bs, 4H), 3.79((s, 2H), 3.92((m, 2H), 4.03((m, 2H), 4.25((d,2H), 6.59((s, 1H), 6.8-7.0((m, 4H), 8.88 ((s, 1H). MH⁺: 435 |

By repeating the procedures described above using appropriate starting materials and conditions the following compounds of formula 6-10 are obtained as identified below in Table 6-10

By repeating the procedures described above using appropriate starting materials and conditions the following compounds of formula 6-11 are obtained as identified below in Table 6-11

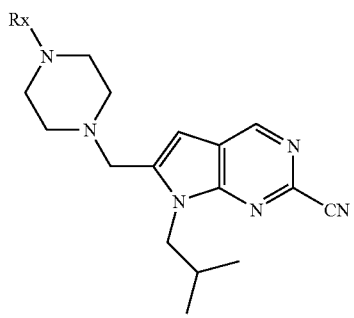

6-10

| | Rx | Name | NMR |
|---|---|---|---|
| 6-104 | 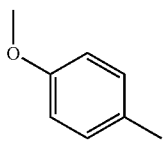 | 6-[4-(4-Methoxy-phenyl)-piperazin-1-ylmethyl]-7-(3-methyl-butyl)-7H-pyrrolo[2,3-d]pyrimidine-2-carbonitrile | CDCl$_3$, 300 MHz: 1.01(d, 6H), 1.72 (m, 3H), 2.67(m, 4H), 3.10(m, 4H), 3.77(m, 5H), 4.42(m, 2H), 6.56(s, 1H), 6.8-6.95(m, 4H), 8.89(s, 1H). MH$^+$: 419. |
| 6-105 | 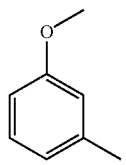 | 6-[4-(3-Methoxy-phenyl)-piperazin-1-ylmethyl]-7-(3-methyl-butyl)-7H-pyrrolo[2,3-d]pyrimidine-2-carbonitrile | CD$_3$OD, 300 MHz: 1.04(d, 6H), 1.65-1.85(m, 3H), 2.67(m, 4H), 3.16(m, 4H), 3.74(s, 3H), 3.85(s, 2H), 4.46(m, 2H), 6.4-6.6(m, 3H), 6.72(s, 1H), 7.11(t, 1H), 8.95(s, 1H). MH$^+$: 419. |
| 6-106 | 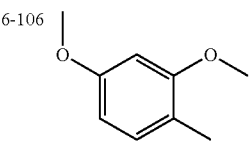 | 6-[4-(2,4-Dimethoxy-phenyl)-piperazin-1-ylmethyl]-7-(3-methyl-butyl)-7H-pyrrolo[2,3-d]pyrimidine-2-carbonitrile | CDCl$_3$, 300 MHz: 1.02(d, 6H), 1.57 (m, 1H), 1.73(m, 2H), 2.68(m, 4H), 3.00(m, 4H), 3.74(m, 5H), 3.82(s, 3H), 4.41(m, 2H), 6.4-6.6(m, 3H), 6.82(d, 1H), 8.87(s, 1H). MH$^+$: 449. |

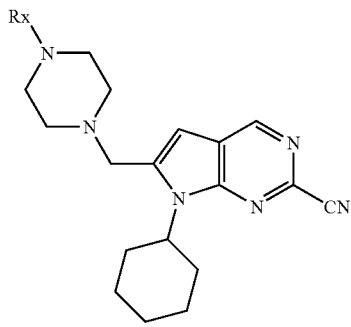

6-11

| 6-107 | 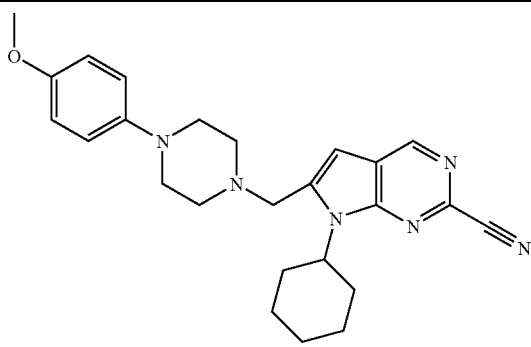 | 7-Cyclohexyl-6-[4-(4-methoxy-phenyl)-piperazin-1-ylmethyl]-7H-pyrrolo[2,3-d]pyrimidine-2-carbonitrile | CDCl$_3$, 300 MHz, 1.3–2.0(m, 8H), 2.66(m, 6H), 3.08(m, 4H), 3.74(s, 2H), 3.76(s, 3H), 4.47(m, 1H), 6.51 (s, 1H), 6.8–7.0(m, 4H), 8.86(s, 1H). MH$^+$: 431. |
|---|---|---|---|
| 6-108 | 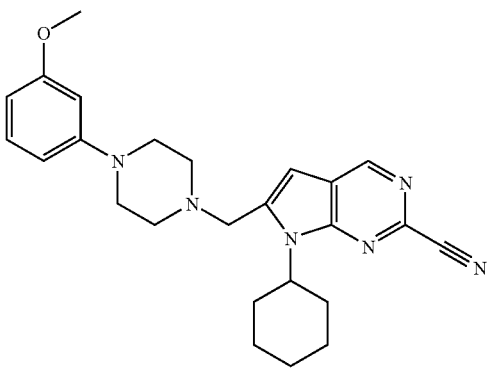 | 7-Cyclohexyl-6-[4-(3-methoxy-phenyl)-piperazin-1-ylmethyl]-7H-pyrrolo[2,3-d]pyrimidine-2-carbonitrile | CDCl$_3$, 300 MHz, 1.3–2.0(m, 8H), 2.65(m, 6H), 3.19(m, 4H), 3.75(s, 2H), 3.80(s, 3H), 4.47(m, 1H), 6.4–6.6(m, 4H), 7.16(t, 1H), 8.87(s, 1H), MH$^+$: 431 |
| 6-109 | 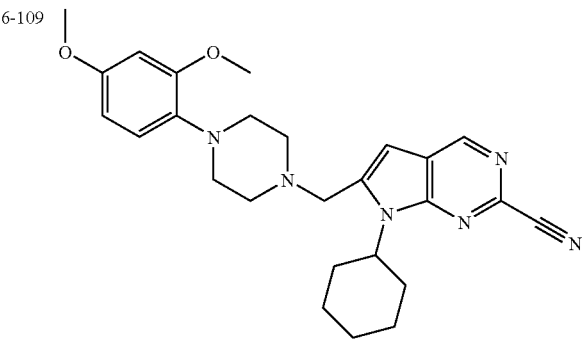 | 7-Cyclohexyl-6-[4-(2,4-dimethoxy-phenyl)-piperazin-1-ylmethyl]-7H-pyrrolo[2,3-d]pyrimidine-2-carbonitrile | CDCl$_3$, 300 MHz: 1.3–2.0(m, 8H), 2.65(m, 6H), 2.98(m, 4H), 3.72(s, 2H), 3.75(s, 3H), 3.83(s, 3H), 4.49 (m, 1H), 6.35–6.55(m, 3H), 6.83(s, 1H), 8.84(s, 1H). MH$^+$: 461. |

Example 7 Describes the Preparation of 6-piperidinylmethyl-7H-pyrrolo[2,3-d]pyrimidine-2-carbonitrile

Example 7-1

7-(2,2-Dimethyl-propyl)-6-(4-oxo-piperidin-1-ylmethyl)-7H-pyrrolo[2,3-d]pyrimidine-2-carbonitrile

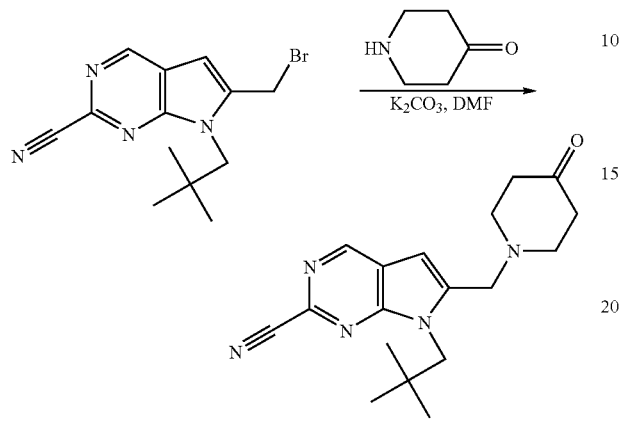

To a solution of 100 mg (0.32 mmoles) of 6-bromomethyl-7-(2,2-dimethyl-propyl)-7H-pyrrolo[2,3-d]pyrimidine-2-carbonitrile and 150 mg (0.96 mmoles) of piperidin-4-one in 5 ml of DMF, 88 mg (0.64 mmoles) of $K_2CO_3$ is added at ambient temperature. After being stirred for 18 hours, the reaction mixture is quenched with $H_2O$ and the mixture is extracted with AcOEt. The combined extracts are washed with brine, dried over $MgSO_4$ and concentrated under reduced pressure. The residue is purified by silica gel column chromatography to give 96 mg of disired 7-(2,2-dimethyl-propyl)-6-(4-oxo-piperidin-1-ylmethyl)-7H-pyrrolo[2,3-d]pyrimidine-2-carbonitrile in 92% yield.

$^1$H NMR (400 MHz, $CDCl_3$, δ); 1.03 (s, 9H), 2.47 (t, 4H), 2.78 (t, 4H), 3.90 (s, 2H), 4.37 (s, 2H), 7.26 (s, 2H), 8.91 (s, 1H) Rf:=0.26 (AcOEt:n-Hexane=1:1)

By repeating the procedures described above using appropriate starting materials and conditions the following compounds of formula 7-1 are obtained as identified below in Table 7-1.

TABLE 7-1

7-1

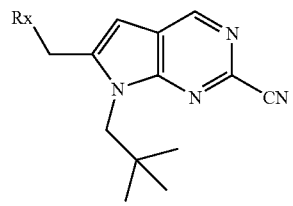

| Expl. No. | Rx | Yield(%) | Rf(solvent) | $^1$H NMR(400 MHz, δ) |
|---|---|---|---|---|
| 7-2 | ![tetrahydroisoquinoline-N-methyl] | 89.7 | 0.85 (n-Hexane:ether = 1:5). | $CDCl_3$: 1.01(s, 9H), 2.76(t, 2H), 2.90(t, 2H), 3.65(s, 2H), 3.96(s, 2H), 4.36(s, 2H), 6.64(s, 1H), 6.97–6.99(m, 1H), 7.11–7.17(m, 3H), 8.91(s, 1H) |
| 7-3 | ![1-methyl-4-pyrrolidin-1-yl-piperidine] | 60 | 0.20 ($CH_2Cl_2$:MeOH = 9:1) | DMSO-$d_6$: 0.96(s, 9H), 1.32–1.47(m, 2H), 1.58–1.71(m, 4H), 1.73–1.85(m, 2H), 1.88–2.15(m, 3H), 2.36–2.51(m, 4H), 2.71–2.81(m, 2H), 3.79(s, 2H), 4.32(s, 2H), 6.78(s, 1H), 9.07(s, 1H) |
| 7-4 | ![4-(4-chlorophenyl)-4-hydroxy-1-methylpiperidine] | 51 | 0.30 (n-Hexane:AcOEt = 1:1) | $CDCl_3$: 1.02(s, 9H), 1.73(brd, 2H), 2.08(m, 2H), 2.55(m, 2H), 2.72(brd, 2H), 3.84(s, 2H), 4.37(s, 2H), 6.61(s, 1H), 7.32(d, 2H), 7.43(d, 2H), 8.90(s, 1H). |

TABLE 7-1-continued

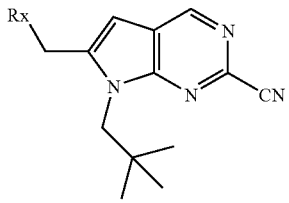

7-1

| Expl. No. | Rx | Yield(%) | Rf(solvent) | ¹H NMR(400 MHz, δ) |
|---|---|---|---|---|
| 7-5 | Cl-[4-chlorophenyl]-tetrahydropyridinyl-N-methyl | 29 | 0.47 (n-Hexane:Ether = 1:1). | CDCl$_3$: 1.02(s, 9H), 2.52(br, 2H), 2.73(t, 2H), 3.16–3.18(m, 2H), 3.91(s, 2H), 4.36(s, 2H), 6.03–6.05(m, 1H), 6.63(s, 1H), 7.27–7.32(m, 4H), 8.90(s, 1H), 9.07(s, 1H) |

7-6

7-(2,2-Dimethyl-propyl)-6-(4-hydroxyimino-piperidin-1-yl-methyl)-7H-pyrrolo[2,3-d]pyrimidine-2-carbonitrile To a solution of 100 mg (0.30 mmoles) of 7-(2,2-dimethyl-propyl)-6-(4-oxo-piperidin-1-ylmethyl)-7H-pyrrolo[2,3-d]pyrimidine-2-carbonitrile and 0.047 ml (0.75 mmoles) of pyridine in 5 ml of CH$_2$Cl$_2$, 52 mg (0.75 mmoles) of hydroxyl amine is added at ambient temperature. After being stirred for 24 hours, the reaction mixture is quenched with H$_2$O and extracted with CH$_2$Cl$_2$. The combined extracts are washed with brine, dried over MgSO$_4$ and concentrated under reduced pressure. The residue is purified by silica gel column chromatography to give 100 mg of desired 7-(2,2-dimethyl-propyl)-6-(4-hydroxyimino-piperidin-1-ylmethyl)-7H-pyrrolo[2,3-d]pyrimidine-2-carbonitrile in 98% yield.

¹H NMR (400 MHz, CDCl$_3$, δ): 1.01 (s, 99H), 1.55 (s, 1H), 2.35 (t, 2H), 2.56 (t, 2H), 2.58 (t, 2H), 2.64 (t, 2H), 3.81 (s, 2H), 4.36 (s, 2H), 6.59 (s, 1H), 8.90 (s, 1H) Rf=0.47 (AcOEt)

7-7

6-(4-Amino-piperidin-1-ylmethyl)-7-(2,2-dimethyl-propyl)-7H-pyrrolo[2,3-d]pyridine-2-carbonitrile

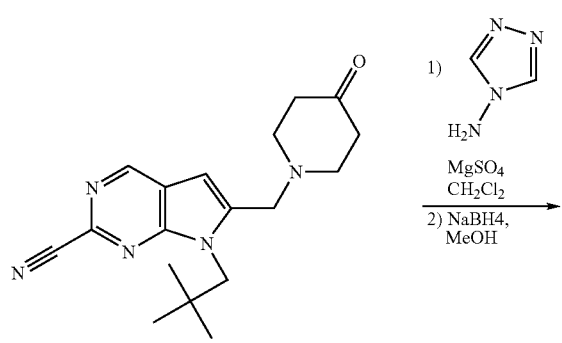

To the mixture of 100 mg (0.30 mmoles) of 7-(2,2-Dimethyl-propyl)-6-(4-oxo-piperidin-1-ylmethyl)-7H-pyrrolo[2,3-d]pyrimidine-2-carbonitrile, 40 mg (0.60 mmoles) of [1,2,4]triazol-4-ylamine and 0.16 ml (1.1 mmoles) of triethylamine in 5 ml of CH$_2$Cl$_2$, 58 mg (0.48 mmoles) of MgSO$_4$ is added at ambient temperature and the mixture is stirred for 17.5 hours at ambient temperature. The reaction mixture is filtered to remove MgSO$_4$ and concentrated under reduced pressure to give crude imine. To a solution of crude imine in 5 ml of MeOH, 13 mg (0.33 mmoles) of NaBH$_4$ is added at −10−−20° C., and the reaction mixture is stirred at 0° C. for 1 h. After addition of 5 ml of acetone, the mixture is concentrated, diluted with H$_2$O, and then extracted with CH$_2$Cl$_2$. The combined extrats are washed with brine, dried over MgSO$_4$ and concentrated under reduced pressure. The residue is purified by silica gel column chromatography to give 85 mg of desired 6-(4-amino-piperidin-1-ylmethyl)-7-(2,2-dimethyl-propyl)-7H-pyrrolo[2,3-d]pyrimidine-2-carbonitrile in 85% yield.

¹H NMR(400 MHz, CDCl$_3$, δ): 1.00 (s, 9H), 1.51-1.62 (m, 4H), 1.87-1.91 (m, 2H), 2.21 (brt, 2H), 2.70-2.71 (m, 2H), 3.76 (s, 3H), 4.35 (s, 2H), 6.55 (s, 1H), 8.88 (s, 1H) Rf=0.16 (AcOEt:n-Hexane=4:1)

7-8

Preparation of 7-(2,2-Dimethyl-propyl)-6-[4-(3-imidazol-1-yl-propylamino)-piperidin-1-ylmethyl]-7H-pyrrolo[2,3-d]pyrimidine-2-carbonitrile

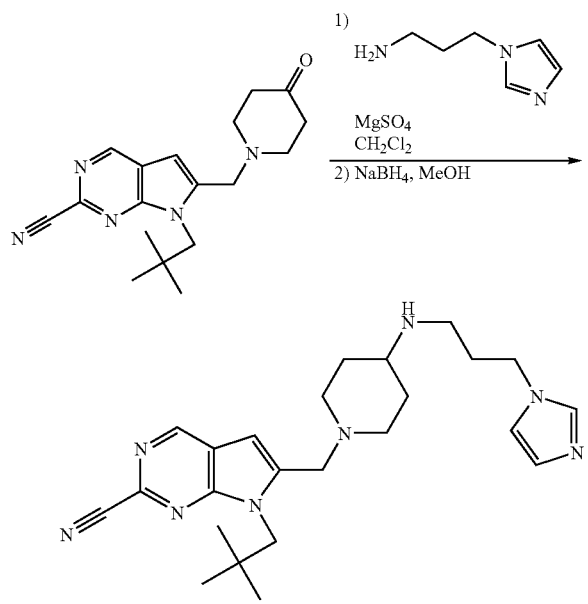

To the mixture of 100 mg (0.30 mmoles) of 7-(2,2-dimethyl-propyl)-6-(4-oxo-piperidin-1-ylmethyl)-7H-pyrrolo[2,3-d]pyrimidine-2-carbonitrile, 60 mg (0.48 mmoles) of 3-Imidazol-1-yl-propylamine and 0.15 ml (1.1 mmoles) of triethylamine in 5 ml of $CH_2Cl_2$, 58 mg (1.1 mmoles) of $MgSO_4$ is added at ambient temperature. The mixture is stirred for 15.5 hours at ambient temperature. The reaction mixture is filterlated to remove $MgSO_4$ and concentrated under reduced pressure to give crude imine. To a solution of crude imine in 5 ml of MeOH, 13 mg (0.33 mmoles) of $NaBH_4$ is added at −10–−20° C., and the reaction mixture is stirred at 0° C. for 4.5 hours. After addition of 5 ml of acetone, the mixture is concentrated, diluted with $H_2O$, and then extracted with $CH_2Cl_2$. The combined extrats are washed with brine, dried over $MgSO_4$ and concentrated under reduced pressure. The residue is purified by silica gel column chromatography to give 95 mg of desired 7-(2,2-dimethyl-propyl)-6-[4-(3-imidazol-1-yl-propylamino)-piperidin-1-ylmethyl]-7H-pyrrolo[2,3-d]pyrimidine-2-carbonitrile in 73% yield.

By repeating the procedures described above using appropriate starting materials and conditions the following compounds of formula 7.2 are obtained as identified below in Table 7-2.

TABLE 7-2

7-2

| Expl. No. | R | Yield(%) | Rf(solvent) | $^1$H NMR(400 MHz, δ) |
|---|---|---|---|---|
| 7-9 | imidazolylpropyl | 73 | 0.09 (MeOH) | MeOH-d$_4$; 1.01(s, 9H), 1.35–1.39(m, 2H), 1.84–1.87(m, 2H), 1.94(m, 2H), 2.12(brt, 2H), 2.38–2.48(m, 1H), 2.56(t, 2H), 2.84(brd, 2H), 3.83(s, 2H), 4.08(t, 2H), 4.40(s, 2H), 6.74(s, 1H), 6.95(s, 1H), 7.12(s, 1H), 7.64(s, 1H), 8.94(s, 1H) |

TABLE 7-2-continued

| Expl. No. | R | Yield(%) | Rf(solvent) | ¹H NMR(400 MHz, δ) |
|---|---|---|---|---|
| 7-10 | cyclopropyl | 76 | 0.07 (AcOEt:MeOH = 9:1) | CDCl₃; 0.25–0.33(m, 2H), 0.43–0.46(m, 2H), 0.99(s, 9H), 1.29–1.42(m, 2H), 1.81–1.93(m, 2H), 2.05–2.17(m, 2H), 2.54–2.67(m, 1H), 2.71–2.83(m, 2H), 3.75(s, 2H), 4.37(s, 2H), 6.54(s, 1H), 8.87(s, 1H) |

7-11

Preparation of 1-[2-Cyano-7-(2,2-dimethyl-propyl)-7H-pyrrolo[2,3-d]pyrimidin-6-ylmethyl]-piperidine-4-carboxylic acid phenylamide

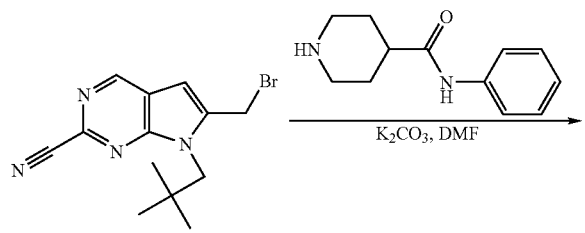

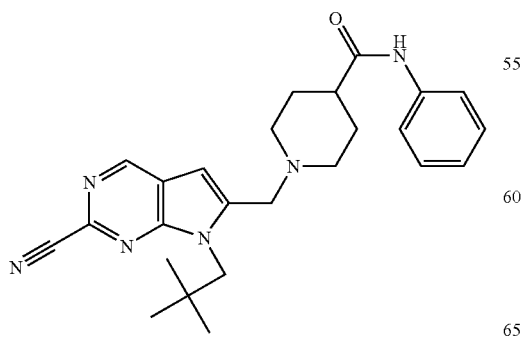

To a solution of 100 mg (0.32 mmoles) of 6-bromomethyl-7-(2,2-dimethyl-propyl)-7H-pyrrolo[2,3-d]pyrimidine-2-carbonitrile and 230 mg (0.96 mmoles) of piperidine-4-carboxylic acid phenylamide in 5 ml of DMF, 130 mg (0.96 mmoles) of $K_2CO_3$ is added at ambient temperature. The reaction mixture is stirred for 18 hours at ambient temperature. The reaction mixture is quenched with $H_2O$ and extracted with AcOEt. The combined extracts are washed with brine, dried over $MgSO_4$ and concentrated under reduced pressure. The residue is purified by silica gel column chromatography to give 130 mg of disired 1-[2-cyano-7-(2,2-dimethyl-propyl)-7H-pyrrolo[2,3-d]pyrimidin-6-ylmethyl]-piperidine-4-carboxylic acid phenylamide in 95% yield.

By repeating the procedures described above using appropriate starting materials and conditions the following compounds of formula 7-3 are obtained as identified below in Table 7-3.

TABLE 7-3

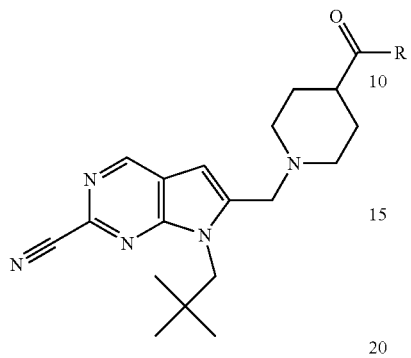

| Expl. No. | R | Yield(%) | Rf(solvent) | $^1$H NMR(400 MHz, δ) |
|---|---|---|---|---|
| 7-11 | —NH—Ph | 95 | 0.19 (AcOEt:Hexane = 1:1) | CDCl$_3$; 1.01(s, 9H), 1.82–1.97(m, 2H), 2.05–2.19(m, 2H), 2.20–2.31 (m, 1H), 2.85–2.96(m, 2H), 3.78 (s, 2H), 4.36(s, 2H), 6.56(s, 1H), 7.12(m, 2H), 7.31(t, 2H), 7.50 (d, 2H), 8.89(s, 1H) |
| 7-12 | —NH-(1,2,4-triazol-3-yl) | 8 | 0.21 (AcOEt:Hexane = 4:1) | Acetone-d$_6$; 0.91(s, 9H), 1.62–1.73 (m, 2H), 1.81–1.93(m, 2H), 2.05–2.15(m, 2H), 2.78–2.89(m, 2H), 3.21–3.33(m, 1H), 3.80(s, 2H), 4.33(s, 2H), 6.67(s, 1H), 6.91(brs, 1H), 7.32(s, 1H), 8.88(s, 1H) |
| 7-13 | 3-amino-1-(4-methylpiperazine-1-carbonyl)pyrazole | 28 | 0.37 (AcOEt:Hexane = 4:1) | MeOH-d$_4$; 1.02(s, 9H), 1.72–1.86(m, 2H), 1.89–1.98(m, 2H), 2.18–2.38(m, 2H), 2.91–2.98(m, 2H), 3.39–3.47(m, 1H), 3.87(s, 2H), 4.43(s, 1H), 5.97(d, 1H), 6.77(s, 1H), 7.99(d, 1H), 8.95(s, 1H) |
| 7-14 | 4-methylpiperazin-1-yl | 93 | 0.26 (MeOH) | CDCl$_3$; 1.00(s, 9H), 1.64–1.72(m, 2H), 1.81–1.95(m, 2H), 2.09(brt, 2H), 2.37(s, 3H), 2.42–2.42(m, 5H), 2.45–2.53(m, 1H), 2.82–2.91 (m, 2H), 3.45–3.52(m, 2H), 3.58–3.67(m, 2H), 3.76(s, 2H), 4.36(s, 2H), 6.54(s, 1H), 8.88(s, 1H) |
| 7-15 | pyrrolidin-1-yl | 92 | 0.38 (AcOEt:MeOH = 9:1) | CDCl$_3$; 1.19(s, 9H), 1.66–1.74(m, 2H), 1.83–1.89(m, 2H), 1.91–1.98 (m, 2H), 2.02–2.13(m, 2H), 2.29–2.39(m, 1H), 2.84–2.93(m, 2H), 3.45(t, 4H), 3.76(s, 2H), 4.37(s, 2H), 6.54(s, 1H), 8.87(s, 1H) |

7-16

Preparation of 7-(2,2-dimethyl-propyl)-6-(1,1-dioxo-1□⁶-thiomorpholin-4-ylmethyl)-7H-pyrrolo[2,3-d]pyrimidine-2-carbonitrile

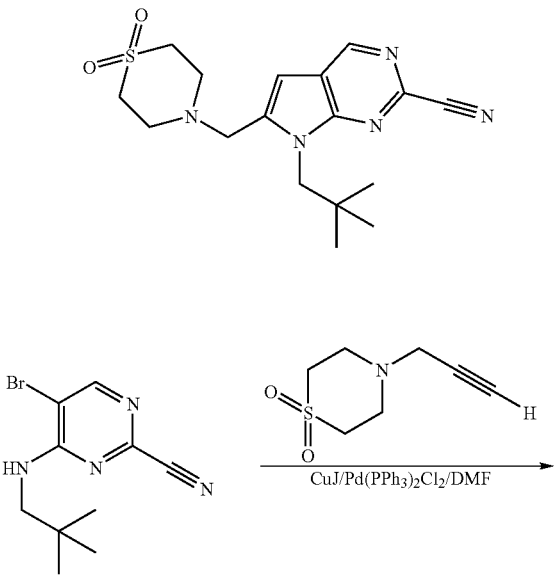

To a solution of 0.54 g (2 mmoles) of 5-bromo-4-(2,2-dimethyl-propylamino)-pyrimidine-2-carbonitrile and 0.75 g (4.3 mmoles) of 4-propargylthiomorpholine-1,1-dioxide in 5 ml of DMF are added 0.841 ml (6 mmoles) of triethylamine, 0.38 g (2 mmoles) of copper(I) iodide and 0.14 g (0.2 mmoles) of Pd(PPh$_3$)$_2$Cl$_2$ under nitrogen atmosphere. The mixture is stirred for 31 hours at 80° C. The mixture is filtered through celite, diluted with AcOEt, washed with H$_2$O and brine, dried over Na$_2$SO$_4$ and concentrated under reduced pressure. The residue is purified by HPLC(H$_2$O—0.1% TFA/CH$_3$CN—0.1% TFA). Fractions are collected, basified with 5% aqueous NaHCO$_3$, extracted with AcOEt, washed with brine, dried over Na$_2$SO$_4$ and concentrated under reduced pressure. The resulting residue is then purified by HPLC (n-Hexane/AcOEt) to give 0.01 g of desired 7-(2,2-dimethyl-propyl)-6-(1,1-dioxo-1λ⁶-thiomorpholin-4-ylmethyl)-7H-pyrrolo[2,3-d]pyrimidine-2-carbonitrile in 1.4% yield.

$^1$H NMR (400 MHz, CDCl$_3$, δ): 1.01(s, 9H), 3.0-3.15 (m, 8H), 3.95 (s, 2H), 4.28 (s, 2H), 6.63 (s, 1H), 8.93 (s, 1H) Rf=0.57 (n-Hexane:AcOEt=1:5)

7-17

Preparation of 6-{4-[4-(2-dimethylamino-ethoxy)-phenyl]-piperidin-1-ylmethyl}-7-(2,2-dimethyl-propyl)-7H-pyrrolo[2,3-d]pyrimidine-2-carbonitrile

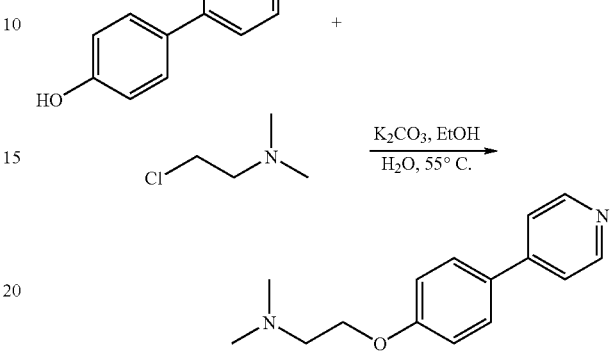

1 g of 4-pyridin-4-yl-phenol, 1.3 g of (2-chloro-ethyl)-dimethyl-amine.HCl and 2.42 g of K$_2$CO$_2$ were heated for 48 h under reflux. The mixture was diluted with chloroform, washed with brine and dried over MgSO$_4$. After evaporation to dryness the residue was chromatographed on silicagel with CH2Cl2/MeOH/NH3conc=90:10:1 to give dimethyl-[2-(4-pyridin-4-yl-phenoxy)-ethyl]-amine as brown powder.

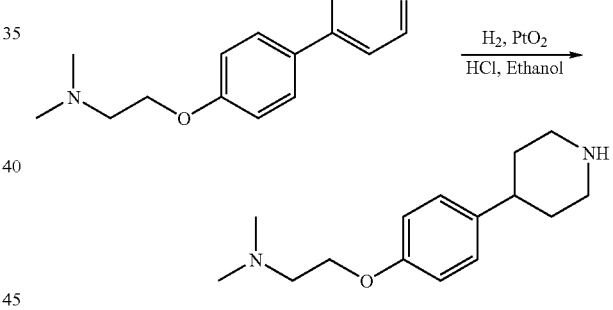

0.38 g of dimethyl-[2-(4-pyridin-4-yl-phenoxy)-ethyl]-amine was dissolved in 15 ml of EtOH/H$_2$O=80:20, 0.35 ml HCl conc and 80 mg of PtO2 were added and the mixture was stirred under 1 atm of hydrogen gas for 6 hours. After filtration over celite and evaporation the dihydrochloride salt of dimethyl-[2-(4-piperidin-4-yl-phenoxy)-ethyl]-amine was obtained as colorless oil.

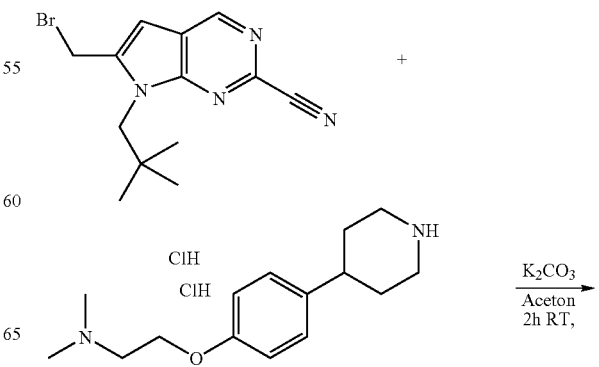

-continued

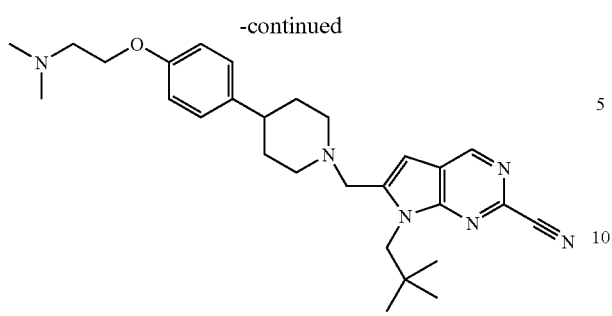

0.22 g of 6-bromomethyl-7-(2,2-dimethyl-propyl)-7H-pyrrolo[2,3-d]pyrimidine-2-carbonitrile, 0.23 g of dimethyl-[2-(4-piperidin-4-yl-phenoxy)-ethyl]-amine bishydrochloride and 0.5 g of potassium carbonate were stirred in 2 ml acetone at 25° C. for 2 hours. The mixture was extracted with ethyl acetate/water, dried over sodium sulfate and evaporated to driness. After chromatography on silicagel using CH₂Cl₂/MeOH=90:10 6-{4-[4-(2-dimethylamino-ethoxy)-phenyl]-piperidin-1-ylmethyl}-7-(2,2-dimethyl-propyl)-7H-pyrrolo[2,3-d]pyrimidine-2-carbonitrile was obtained as yellow solid.

By repeating the procedures described above using appropriate starting materials and conditions the following compounds of formula 7-4 are obtained as identified below in Table 7-4.

TABLE 7-4

7-4

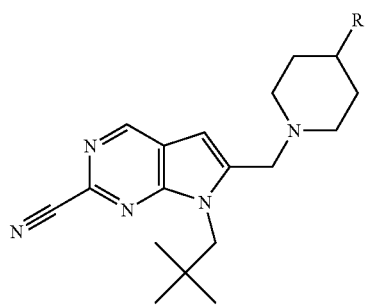

| | | | |
|---|---|---|---|
| 7-18 | 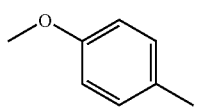 | 7-(2,2-Dimethyl-propyl)-6-[4-(4-methoxy-phenyl)-piperidin-1-ylmethyl]-7H-pyrrolo[2,3-d]pyrimidine-2-carbonitrile | CDCl₃, 300 MHz: 1.02(s, 9H), 2.55–2.90(m, 4H), 2.16(t, 2H), 2.48(m, 1H), 2.93(m, 2H), 3.80(m, 5H), 4.38(s, 2H), 6.58(bs, 1H), 6.85(d, 2H), 7.14(d, 2H), (8.89 1H). MH⁺: 418 |
| 7-19 | 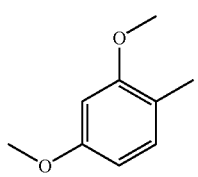 | 6-[4-(2,4-Dimethoxy-phenyl)-piperidin-1-ylmethyl]-7-(2,2-dimethyl-propyl)-7H-pyrrolo[2,3-d]pyrimidine-2-carbonitrile | CDCl₃, 300 MHz: 1.03(s, 9H), 1.6–1.85(m, 4H), 2.19(m, 2H), 2.89(m, 3H), 3.79(m, 8H), 4.39(s, 2H), 6.43(s, 1H), 6.44(d, 1H), 6.55(s, 1H), 7.07(d, 1H), 8.88(s, 1H).MH⁺: 448. |
| 7-20 | 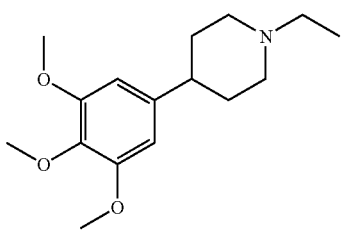 | 7-(2,2-Dimethyl-propyl)-6-[4-(3,4,5-trimethoxy-phenyl)-piperidin-1-ylmethyl]-7H-pyrrolo[2,3-d]pyrimidine-2-carbonitrile | CDCl₃, 300 MHz: 1.03(s, 9H), 1.5–1.9(m, 4H), 2.16 (m, 2H), 2.46(m, 1H), 2.95(m, 2H), 3.81(s, 2H), 3.82(s, 3H), 3.86(s, 6H), 4.37(s, 2H), 6.42(s, 2H), 6.59(s, 1H),8.88(s, 1H). MH⁺: 478 |
| 7-21 | 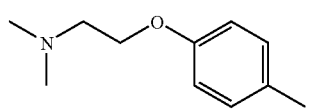 | 6-{4-[4-(2-Dimethylamino-ethoxy)-phenyl]-piperidin-1-ylmethyl}-7-(2,2-dimethyl-propyl)-7H-pyrrolo[2,3-d]pyrimidine-2-carbonitrile | CDCl₃, 300 MHz: 1.02(s, 9H), 1.6-1-85(m, 4H), 2.15(m, 2H), 2.34(s, 6H), 2.46(m, 1H), 2.72(t, 2H), 2.9(2m, 2H), 3.78(s, 2H), 4.04(t, 2H),4.38(s, 2H), 6.57(s, 1H), 6.85(d, 2H), 7.11(d, 2H), 8.87(s, 1H). MH⁺: 475 |

TABLE 7-4-continued 7-4

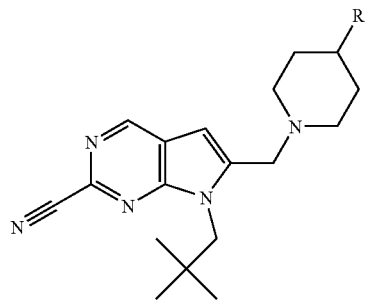

| | R | | |
|---|---|---|---|
| 7-22 | (structure) | 6-{4-[3-(2-Di-methylamino-ethoxy)-phenyl]-piperidin-1-yl-methyl}-7-(2,2-dimethyl-propyl)-7H-pyrrolo[2,3-d]pyrimidine-2-carbonitrile | CD$_3$OD, 300 MHz: 1.03 (s, 9H), 1.80(m, 4H), 2.22 (m, 2H), 2.37(s, 6H), 2.52 (m, 1H), 2.86(t, 2H), 2.99 (m, 2H), 3.88(s, 2H), 4.08 (t, 2H), 4.44(s,2H), 6.78(m, 4H), 7.17(t, 1H), 8.95 (s, 1H). MH$^+$: 475. |
| 7-23 | (structure) | 6-{4-[2-(2-Di-methylamino-ethoxy)-phenyl]-piperidin-1-yl-methyl}-7-(2,2-dimethyl-propyl)-7H-pyrrolo[2,3-d]pyrimidine-2-carbonitrile | CDCl$_3$, 300 MHz: 1.03(s, 9H), 1.6–1.9(m, 4H), 2.17 (m, 2H), 2.36(s, 6H), 2.76 (t, 2H), 2.93(m, 3H), 3.80 (s, 2H), 4.08(t, 2H), 4.41 (s, 2H), 6.58(s, 1H),6.8–6.95(m, 2H), 7.16(m, 2H), 8.88(s, 1H). MH$^+$: 475. |
| 7-24 | (structure) | 6-{4-[4-(2-Diethylamino-ethoxy)-phenyl]-piperidin-1-yl-methyl}-7-(2,2-dimethyl-propyl)-7H-pyrrolo[2,3-d]pyrimidine-2-carbonitrile | CDCl$_3$, 300 MHz: 1.02(s, 9H), 1.08(t, 6H), 1.6–1.9 (m, 4H), 2.15(m, 2H), 2.44(m, 1H), 2.67(m, 4H), 2.92(m, 4H), 3.78(s, 2H), 4.06(t, 2H), 4.39(s, 2H), 6.57(s,1H 6.83(d, 2H), 7.12(d, 2H), 8.88(s, 1H). MH$^+$: 503. |
| 7-25 | (structure) | 6-{4-[3-(2-Diethylamino-ethoxy)-phenyl]-piperidin-1-ylmethyl}-7-(2,2-dimethyl-propyl)-7H-pyrrolo[2,3-d]pyrimidine-2-carbonitrile | CDCl$_3$, 300 MHz: 1.02(s, 9H), 1.08(t, 6H), 1.6–1.9 (m, 4H), 2.16(m, 2H), 2.48(m, 1H), 2.67(m, 4H), 2.92(m, 4H), 3.79(s, 2H), 4.05(t, 2H), 4.39(s, 2H), 6.58(s,1H), 6.78(m, 3H), 7.20 (t, 1H), 8.88(s, 1H). MH$^+$: 503. |
| 7-26 | (structure) | 6-{4-[2-(2-Diethylamino-ethoxy)-phenyl]-piperidin-1-yl-methyl}-7-(2,2-dimethyl-propyl)-7H-pyrrolo[2,3-d]pyrimidine-2-carbonitrile | CDCl$_3$, 300 MHz: 1.02(s, 9H), 1.12(t, 6H), 1.6–1.9 (m, 4H), 2.17(m, 2H), 2.69(m, 4H), 2.95(m, 5H), 3.80(s, 2H), 5.06(m, 2H), 4.39(s, 2H), 6.58(s, 1H), 6.88(m,2H), 7.17 (m, 2H), 8.88(s, 1H). MH$^+$: 503. |
| 7-27 | (structure) | 7-(2,2-Dimethyl-propyl)-6-(4-{4-[2-(4-methyl-piperazin-1-yl)-ethoxy]-phenyl}-piperidin-1-yl-methyl)-7H-pyrrolo[2,3-d]pyrimidine-2-carbonitrile | CDCl$_3$, 300 MHz: 1.02(s, 9H), 1.6–1.9(m, 4H), 2.15 (m, 2H), 2.32(s, 3H), 2.3–2.8(m, 9H), 2.82(t, 2H), 2.92(m, 2H), 3.79(s, 2H), 4.10(t, 2H),4.38(s, 2H), 6.58(s, 1H), 6.84(d, 2H), 7.12(d, 2H), 8.88(s, 1H). MH$^+$: 530. |

TABLE 7-4-continued

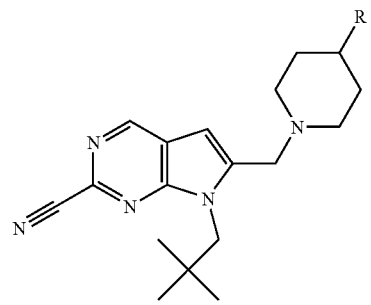

7-4

| | | | |
|---|---|---|---|
| 7-28 | ![structure] | 7-(2,2-Dimethyl-propyl)-6-(4-{3-[2-(4-methyl-pipera-zin-1-yl)-ethoxy]-phenyl}-piperidin-1-yl-methyl)-7H-pyrrolo[2,3-d]pyrimidine-2-carbonitrile | CDCl₃, 300 MHz: 1.02(s, 9H), 1.6–1.9(m, 4H), 2.15 (m, 2H), 2.31(s, 3H), 2.4–2.8(m, 9H), 2.82(s, 2H), 2.93(m, 2H), 3.79(s, 2H), 4.09(m, 2H),4.38(s, 2H), 6.57(s, 1H), 6.7–6.85(m, 3H), 7.20(t. 1H), 8.88(s, 1H). MH⁺: 530. |
| 7-29 | ![structure] | 7-(2,2-Dimethyl-propyl)-6-(4-{2-[2-(4-methyl-pipera-zin-1-yl)-ethoxy]-phenyl}-piperidin-1-yl-methyl)-7H-pyrrolo[2,3-d]pyrimidine-2-carbonitrile | CDCl₃, 300 MHz: 1.02(s, 9H), 1.6–1.9(m, 4H), 2.16 (m, 2H), 2.32(s, 3H), 2.3–2.8(m, 8H), 2.85(t, 2H), 2.93(m, 3H), 3.80(s, 2H), 4.12(m, 2H),4.41(s, 2H), 6.58(s, 1H), 6.83(d, 1H), 6.93(t, 1H), 7.16(m, 2H), 8.89(s, 1H). MH⁺: 530. |
| 7-30 | ![structure] | 7-(2,2-Dimethyl-propyl)-6-(4-{4-[3-(4-methyl-pipera-zin-1-yl)-propoxy]-phenyl}-piperidin-1-yl-methyl)-7H-pyrrolo[2,3-d]pyrimidine-2-carbonitrile | CDCl₃, 300 MHz: 1.01(s, 9H), 1.6–1.85(m, 4H), 1.96(m, 2H), 2.15(m, 2H), 2.30(s, 3H), 2.35–2.65(m, 11H), 2.90(m, 2H), 3.79(s,2H), 3.88(t, 2H), 4.38(s, 2H), 6.57(s, 1H), 6.82(d, 2H), 7.11(d, 2H), 8.87 (s, 1H). MH⁺: 544 |
| 7-31 | ![structure] | 7-(2,2-Dimethyl-propyl)-6-(4-{3-[3-(4-methyl-piperazin-1-yl)-propoxy]-phenyl}-piperidin-1-yl-methyl)-7H-pyrrolo[2,3-d]pyrimidine-2-carbonitrile | CDCl₃, 300 MHz: 1.02(s, 9H), 1.6–1.9(m, 4H), 1.97 (m, 2H), 2.15(m, 2H), 2.31(s, 3H), 2.3–2.7(m, 11H), 2.82(m, 2H), 3.80 (s, 2H), 4.00(t, 2H),4.38 (s, 2H), 6.58(s, 1H), 6.75 (m, 3H), 7.20(t, 1H), 8.88 (s, 1H). MH⁺: 544. |
| 7-32 | ![structure] | 7-(2,2-Dimethyl-propyl)-6-(4-{2-[3-(4-methyl-pipera-zin-1-yl)-propoxy]-phenyl}-piperidin-1-yl-methyl)-7H-pyrrolo[2,3-d]pyrimidine-2-carbonitrile | CD₃OD, 300 MHz: 1.04 (s, 9H), 1.7–1.9(m, 4H), 2.01(m, 2H), 2.23(m, 2H), 2.35(s, 3H), 2.4–3.1 (m, 13H), 3.90(s, 2H), 4.02(t, 2H), 4.45(s, 2H),6.79(s, 1H), 6.88(m, 2H), 7.14(m, 2H), 8.96(s, 1H). MH⁺: 544. |

TABLE 7-4-continued

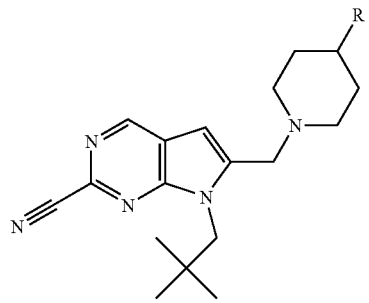

7-4

| | | | |
|---|---|---|---|
| 7-33 | 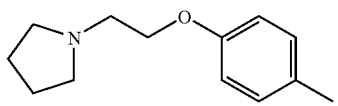 | 7-(2,2-Dimethyl-propyl)-6-{4-[4-(2-pyr-rolidin-1-yl-eth-oxy)-phenyl]-piperidin-1-yl-methyl}-7H-pyr-rolo[2,3-d]pyrimidine-2-carbo-nitrile | CDCl$_3$, 300MHz: 1.02(s, 9H), 1.6–1.9(m, 8H), 2.15 (m, 2H), 2.46(m, 1H), 2.66(m, 4H), 2.83(m, 4H), 3.79(s, 2H), 4.12(t, 2H), 4.38(s, 2H), 6.57(s, 1H), 6.85(d, 2H),7.11(d, 2H), 8.87(s, 1H). MH$^+$: 501. |
| 7-34 | 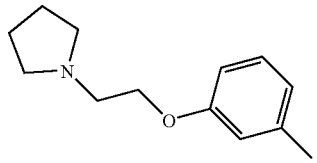 | 7-(2,2-Dimethyl-propyl)-6-{4-[3-(2-pyr-rolidin-1-yl-eth-oxy)-phenyl]-piperidin-1-yl-methyl}-7H-pyr-rolo[2,3-d]pyrimidine-2-carbo-nitrile | CDCl$_3$, 300 MHz: 1.02(s, 9H), 1.6–1.9(m, 8H), 2.15 (m, 2H), 2.48(m, 1H), 2.62(m, 4H), 2.91(m, 4H), 3.79(s, 2H), 4.10(t, 2H), 4.39(s, 2H), 6.58(s, 1H), 6.77(m, 3H),7.20(t, 1H), 8.88(s, 1H). MH$^+$: 501. |
| 7-35 | 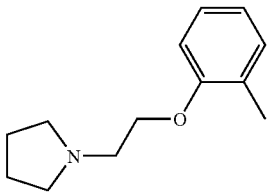 | 7-(2,2-Dimethyl-propyl)-6-{4-[2-(2-pyr-rolidin-1-yl-eth-oxy)-phenyl]-piperidin-1-yl-methyl}-7H-pyr-rolo[2,3-d]pyrimidine-2-carbo-nitrile | CDCl$_3$, 300 MHz: 1.02(s, 9H), 1.6–1.95(m, 8H), 2.16(m, 2H), 2.74(m, 4H), 2.95(m, 5H), 3.80(s, 2H), 4.16(m, 2H), 4.40(s, 2H), 6.58(s, 1H), 6.88(m, 2H), 7.16(m, 2H),8.88(s, 1H). MH$^+$: 501. |
| 7-36 | 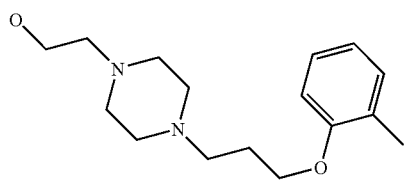 | 7-(2,2-Dimethyl-propyl)-6-[4-(2-{3-[4-(2-hy-droxy-eth-yl)-piperazin-1-yl]-pro-poxy}-phenyl)-piperi-din-1-ylmethyl]-7H-pyr-rolo[2,3-d]pyrimidine-2-carbo-nitrile | CDCl$_3$, 300 MHz: 1.02(s, 9H), 1.26(m, 2H), 1.6–1.9 (m, 4H), 2.00(m, 2H), 2.17(m, 2H), 2.56(m, 10H), 2.93(m, 3H), 3.74 (m, 2H), 3.91(s,2H), 4.02 (t, 2H), 4.41(s, 2H), 6.59 (s, 1H), 6.84(d, 1H), 6.92 (t, 1H), 7.17(m, 2H), 8.88 (s, 1H). MH$^+$: 574 |

7-37

7-(2,2-Dimethyl-propyl)-6-(3-methyl-2,4-dioxo-1,3,8-triaza-spiro[4.5]dec-8-ylmethyl)-7H-pyrrolo[2,3-d]pyrimidine-2-carbonitrile

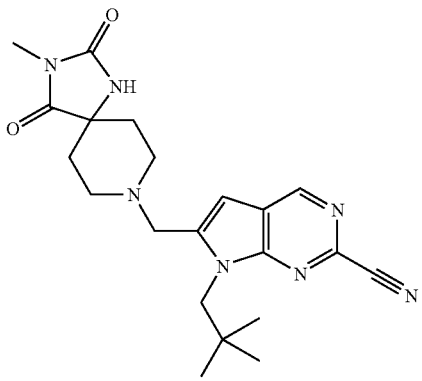

A. 4-Oxo-piperidine-1-carboxylic acid tert-butyl ester

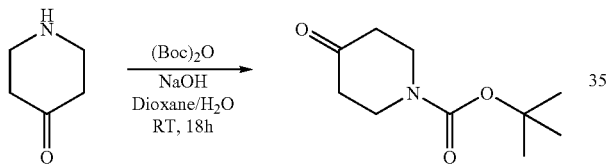

To a solution of piperidin-4-one.H$_2$O.HCl (86.9 g, 0.57 mol) in dioxane/H$_2$O (600 ml/400 ml), di-t-butyl dicarbonate (135.9 g, 0.62 mol) and NaOH (47.5 g, 1.18 mol) are added at ambient temperature. The reaction mixture is stirred at ambient temperature for 18 h. After removal of the solvent, the residue is extracted with CH$_2$Cl$_2$ and the combined extracts are washed with brine, dried over magnesium sulfate, concentrated to give yellow solid.

Yield: quant. $^1$H-NMR (400Mz, δ, CDCl$_3$): 1.50 (s, 9H), 2.44 (t, 4H), 3.72 (t, 4H)

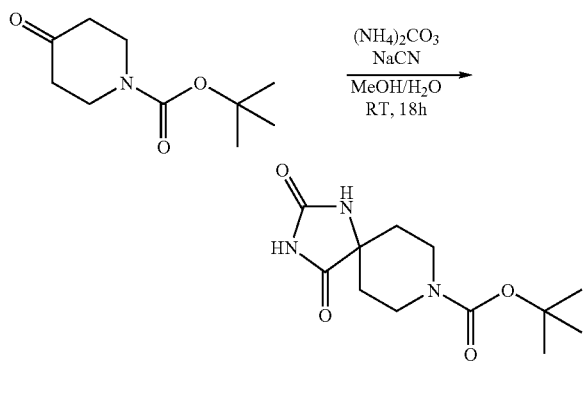

B. 2,4-Dioxo-1,3,8-triaza-spiro[4.5]decane-8-carboxylic acid tert-butyl ester To a solution of 4-oxo-piperidine-1-carboxylic acid tert-butyl ester (30.0 g, 151 mmol) in MeOH (100 ml), H$_2$O (40 ml), ammonium carbonate (331 mmol) and sodium cyanide (226 mmol) in H$_2$O (60 ml) are added successively at ambient temperature. The reaction mixture is stirred at ambient temperature for 18 h to give precipitates, which are filtered off and washed with H$_2$O and ether on the filter.

Yield: 88% $^1$H-NMR (400 MHz, δ, DMSO-d$_6$): 1.40 (s, 9H), 1.44-1.51 (m, 2H), 1.63-1.70 (m, 2H), 3.10 (br, 2H), 3.78-3.81 (m, 2H), 8.39 (brs, 1H), 10.7 (br, 1H).

C. 3-Methyl-2,4-dioxo-1,3,8-triaza-spiro[4.5]decane-8-carboxylic acid tert-butyl ester

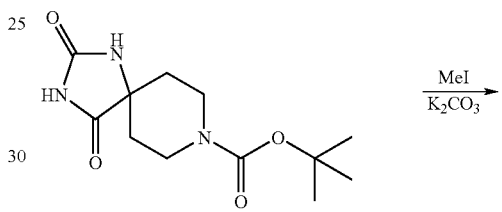

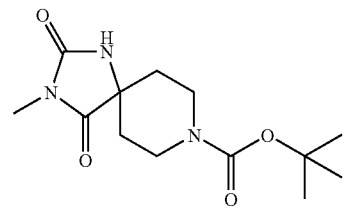

To a solution of 2,4-dioxo-1,3,8-triaza-spiro[4.5]decane-8-carboxylic acid tert-butyl ester (3.60 g, 13 mmol) in DMSO (30 ml), MeI (2.27 g, 16 mmol) and potassium carbonate (2.40 g, 17 mmol) are added at ambient temperature. The mixture is stirred for 18 h at ambient temperature. The reaction mixture is quenched with water and extracted with AcOEt. The combined extracts are washed with brine, dried over magnesium sulfate, filtrated and evaporated to afford 3.8 g of the desired product.

Yield: quant. Rf=0.60 (CH$_2$Cl$_2$:MeOH=10:1). $^1$H-NMR (400 MHz, δ, CDCl$_3$): 1.47 (s, 9H), 1.59-1.62 (m, 2H), 1.98-2.04 (m, 2H), 3.03 (s, 3H), 3.18-3.24 (m, 2H), 3.97-4.00 (m, 2H), 6.08 (brs, 1H).

D. 7-(2,2-Dimethyl-propyl)-6-(3-methyl-2,4-dioxo-1,3,8-triaza-spiro[4.5]dec-8-ylmethyl)-7H-pyrrolo[2,3-d]pyrimidine-2-carbonitrile

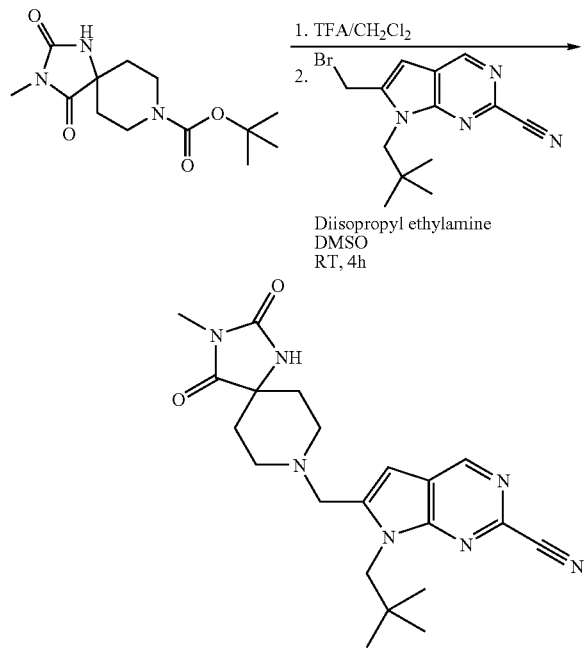

To a solution of 3-methyl-2,4-dioxo-1,3,8-triaza-spiro[4.5]decane-8-carboxylic acid tert-butyl ester (10.0 g, 35 mmol) in $CH_2Cl_2$ (50 ml), TFA (27.2 ml, 353 mmol) is added at 0° C. The reaction mixture is stirred at room temperature for 1 h. After removal of the solvent, ether is added to the residue and amorphase is filtrated and dried (yield: 96%, Rf=0.21 ($CH_2Cl_2$:MeOH=10:1)). To the crude product (10.1 g, 34 mmol) in DMSO (100 ml), diisopropyl ethylamine (12.23 ml, 70 mmol) and 6-bromomethyl-7-(2,2-dimethyl-propyl)-7H-pyrrolo[2,3-d]pyrimidine-2-carbonitrile (7.99 g, 26 mmol) are added to the mixture at ambient temperature. The reaction mixture is stirred at ambient temperature for 4 h, quenched with saturated ammonium chloride and extracted with AcOEt. The combined extracts are washed with $H_2O$, brine and dried over magnesium sulfate. The solvent is concentrated and diethyl ether is added to the residue to give pale yellow solid, which are filtrated and recrystallized by $CH_3CN$ to give the product in 81% yield.

Rf=0.30 (AcOEt). $^1$H-NMR (400 MHz, δ, $CDCl_3$): 1.01 (s, 9H), 1.64-1.68 (m, 2H), 2.10-2.17 (m, 2H), 2.24-2.29 (m, 2H), 2.88-2.93 (m, 2H), 3.03 (s, 3H), 3.84 (s, 2H), 4.34 (s, 2H), 5.95 (brs, 1H), 6.59 (s, 1H), 8.91 (s, 1H).

By repeating the procedures described above using appropriate starting materials and conditions the following compounds of formula I are obtained as identified below in Table 7-5.

TABLE 7-5

Formula 1

| Expl. No | R1 | R2 | Rf(Solvent) | $^1$H NMR(400 MHz, □) |
|---|---|---|---|---|
| 7-38 | n-propyl | H | 0.12 (n-Hexane:AcOEt = 1:1) | ($CDCl_3$): 0.91(t, 3H), 1.01(s, 9H), 1.55–1.68(m, 4H), 2.09–2.16(m, 2H), 2.25(m, 2H), 2.89–2.92(m, 2H), 3.47(dd, 2H), 3.83 (s, 2H), 4.33(s, 2H), 5.65(brs, 1H), 6.59 (s, 1H), 8.91(s, 1H). |
| 7-39 | isopropyl | H | 0.11 (n-Hexane:AcOEt = 1:1) | ($CDCl_3$): 0.89(d, 6H), 1.01(s, 9H), 1.62–1.68(s, 2H), 2.06–2.17(m, 3H), 2.23–2.27(m, 2H), 2.89–2.92(m, 2H), 3.32(d, 2H), 3.83(s, 2H), 4.33(s, 2H), 5.60(brs, 1H), 6.59(s, 1H), 8.90(s, 1H). |
| 7-40 | cyclopropylmethyl | H | 0.08 (n-Hexane:AcOEt = 1:1) | ($CDCl_3$): 0.32–0.36(m, 2H), 0.47–0.52(m, 2H), 1.02(s, 9H), 1.02–1.18(m, 1H), 1.65–1.68(m, 2H), 2.10–2.17(m, 2H), 2.24(dd, 2H), 2.88–2.94 (m, 2H), 3.37(d, 2H), 3.39(s, 2H), 4.34(s, 2H), 5.85(brs, 1H), 6.59(s, 1H), 8.91(s, 1H) |

TABLE 7-5-continued

Formula 1

[Structure 102: hydantoin-spiro-piperidine linked via CH2 to pyrrolopyrimidine-2-carbonitrile with N-neopentyl group; R1 and R2 on hydantoin nitrogens]

| Expl. No | R1 | R2 | Rf(Solvent) | ¹H NMR(400 MHz, □) |
|---|---|---|---|---|
| 7-41 | CH2-CH=CH2 (allyl) | H | 0.66 (CH₂Cl₂:MeOH = 9:1) | (CDCl₃): 1.01(s, 9H), 1.65–1.69(m, 2H), 2.10–2.17(m, 2H), 2.27(dd, 2H), 2.88–2.94(m, 2H), 3.84(s, 2H), 4.11(dd, 2H), 4.33(s, 2H), 5.19–5.23(m, 2H), 5.75–5.86(m, 2H), 6.59(s, 1H), 8.91(s, 1H) |
| 7-42 | cyclohexylmethyl | H | 0.48 (CH₂Cl₂:MeOH = 9:1) | (CDCl₃): 0.94–1.13(m, 11H), 1.17–1.22(m, 3H), 1.60–1.77(m, 8H), 2.10–2.17(m, 2H), 2.23–2.28(m, 2H), 2.88–2.93(m, 2H), 3.33(d, 2H), 3.83(s, 2H), 4.33(s, 2H), 5.71(brs, 1H), 6.59(s, 1H), 8.91(s, 1H). |
| 7-43 | 3-(piperidin-1-yl)propyl | H | 0.41 (CH₂Cl₂:MeOH = 9:1) | (CDCl₃): 1.01(s, 9H), 1.35–1.40(m, 2H), 1.45–1.50(m, 4H), 1.65–1.68(m, 2H), 2.09–2.16(m, 2H), 2.24–2.29(m, 2H), 2.36–2.44(m, 4H), 2.52(t, 2H), 2.88–2.93(m, 2H), 3.61(t, 2H), 3.83(s, 2H), 4.34(s, 2H), 5.70(brs, 1H), 6.59(s, 1H), 8.90(s, 1H) |
| 7-44 | 4-fluorobenzyl (via CH2CH2) | H | 0.13 (n-Hexane:AcOEt = 1:1) | (CDCl₃): 1.01(s, 9H), 1.61–1.65(m, 2H), 2.07–2.14(m, 2H), 2.25(dd, 2H), 2.86–2.91(m, 2H), 3.82(s, 2H), 4.32(s, 2H), 4.61(s, 2H), 5.65(brs, 1H), 6.58(s, 1H), 6.99(ddd, 2H), 7.34–7.37(m, 2H), 8.90(s, 2H). |
| 7-45 | H | H | 0.35 (AcOEt) | (CDCl₃): 1.01(s, 9H), 1.70–1.83(m, 2H), 2.09–2.22(m, 2H), 2.24–2.32(m, 2H), 2.87–2.93(m, 2H), 3.84(s, 2H), 4.33(s, 2H), 5.99(brs, 1H), 6.58(s, 1H), 7.60(brs, 1H), 8.91(s, 1H) |

7-46

7-(2,2-Dimethyl-propyl)-6-(1-methyl-2,4-dioxo-3-propyl-1,3,8-triaza-spiro[4.5]dec-8-ylmethyl)-7H-pyrrolo[2,3-d]pyrimidine-2-carbonitrile

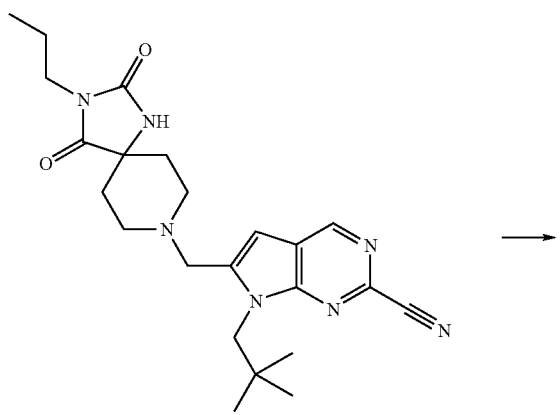

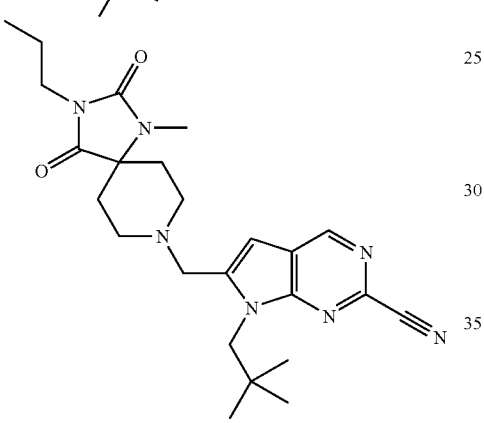

To a solution of 7-(2,2-dimethyl-propyl)-6-(2,4-dioxo-3-propyl-1,3,8-triaza-spiro[4.5]dec-8-ylmethyl)-7H-pyrrolo[2,3-d]pyrimidine-2-carbonitrile (0.2 g, 0.48 mmol) in DMF (2 ml), NaH (22 mg, 0.55 mmol) and MeI (50 □l, 0.55 mmol) are added at 0° C. The reaction mixture is stirred at ambient temperature for 4 h, quenched with saturated ammonium chloride and extracted with AcOEt. The organic layer is washed with brine, dried over magnesium sulfate and filtrated The combined extracts are concentrated and the residue is purified by column chromatography on silica gel using $CH_2Cl_2$:MeOH=25:1 (v/v) and $CH_2Cl_2$:MeOH=15:1 (v/v) to give 71 mg of desired product in 34% yield.

Rf=0.80 ($CH_2Cl_2$:MeOH=9:1). $^1$H-NMR (400 MHz, δ, CDCl$_3$): 0.90 (t, 3H), 1.02 (s, 9H), 1.57-1.68 (m, 4H), 1.96-2.04 (m, 2H), 2.74-2.77 (m, 2H), 2.87 (s, 3H), 2.89-2.96 (m, 2H), 3.46 (t, 3H), 3.87 (s, 3H), 4.32 (s, 2H), 6.60 (s, 1H), 8.90 (s, 1H).

By repeating the procedures described above using appropriate starting materials and conditions the following compounds of formula II are obtained as identified below in Table 7-6.

TABLE 7-6

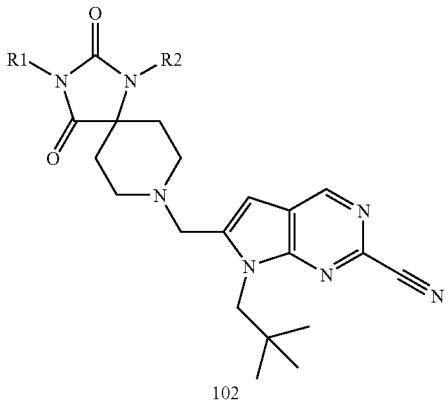

Formula II

102

| Expl. No | R1 | R2 | Rf(Solvent) | $^1$H NMR(400 MHz, □) |
|---|---|---|---|---|
| 7-47 | CH$_3$ | CH$_3$ | 0.24 (n-Hexane:AcOEt = 1:3) | (CDCl$_3$): 1.02(s, 9H), 1.62–1.66 (m, 2H), 1.96–2.04(m, 2H), 2.74–2.76(m, 2H), 2.88–2.96(m, |

TABLE 7-6-continued

Formula II

| Expl. No | R1 | R2 | Rf(Solvent) | ¹H NMR(400 MHz, ☐) |
|---|---|---|---|---|
| | | | | 5H), 3.01(s, 3H), 3.88(s, 2H), 4.32(s, 2H), 6.61(s, 1H), 8.90 (s, 1H). |
| 7-48 | isobutyl | CH₃ | 0.34 (n-Hexane:AcOEt = 1:3) | (CDCl₃): 0.89(d, 6H), 1.02(s, 9H), 1.58–1.64(m, 2H), 1.97–2.08(m, 3H), 2.74–2.77(m, 2H), 2.88(s, 3H), 2.89–2.96(m, 2H), 3.30(d, 2H), 3.87(s, 2H), 4.32 (s, 2H), 6.60(s, 1H), 8.90(s, 1H). |
| 7-49 | cyclopropylmethyl | CH₃ | 0.68 (CH₂Cl₂:MeOH = 9:1) | (CDCl₃): 0.32–0.34(m, 2H), 0.46–0.49(m, 2H), 1.02(s, 9H), 1.13–1.16(m, 1H), 1.63–1.67(m, 2H), 1.97–2.04(m, 2H), 2.75–2.77(m, 2H), 2.88–2.96(m, 5H), 3.35(d, 2H), 3.87(s, 2H), 4.32 (s, 2H), 6.61(s, 1H), 8.90(s, 1H). |
| 7-50 | 4-fluorobenzyl | CH₃ | 0.07 (n-Hexane:AcOEt = 1:1) | (CDCl₃): 1.01(s, 9H), 1.59–1.61 (m, 2H), 1.95–2.04(m, 2H), 2.73–2.76(m, 2H), 2.87–2.93(m, 5H), 3.87(s, 2H), 4.31(s, 2H), 4.60(s, 2H), 6.59(s, 1H), 6.99 (ddd, 2H), 7.34–7.37(m, 2H), 8.90(s, 1H). |
| 7-51 | | | | |

143

7-(2,2-Dimethyl-propyl)-6-(3-methyl-2,4-dioxo-1-propyl-1,3,8-triaza-spiro[4.5]dec-8-ylmethyl)-7H-pyrrolo[2,3-d]pyrimidine-2-carbonitrile

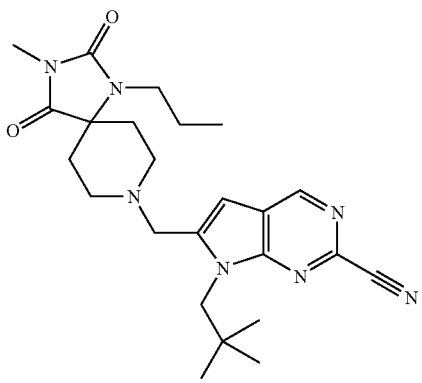

7-(2,2-Dimethyl-propyl)-6-(3-methyl-2,4-dioxo-1-propyl-1,3,8-triaza-spiro[4.5]dec-8-ylmethyl)-7H-pyrrolo[2,3-d]pyrimidine-2-carbonitrile

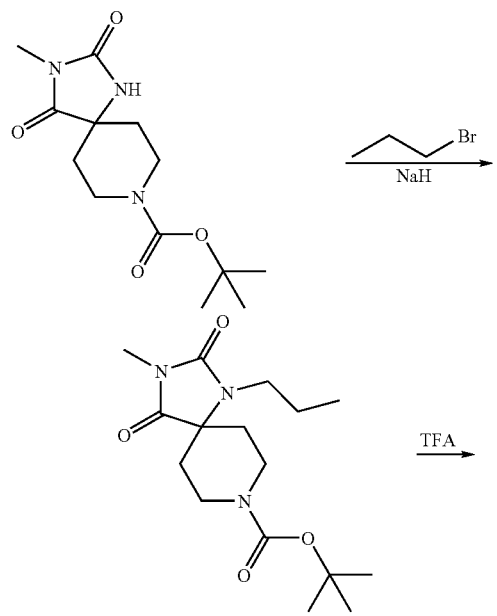

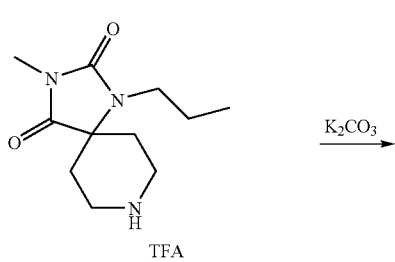

144

-continued

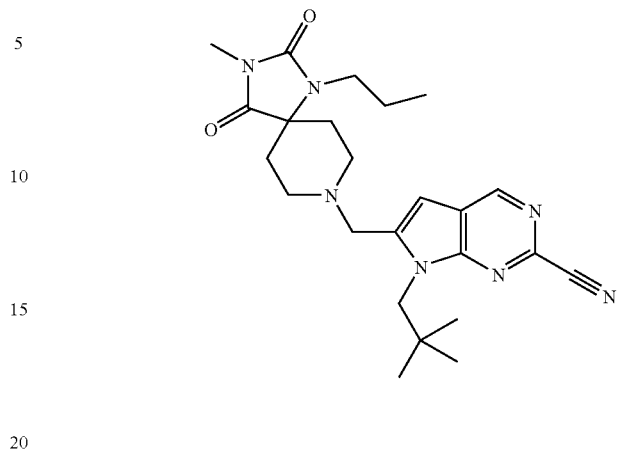

To a solution of 3-methyl-2,4-dioxo-1,3,8-triaza-spiro[4.5]decane-8-carboxylic acid tert-butyl ester (1 g, 3.53 mmol) in DMF (10 ml), Na (211 mg, 5.4 mmol) and n-propryl bromide (384 □1, 4.24 mmol) are added at 0° C. The reaction mixture is stirred at ambient temperature for 4 h, quenched with saturated ammonium chloride and extracted with AcOEt. The organic layer is washed with brine, dried over magnesium sulfate and filtrated. To a solution of 3-methyl-2,4-dioxo-1-propyl-1,3,8-triaza-spiro[4.5]decane-8-carboxylic acid tert-butyl ester (3.53 mmol) in $CH_2Cl_2$ (5 ml), TFA (5 ml) are added at 0° C. The reaction mixture is stirred at room temperature for 1 h. After removal of the solvent, $H_2O$ is added to the residue and lyophilized. To the crude product (1.5 g, 4.42 mmol) in DMSO (10 ml), potassium carbonate (1.2 g, 8.82 mmol) and 6-bromomethyl-7-(2,2-dimethyl-propyl)-7H-pyrrolo[2,3-d]pyrimidine-2-carbonitrile (0.7 g, 2.28 mmol) are added to the mixture at ambient temperature. The reaction mixture is stirred at ambient temperature for 3 h, quenched with saturated ammonium chloride and extracted with AcOEt. The combined extracts are washed with $H_2O$, brine and dried over magnesium sulfate. The combined extracts are concentrated and the residue is purified by column chromatography on silica gel using n-hexane:AcOEt=3:1 to give 386 mg of desired product in 24% yield.

Rf=0.33 (n-Hexane:AcOEt=1:3) $^1$H-NMR (400 MHz, δ, $CDCl_3$): 0.94 (t, 3H), 1.02 (s, 9H), 1.62-1.70 (m, 4H), 1.93-2.01 m, 2H), 2.74-2.77 (m, 2H), 2.91-3.00 (m, 5H), 3.17 (dd, 2H), 3.87 (s, 2H), 4.32 (s, 2H), 6.62 (s, 1H), 8.90 (s, 1H).

By repeating the procedures described above using appropriate starting materials and conditions the following compounds of formula III are obtained as identified below in Table 7-7.

TABLE 7-7

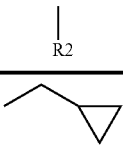

Formula III

| Expl No | R1 | R2 | Yield(%) | Rf(Solvent) | ¹H NMR(400 MHz, ☐) |
|---|---|---|---|---|---|
| 7-52 | CH₃ | 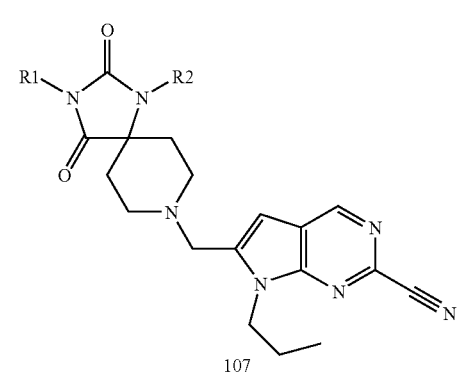 | 30 | 0.30 (n-Hexane:AcOEt = 1:3) | (CDCl₃): 0.35–0.37(m, 2H), 0.54–0.58(m, 2H), 1.02(s, 9H), 1.17–1.25(m, 1H), 1.68–1.71(m, 2H), 2.02–2.09(m, 2H), 2.74–2.77(m, 2H), 2.74–2.99(m, 2H), 3.01(s, 3H), 3.16(d, 2H), 3.88(s, 2H), 4.33(s, 2H), 6.61(s, 1H), 8.90 (s, 1H). |
| 7-53 | CH₃ | 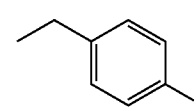 | 21 | 0.08 (n-Hexane:AcOEt = 1:1) | (CDCl₃): 1.00(s, 9H), 1.55–1.59(m, 2H), 1.87–1.93(m, 2H), 2.67–2.69(m, 2H), 2.86–2.92(m, 2H), 3.06(s, 3H), 3.84(s, 2H), 4.29(s, 2H), 4.51 (s, 2H), 6.56(s, 1H), 6.99–7.04 (m, 2H), 7.27–7.29(m, 2H), 8.89(s, 1H). |

7-54

7-(2,2-Dimethyl-propyl)-6-(1-ethyl-2,4-dioxo-1,3,8-triaza-spiro[4.5]dec-8-ylmethyl)-7H-pyrrolo[2,3-d]pyrimidine-2-carbonitrile

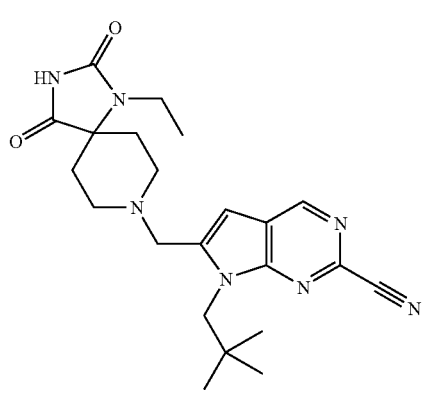

A. 2,4-Dioxo-1,3,8-triaza-spiro[4.5]decane-3,8-dicarboxylic acid di-tert-butyl ester

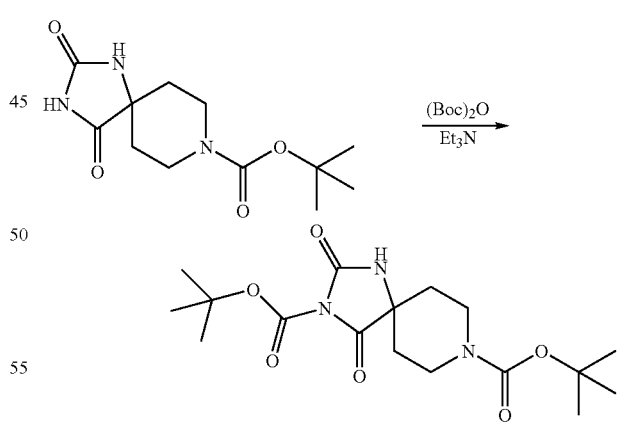

To a solution of 2,4-dioxo-1,3,8-triaza-spiro[4.5]decane-8-carboxylic acid tert-butyl ester (3 g, 11.1 mmol) in DMF (10 ml), (Boc)₂O (4.9 g, 22.2 mmol) and triethyl amine (3.1 ml, 22.2 mmol) are added at ambient temperature. The mixture is stirred for 18 h at ambient temperature. The reaction mixture is quenched with water and extracted with AcOEt. The combined extracts are washed with brine, dried over magnesium sulfate, filtrated and evaporated. AcOEt is added to the residue to give white powder.

Yield: 2.5 g (62%). Rf=0.50 (CH$_2$Cl$_2$:MeOH=10:1). $^1$H-NMR (400 MHz, δ, CDCl$_3$): 1.47 (s, 9H), 1.58 (s, 9H), 1.65-1.68 (m, 2H), 2.01-2.07 m, 2H), 3.22-3.28 (m, 2H), 3.94-3.98 (m, 2H), 6.41 (brs, 1H).

B. 7-(2,2-Dimethyl-propyl)-6-(1-ethyl-2,4-dioxo-1,3,8-triaza-spiro[4.5]dec-8-ylmethyl)-7H-pyrrolo[2,3-d]pyrimidine-2-carbonitrile

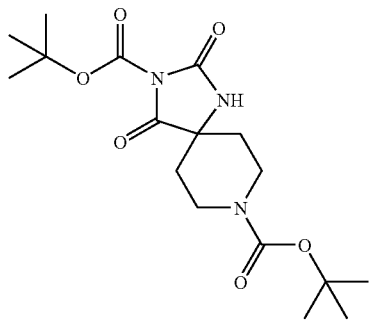

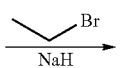

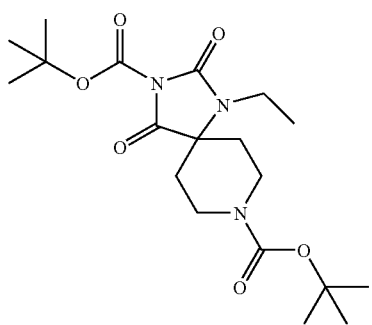

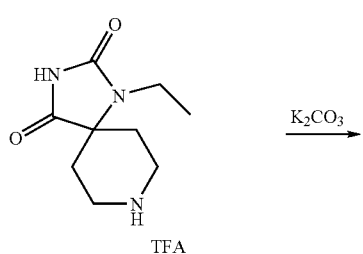

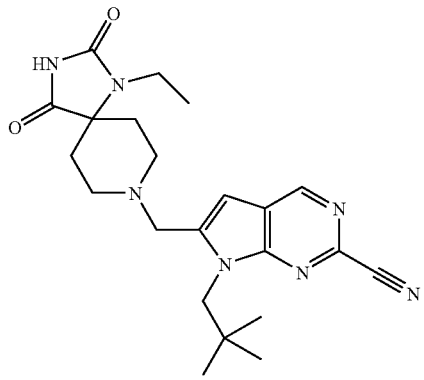

To a solution of 2,4-dioxo-1,3,8-triaza-spiro[4.5]decane-3,8-dicarboxylic acid di-tert-butyl ester (0.4 g, 1.1 mmol) in DMF (8 ml), NaH (80 mg, 2.2 mmol) and ethyl bromide (166 □l, 2.16 mmol) are added at room temperature. The reaction mixture is stirred at ambient temperature for 15 h, quenched with saturated ammonium clroride and extracted with AcOEt. The organic layer is washed with brine, dried over magnesium sulfate and filtrated. To a solution of 1-ethyl-2,4-dioxo-1,3,8-triaza-spiro[4.5]decane-3,8-dicarboxylic acid di-tert-butyl ester (1.1 mmol) in CH$_2$Cl$_2$ (10 ml), TFA (10 ml) are added at 0° C. The reaction mixture is stirred at room temperature for 1 h. After removal of the solvent, ethyl ether is added to the residue to give 34 mg of desired product in 10% yield. To a solution of 1-ethyl-1,3,8-triaza-spiro[4.5]decane-2,4-dione (30 mg, 0.096 mmol) in DMSO (1 ml), potassium carbonate (13.8 mg, 0.1 mmol) and 6-bromomethyl-7-(2,2-dimethyl-propyl)-7H-pyrrolo[2,3-d]pyrimidine-2-carbonitrile (30.7 mg, 0.1 mmol) are added to the mixture at ambient temperature. The reaction mixture is stirred at ambient temperature for 3 h, quenched with saturated ammonium clroride and extracted with AcOEt. The combined extracts are washed with H$_2$O, brine and dried over magnesium sulfate. The combined extracts are concentrated and the residue is purified by reverse phase preparative HPLC to give 20 mg of desired product in 3.6% yield.

Rf=0.19 (n-Hexane:AcOEt=1:3) $^1$H-NMR (400 MHz, δ, CDCl$_3$): 1.01 (s, 9H), 1.22 (t, 3H), 1.63-1.66 (m, 2H), 2.09-2.16 (m, 2H), 2.23-2.28 (m, 2H), 2.88-2.93 (m, 2H), 3.56 (q, 2H), 3.84 (s, 2H), 4.34 (s, 2H), 5.76 (brs, 1H), 6.59 (s, 1H), 8.91 (s, 1H)

By repeating the procedures described above using appropriate starting materials and conditions the following compounds of formula III are obtained as identified below in Table 7-8.

TABLE 7-8
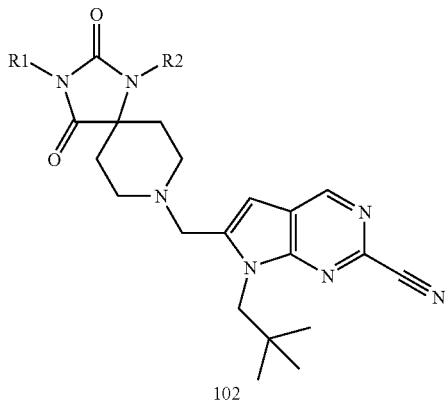
Formula III
| Expl No | R1 | R2 | Yield(%) | Rf(Solvent) | $^1$H NMR(400 MHz, ☐) |
|---|---|---|---|---|---|
| 7-55 | H | n-propyl | 4.5 | 0.28 (n-Hexane:AcOEt = 1:3) | (CDCl$_3$): 0.91(t, 3H), 1.02(s, 9H), 1.61–1.70(m, 4H), 2.05–2.17(m, 2H), 2.25–2.31(m, 2H), 2.88–2.93(m, 2H), 3.48(t, 2H), 3.84(s, 2H), 4.34(s, 2H), 6.22(brs, 1H), 6.59(s, 1H), 8.91(s, 1H). |
| 7-56 | H | cyclopropylmethyl | 4.2 | 0.22 (n-Hexane:AcOEt = 1:3) | (CDCl$_3$): 0.35–0.37 (m, 2H), 0.47–0.52 (m, 2H), 1.02(s, 9H), 1.13–1.19(m, 1H), 1.65–1.69(m, 2H), 2.10–2.17(m, 2H), 2.24–2.30(m, 2H), 2.89–2.93(m, 2H), 3.37(d, 2H), 3.83(s, 2H), 4.34(s, 2H), 5.88(br, 1H), 6.59(s, 1H), 8.91(s, 1H). |

7-57

7-(2,2-Dimethyl-propyl)-6-(2,4-dioxo-3-propyl-1-oxa-3,8-diaza-spiro[4.5]dec-8-ylmethyl)-7H-pyrrolo[2,3-d]pyrimidine-2-carbonitrile

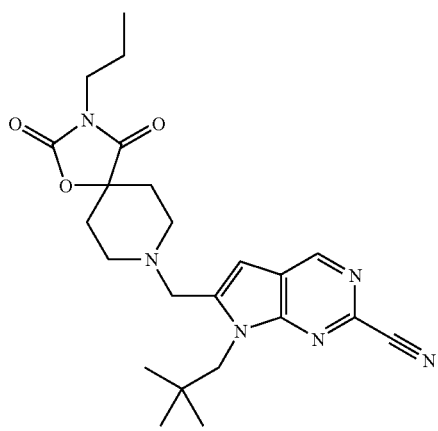

A. 2,4-Dioxo-1-oxa-3,8-diaza-spiro[4.5]decane-8-carboxylic acid benzyl ester

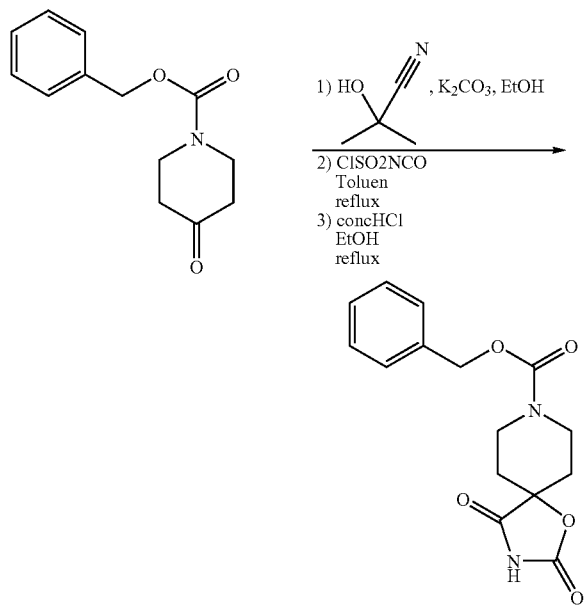

To a solution of 4-oxo-piperidine-1-carboxylic acid benzyl ester (25 g, 0.11 mol) in EtOH (400 ml), potassium carbonate (4.4 g, 0.03 mol) and 2-hydroxy-2-methyl-propionitrile (68.5 ml, 0.75 mol) are added at ambient temperature. The reaction mixture is stirred at ambient temperature for 18 h. After removal of the solvent, the residue is extracted with AcOEt and the combined extracts are washed with brine, dried over magnesium sulfate, concentrated to give yellow solid (36.2 g). To a solution of crude yellow solid (36.2 g) in toluene (450 ml), chlorosulfonyl isocyanate (10.3 ml, 0.12 mol) and triethylamine (18 ml, 0.13 mol) are added at ambient temperature. The reaction mixture is refluxed for 2.5 h. After removal of the solvent, conc.HCl (30 ml) and EtOH (250 ml) was added to the residue. The reaction mixture is refluxed for 1.5 h and evaporated down. The reaction mixture is quenched with water and extracted with AcOEt. The combined extracts are washed with brine, dried over magnesium sulfate, filtrated and evaporated to afford 24.8 g of the desired product.

Yield: 70%. $^1$H-NMR (400 MHz, δ, DMSO-$d_6$): 1.47-1.93 (m, 4H), 3.12-3.23 (m, 2H), 3.90-3.96 (m, 2H), 5.10 (s, 2H), 7.31-7.38 (m, 5H)

B. 3-Propyl-1-oxa-3,8-diaza-spiro[4.5]decane-2,4-dione

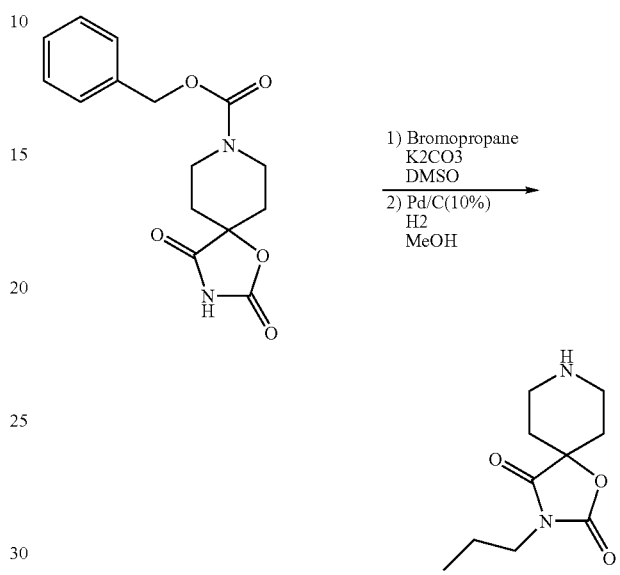

To a solution of 2,4-dioxo-1-oxa-3,8-diaza-spiro[4.5]decane-8-carboxylic acid benzyl ester (24.4 g, 80 mmol) in DMSO (240 ml), potassium carbonate (16.5 g, 120 mmol) and bromopropane (11 ml, 120 mmol) are added to the mixture at ambient temperature. The reaction mixture is stirred at ambient temperature for 12 h, quenched with water and extracted with AcOEt:ether (1:1 (v/v)). The combined extracts are washed with brine, dried over magnesium sulfate, filtrated and concentrated. The residue is purified by column chromatography on silica gel using n-hexane:AcOEt=2:1 (v/v). to give 21.2 g of desired product in 76% yield. Rf=0.8 (n-hexane:AcOEt=1:1). To white solid (21.2 g) and 10% Pd/C (3 g), MeOH (300 ml) is added. The reaction mixture is stirred at ambient temperature for 18 h under $H_2$. After the filtration, the solvent is evaporated down to give the desired product.

Yield: 78%. Rf=0.6 (n-hexane:AcOEt=1:1) $^1$H-NMR (400 MHz, δ, DMSO-d6): 0.83 (t, 3H), 1.56 (q, 2H), 1.68-1.71 (m, 2H), 1.77-1.85 (m, 2H), 2.66-2.73 (m, 2H), 2.88-2.93 (m, 2H)

C. 7-(2,2-Dimethyl-propyl)-6-(2,4-dioxo-3-propyl-1-oxa-3,8-diaza-spiro[4.5]dec-8-ylmethyl)-7H-pyrrolo[2,3-d]pyrimidine-2-carbonitrile

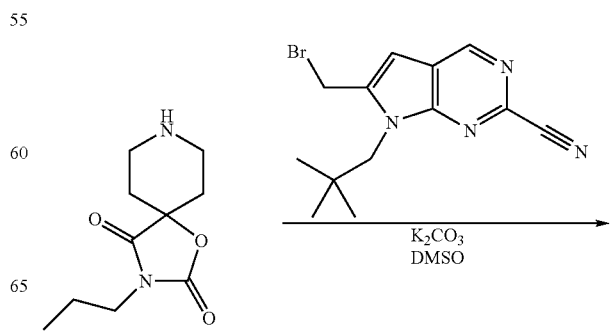

-continued

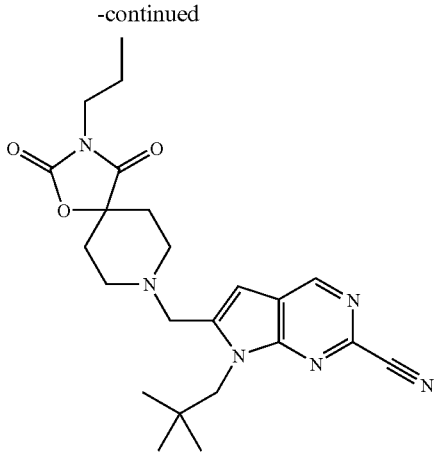

To a solution of 3-propyl-1-oxa-3,8-diaza-spiro[4.5]decane-2,4-dione (332 mg, 1.6 mmol) in DMSO (4 ml), potassium carbonate (234 mg, 1.7 mmol) and 6-bromomethyl-7-(2,2-dimethyl-propyl)-7H-pyrrolo[2,3-d]pyrimidine-2-carbonitrile (400 mg, 1.3 mmol) are added to the mixture at ambient temperature. The reaction mixture is stirred at ambient temperature for 2 h, quenched with saturated water and extracted with AcOEt. The combined extracts are washed with H$_2$O, brine and dried over magnesium sulfate. The solvent is concentrated and diethyl ether is added to the residue to give pale yellow solid, which are filtrated and recrystallized by MeOH to give the product in 81% yield.

Rf=0.50 (AcOEt). $^1$H-NMR (400 MHz, δ, CDCl$_3$): 0.92 (t, 3H), 1.01 (s, 9H), 1.68 (q, 2H), 1.75-1.79 (m, 2H), 2.13-2.20 (m, 2H), 2.45-2.52 (m, 2H), 2.80-2.84 (m, 2H), 3.84 (s, 2H), 4.33 (s, 2H), 6.60 (s, 1H), 8.91 (s, 1H)

By repeating the procedures described above using appropriate starting materials and conditions the following compounds of formula I are obtained as identified below in Table 7-9.

TABLE 7-9

Formula I

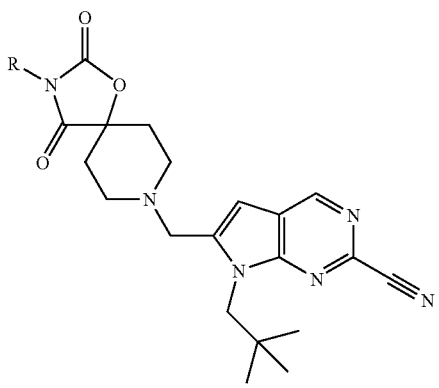

| Expl No | R | Yield(%) | Rf(Solvent) | $^1$H NMR(400 MHz, ☐) |
|---|---|---|---|---|
| 7-58 | ![cyclopropylmethyl] | 46 | 0.48 (n-Hexane:AcOEt = 1:1) | (CDCl$_3$): 0.36(q, 2H), 0.53(q, 2H), 1.01(s, 9H), 1.16–1.20(m, 1H), 1.79(d, 2H), 2.13–2.21(m, 2H), 2.81–2.84(m, 2H), 3.39–3.41(m, 2H), 3.85(s, 2H), 4.33(s, 2H), 6.60(s, 1H), 8.91(s, 1H) |
| 7-59 | ![cyclopropylethyl] | 7.3 (overall) | 0.44 (n-Hexane:AcOEt = 1:1) | (CDCl$_3$): 0.01–0.05(m, 2H), 0.43–0.46(m, 2H), 0.63–0.66(m, 1H), 1.02(s, 9H), 1.54–1.57(m, 2H), 1.76–1.80(m, 2H), 2.13–2.20(m, 2H), 2.46–2.52(m, 2H), 2.81–2.83(m, 2H), 3.64(t, 2H), 3.84(s, 2H), 4.33(s, 2H), 6.60(s, 1H), 8.90(s, 1H) |
| 7-60 | ![isopentyl] | 9.4 (overall) | 0.48 (n-Hexane:AcOEt = 1:1) | (CDCl$_3$): 0.94(d, 6H), 1.01(s, 9H), 1.50–1.57(m, 2H), 1.76(d, 2H), 2.12–2.19(m, 2H), 2.45–2.52(m, 2H), 2.80–2.84(m, 2H), 3.55(t, 2H), 3.84(s, 2H), 4.33(s, 2H), 6.60(s, 1H), 8.90(s, 1H) |
| 7-61 | ![propyl] | 13.2 (overall) | 0.35 (n-Hexane:AcOEt = 1:1) | (CDCl$_3$): 1.01(s, 9H), 1.26(t, 3H), 1.77(d, 2H), 2.04–2.20(m, 2H), 2.45–2.52(m, 2H), 2.81–2.84(m, 2H), 3.59(q, 2H), 3.84(s, 2H), 4.33(s, 2H), 6.60(s, 1H), 8.90(s, 1H) |

TABLE 7-9-continued

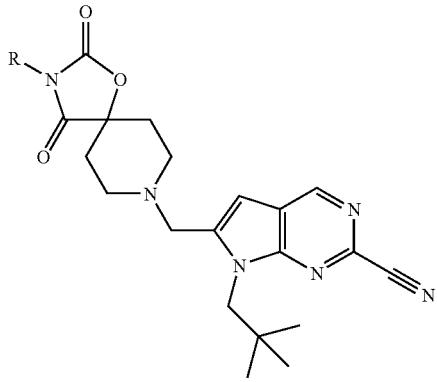

Formula I

| Expl No | R | Yield(%) | Rf(Solvent) | ¹H NMR(400 MHz, ☐) |
|---|---|---|---|---|
| 7-62 | ~~~~~ | 12.0 (overall) | 0.44 (n-Hexane:AcOEt = 1:1) | (CDCl$_3$): 0.94(t, 3H), 1.01(s, 9H), 1.26–1.30(m, 2H), 1.59–1.67(m, 2H), 1.77(d, 2H), 2.13–2.20(m, 2H), 2.45–2.52(m, 2H), 2.80–2.81(m, 2H), 3.53(t, 2H), 3.84(s, 2H), 4.33(s, 2H), 6.60(s, 1H), 8.90(s, 1H) |
| 7-63 | ~⟨ | 5.5 (overall) | 0.44 (n-Hexane:AcOEt = 1:1) | (CDCl$_3$): 0.91(d, 6H), 1.01(s, 9H), 1.76–1.79(m, 2H), 2.09–2.21(m, 3H), 2.46–2.52(d, 2H), 2.80–2.83(m, 2H), 3.35(d, 2H), 3.84(s, 2H), 4.33(s, 2H), 6.60(s, 1H), 8.91(s, 1H) |
| 7-64 | ~~N(piperidine) | 8.4 (overall) | 0.23 (AcOEt) | (CDCl$_3$): 1.02(s, 9H), 1.38–1.46(m, 6H), 1.80(d, 2H), 2.13–2.20(m, 2H), 2.38(brs, 4H), 2.46–2.60(m, 4H), 2.81–2.82(m, 2H), 3.63(t, 2H), 3.85(s, 2H), 4.34(s, 2H), 6.60(s, 1H), 8.90(s, 1H) |

By repeating the procedures described above using appropriate starting materials and conditions the following compounds of formula 7-10 are obtained as identified below in Table 7-10

7-10

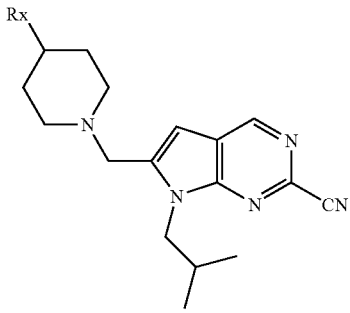

| 7-65 |  | 7-Isobutyl-6-(3-methyl-2,4-dioxo-1,3,8-triaza-spiro[4.5]dec-8-yl-methyl)-7H-pyrrolo[2,3-d]pyrimidine-2-carbonitrile | CDCl$_3$, 300 MHz, 0.93(d, 6H), 1.72(m, 2H), 2.05–2.45(m, 5H), 2.97(m, 2H), 3.03(s, 3H), 3.80 (m, 2H), 4.25(d, 2H), 6.46(m, 1H), 6.59(bs, 1H), 8.91(s, 1H). MH$^+$: 396. |

7-10

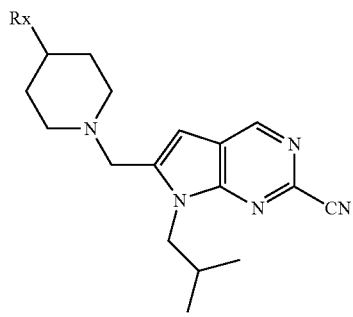

| | | | |
|---|---|---|---|
| 7-66 | 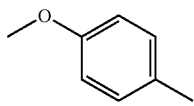 | 7-Isobutyl-6-[4-(4-methoxy-phenyl)-piperidin-1-ylmethyl]-7H-pyrrolo[2,3-d]pyrimidine-2-carbonitrile | CDCl$_3$, 300 MHz: 0.94(d, 6H), 1.6–1.9(m, 4H), 2.21(m, 2H), 2.36(m, 1H), 2.50(m, 1H), 3.00 (m, 2H), 3.75(bs, 2H), 3.79(s, 3H), 4.28(d, 2H), 6.58(m, 1H), 6.84(d, 2H), 7.13(d, 2H), 8.89(s, 1H). MH$^+$: 404. |
| 7-67 | 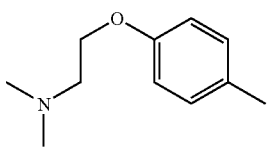 | 6-{4-[4-(2-Dimethylamino-ethoxy)-phenyl]-piperidin-1-ylmethyl}-7-isobutyl-7H-pyrrolo[2,3-d]pyrimidine-2-carbonitrile | CDCl$_3$, 300 MHz: 0.92(d, 6H), 1.6–1.9(m, 4H), 2.18(m, 2H), 2.36(m, 1H), 2.39(s, 6H), 2.47 (m, 1H), 2.81(t, 2H), 2.98(m, 2H), 3.71(s, 2H), 4.07(t, 2H), 4.27(d, 2H), 6.54(s, 1H), 6.85(d, 2H), 7.11(d, 2H), 8.87(s, 1H). MH$^+$: 461. |
| 7-68 | 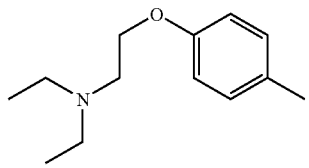 | 6-{4-[4-(2-Diethylamino-ethoxy)-phenyl]-piperidin-1-ylmethyl}-7-isobutyl-7H-pyrrolo[2,3-d]pyrimidine-2-carbonitrile | CDCl$_3$, 300 MHz: 0.92(d, 6H), 1.06(t, 6H), 1.6–1.9(m, 4H), 2.18 (m, 2H), 2.35(m, 1H), 2.47(m, 1H), 2.65(q, 4H), 2.88(t, 2H), 2.96(m, 2H), 2.71(s, 2H), 4.03(t, 2H), 4.17(d, 2H), 6.54(s, 1H), 6.83(d, 2H), 7.10(d, 2H), 8.86(s, 1H). MH$^+$: 489. |
| 7-69 | 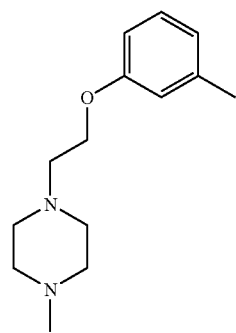 | 7-Isobutyl-6-(4-{3-[2-(4-methyl-piperazin-1-yl)-ethoxy]-phenyl}-piperidin-1-ylmethyl)-7H-pyrrolo[2,3-d]pyrimidine-2-carbonitrile | CDCl$_3$, 300 MHz: 0.92(d, 6H), 1.6–1.9(m, 4H), 2.17(m, 2H), 2.29(s, 3H), 2.3–2.7(m, 10H), 2.81(t, 2H), 2.97(m, 2H), 3.71(s, 2H), 4.09(t, 2H), 4.18(d, 2H), 6.54(s, 1H), 6.7–6.85(m, 3H), 7.19(t, 1H), 8.86(s, 1H). MH$^+$: 516. |
| 7-70 | 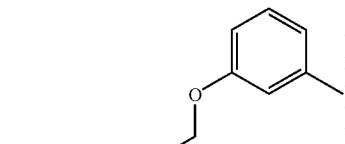 | 7-Isobutyl-6-(4-{3-[3-(4-methyl-piperazin-1-yl)-propoxy]-phenyl}-piperidin-1-ylmethyl)-7H-pyrrolo[2,3-d]pyrimidine-2-carbonitrile | CDCl$_3$, 300 MHz: 0.92(d, 6H), 1.6–2.1(m, 6H), 2.18(m, 2H), 2.29(s, 3H), 2.3–2.7(m, 12H), 2.98(m, 2H), 2.71(s, 2H), 2.99(t, 2H), 4.28(d, 2H), 6.54(s, 1H), 6.7–6.8(m, 3H), 7.18(t, 1H), 8.87 (s, 1H). MH$^+$: 530. |

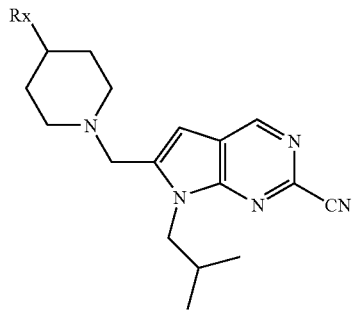

7-10

| 7-71 | 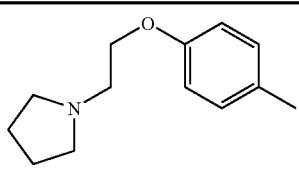 | 7-Isobutyl-6-{4-[4-(2-pyrrolidin-1-yl-ethoxy)-phenyl]-piperidin-1-yl-methyl}-7H-pyrrolo[2,3-d]pyrimidine-2-carbonitrile | CDCl$_3$, 300 MHz: 0.94(d, 6H), 1.6–1.9(M, 8H), 2.17(m, 2H), 2.36(m, 1H), 2.47(m, 1H), 2.70 (m, 4H), 2.96(m, 4H), 3.71(s, 2H), 4.12(t, 2H), 4.27(d, 2H), 6.55(s, 1H), 6.85(d, 2H),7.12(d, 2H), 8.87(s, 1H). MH$^+$: 487. |

By repeating the procedures described above using appropriate starting materials and conditions the following compounds of formula 7-11 are obtained as identified below in Table 7-11

By repeating the procedures described above using appropriate starting materials and conditions the following compounds of formula 7-12 are obtained as identified below in Table 7-12

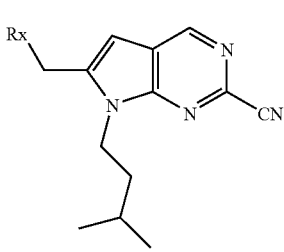

7-11

| 7-72 | 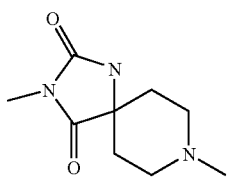 | 7-(3-Methyl-butyl)-6-(3-methyl-2,4-dioxo-1,3,8-tri-aza-spiro[4.5]dec-8-yl-methyl)-7H-pyrrolo[2,3-d]pyrimidine-2-carbonitrile | CDCl$_3$, 300 MHz: 1.02(d, 6H), 1.70(m, 5H), 2.13(m, 2H), 2.35 (m, 2H), 2.95(m, 2H), 3.03(s, 3H), 3.78(s, 2H), 4.42(m, 2H), 6.54(s, 1H), 6.79(bs, 1H), 8.88 (s, 1H). MH$^+$: 410. |
| 7-73 | 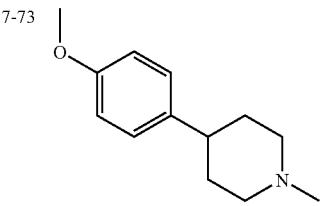 | 6-[4-(4-Methoxy-phenyl)-piperidin-1-yl-methyl]-7-(3-methyl-butyl)-7H-pyrrolo[2,3-d]pyrimidine-2-carbonitrile | CDCl$_3$, 300 MHz: 1.04(d, 6H), 1.61–1.95(m, 7H), 2.22(m, 2H), 2.51(m, 1H), 3.02(m, 2H), 3.76 (m, 2H), 3.78(s, 3H). 4.45(m, 2H), 6.56(s, 1H), 6.86(d, 2H), 7.12(d, 2H), 8.88(s, 1H).MH$^+$: 418. |

| | | 7-12 |
|---|---|---|
| | 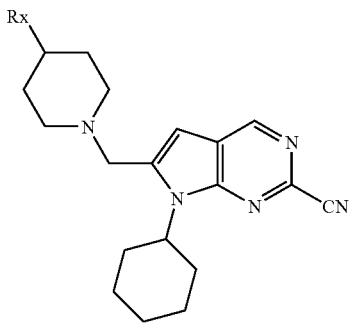 | |
| 7-74 | 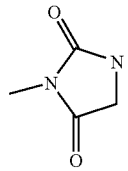 7-Cyclohexyl-6-(3-methyl-2,4-dioxo-1,3,8-triaza-spiro[4.5]dec-8-ylmethyl)-7H-pyrrolo[2,3-d]pyrimidine-2-carbonitrile | CDCl$_3$, 300 MHz: 1.3–1.9(m, 8H), 1.95–2.2(m, 4H), 2.30(m, 2H), 2.65(m, 2H), 2.95(m, 2H), 3.03 (s, 3H), 3.73(s, 2H), 4.42(m, 1H), 6.08(bs, 1H), 6.49(s, 1H), 8.86 (s, 1H). MH$^+$: 422. |
| 7-75 | 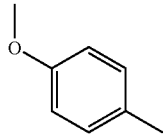 7-Cyclohexyl-6-[4-(4-methoxy-phenyl)-piperidin-1-ylmethyl]-7H-pyrrolo[2,3-d]pyrimidine-2-carbonitrile | CD$_3$OD, 300 MHz: 1.4–2.1(m, 12H), 2.22(m, 2H), 2.50(m, 1H), 2.71(m, 2H), 2.98(m, 2H), 3.75 (s, 3H), 3.79(s, 2H), 4.67(m, 1H), 6.65(s, 1H), 6.83(d, 2H), 7.10(d, 2H), 8.91(s, 1H). MH$^+$: 430. |

Example 8 Describes the Preparation of 6-benzyl-7H-pyrrolo[2,3-d]pyrimidine-2-carbonitriles Example 8-1

6-Benzyl-7-isobutyl-7H-pyrrolo[2,3-d]-pyrimidine-2-carbonitrile

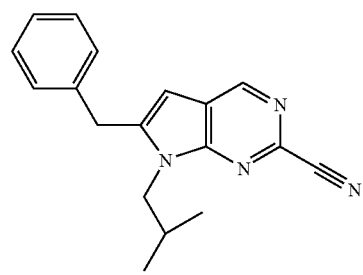

A. (5-Bromo-2-chloro-pyrimidin-4-yl)-isobutyl-amine

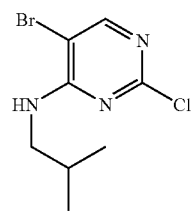

To a solution of 5-bromo-2,4-dichloropyrimidine (14.0 mmol) in methanol (30 ml) is added isobutylamine (28.0 mmol) at room temperature. The mixture is stirred at room temperature for one day and diluted with AcOEt. The organic layer is washed with water and brine, dried over sodium sulfate and concentrated. Chromatography on silica gel (n-hexane and n-hexane:AcOEt=25:1) gives the product in 78% yield. Rf=0.52 (n-hexane:AcOEt=4:1)

B. 5-Bromo-4-isobutylamino-pyrimidine-2-carbonitrile

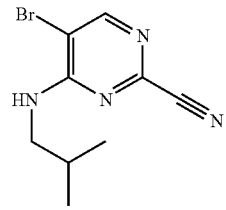

To a solution of (5-bromo-2-chloro-pyrimidin-4-yl)-isobutyl-amine (11.2 mmol) in DMSO (30 ml) is added potassium cyanide (22.5 mmol) and sodium p-toluenesulfonic acid (3.75 mmol) in DMSO(17 ml) at room temperature. The mixture is stirred at 75° C. for 18 h and diluted with AcOEt. The organic layer is washed with water and brine, dried over sodium sulfate and concentrated. Chromatography on silica gel (n-hexane:AcOEt=25:1, 15:1 and 12:1) gives the product in 84% yield. Rf=46 (n-hexane:AcOEt=3:1)

C. 6-Benzyl-7-isobutyl-7H-pyrrolo[2,3-d]pyrimidine-2-carbonitrile

5-Bromo-4-isobutylamino-pyrimidine-2-carbonitrile (0.39 mmol), 3-phenyl-1-propyne (0.78 mmol), dichlorobis (triphenylphosphine)palladium (II) (0.02 mmol), copper (I) iodide (0.04 mmol) and triethylamine (1.2 mmol) in DMF (3 ml) is stirred at 75° C. for 2.5 h. After the reaction mixture is treated with saturated ammonium chloride, the mixture is extracted with AcOEt. The organic layer is washed with brine, dried over magnesium sulfate and evaporated down. The crude product is applied to a column chromatography on silica gel, which is eluted with following solvents: n-hexane: AcOEt=10:1 (v/v) and n-hexane:AcOEt=8:1 (v/v). The solvent of the latter effluent is removed by evaporation and dried in vacuo to afford the title compound. yield 40.6%, Rf=0.53 (n-hexane:AcOEt=1:1).

By repeating the procedures described above using appropriate starting materials and conditions the following compounds of formula 8-1 are obtained as identified below in Table 8-1.

To a suspension of Mg powder (5.3 mmol) and one piece of iodine in THF (4 ml) is added 2-bromonaphthalene (4.6 mmol) in THF (2 ml) at room temperature and the mixture is stirred at 85° C. for 0.5 h. Copper(I) bromide (0.32 mmol) is added at room temperature then methoxyallene (4.6 mmol) in THF (3 ml) is added at 0° C. and the mixture is stirred at room temperature for 2 h. The mixture is poured into saturated ammonium chloride, extracted with AcOEt. The organic layer is washed with brine, dried over sodium sulfate and concentrated. Chromatography on silica gel (n-hexane: AcOEt=20:1) gives the product in 18% yield. Rf=0.5 (n-hexane:AcOEt=10:1)

TABLE 8-1

8-1

| Expl. No. | Rx | Yield(%) | Rf(Solvent) | $^1$H-NMR(400 MHz, δ) |
|---|---|---|---|---|
| 8-1 | 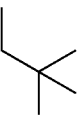 | 41 | 0.53 (n-hexane:AcOEt = 1:1) | (CDCl$_3$): 0.90(d, 6H), 2.19–2.30(m, 1H), 4.02(d, 2H), 4.19(s, 2H), 6.28(s, 1H), 7.19(d, 2H), 7.26–7.38(m, 3H), 8.84(s, 1H) |
| 8-2 | | 74 | 0.50 (n-hexane:AcOEt = 2:1) | (CDCl$_3$): 1.05(d, 9H), 4.07(s, 2H), 4.22(s, 2H), 6.24(s, 1H), 7.19(d, 2H), 7.26–7.38(m, 3H), 8.82(s, 1H) |

8-3

7-(2,2-dimethyl-propyl)-6-naphthalen-2-ylmethyl-7H-pyrrolo[2,3-d]pyrimidine-2-carbonitrile

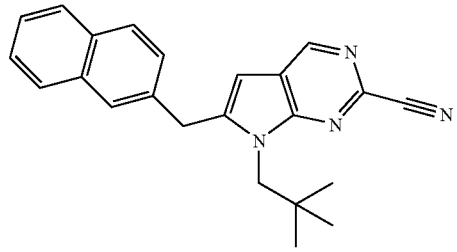

A. 2-Prop-2-ynyl-naphthalene

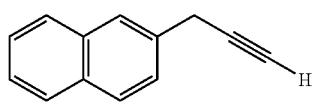

B. 7-(2,2-Dimethyl-propyl)-6-naphthalen-2-ylmethyl-7H-pyrrolo[2,3-d]pyrimidine-2-carbonitrile

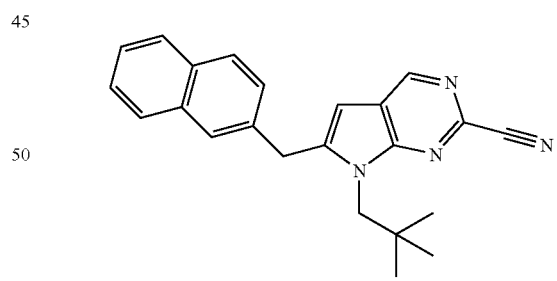

This compound is obtained analogously to 8-1 above.

Rf=0.4(n-hexane:AcOEt=3:1) $^1$H NMR(400 MHz, CDCl$_3$) δ 1.08(s, 9H), 4.11(s, 2H), 4.38(s, 2H), 6.27(s, 1H), 7.26-7.30(m, 1H), 7.47-7.52(m, 2H), 7.61(br s, 1H), 7.75-7.88(m, 3H), 8.82(s, 1H)

By repeating the procedures described above using appropriate starting materials and conditions the following compounds of formula 8-2 are obtained as identified below in T

TABLE 8-2

8-2

[Structure shown: pyrrolo[2,3-d]pyrimidine-2-carbonitrile with Rx-CH2- at 6-position and 2,2-dimethylpropyl at N-7]

| Expl. No. | Rx (group) | Rf(Solvent) | ¹H NMR(400 MHz, δ) |
|---|---|---|---|
| 8-3 | 2-naphthyl | 0.4 (n-hexane:AcOEt = 3:1) | (CDCl₃) 1.08(s, 9H), 4.11(s, 2H), 4.38(s, 2H), 6.27(s, 1H), 7.26–7.30(m, 1H), 7.47–7.52(m, 2H), 7.61(brs, 1H), 7.75–7.88(m, 3H), 8.82(s, 1H) |
| 8-4 | 4-(1,3-dioxolan-2-yl)phenyl | 0.54 (n-hexane:AcOEt = 1:1) | (CDCl₃) 1.05(s, 9H), 4.02–4.17(m, 6H), 4.23(s, 2H), 5.80(s, 1H), 6.23(s, 1H), 7.17–7.22(m, 2H), 7.46–7.51(m, 2H), 8.82(s, 1H) |
| 8-5 | 3,4-methylenedioxyphenyl | 0.31 (n-hexane:AcOEt = 3:1) | (CDCl₃) 1.04(s, 9H), 4.06(s, 2H), 4.15(s, 2H), 5.97(s, 2H), 6.28(s, 1H), 6.59–6.65(m, 2H), 6.75–6.80(m, 1H), 8.84(s, 1H) |

8-6

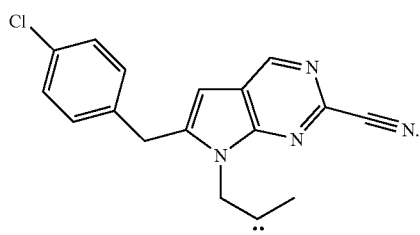

6-(4-Chloro-benzyl)-7-(2,2-diethyl-propyl)-7H-pyrrolo[2,3-d]pyrimidine-2-carbonitrile A. (5-Bromo-2-chloro-pyrimidin-4-yl)-(2,2-dimethyl-propyl)-amine

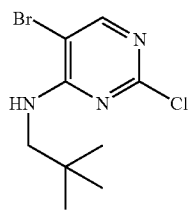

To a solution of 5-bromo-2,4-dichloropyrimidine (13.2 mmol) in MeOH (20 ml) is added neopentylamine (25.5 mmol) at room temperature. The mixture is stirred at room temperature for one day, diluted with AcOEt. The organic layer is washed with water and brine, dried over sodium sulfate and concentrated. Chromatography on silica gel (n-hexane:AcOEt=30:1 and 3:1) gives the product in 78% yield.

Rf=0.62 (n-hexane:AcOEt=3:1)

B. 5-Bromo-4-(2,2-dimethyl-propylamino)-pyrimidine-2-carbonitrile

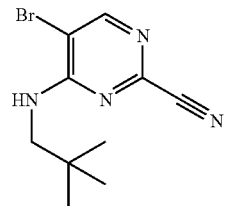

To a solution of sodium cyanide(10.4 mmol) and 1,4-diazabicyclo[2.2.2]octane(1.1 mmol) in water(2 ml) and DMSO(1 ml) is added (5-bromo-2-chloro-pyrimidinyl)-(2,2-dimethyl-propyl)-amine(10.3 mmol) in DMSO(17 ml) at room temperature. The mixture is stirred at 60° C. for 6 h and diluted with AcOEt. The organic layer is washed with water and brine, dried over sodium sulfate and concentrated. Chromatography on silica gel (n-hexane:AcOEt=30:1, 10:1 and 3:1) gives the product in 84% yield.

Rf=0.46 (n-hexane:AcOEt=3:1)

C. 1-Chloro-4-prop-2-ynyl-benzene

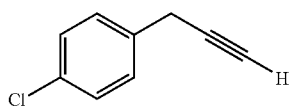

D. 6-(4-Chloro-benzyl)-7-(2,2-dimethyl-propyl)-7H-pyrrolo[2,3-d]pyrimidine-2-carbonitrile

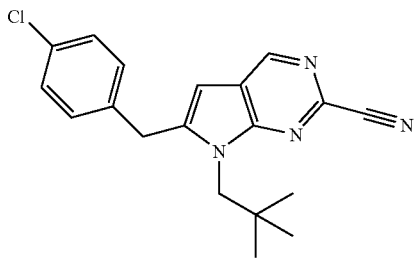

To a solution of 5-bromo-4-(2,2-dimethyl-propylamino)-pyrimidine-2-carbonitrile(8.7 mmol) and 1-chloro-4-prop-2-ynyl-benzene(13.1 mmol) in DMF(30 ml) are added triethylamine(25.8 mmol), copper(I) iodide(0.87 mmol) and dichlorobis(triphenylphosphine)palladium (II) (0.44 mmol) under nitrogen. The mixture is stirred at 80° C. for 2 h and diluted with AcOEt. The organic layer is washed with water, saturated ammonium chloride and brine, dried over sodium sulfate and concentrated. The crude product is purified by chromatography on silica gel (n-hexane:AcOEt=25:1, 15:1, 10:1 and 5:1) to give the product in 95% yield.

Rf=0.43(n-hexane:AcOEt=3:1) $^1$H NMR (400 MHz, CDCl$_3$) δ 1.05(s, 9H), 4.06(s, 2H), 4.19(s, 2H), 6.22(s, 1H), 7.08-7.13(m, 2H), 7.30-7.35(m, 2H), 8.84(s, 1H)

By repeating the procedures described above using appropriate starting materials and conditions the following compounds of formula 8-3 are obtained as identified below in Table 8-3.

TABLE 8-3

8-3

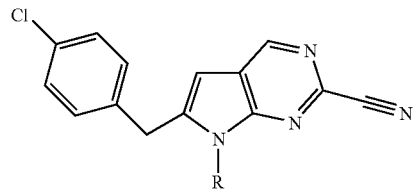

| Expl. No. | R | Rf(Solvent) | $^1$H NMR(400 MHz, δ) |
|---|---|---|---|
| 8-6 | neopentyl | 0.43 (n-hexane:AcOEt = 3:1) | (CDCl$_3$): 1.05(s, 9H), 4.06(s, 2H), 4.19(s, 2H), 6.22(s, 1H), 7.08–7.13(m, 2H), 7.30–7.35(m, 2H), 8.84(s, 1H) |
| 8-7 | cyclohexyl | 0.24 (n-hexane:AcOEt = 4:1) | (CDCl$_3$): 1.21–1.90(m, 8H), 2.52–2.59(m, 2H), 4.06–4.13(m, 1H), 4.16(s, 2H), 6.31(s, 1H), 7.12(d, 2H), 7.33(d, 2H), 8.84(s, 1H) |
| 8-8 | isobutyl | 0.36 (n-hexane:AcOEt = 3:1) | (CDCl$_3$): 0.91(d, 6H), 2.19–2.31(m, 1H), 4.02(d, 2H), 4.16(s, 2H), 6.26(s, 1H), 7.11–7.16(m, 2H), 7.30–7.36(m, 2H), 8.85(s, 1H) |
| 8-9 | cyclopropylmethyl | 0.35 (n-hexane:AcOEt = 3:1) | (CDCl$_3$): 0.43–0.58(m, 4H), 1.03–1.17(m, 1H), 4.12(d, 2H), 4.22(s, 2H), 6.29(s, 1H), 7.12–7.18(m, 2H), 7.30–7.36(m, 2H), 8.86(s, 1H) |
| 8-10 | cyclohexylmethyl | 0.37 (n-hexane:AcOEt = 3:1) | (CDCl$_3$): 1.0–1.22(m, 5H), 1.44–1.52(m, 2H), 1.66–1.89(m, 4H), 4.03(d, 2H), 4.16(s, 2H), 6.26(s, 1H), 7.11–7.16(m, 2H), 7.30–7.36(m, 2H), 8.84(s, 1H) |

TABLE 8-3-continued 8-3

| Expl. No. | R | Rf(Solvent) | ¹H NMR(400 MHz, δ) |
|---|---|---|---|
| 8-11 | isopentyl | 0.31 (n-hexane:AcOEt = 3:1) | (CDCl$_3$): 0.95(d, 6H), 1.49–1.68(m, 3H), 4.16–4.22(m, 4H), 6.31(s, 1H), 7.11–7.17(m, 2H), 7.30–7.37(m, 2H), 8.85(s, 1H) |
| 8-12 | 2-ethylbutyl | 0.37 (n-hexane:AcOEt = 3:1) | (CDCl$_3$): 0.8(t, 6H), 1.18–1.42(m, 4H), 1.77–1.89(m, 1H), 4.09(d, 2H), 4.16(s, 2H), 6.28(s, 1H), 7.11–7.17(m, 2H), 7.30–7.37(m, 2H), 8.86(s, 1H) |

8-13

7-Cyclohexyl-6-[4-(4-methyl-piperazin-1-yl)-benzyl]-7H-pyrrolo[2,3-d]pyrimidine-2-carbonitrile

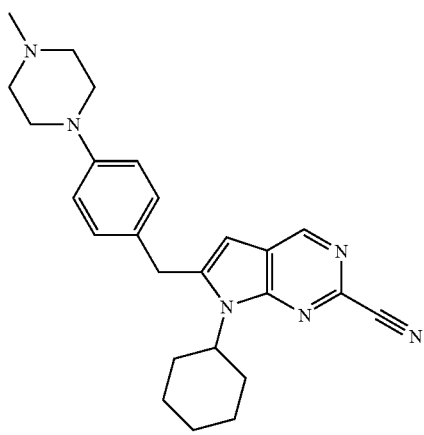

A mixture of 6-(4-chloro-benzyl)-7-cyclohexyl-7H-pyrrolo[2,3-d]pyrimidine-2-carbonitrile (1.5 mmol), 1-methylpiperazine (1.8 mmol), cesium carbonate (1.4 mmol), 2-(di-t-butylphosphino)-biphenyl (0.3 mmol) and palladium (II) acetate in toluene (6 ml) is stirred at 100° C. for 3 h. After the reaction mixture is quenched with saturated ammonium chloride, the mixture is extracted with AcOEt. The organic layer is washed with brine, dried over magnesium sulfate and evaporated down. The crude product is applied to a silica gel column chromatography, which is eluted with following solvents: 2% MeOH in CH$_2$Cl$_2$ and 3% MeOH in CH$_2$Cl$_2$. The solvent of the latter effluent is removed by evaporation and dried in vacuo to afford the title compound. yield 40.0%, By repeating the procedures described above using appropriate starting materials and conditions the following compounds of formula 8-4 are obtained as identified below in Table 8-4.

Dichlorobis(triphenylphosphine)palladium (II) is used instead of palladium (II) acetate for the synthesis of 8-15. 1,4-Dioxane is used instead of toluene for the syntheses of 8-17 and 8-19 to 8-27.

TABLE 8-4

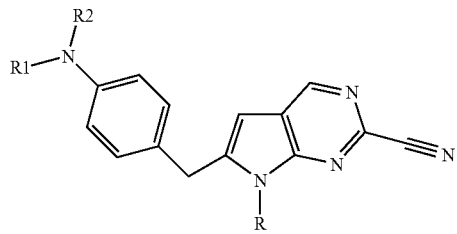

8-4

| Expl. No. | R1\N/R2 (with Me) | R | Rf(Solvent) | $^1$H NMR(400 MHz, δ) |
|---|---|---|---|---|
| 8-13 | 4-methylpiperazin-1-yl | cyclohexyl | 0.47 (CH$_2$Cl$_2$:methanol = 9:1) | (CDCl$_3$): 1.20–1.88(m, 8H), 2.35(s, 3H), 2.50–2.60(m, 6H), 3.18–3.21(m, 4H), 4.09(s, 2H), 4.13–4.19(m, 1H), 6.30(s, 1H), 6.95(d, 2H), 7.02(d, 2H), 8.81(s, 1H) |
| 8-14 | morpholin-4-yl | cyclohexyl | 0.48 (n-hexane:AcOEt = 1:1) | (CDCl$_3$): 1.20–1.45(m, 4H), 1.45–1.75(m, 2H), 1.80–1.90(m, 2H), 2.49–2.51(m, 2H), 3.14(t, 4H), 4.10(s, 2H), 4.10–4.20(m, 1H), 6.3(s, 1H), 6.88(d, 2H), 7.09(d, 2H), 8.82(s, 1H) |
| 8-15 | 4-methylpiperazin-1-yl | cyclopentyl | 0.39 (CH$_2$Cl$_2$:MeOH = 9:1) | (CDCl$_3$): 1.56–1.70(m, 2H), 1.78–1.90(m, 2H), 2.03–2.17(m, 2H), 2.30–2.42(m, 5H), 2.57–2.60(m, 4H), 3.19–3.22(m, 4H), 4.12(s, 2H), 4.64–4.72(m, 1H), 6.30(s, 1H), 6.88–6.91(m, 2H), 7.03–7.06(m, 2H), 8.82(s, 1H) |
| 8-16 | 4-methylpiperazin-1-yl | isobutyl | 0.45 (CH$_2$Cl$_2$:MeOH = 9:1) | (CDCl$_3$): 0.90(d, 6H), 2.18–2.30(m, 1H), 2.36(s, 3H), 2.55–2.61(m, 4H), 3.19–3.22(m, 4H), 4.02(d, 2H), 4.09(s, 2H), 6.27(s, 1H), 6.88–6.92(m, 2H), 7.05–7.10(m, 2H), 8.82(s, 1H) |
| 8-17 | morpholin-4-yl | isobutyl | 0.54 (n-hexane:AcOEt = 1:1) | (CDCl$_3$+DMSO-d$_6$): 0.91(d, 6H), 2.20–2.31(m, 1H), 3.10–3.18(m, 4H), 3.82–3.89(m, 4H), 4.03(d, 2H), 4.12(s, 2H), 6.30(s, 1H), 6.88–6.92(m, 2H), 7.08–7.12(m, 2H), 8.83(s, 1H) |
| 8-18 | 4-methylpiperazin-1-yl | neopentyl | 0.46 (CH$_2$Cl$_2$:MeOH = 9:1) | (CDCl$_3$+CD$_3$OD): 1.05(s, 9H), 2.39(s, 3H), 2.60–2.70(m, 4H), 3.20–3.28(m, 4H), 4.07(s, 2H), 4.14(s, 2H), 6.26(s, 1H), 6.88–6.92(m, 2H), 7.02–7.08(m, 2H), 8.81(s, 1H) |
| 8-19 | 4-isopropylpiperazin-1-yl | isobutyl | 0.61 (CH$_2$Cl$_2$:MeOH = 9:1) | (CDCl$_3$): 0.90(d, 6H), 1.10(d, 6H), 2.20–2.32(m, 1H), 2.67–2.80(m, 5H), 3.18–3.25(m, 4H), 4.02(d, 2H), 4.09(s, 2H), 6.27(s, 1H), 6.88–6.92(m, 2H), 7.03–7.08(m, 2H), 8.82(s, 1H) |
| 8-20 | 4-(2-methoxyethyl)piperazin-1-yl | isobutyl | 0.56 (CH$_2$Cl$_2$:MeOH = 9:1) | (CDCl$_3$): 0.90(d, 6H), 2.19–2.31(m, 1H), 2.60–2.82(m, 6H), 3.18–3.28(m, 4H), 3.37(s, 3H), 3.53–3.58(m, 2H), 4.02(d, 2H), 4.09(s, 2H), 6.27(s, 1H), 6.87–6.92(m, 2H), 7.03–7.08(m, 2H), 8.82(s, 1H) |

TABLE 8-4-continued 8-4

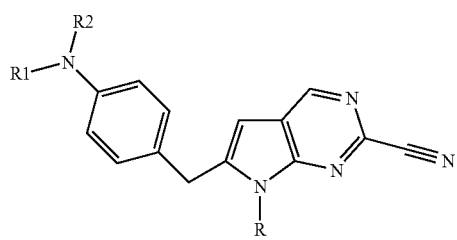

| Expl. No. | R1\N/R2 with Me | R | Rf(Solvent) | $^1$H NMR(400 MHz, δ) |
|---|---|---|---|---|
| 8-21 | isopropyl-piperazine-N-Me | t-Bu-CH2 | 0.59 (CH$_2$Cl$_2$:MeOH = 9:1) | (CDCl$_3$): 1.04(s, 9H), 1.09(d, 6H), 2.65–2.76(m, 5H), 3.17–3.23(m, 4H), 4.06(s, 2H), 4.13(s, 2H), 6.25(s, 1H), 6.88–6.92(m, 2H), 7.02–7.06(m, 2H), 8.81(s, 1H) |
| 8-22 | MeOCH2CH2-piperazine-N-Me | t-Bu-CH2 | 0.56 (CH$_2$Cl$_2$:MeOH = 9:1) | (CDCl$_3$): 1.04(s, 9H), 2.60–2.72(m, 6H), 3.20–3.27(m, 4H), 3.38(s, 3H), 3.53–3.58(m, 2H), 4.07(s, 2H), 4.13(s, 2H), 6.24(s, 1H), 6.85–6.91(m, 2H), 7.01–7.06(m, 2H), 8.81(s, 1H) |
| 8-23 | morpholine-N | t-Bu-CH2 | 0.66 (n-hexane:AcOEt = 1:1) | (CDCl$_3$): 1.04(s, 9H), 3.03–3.09(m, 4H), 3.82–3.89(m, 4H), 4.07(s, 2H), 4.14(s, 2H), 6.24(s, 1H), 6.85–6.91(m, 2H), 7.03–7.09(m, 2H), 8.81(s, 1H) |
| 8-24 | Ac-piperazine-N | t-Bu-CH2 | 0.52 (CH$_2$Cl$_2$:MeOH = 9:1) | (CDCl$_3$): 1.04(s, 9H), 2.14(s, 3H), 3.12–3.22(m, 4H), 3.60–3.65(m, 2H), 3.75–3.80(m, 2H), 4.07(s, 2H), 4.14(s, 2H), 6.24(s, 1H), 6.87–6.93(m, 2H), 7.04–7.10(m, 2H), 8.82(s, 1H) 7.04–7.10(m, 2H), 8.82(s, 1H) |
| 8-25 | Boc-piperazine-N | t-Bu-CH2 | 0.62 (n-hexane:AcOEt = 1:1) | (CDCl$_3$): 1.04(s, 9H), 1.48(s, 9H), 3.08–3.17(m, 4H), 3.53–3.62(m, 4H), 4.06(s, 2H), 4.14(s, 2H), 6.24(s, 1H), 6.86–6.92(m, 2H), 7.02–7.08(m, 2H), 8.81(s, 1H) |
| 8-26 | EtSO2-piperazine-N | t-Bu-CH2 | 0.24 (n-hexane:AcOEt = 1:1) | (CDCl$_3$+DMSO-d$_6$): 1.05(s, 9H), 1.41(t, 3H), 3.01(q, 2H), 3.23–3.30(m, 4H), 3.43–3.50(m, 4H), 4.09(s, 2H), 4.15(s, 2H), 6.25(s, 1H), 6.88–6.95(m, 2H), 7.05–7.12(m, 2H), 8.82(s, 1H) |
| 8-27 | N,N'-dimethyl-homopiperazine | t-Bu-CH2 | 0.37 (CH$_2$Cl$_2$:MeOH = 9:1) | (CDCl$_3$): 1.04(s, 9H), 2.0–2.1(m, 2H), 2.41(s, 3H), 2.58–2.65(m, 2H), 2.7–2.78(m, 2H), 3.45–3.51(m, 2H), 3.55–3.62(m, 2H), 4.08(s, 2H), 4.10(s, 2H), 6.26(s, 1H), 6.62–6.68(m, 2H), 6.97–7.02(m, 2H), 8.81(s, 1H) |

8-28

7-Cyclohexyl-6-(4-hydroxymethyl-benzyl)-7H-pyr-rolo[2,3-d]pyrimidine-2-carbonitrile

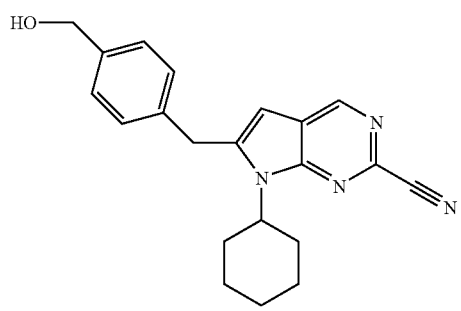

To a solution of (4-prop-2-ynyl-phenyl)-methanol (10 mmol) and 5-bromo-4-cyclohexylamino-pyrimidine-2-carbonitrile (7 mmol) in DMF (20 ml) are added triethylamine (21 mmol), dichlorobis(triphenylphosphine)palladium (II) (0.35 mmol) and copper (I) iodide (0.7 mmol). The reaction mixture is heated at 85° C. ca. for 2 h. The reaction mixture is quenched with saturated ammonium chloride and extracted with AcOEt. The organic layer is washed with brine and then dried over sodium sulfate and concentrated under vacuum to give 2.6 g of crude product, which is purified by silica gel column chromatography. Yield 58%.

By repeating the procedures described above using appropriate starting materials and conditions the following compounds of formula 8-5 are obtained as identified below in Table 8-5.

8-30

6-(4-Bromomethyl-benzyl)-7-cyclohexyl-7H-pyrrolo[2,3-d]pyrimidine-2-carbonitrile

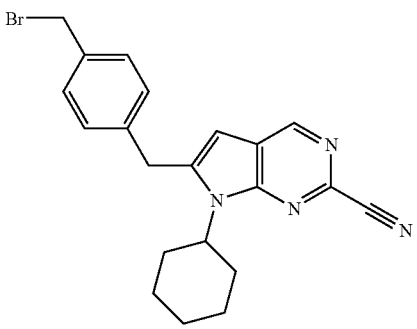

To a solution of 7-cyclohexyl-6-(4-hydroxymethyl-benzyl)-7H-pyrrolo[2,3-d]pyrimidine-2-carbonitrile (0.43 mmol) in $CH_2Cl_2$ (5 ml), triphenylphosphine (0.47 mmol) and carbontetrabromide (0.47 mmol) are added at 0° C. under nitrogen. The reaction mixture is stirred at 0° C. for 1 h and at room temperature for 1 h. The crude product is applied to a column of silica gel, which is eluted with following solvents: n-hexane:AcOEt=10:1 (v/v), n-hexane:AcOEt=8:1 (v/v) and n-hexane:AcOEt=5:1 (v/v). The solvent of the latter effluent is removed by evaporation and dried in vacuo to afford the title compound. yield 73.9%, Rf=0.72 (n-hexane:AcOEt=1:1).

By repeating the procedures described above using appropriate starting materials and conditions the following compounds of formula 8-6 are obtained as identified below in Table 8-6.

TABLE 8-5

8-5

| Expl. No. | R | Rf(Solvent) | $^1$H NMR(400 MHz, δ) |
|---|---|---|---|
| 8-28 | cyclohexyl | 0.1 (n-hexane:AcOEt = 4:1) | ($CDCl_3$): 1.15–1.45(m, 4H), 1.5–1.9(m, 4H), 2.49–2.61(m, 2H), 4.08–4.2(m, 1H), 4.18(s, 2H), 4.71(d, 2H), 6.32(s, 1H), 7.19(d, 2H), 7.35(d, 2H), 8.83(s, 1H) |
| 8-29 | neopentyl | 0.31 (n-hexane:AcOEt = 1:1) | ($CDCl_3$): 1.05(s, 9H), 1.70–1.76(m, 1H), 4.07(s, 2H), 4.22(s, 2H), 4.72(d, 2H), 6.24(s, 1H), 7.16(d, 2H), 7.36(d, 2H), 8.82(s, 1H) |

TABLE 8-6

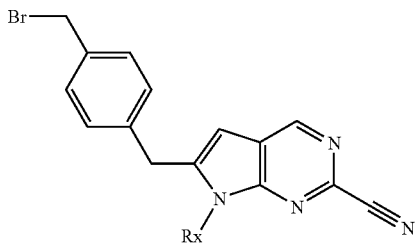

| Expl. No. | Rx | Rf(Solvent) | $^1$H-NMR(400 MHz, δ) |
|---|---|---|---|
| 8-30 | cyclohexyl-methyl | 0.72 (n-hexane:AcOEt = 1:1) | (CDCl$_3$): 1.19–1.85(m, 8H), 2.51–2.58(m, 2H), 4.07–4.15(m, 1H), 4.49(s, 2H), 6.38(s, 1H), 7.16(d, 2H), 7.37(d, 2H), 8.84(s, 1H) |
| 8-31 | 2,2-dimethylbutyl | 0.38 (n-hexane:AcOEt = 7:3) | (CDCl$_3$): 1.05(s, 9H), 4.07(s, 2H), 4.22(s, 2H), 4.50(s, 2H), 6.25(s, 1H), 7.15(d, 2H), 7.38(d, 2H), 8.83(s, 1H) |

8-32

7-Cyclohexyl-6-(4-diethylaminomethyl-benzyl)-7H-pyrrolo[2,3-d]pyrimidine-2-carbonitrile

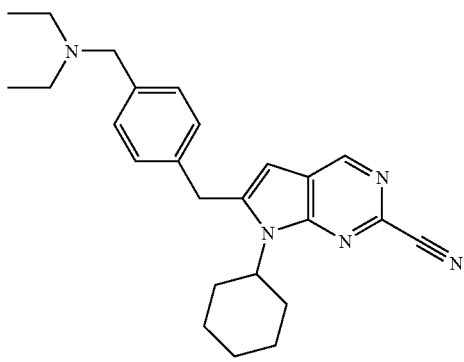

To (4-bromomethyl-benzyl)-7-cyclohexyl-7H-pyrrolo[2,3-d]pyrimidine-2-carbonitrile (0.27 mmol) in THF (2 ml), diethyamine (0.54 mmol) is added at 0° C. and stirred at room temperature for 18 h. After the reaction mixture is quenched with saturated ammonium chloride, the mixture is extracted with AcOEt. The organic layer is washed with brine, dried over magnesium sulfate and evaporated down. The crude product is applied to a chromatography on silica gel, which is eluted with following solvents: 2% MeOH in CH$_2$Cl$_2$ and 3% MeOH in CH$_2$Cl$_2$. The solvent of the latter effluent is removed by evaporation and dried in vacuo to afford the title compound. yield 83.3%, Rf=0.39 (CH$_2$Cl$_2$:MeOH=9:1).

By repeating the procedures described above using appropriate starting materials and conditions the following compounds of formula 8-7 are obtained as identified below in Table 8-7.

TABLE 8-7

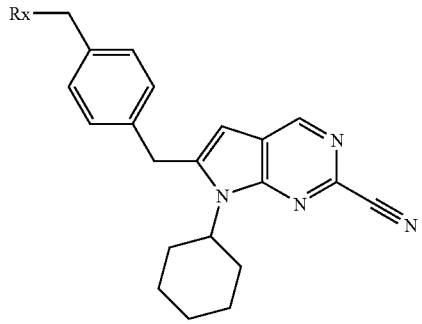

| Expl. No. | Rx | Rf(Solvent) | ¹H-NMR(400 MHz, δ) |
|---|---|---|---|
| 8-32 | (diethylaminomethyl) | 0.39 (CH$_2$Cl$_2$:MeOH = 9:1) | (CDCl$_3$): 1.03(t, 6H), 1.17–1.84(m, 8H), 2.49–2.58(m, 6H), 3.56(s, 2H), 4.06–4.19(m, 1H), 4.17(s, 2H), 6.36(s, 1H), 7.11(d, 2H), 7.30(d, 2H), 8.84(s, 1H) |
| 8-33 | (2,2-dimethoxyethyl)(methyl)amino | 0.43 (CH$_2$Cl$_2$:MeOH = 9:1) | (CDCl$_3$): 1.20–1.87(m, 8H), 2.50–2.60(m, 2H), 2.71(d, 2H), 3.37(s, 6H), 3.78(s, 2H), 4.10–4.14(m, 1H), 4.16(s, 2H), 4.48(s, 1H), 6.32(s, 1H), 7.17(d, 2H), 7.30(d, 2H), 8.83(s, 1H) |
| 8-34 | morpholino | 0.56 (CH$_2$Cl$_2$:MeOH = 9:1) | (CDCl$_3$): 1.17–1.84(m, 8H), 2.40–2.42(m, 4H), 2.49–2.59(m, 2H), 3.48(s, 2H), 3.68–3.70(m, 4H), 4.06–4.13(m, 1H), 4.17(s, 2H), 6.35(s, 1H), 7.15(d, 2H), 7.29(d, 2H), 8.84(s, 1H) |
| 8-35 | 4-methylpiperazin-1-yl | 0.37 (CH$_2$Cl$_2$:MeOH = 9:1) | (CDCl$_3$): 1.14–1.84(m, 8H), 2.29(s, 3H), 2.45–2.60(m, 10H), 3.49(s, 2H), 4.07–4.16(m, 1H), 4.16(s, 2H), 6.35(s, 1H), 7.14(d, 2H), 7.28(d, 2H), 8.84(s, 1H) |
| 8-36 | 4-(2-hydroxyethyl)piperazin-1-yl | 0.44 (CH$_2$Cl$_2$:MeOH = 9:1) | (CDCl$_3$): 1.17–1.84(m, 8H), 2.46–2.58(m, 12H), 2.71–2.86(br, 1H), 3.51(s, 2H), 3.59–3.61(m, 2H), 4.07–4.13(m, 1H), 4.17(s, 2H), 6.36(s, 1H), 7.12(d, 2H), 7.28(d, 2H), 8.84(s, 1H) |
| 8-37 | (2-(diethylamino)ethyl)(methyl)amino | 0.21 (CH$_2$Cl$_2$:MeOH = 9:1) | (CDCl$_3$): 1.02(t, 6H), 1.17–1.87(m, 9H), 2.53–2.70(m, 10H), 3.80(s, 2H), 3.68–.370(m, 4H), 4.10–4.16(m, 1H), 4.16(s, 2H), 6.32(s, 1H), 7.13(d, 2H), 7.29(d, 2H), 8.83(s, 1H) |
| 8-38 | (2-(piperidin-1-yl)ethyl)amino | 0.15 (CH$_2$Cl$_2$:MeOH = 9:1) | (CDCl$_3$): 1.20–1.87(m, 15H), 2.42–2.60(m, 8H), 2.70–2.73(m, 2H), 3.80(s, 2H), 4.10–4.16(m, 1H), 4.16(s, 2H), 6.32(s, 1H), 7.13(d, 2H), 7.29(d, 2H), 8.83(s, 1H) |
| 8-39 | 4-ethylpiperazin-1-yl | 0.26 (CH$_2$Cl$_2$:MeOH = 9:1) | (CDCl$_3$): 1.09(t, 3H), 1.18–1.85(m, 8H), 2.43–2.59(m, 12H), 3.50(s, 2H), 4.07–4.16(m, 1H), 4.16(s, 2H), 6.35(s, 1H), 7.12(d, 2H), 7.28(d, 2H), 8.84(s, 1H) |
| 8-40 | (2-(diethylamino)ethyl)(methyl)amino | 0.37 (CH$_2$Cl$_2$:MeOH = 9:1) | (CDCl$_3$): 1.05(t, 9H), 1.18–1.89(m, 8H), 2.51–2.66(m, 12H), 3.57(s, 2H), 4.12–4.18(m, 1H), 6.36(s, 1H), 7.14(d, 2H), 7.32(d, 2H), 8.85(s, 1H) |

8-41

7-(2,2-Dimethyl-propyl)-6-(4-methoxybenzyl)-7H-pyrrolo[2,3-d]pyrimidine-2-carbonitrile

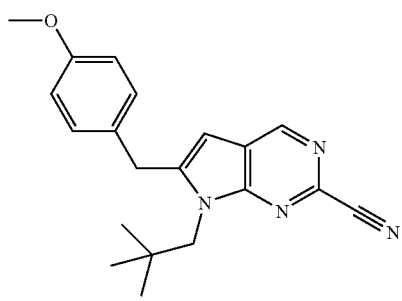

1-Methoxy-4-prop-2-ynyl-benzene (3.01 mmol) is dissolved in DMF (7 ml) at room temperature under nitrogen atmosphere. To the solution, 5-bromo-4-(2,2-dimethyl-propylamino)-pyrimidine-2-carbonitrile (2.01 mmol), triethylamine (6 mmol), copper(I) iodide (0.2 mmol), and dichlorobis(triphenylphosphine)palladium (II) (0.1 mmol) are added successively. The mixture is heated at 80° C. under nitrogen atmosphere for 3 h. After cooling at room temperature, the mixture is diluted with $H_2O$ and extracted with AcOEt. The organic layer is dried over $MgSO_4$ and evaporated in vacuo. The residue is purified by silica gel column chromatography (n-hexane:AcOEt=7:1) to give 7-(2,2-dimethyl-propyl)-6-(4-methoxy-benzyl)-7H-pyrrolo[2,3-d]pyrimidine-2-carbonitrile in 57%.

By repeating the procedure described above using appropriate starting materials and conditions, the following compounds of formula 8-8 are obtained as identified below in Table 8.

TABLE 8-8

8-8

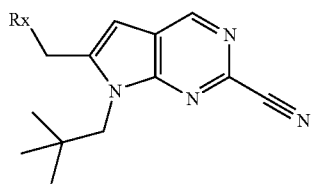

| Expl. No. | Rx | Rf(Solvent) | $^1$H NMR(400 MHz, δ) |
|---|---|---|---|
| 8-41 | 4-methoxybenzyl | 0.30 (n-hexane:AcOEt = 3:1) | (CDCl$_3$): 1.05(s, 9H), 3.81(s, 3H), 4.07(s, 2H), 4.16(s, 2H), 6.23(s, 1H), 6.88(d, 2H), 7.08(d, 2H), 8.82(s, 1H) |
| 8-42 | 4-propoxybenzyl | 0.40 (n-hexane:AcOEt = 5:1) | (CDCl$_3$): 1.02–1.06(m, 12H), 1.79–1.84(m, 2H), 3.92(t, 2H), 4.06(s, 2H), 4.15(s, 2H), 6.23(s, 1H), 6.87(d, 2H), 7.06(d, 2H), 8.82(s, 1H) |
| 8-43 | 4-fluorobenzyl | 0.38 (n-hexane:AcOEt = 5:1) | (CDCl$_3$): 1.05(s, 9H), 4.07(s, 2H), 4.19(s, 2H), 6.21(s, 1H), 7.03–7.07(m, 2H), 7.12–7.16(m, 2H), 8.83(s, 1H) |
| 8-44 | 4-trifluoromethylbenzyl | 0.30 (n-hexane:AcOEt = 5:1) | (CDCl$_3$): 1.06(s, 9H), 4.08(s, 2H), 4.28(s, 2H), 6.22(s, 1H), 7.30(d, 2H), 7.62(d, 2H), 8.85(s, 1H) |
| 8-45 | 4-methylbenzyl | 0.44 (n-hexane:AcOEt = 3:1) | (CDCl$_3$): 1.04(s, 9H), 2.35(s, 3H), 4.07(s, 2H), 4.18(s, 2H), 6.24(s, 1H), 7.15(d, 1H), 7.04(d, 2H), 8.82(s, 1H) |
| 8-46 | 4-ethylbenzyl | 0.56 (n-hexane:AcOEt = 3:1) | (CDCl$_3$): 1.05(s, 9H), 1.24(t, 3H), 2.65(q, 2H), 4.07(s, 2H), 6.25(s, 1H), 7.07(d, 2H), 7.18(d, 2H), 8.82(s, 1H) |
| 8-47 | 4-butylbenzyl | 0.67 (n-hexane:AcOEt = 3:1) | (CDCl$_3$): 0.93(t, 3H), 1.35–1.37(m, 2H), 1.58–1.62(m, 2H), 2.61(t, 2H), 4.07(s, 2H), 4.18(s, 2H), 6.25(s, 1H), 7.06(d, 2H), 7.16(d, 2H), 8.83(s, 1H) |

8-48

7-(2,2-Dimethyl-propyl)-6-[4-(4-ethyl-piperazin-1-ylmethyl)-benzyl]-7H-pyrrolo[2,3-d]pyrimidine-2-carbonitrile

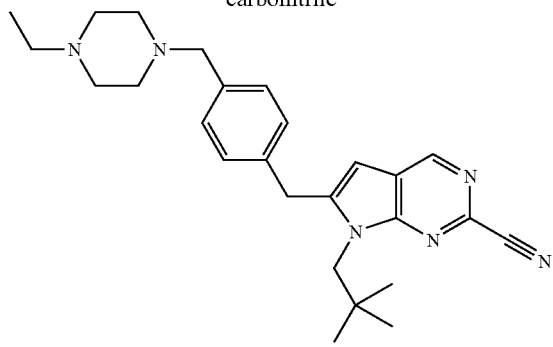

1-Ethyl-piperazine (1.1 mmol) and 6-(4-bromomethyl-benzyl)-7-(2,2-dimethyl-propyl)-7H-pyrrolo[2,3-d]pyrimidine-2-carbonitrile (0.35 mmol) are dissolved in DMF (3 ml) and stirred at room temperature for 3 h. After the reaction mixture is diluted with AcOEt, the organic layer is washed with brine, dried over magnesium sulfate and filtrated. The solvent is evaporated and the residue is purified by chromatography on silica gel using 2% MeOH in $CH_2Cl_2$ and 7% MeOH in $CH_2Cl_2$. The solvent of the latter effluent is removed by evaporation and dried in vacuo to afford crystals. yield 81.8%, Rf=0.34 ($CH_2Cl_2$:MeOH=9:1).

By repeating the procedures described above using appropriate starting materials and conditions the following compounds of formula 8-9 are obtained as identified below in Table 8-9.

TABLE 8-9

8-9

| Expl. No. | Rx | Rf(Solvent) | $^1$H-NMR(400 MHz, δ) |
|---|---|---|---|
| 8-48 | | 0.34 ($CH_2Cl_2$:MeOH = 9:1) | ($CDCl_3$): 1.05(s, 9H), 1.09(t, 3H), 2.41–2.52(m, 10H), 3.52(s, 2H), 4.07(s, 2H), 4.20(s, 2H), 6.24(s, 1H), 7.10(d, 2H), 7.29(d, 2H), 8.88(s, 1H), |
| 8-49 | | 0.57 ($CH_2Cl_2$:MeOH = 9:1) | ($CDCl_3$): 1.05(s, 9H), 2.43–2.46(m, 4H), 3.50(s, 2H), 3.70–3.72(m, 4H), 4.07(s, 2H), 4.20(s, 2H), 6.24(s, 1H), 7.20(d, 2H), 7.30(d, 2H), 8.83(s, 1H), |
| 8-50 | | 0.31 ($CH_2Cl_2$:MeOH = 9:1) | ($CDCl_3$): 1.05(s, 9H), 2.50–2.57(m, 11H), 3.51(s, 2H), 3.61(t, 2H), 4.07(s, 2H), 4.20(s, 2H), 6.25(s, 1H), 7.10(d, 2H), 7.29(d, 2H), 8.83(s, 1H), |
| 8-51 | | 0.30 (n-hexane:AcOEt = 2:1) | ($CDCl_3$): 1.04(s, 9H), 1.56(s, 6H), 4.05(s, 2H), 4.20(s, 2H), 4.67(s, 2H), 6.23(s, 1H), 7.14(d, 2H), 7.35(d, 2H), 8.83(s, 1H), |
| 8-52 | | 0.50 (n-hexane:AcOEt = 1:5) | ($CDCl_3$): 1.04(s, 9H), 3.00(s, 3H), 3.87(s, 2H), 4.10(s, 2H), 4.23(s, 2H), 4.66(s, 2H), 6.22(s, 1H), 7.12(d, 2H), 7.39(d, 2H), 8.82(s, 1H), |

TABLE 8-9-continued

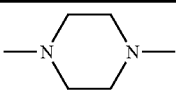

8-9

| Expl. No. | Rx | Rf(Solvent) | $^1$H-NMR(400 MHz, δ) |
|---|---|---|---|
| 8-53 | —N⌒N— | 0.33 (CH$_2$Cl$_2$:MeOH = 9:1) | (CDCl$_3$): 1.05(s, 9H), 2.31(s, 3H), 2.50(m, 8H), 3.52(s, 2H), 4.07(s, 2H), 4.20(s, 2H), 6.24(s, 1H), 7.11(d, 2H), 7.30(d, 2H), 8.83(s, 1H) |
| 8-54 | Et$_2$N— | 0.34 (CH$_2$Cl$_2$:MeOH = 9:1) | (CDCl$_3$): 1.05(s, 9H), 1.07(t, 6H), 2.56(q, 4H), 3.59(s, 2H), 4.07(s, 2H), 4.20(s, 2H), 6.24(s, 1H), 7.11(d, 2H), 7.34(d, 2H), 8.82(s, 1H) |
| 8-55 | Ac-N⌒N— | 0.5 (CH$_2$Cl$_2$:MeOH = 9:1) | (CDCl$_3$): 1.05(s, 9H), 2.08(s, 3H), 2.43(m, 4H), 3.46(t, 2H), 3.52(s, 2H), 4.08(s, 2H), 4.21(s, 2H), 6.25(s, 1H), 7.12(d, 2H), 7.30(d, 2H), 8.83(s, 1H) |
| 8-56 | imidazol-1-yl | 0.58 (CH$_2$Cl$_2$:MeOH = 9:1) | (CDCl$_3$): 1.04(s, 9H), 4.05(s, 2H), 4.22(s, 2H), 4.75(s, 2H), 5.36(s, 1H), 7.18(d, 2H), 7.24–7.30(m, 2H), 7.99(s, 1H), 8.09(s, 1H), 8.83(s, 1H) |

8-57

7-(2,2-Dimethyl-propyl)-6-(4-[1,2,4]triazol-1-ylmethyl-benzyl)-7H-pyrrolo[2,3-d]pyrimidine-2-carbonitrile

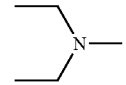

1,2,4-Triazole (0.6 mmol) is dissolved in DMF (1 ml) and sodium hydride (0.6 mmol) is added. The mixture is stirred and 6-(4-bromomethyl-benzyl)-7-(2,2-dimethyl-propyl)-7H-pyrrolo[2,3-d]pyrimidine-2-carbonitrile (0.5 mmol) in DMF (1 ml) is added at 0° C. The mixture is stirred at room temperature for 0.5 h, and quenched with H$_2$O. The mixture is extracted with AcOEt. The organic layer is washed with water and brine, dried over magnesium sulfate and concentrated. The crude product is purified by silica gel column chromatography to give the product in 57% yield. Rf=0.50 (CH$_2$Cl$_2$:MeOH=9:1). $^1$H NMR (400 MHz, CDCl$_3$) δ 1.04(s, 9H), 4.06(s, 2H), 4.22(s, 2H), 5.36(s, 2H), 6.22(s, 1H), 7.18(d, 2H), 7.23-7.39(m, 2H), 7.98(s, 1H), 8.09(s, 1H), 8.83(s, 1H).

8-58

7-(2,2-Dimethyl-propyl)-6-[4-(morpholine-4-carbonyl)-benzyl]-7H-pyrrolo[2,3-d]pyrimidine-2-carbonitrile

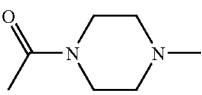

A. 4-Prop-2-ynyl-benzoic acid

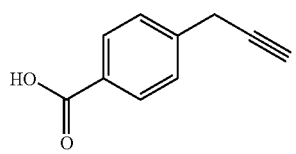

To a solution of 4-prop-2-ynyl-benzaldehyde (10 mmol) in THF (30 ml), amidosurfulic acid (16 mmol) and water (15 ml) solution of sodium chlorite (30 mmol) are added. The reaction mixture is stirred at room temperature for 2 h. Water is added and then aqueous layer is extracted with two 50 ml portions of $CH_2Cl_2$. The combined extracts are washed with brine, dried over sodium sulfate and concentrated under vacuum to give crude product which is purified by silica gel column chromatography. Yield: 62%. Rf=0.44 (n-hexane:AcOEt=7:3)

B. 4-[2-Cyano-7-(2,2-dimethyl-propyl)-7H-pyrrolo[2,3-d]pyrimidin-6-ylmethyl]-benzoic acid

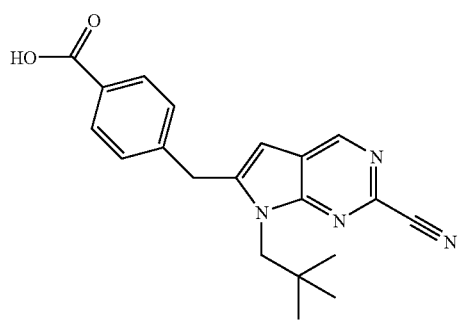

To a solution of 4-prop-2-ynyl-benzoic acid (6.3 mmol) and 5-bromo-4-(2,2-dimethyl-propylamino)-pyrimidine-2-carbonitrile (4.8 mmol) in DMF (30 ml), triethylamine(14.4 mmol), dichlorobis(triphenylphosphine)palladium (II) (0.48 mmol) and copper (I) iodide (0.96 mmol) are added. The reaction mixture is heated at 75° C. ca. for 18 h. Saturated aqueous solution of ammonium chloride is added to the reaction mixture and then aqueous layer is extracted with two 150 ml portions of AcOEt. The combined extracts are washed with brine, dried over sodium sulfate and concentrated under vacuum to give crude product which is purified by silica gel column chromatography. Yield: 51%. Rf=0.18 (AcOEt only)

C. 7-(2,2-Dimethyl-propyl)-6-[4-(morpholine-4-carbonyl-benzyl]-7H-pyrrolo[2,3-d]pyrimidine-2-carbonitrile

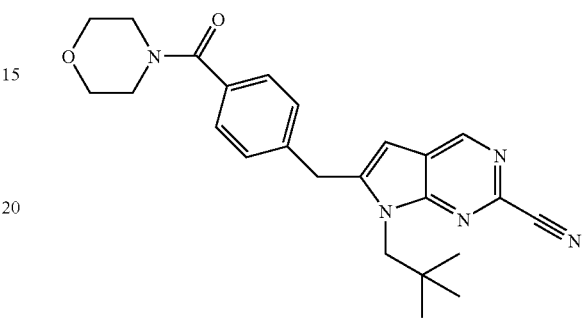

To a solution of 4-[2-cyano-7-(2,2-dimethyl-propyl)-7H-pyrrolo[2,3-d]pyrimidin-6-ylmethyl]-benzoic acid (0.3 mmol) in DMF (3 ml), morpholine (0.6 mmol), water soluble carbodiimide hydrochloride (0.45 mmol) and 1-hydroxybenzotriazole hydrate (0.45 mmol) are added at 0° C. The reaction mixture is stirred at room temperature for 2 days. The mixture is quenched with saturated ammonium chloride and extracted with two 50 ml portions of AcOEt. The combined extracts are washed with brine, dried over sodium sulfate and concentrated under vacuum to give crude product. Purification of the residue by silica gel column chromatography affords title compound in 90% yield.

By repeating the procedures described above using appropriate starting materials and conditions the following compounds of formula 8-10 are obtained as identified below in Table 8-10.

TABLE 8-10

Formula 8-10

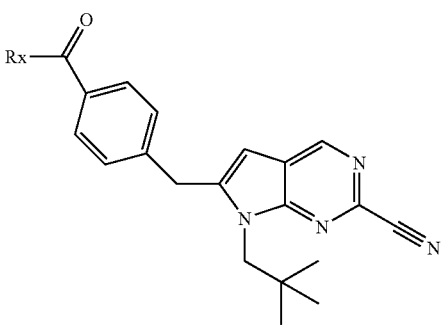

| Expl. No. | Rx | Rf(Solvent) | $^1$H NMR(400 MHz, δ) |
|---|---|---|---|
| 8-58 | ![morpholine] | 0.43 (AcOEt only) | (CDCl$_3$): 1.05(s, 9H), 3.71(m, 8H), 4.07(s, 2H), 4.25(s, 2H), 6.26(s, 1H), 7.22(d, 2H), 7.41(d, 2H), 8.85(s, 1H) |

TABLE 8-10-continued

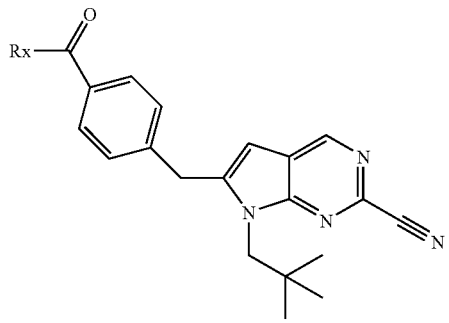

Formula 8-10

| Expl. No. | Rx | Rf(Solvent) | ¹H NMR(400 MHz, δ) |
|---|---|---|---|
| 8-59 | \N—<br>/ | 0.47<br>(n-hexane:AcOEt = 1:1) | (CDCl₃): 1.05(s, 9H), 3.00(brs, 3H), 3.12(brs, 3H), 4.07(s, 2H), 4.25(s, 2H), 6.26(s, 1H), 7.20(d, 2H), 7.42(d, 2H), 8.85(s, 1H) |
| 8-60 | —N⌒N— | 0.46<br>(CH₂Cl₂:MeOH = 9:1) | (CDCl₃): 1.05(s, 9H), 2.33(s, 3H), 2.43(m, 4H), 3.46(m, 2H), 3.80(m, 2H), 4.07(s, 2H), 4.25(s, 2H), 6.26(s, 1H), 7.21(d, 2H), 7.41(d, 2H), 8.85(s, 1H) |
| 8-61 | O⌒N—N—<br>H | 0.14<br>(AcOEt only) | (CDCl₃): 1.05(s, 9H), 2.97(m, 4H), 3.88(m, 4H), 4.06(s, 2H), 4.27(s, 2H), 6.22(s, 1H), 6.78(brs, 1H), 7.24(d, 2H), 7.74(d, 2H), 8.84(s, 1H) |

8-62

N.-{4-[2-Cyano-7-(2,2-dimethyl-propyl)-7H-pyrrolo[2,3-d]pyrimidin-6-ylmethyl]-phenyl}-methanesulfonamide

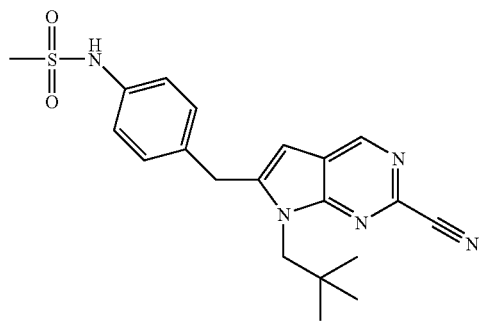

A. N.-(4-Prop-2-ynyl-phenyl)-methanesulfonamide

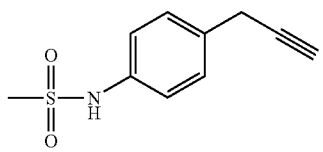

To a solution of 4-prop-2-ynyl-phenylamine (3.05 mmol) in pyridine(3 ml), methanesulfonyl chloride (4.6 mmol) is added. The reaction mixture is stirred at room temperature for 1 h. The mixture is quenched with saturated ammonium chloride and extracted with two 50 ml portions of AcOEt. The combined extracts are washed with brine, dried over magnesium sulfate and concentrated under vacuum to give 600 mg of crude product.

Rf=0.54 (n-hexane:AcOEt=7:3)

B. N.-{4-[2-Cyano-7-(2,2-dimethyl-propyl)-7H-pyrrolo[2,3-d]pyrimidin-6-ylmethyl]-phenyl}-methanesulfonamide

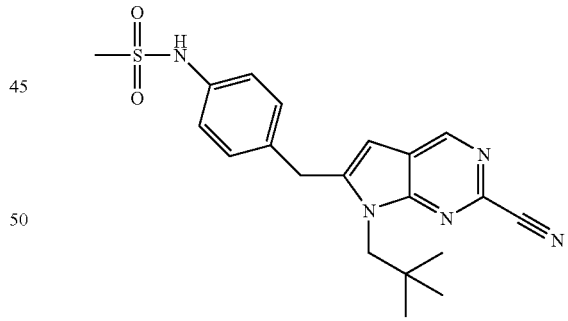

To a solution of N.-(4-prop-2-ynyl-phenyl)-methanesulfonamide (1.0 mmol) and 5-bromo-4-(2,2-dimethyl-propylamino)-pyrimidine-2-carbonitrile (0.5 mmol) in DMF (5 ml), triethylamine (1.5 mmol), dichlorobis-dichlorobis(triphenylphosphine)palladium (II) (0.05 mmol) and copper (I) iodide (0.1 mmol) is added. The reaction mixture is heated at 70° C. ca. for 2.5 h. The mixture is quenched with saturated ammonium chloride and extracted with two 50 ml portions of AcOEt. The combined extracts are washed with brine, dried over sodium sulfate and concentrated under vacuum to give crude product, which is purified by silica gel column chromatography. Yield: 60.7%. Rf=0.55 (n-hexane:AcOEt=1:1)

¹H NMR (400 MHz, CDCl₃) δ1.05(s, 9H), 3.04(s, 3H), 4.07(s, 2H), 4.20(s, 2H), 6.24(s, 1H), 6.40(brs, 1H), 7.16 (d, 2H), 7.21(d, 2H), 8.84(s, 1H).

8-63

N.-{4-[2-Cyano-7-(2,2-dimethyl-propyl)-7H-pyrrolo[2,3-d]pyrimidin-6-ylmethyl]-phenyl}-methanesulfonamide

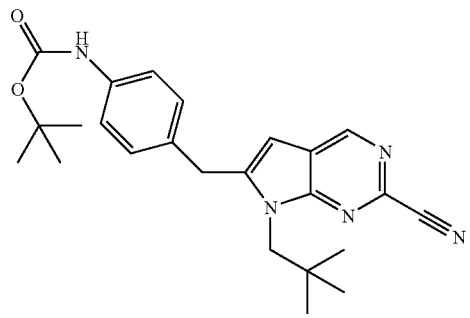

A. (4-Prop-2-ynyl-phenyl)-carbamic acid tert-butyl ester

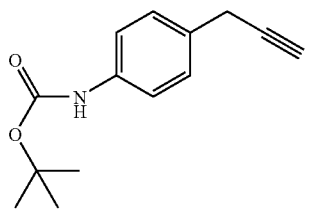

To a solution of 4-prop-2-ynyl-phenylamine (85.4 mmol) and triethylamine (102.5 mmol) in THF (200 ml), di-t-butyl dicarbonate (128.1 mmol) is added. The reaction mixture is stirred at room temperature for 17 h. The reaction mixture is quenched with saturated ammonium chloride and extracted with two 150 ml portions of AcOEt. The combined extracts are washed with brine, dried over sodium sulfate and concentrated under vacuum to give 22.6 g of crude product. Purification of the residue by silica gel column chromatography affords title compound in quantitative yield.

Rf=0.70 (n-hexane:AcOEt=7:3)

B. N.-{4-[2-Cyano-7-(2,2-di(ethyl-propyl)-7H-pyrrolo[2,3-d]pyrimidin-6-ylmethyl]-phenyl}-methanesulfonamide

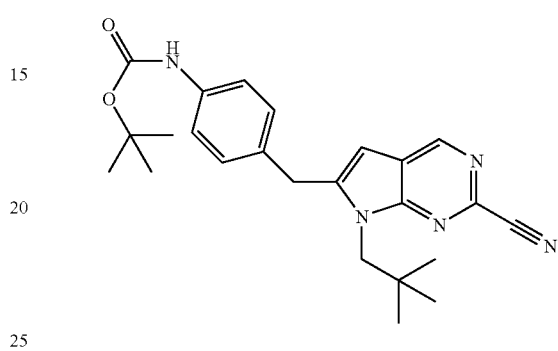

To a solution of (4-prop-2-ynyl-phenyl)-carbamic acid .tert.-butyl ester (7.5 mmol) and 5-bromo-4-(2,2-dimethyl-propylamino)-pyrimidine-2-carbonitrile (5.0 mmol) in DMF (30 ml), triethylamine (15.0 mmol), dichlorobisdichlorobis(triphenylphosphine)palladium (II) (0.5 mmol) and copper (I) iodide (1.0 mmol) are added. The reaction mixture is heated at 80° C. ca. for 6 h. The mixture is quenched with saturated ammonium chloride and extracted with two 200 ml portions of AcOEt. The combined extracts are washed with brine, dried over sodium sulfate and concentrated under vacuum to give 3.01 g of crude product which is purified by silica gel column chromatography. Yield: 63%.

By repeating the procedures described above using appropriate starting materials and conditions the following compounds of formula 8-11 are obtained as identified below in Table 8-11.

TABLE 8-11

8-11

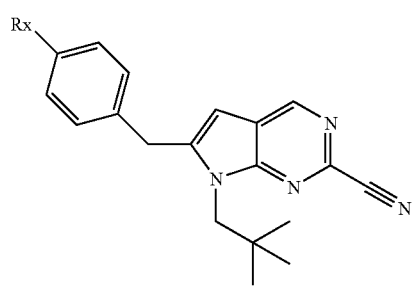

| Expl. No. | Rx | Rf(Solvent) | ¹H NMR(400 MHz, δ) |
|---|---|---|---|
| 8-64 | —N(CH₃)₂ group | 0.71 (n-hexane:AcOEt = 1:1) | (CDCl₃): 1.04(s, 9H), 2.95(s, 6H), 4.07(s, 2H), 4.11(s, 2H), 6.25(s, 1H), 6.70(d, 2H), 7.01(d, 2H), 8.80(s, 1H) |

TABLE 8-11-continued 8-11

| Expl. No. | Rx | Rf(Solvent) | ¹H NMR(400 MHz, δ) |
|---|---|---|---|
| 8-63 | [tert-butyl carbamate group] | 0.40 (n-hexane:AcOEt = 7:3) | (CDCl₃): 1.04(s, 9H), 1.52(s, 9H), 4.06(s, 2H), 4.16(s, 2H), 6.23(s, 1H), 6.48(brs, 1H), 7.08(d, 2H), 7.35(d, 2H), 8.82(s, 1H) |

8-65

6-(4-Amino-benzyl)-7-(2,2-dimethyl-propyl)-7H-pyrrolo[2,3-d]pyrimidine-2-carbonitrile To a solution of N.-{(4-[2-Cyano-7-(2,2-dimethyl-propyl)-7H-pyrrolo[2,3-d]pyrimidin-6-ylmethyl]-phenyl}-methanesulfonamide (91 mmol) in 1,2-dichloroethan(5 ml), montmorillonite K-10 (5.72 g) is added. The reaction mixture is refluxed for 15 h and then filtered on glass filter. The filtrates are concentrated under vacuum. Purification of the residue by silica gel column chromatography affords title compound in 79% yield. Rf=0.37 (n-hexane:AcOEt=1:1)

¹H NMR(400 MHz, CDCl₃) δ 1.02(s, 9H), 2.38(s, 3H), 3.55 (s, 3H), 4.02(s, 2H), 4.14(s, 2H), 6.21(s, 1H), 7.04(d, 2H), 7.19(d, 2H), 7.31(s, 1H), 7.52(brs, 1H), 8.82(s, 1H)

8-66

7-(2,2-Dimethyl-propyl)-6-(4-pyrrol-1-yl-benzyl)-7H-pyrrolo[2,3-d]pyrimidine-2-carbonitrile To a solution of 6-(4-amino-benzyl)-7-(2,2-dimethyl-propyl)-7H-pyrrolo[2,3-d]pyrimidine-2-carbonitrile (0.32 mmol) in acetic acid (1 ml) is slowly added 2,5-dimethoxy-tetrahydro-furan (0.35 mmol). The reaction mixture is refluxed for 2 h and cooled. The mixture is quenched with saturated ammonium chloride and extracted with AcOEt. The organic layer is washed with saturated ammonium chloride and brine, dried over magnesium sulfate and evaporated down. The crude product is applied to a silica gel column chromatography, which is eluted with following solvents: n-hexane:AcOEt=6:1 (v/v) and n-hexane:AcOEt=4:1 (v/v). The solvent of the latter effluent is removed by evaporation and dried in vacuo to afford the title compound. yield 60.2%, Rf=0.55 (n-hexane:AcOEt=2:1). ¹H-NMR (400 MHz, CDCl₃) δ 1.06(s, 9H), 4.09(s, 2H), 4.24(s, 2H), 6.27(s, 1H), 6.35-6.36(m, 2H), 7.16-7.17(m, 2H), 7.21(d, 2H), 7.38(d, 2H), 8.84(s, 1H)

8-67

Butane-1-sulfonic acid {4-[2-cyano-7-(2,2-dimethyl-propyl)-7H-pyrrolo[2,3-d]pyrimidin-6-ylmethyl]-phenyl}-amide

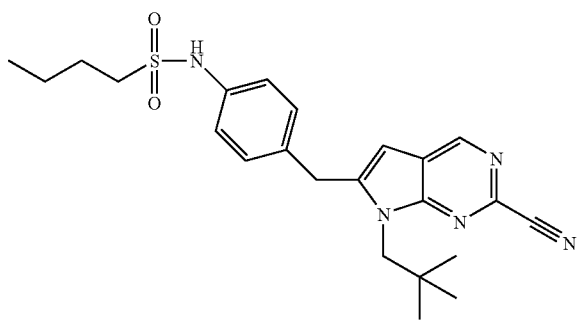

To a solution of 6-(4-amino-benzyl)-7-(2,2-dimethyl-propyl)-7H-pyrrolo[2,3-d]pyrimidine-2-carbonitrile (0.3 mmol) in $CH_2Cl_2$ (5 ml) are slowly added triethylamine (0.36 mmol) and 1-butanesulfonyl chloride (0.36 mmol) at 0° C. The reaction mixture is stirred at room temperature for 15 h. The mixture is quenched with saturated ammonium chloride and extracted with two 50 ml portions of $CH_2Cl_2$. The combined extracts are washed with brine, dried over sodium sulfate and concentrated under vacuum to give crude product. Purification of the residue by silica gel column chromatography affords title compound in 39% yield.

By repeating the procedures described above using appropriate starting materials and conditions the following compounds of formula 8-12 are obtained as identified below in Table 8-12.

TABLE 8-12

8-12

| Expl. No. | Rx | Rf(Solvent) | $^1$H NMR(400 MHz, δ) |
|---|---|---|---|
| 8-67 | n-butyl | 0.57 (n-hexane:AcOEt = 1:1) | (CDCl$_3$): 0.91(t, 3H), 1.05(s, 9H), 1.43(hex, 2H), 1.82(qui, 2H), 3.10(t, 2H), 4.20(s, 2H), 6.24(s, 1H), 6.53(brs, 1H), 7.14(d, 2H), 7.20(d, 2H), 8.84(s, 1H). |
| 8-68 | isopropyl | 0.63 (n-hexane:AcOEt = 1:1) | (CDCl$_3$): 1.05(s, 9H), 1.41(s, 3H), 1.42(s, 3H), 3.31(m, 1H), 4.07(s, 2H), 4.18(s, 2H), 6.24(s, 1H), 6.28(brs, 1H), 7.13(d, 2H), 7.21(d, 2H), 8.84(s, 1H) |
| 8-69 | 4-chlorophenyl | 0.64 (n-hexane:AcOEt = 1:1) | (CDCl$_3$): 1.03(s, 9H), 4.02(s, 2H), 4.16(s, 2H), 6.16(s, 1H), 6.45(brs, 1H), 7.05(d, 2H), 7.43(d, 2H), 7.70(d, 2H), 8.84(s, 1H) |
| 8-70 | 1,2-dimethylimidazolyl | 0.75 (CH$_2$Cl$_2$:MeOH = 9:1) | (CDCl$_3$): 1.02(s, 9H) 2.38(s, 3H), 3.55(s, 3H), 4.02(s, 2H), 4.14(s, 2H), 6.21(s, 1H), 7.04(d, 2H), 7.19(d, 2H), 7.31(s, 1H), 7.52(brs, 1H), 8.82(s, 1H) |
| 8-71 | dimethylamino | 0.52 (n-hexane:AcOEt = 1:1) | (CDCl$_3$): 1.04(s, 9H), 2.87(s, 6H), 4.06(s, 2H), 4.18(s, 2H), 6.23(s, 1H), 6.32(brs, 1H), 7.11(d, 2H), 7.15(d, 2H), 8.84(s, 1H) |
| 8-72 | ethyl | 0.55 (n-hexane:AcOEt = 1:1) | (CDCl$_3$): 1.05(s, 9H), 1.40(t, 3H), 3.15(q, 3H), 4.07(s, 2H), 4.19(s, 2H), 6.24(s, 1H), 6.30(brs, 1H), 7.14(d, 2H), 7.20(d, 2H), 8.84(s, 1H) |
| 8-73 | n-propyl | 0.50 (n-hexane:AcOEt = 1:1) | (CDCl$_3$): 1.05(s, 9H), 1.05(t, 3H), 1.88(m, 2H), 3.09(t, 2H), 4.07(s, 2H), 4.19(s, 2H), 6.24(s, 1H), 6.27(brs, 1H), 7.14(d, 2H), 7.19(d, 2H), 8.84(s, 1H) |

TABLE 8-12-continued 8-12

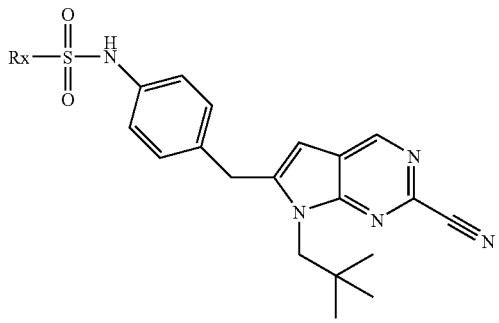

| Expl. No. | Rx | Rf(Solvent) | ¹H NMR(400 MHz, δ) |
|---|---|---|---|
| 8-74 | ⟋⟍ (allyl) | 0.42 (n-hexane:AcOEt = 1:1) | (CDCl$_3$): 1.04(s, 9H), 4.06(s, 2H), 4.18(s, 2H), 5.99(d, 1H), 6.23(s, 1H), 6.31(d, 1H), 6.58(q, 1H), 6.60(brs, 1H), 7.12(d, 2H), 7.17(d, 2H), 8.84(s, 1H) |
| 8-75 | ⟋O⟍ | 0.42 (n-hexane:AcOEt = 1:1) | (CDCl$_3$): 1.05(s, 9H), 3.24(t, 2H), 3.43(s, 3H), 3.85(t, 2H), 4.07(s, 2H), 4.20(s, 2H), 6.25(s, 1H), 6.47(brs, 1H), 7.14(d, 2H), 7.24(d, 2H), 8.84(s, 1H) |
| 8-76 | Cl⟍⟋⟍ | 0.30 (n-hexane:AcOEt = 7:3) | (DMSO-d$_6$): 0.99(s, 9H), 2.11(m, 2H), 3.22(t, 2H), 3.72(t, 2H), 4.13(s, 2H), 4.26(s, 2H), 6.35(s, 1H), 7.04(d, 2H), 7.20(d, 2H), 7.25(s, 1H), 9.01(s, 1H), 9.89(brs, 1H) |
| 8-77 | N-methylimidazolyl | 0.68 (CH$_2$Cl$_2$:MeOH = 9:1) | (DMSO-d$_6$): 0.97(s, 9H), 3.64(s, 3H), 4.10(s, 2H), 4.19(s, 2H), 6.30(s, 1H), 7.12(s, 4H), 7.73(s, 1H), 7.79(s, 1H), 9.00(s, 1H), 10.17(brs, 1H) |
| 8-78 | H$_2$N— | 0.31 (n-hexane:AcOEt = 1:1) | (CDCl$_3$): 1.05(s, 9H), 3.82(m, 2H), 4.08(s, 2H), 4.22(s, 2H), 6.25(s, 1H), 6.84(brs, 1H), 7.20(d, 2H), 7.26(d, 2H), 8.86(s, 1H) |
| 8-79 | CF$_3$-ethyl | 0.65 (n-hexane:AcOEt = 1:1) | (CDCl$_3$): 1.02(s, 9H), 2.38(s, 3H), 3.55(s, 3H), 4.02(s, 2H), 4.14(s, 2H), 6.21(s, 1H), 7.04(d, 2H), 7.19(d, 2H), 7.31(s, 1H), 7.52(brs, 1H), 8.82(s, 1H) |

8-80

N-{4-[2-Cyano-7-(2,2-dimethyl-propyl)-7H-pyrrolo[2,3-d]pyrimidin-6-ylmethyl]-phenyl}-N-methyl-methanesulfonamide

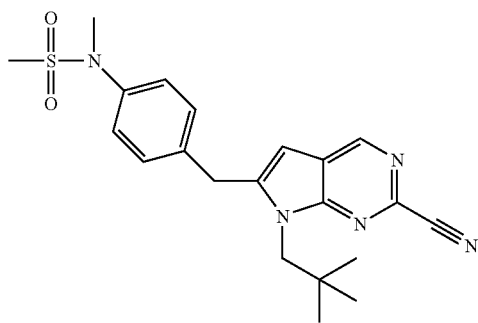

To a solution of .N.-{4-[2-cyano-7-(2,2-dimethyl-propyl)-7H-pyrrolo[2,3-d]pyrimidin-6-ylmethyl]-phenyl}-methanesulfonamide (0.377 mmol) in DMF (5ml), potassium carbonate (0.453 mmol) and methyliodide (0.453 mmol) is added at 0° C. The reaction mixture is stirred at room temperature for 21 h. The mixture is quenched with saturated ammonium chloride and extracted with two 50 ml portions of AcOEt. The combined extracts are washed with brine, dried over sodium sulfate and concentrated under vacuum to give 220 mg of crude product. Purification of the residue by column chromatography affords title compound in 92% yield. Rf=0.35 (n-hexane:AcOEt=7:3)

¹H NMR(400 MHz, CDCl$_3$) δ 1.05(s, 9H), 2.86(s, 3H), 3.33(s, 3H), 4.08(s, 2H), 4.22(s, 2H), 6.26(s, 1H), 7.19 (d, 2H), 7.36(d, 2H), 8.85(s, 1H).

8-81

N-{4-[2-Cyano-7-(2,2-dimethyl-propyl)-7H-pyrrolo[2,3-d]pyrimidin-6-ylmethyl]-phenyl}-acetamide

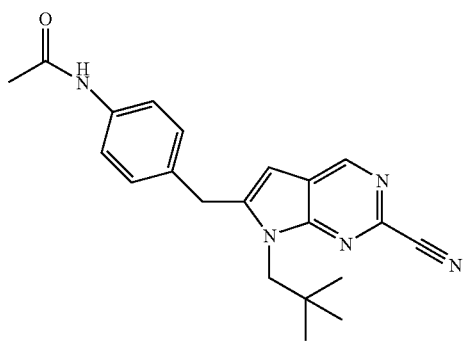

To a solution of 6-(4-amino-benzyl)-7-(2,2-dimethyl-propyl)-7H-pyrrolo[2,3-d]pyrimidine-2-carbonitrile (0.3 mmol) in $CH_2Cl_2$ (4 mL), triethylamine(0.36 mmol) and acetyl chloride (0.36 mmol) is added at 0° C. The reaction mixture stirred at room temperature for 1 day. The mixture is quenched with saturated ammonium chloride and extracted with two 50 ml portions of AcOEt. The combined extracts are washed with brine, dried over sodium sulfate and concentrated under vacuum to crude product. Purification of the residue by silica gel column chromatography affords title compound in 84% yield.

Rf=0.22 (n-hexane:AcOEt=1:1) $^1$H NMR (400 MHz, $CDCl_3$) δ 1.04(s, 9H), 2.19(s, 3H), 4.06(s, 2H), 4.18 (s, 2H), 6.24(s, 1H), 7.11(d, 2H), 7.18(br s, 1H), 7.49(d, 2H), 8.83(s, 1H).

8-82

N-{4-[2-Cyano-7-(2,2-dimethyl-propyl)-7H-pyrrolo[2,3-d]pyrimidin-6-ylmethyl]-phenyl}-butyramide

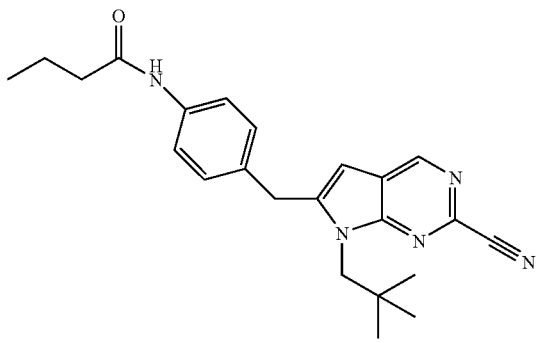

To a solution of 6-(4-amino-benzyl)-7-(2,2-dimethyl-propyl)-7H-pyrrolo[2,3-d]pyrimidine-2-carbonitrile (0.3 mmol) in DMF (4 ml), butyric acid (0.36 mmol), water soluble carbodiimide (0.45 mmol) and 1-hydroxybenzotriazole hydrate (0.45 mmol) are added at 0° C. and then the reaction mixture is stirred at room temperature for 1 day. The reaction mixture is quenched with ammonium chloride and extracted with AcOEt. The organic layer is washed with brine, dried over sodium sulfate and evaporated in vacuo to give 129 mg of crude product. Purification of the residue by silica gel column chromatography affords the title compound in 96% yield. Rf=0.46 (n-hexane:AcOEt=1:1)

$^1$H NMR(400 MHz, $CDCl_3$) δ 1.02(t, 3H), 1.04(s, 9H), 1.70.1.85(m, 2H), 2.35(t, 2H), 4.06(s, 2H), 4.18(s, 2H), 6.24(s, 1H), 7.11 (d, 2H), 7.12(br s, 1H), 7.51(d, 2H), 8.82(s, 1H).

8-83

N-{4-[2-Cyano-7-(2,2-dimethyl-propyl)-7H-pyrrolo[2,3-d]pyrimidin-6-ylmethyl]-phenyl}-succinamic acid

146

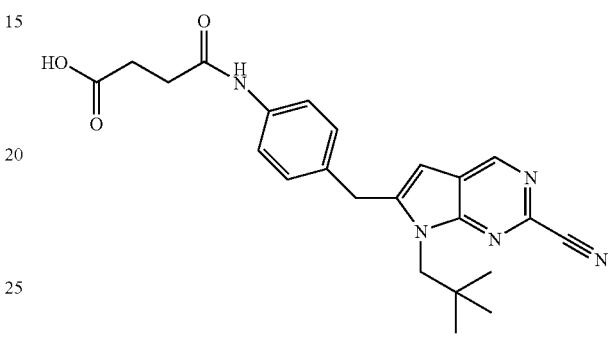

To a solution of 6-(4-amino-benzyl)-7-(2,2-dimethyl-propyl)-7H-pyrrolo[2,3-d]pyrimidine-2-carbonitrile (0.626 mmol) in THF (3 ml), succinic anhydride (0.626 mmol) is added. The reaction mixture is stirred at room temperature for 16 h. The reaction mixture is concentrated under vacuum. Purification of the residue by silica gel column chromatography affords the title compound in quantitative yield.

Rf=0.49($CH_2Cl_2$:MeOH=9:1) $^1$H NMR(400 MHz, $CDCl_3$) δ 1.05(s, 9H), 2.56(s, 4H), 4.18(s, 2H), 4.30(s, 2H), 6.40(s, 1H), 7.25(d, 2H), 7.63(d, 2H), 9.06(s, 1H), 10.25(br s, 1H).

8-84

N-{1-[2-Cyano-7-(2,2-dimethyl-propyl)-7H-pyrrolo[2,3-d]pyrimidin-6-ylmethyl]-phenyl}-succinamic acid

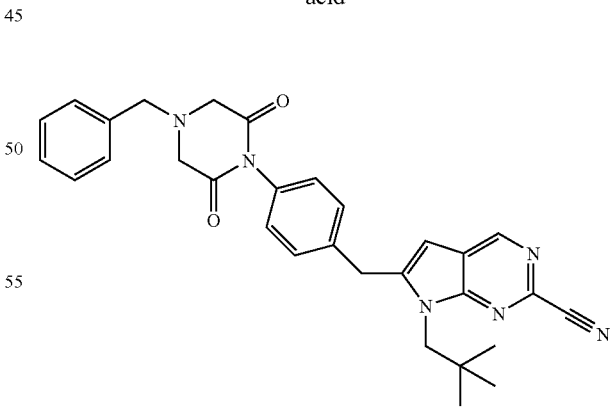

To a suspension of N-benzyliminodiacetic acid (2 mmol) in THF (15 ml), 1,1'-carbonyldiimidazole (4.4 mmol) is added. The reaction mixture is refluxed for 10 minutes. 6-(4-Amino-benzyl)-7-(2,2-dimethyl-propyl)-7.H.-pyrrolo[2,3-.d.]pyrimidine-2-carbonitrile is added to the reaction mixture and then the mixture is stirred at 80° C. for 1 day. The mixture is quenched with saturated ammonium chloride and extracted with two 100 ml portions of AcOEt. The organic layer is washed with brine, dried over sodium sulfate and concentrated under vacuum. Purification of the residue by silica gel column chromatography affords 874 mg of title compound in 86% yield.

Rf=0.48 (n-hexane:AcOEt=7:3) ¹H NMR (400 MHz, CDCl₃) δ 1.05(s, 9H), 3.58(s, 4H), 3.73 (s, 2H), 4.10(s, 2H), 4.25(s, 2H), 6.30(s, 1H), 7.12(d, 2H), 7.25(d, 2H), 7.35(m, 5H), 8.85(s, 1H)

Example 9 Describes the Preparation of phthalimide, hydantoin, oxazolidinone and 2,6-dioxo-piperazine Derivatives

Example 9-1

7-(2,2-Dimethyl-propyl)-6-(1,3-dioxo-1,3-dihydro-isoindol-2-ylmethyl)-7H-pyrrolo[2,3-d]pyrimidine-2-carbonitrile

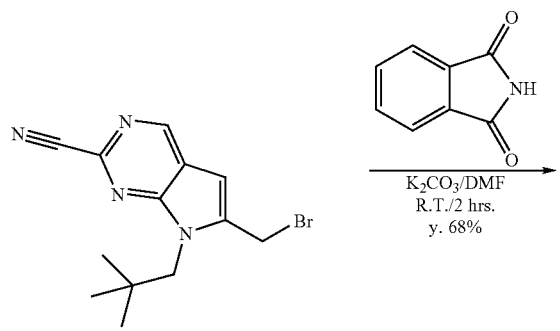

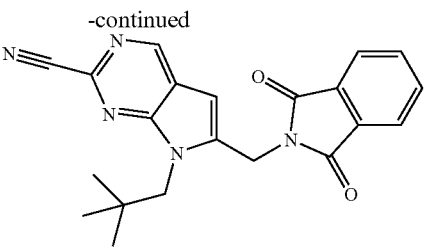

To a solution of 500 mg (1.63 mmoles) of phenylphthalimide in 20 ml of DMF, 315 mg (2.28 mmoles) of $K_2CO_3$ and 500 mg (1.63 mmoles) of 6-bromomethyl-7-(2,2-dimethyl-propyl)-7H-pyrrolo[2,3-d]pyrimidine-2-carbonitrile are added successively and the mixture is stirred for 2 hours at ambient temperature. The reaction mixture is quenched with ice-water and extracted with AcOEt. The combined extracts are washed with $H_2O$, brine and dried over $MgSO_4$. Chromatography on silica gel (eluent: n-Hexane:AcOEt=2:1) give 412 mg of desired 7-(2,2-dimethyl-propyl)-6-(1,3-dioxo-1,3-dihydro-isoindol-2-ylmethyl)-7H-pyrrolo[2,3-d]pyrimidine-2-carbonitrile in 68% yield.

NMR (400 MHz, CDCl₃, □): 1.08 (s, 9H), 4.39 (s, 2H), 5.12 (s, 2H), 6.70 (s, 1H), 7.75-7.80 (m, 22), 7.85-7.92 (m, 2 H), 8.88 (s, 1 H) Rf=0.24 (n-Hexane:AcOEt=1:1)

By repeating the procedures described above using appropriate starting materials and conditions the following compounds of formula 9-1 are obtained as identified below in Table 9-1.

TABLE 9-1

9-1

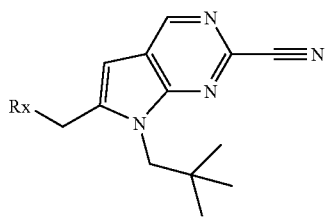

| Expl. No. | Rx | Rf(solvent) | ¹H NMR(400 MHz, δ) |
|---|---|---|---|
| 9-2 | ![structure: N-methylglutarimide] | 0.51 (n-Hexane:AcOEt = 1:5) | CDCl₃: 1.02(s, 9H), 1.97–2.04(m, 2H), 2.73(t, 4H), 4.54(s, 2H), 5.17(s, 2H), 6.48(s, 1H), 8.86(s, 1H) |
| 9-3 | ![structure: 1,3-dimethylquinazoline-2,4-dione] | 0.32 (nHexane:AcOEt = 1:1) | CDCl₃: 1.06(s, 9H), 3.76(s, 3H), 4.30(s, 2H), 5.63(s, 2H), 6.85(s, 1H), 7.77–7.83(m, 2H), 8.42–8.44(m, 1H), 8.99(s, 1H) |

TABLE 9-1-continued
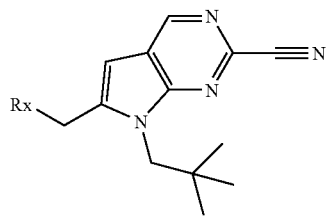
9-1
| Expl. No. | Rx | Rf(solvent) | $^1$H NMR(400 MHz, δ) |
|---|---|---|---|
| 9-4 | | 0.36(AcOEt) | CDCl$_3$: 1.03(s, 9H), 3.03(s, 3H), 3.92(s, 2H), 4.37(s, 2H), 4.93(s, 2H), 6.75(s, 1H), 8.90(s, 1H) |
| 9-5 | | 0.7 (CH$_2$Cl$_2$:Acetone = 9:1) | CDCl$_3$: 1.04(s, 9H), 1.59(s, 6H), 4.34(s, 2H), 4.96(s, 2H), 6.71(s, 1H), 8.95 (s, 1H) |
| 9-6 | | 0.52 (n-Hexane:AcOEt = 1:1) | CDCl$_3$: 1.08(s, 9H), 4.39(s, 2H), 5.18(s, 2H), 6.73(s, 1H), 8.08(d, 1H), 8.63(dd, 1H), 8.69(d, 1H), 8.90(s, 1H) |
| 9-7 | | 0.20 (n-Hexane:AcOEt = 1:1) | CDCl$_3$: 1.08(s, 9H), 4.38(s, 2H), 5.15(s, 2H), 6.72(s, 1H), 7.78(dd, 1H), 8.90(s, 1H), 9.11(d, 1H), 9.19(d, 1H) |
| 9-8 | | 0.52(AcOEt) | CDCl$_3$: 1.03(s, 9H), 1.40(s, 6H), 2.90(s, 3H), 4.35(s, 2H), 4.93(s, 2H), 6.65 (s, 1H), 8.90(s, 1H) |
| 9-9 | | 0.27 (n-Hexane:AcOEt = 1:3) | (CDCl$_3$: 1.13(s, 9H), 2.66(s, 3H), 4.28(s, 2H), 5.54(s, 2H), 6.18(s, 1H), 7.48–7.53(m, 1H), 7.68–7.72(m, 1H), 7.78–7.84(m, 1H), 8.22–8.27(m, 1H), 8.81(s, 1H) |
| 9-10 | | 0.34(AcOEt) | CDCl$_3$: 1.03(s, 9H), 4.04(s, 2H), 4.36(s, 2H), 4.95(s, 2H), 5.15(brs, 2H), 6.74(s, 1H), 8.91(s, 1H) |

TABLE 9-1-continued
9-1
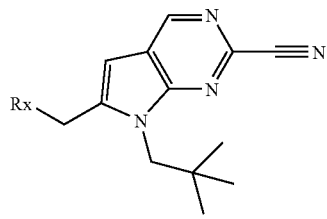
| Expl. No. | Rx | Rf(solvent) | ¹H NMR(400 MHz, δ) |
|---|---|---|---|
| 9-11 | | 0.24(AcOEt) | CDCl₃: 1.02(s, 9H), 2.75–2.85(m, 2H), 3.45–3.55(m, 2H), 4.35(s, 2H), 5.18(s, 2H), 5.74(brs, 2H), 6.57(s, 1H), 8.87(s, 1H) |
| 9-12 | | 0.48 (n-Hexane:AcOEt = 1:1) | CDCl₃: 1.08(s, 9H), 4.43(s, 2H), 5.57(s, 2H), 6.54(s, 1H), 6.95–7.05(m, 1H), 7.25–7.35(m, 1H), 7.99(s, 1H), 8.82(s, 1H) |
| 9-13 | | 0.46 (CHCl₃:Acetone = 9:1) | CDCl₃: 1.02(s, 9H), 4.01(s, 2H), 4.35(s, 2H), 5.04(s, 2H), 6.70(s, 1H), 8.92(s, 1H) |
| 9-14 | | 0.36 (n-Hexane:AcOEt = 1:1) | CDCl₃: 1.03(s, 9H), 1.33–1.44(m, 3H), 1.57–1.74(m, 2H), 1.83–1.94(m, 5H), 4.33(s, 2H), 4.91(s, 2H), 6.04(s, 1H), 6.63(s, 1H), 8.91(s, 1H) |
| 9-15 | | 0.50(AcOEt) | CDCl₃: 1.04(s, 9H), 1.76–1.85(m, 4H), 1.88–1.97(m, 2H), 2.13–2.24(m, 2H), 4.34(s, 2H), 4.93(s, 2H), 5.51(bs, 1H), 6.66(s, 1H), 8.91(s, 1H) |
| 9-16 | | 0.50(AcOEt) | CDCl₃: 1.04(s, 9H), 1.22(s, 6H), 1.25(s, 6H), 1.64(d, 2H), 1.80(d, 2H), 4.34(s, 2H), 4.93(s, 2H), 6.01(brs, 1H), 6.66(s, 1H), 8.93(s, 1H) |
| 9-17 | | 0.64 (n-Hexane:AcOEt = 1:1) | CDCl₃: 1.07(s, 9H), 4.37(s, 2H), 5.11(s, 2H), 6.69(s, 1H), 7.73(d, 1H), 7.90(dd, 1H), 8.01(d, 1H), 8.88(s, 1H) |

TABLE 9-1-continued
9-1
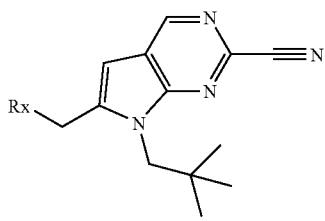
| Expl. No. | Rx | Rf(solvent) | $^1$H NMR(400 MHz, δ) |
|---|---|---|---|
| 9-18 | | 0.5 (n-Hexane:AcOEt = 1:1) | CDCl$_3$: 1.03(s, 9H), 1.32–1.45(m, 1H), 1.50–1.58(m, 1H), 1.61–1.96(m, 8H), 4.32(s, 2H), 4.94(s, 2H), 6.68(s, 1H), 8.93(s, 1H) |
| 9-19 | | 0.64 (n-Hexane:AcOEt = 1:3) | (CDCl$_3$+DMSO-d$_6$): 1.04(s, 9H), 4.35(s, 2H), 4.78(s, 2H)5.00(s, 2H), 6.81(s, 1H), 8.95(s, 1H) |
| 9-20 | | 0.31 (n-Hexane:AcOEt = 1:1) | CDCl$_3$: 1.04(s, 9H), 1.73(brd, 2H), 2.15–2.23(m, 2H), 3.79(brt, 2H), 3.97–4.02(m, 2H), 4.34(s, 2H), 4.98(s, 2H), 6.71(s, 1H), 8.95(s, 1H) |
| 9-21 | | 0.5 (n-Hexane:AcOEt = 1:1) | CDCl$_3$: 0.85(t, 6H), 1.03(s, 9H), 1.91(q, 4H), 4.35(s, 2H), 4.96(s, 2H), 6.73 (s, 1H), 8.95(s, 1H) |
| 9-22 | | 0.49 (n-Hexane:AcOEt = 1:1) | CDCl$_3$: 1.04(s, 9H), 1.88–1.99(m, 4H), 2.02–2.08(m, 2H), 2.15–2.22(m, 2H), 4.34(s, 2H), 4.97(s, 2H), 6.71(s, 1H), 8.95(s, 1H) |
| 9-23 | | 0.57 (AcOEt:MeOH = 4:1) | CDCl$_3$: 1.04(s, 9H), 1.62–1.68(m, 2H), 2.08–2.17(m, 2H), 3.60–3.68(m, 2H), 4.04–4.11(m, 2H), 4.34(s, 2H), 4.93(s, 2H), 5.96(brs, 1H), 6.65(s, 1H), 8.91 (s, 1H) |

TABLE 9-1-continued 9-1

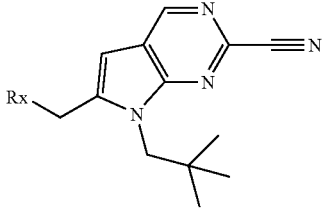

| Expl. No. | Rx | Rf(solvent) | ¹H NMR(400 MHz, δ) |
|---|---|---|---|
| 9-24 | (structure) | 0.41 (n-Hexane:AcOEt = 1:1) | CDCl₃: 1.03(s, 9H), 1.97–2.11(m, 2H), 2.59–2.64(m, 4H), 4.34(s, 2H), 4.95(s, 2H), 6.74(s, 1H), 8.94(s, 1H) |
| 9-25 | (structure) | 0.65 (n-Hexane:Ether = 1:1). | CDCl₃: 1.03(s, 9H), 1.73(s, 6H), 4.33(s, 2H), 5.02(s, 2H), 6.61(s, 1H), 8.92 (s, 1H) |

9-26

N.-{2-[2-Cyano-7-(2,2-dimethyl-propyl)-7H-pyrrolo[2,3-d]pyrimidin-6-ylmethyl]-1,3-dioxo-2,3-dihydro-1H-pyrrolo[3,4-c]pyridin-5-yl}-methanesulfonamide

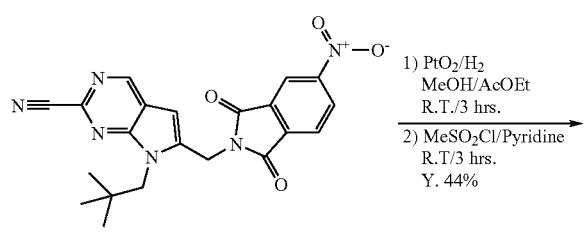

To a suspension of catalytic amount of PtO₂ in 10 ml of MeOH and 10 ml of AcOEt, 200 mg (0.48 mmoles) of 7-(2,2-dimethyl-propyl)-6-(5-nitro-1,3-dioxo-1,3-dihydro-pyrrolo[3,4-c]pyridin-2-ylmethyl)-7H-pyrrolo[2,3-d]pyrimidine-2-carbonitrile is added and the mixture is stirred under H₂ atmosphere. After being stirred for 3 hours, the reaction mixture is filtered through celite and concentrated under reduced pressure to give crude amine. To the crude amine, 0.052 ml (0.67 mmoles) of methanesulfonyl chloride is added at 0° C. and the mixture is allowed to warm to ambient temperature and stirred for 3 hours. The reaction mixture is poured into ice water and extracted with AcOEt. The combined extracts are washed with brine, dried over MgSO₄ and concentrated under reduced pressure. The residue is purified by silica gel column chromatography (eluent: n-Hexane:AcOEt=1:1) to give 98 mg of desired N.-{2-[2-cyano-7-(2,2-dimethyl-propyl)-7H-pyrrolo[2,3-d]pyrimidin-6-ylmethyl]-1,3-dioxo-2,3-dihydro-1H-pyrrolo[3,4-c]pyridin-5-yl}-methanesulfonamide in 44% yield.

¹H NMR(400 MHz, CDCl₃, δ): 1.03 (s, 9H), 3.18 (s, 3H), 4.30 (s, 2H), 5.11 (s, 2H), 6.72(s, H), 7.57 (dd, 1 H), 7.65 (s, 1 H), 7.90 (d, 1 H), 9.03 (s, 1 H), 10.70 (s, 1 H) Rf=0.62 (AcOEt)

9-27

7-(2,2-Dimethyl-propyl)-6-(3-methyl-1,4-dioxo-3,4-dihydro-1H-phthalazin-2-ylmethyl)-7H-pyrrolo[2,3-d]pyrimidine-2-carbonitrile

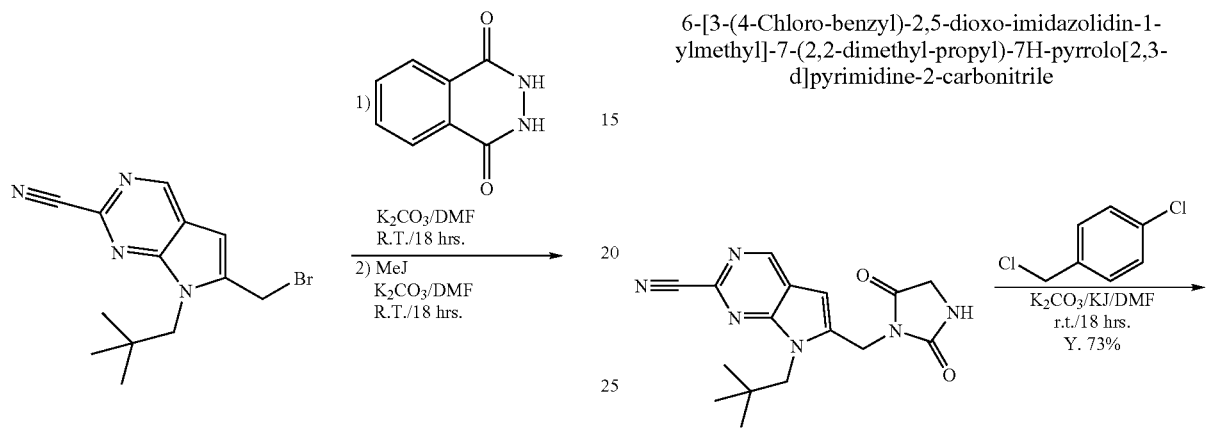

2-Dimethyl-propyl)-6-(3-methyl-1,4dioxo-3,4-dihydro-1H-phthalazin-2-ylmethyl)-7H-pyrrolo[2,3-d]pyrimidine-2-carbonitrile in 78% yield.

$^1$H NMR(400 MHz, CDCl$_3$, δ): 1.07 (s, 9H), 3.63 (s, 3H), 4.47 (s, 2H), 5.51 (s, 2H), 6.63 (s, 1H), 7.25 (d, 1H), 7.28-7.45 (m, 1H), 7.70-7.80 (m, 1H), 8.24 (dd, 1H), 8.82 (s, 1H) Rf=0.40 (n-Hexane:AcOEt=1:4)

9-28

6-[3-(4-Chloro-benzyl)-2,5-dioxo-imidazolidin-1-ylmethyl]-7-(2,2-dimethyl-propyl)-7H-pyrrolo[2,3-d]pyrimidine-2-carbonitrile

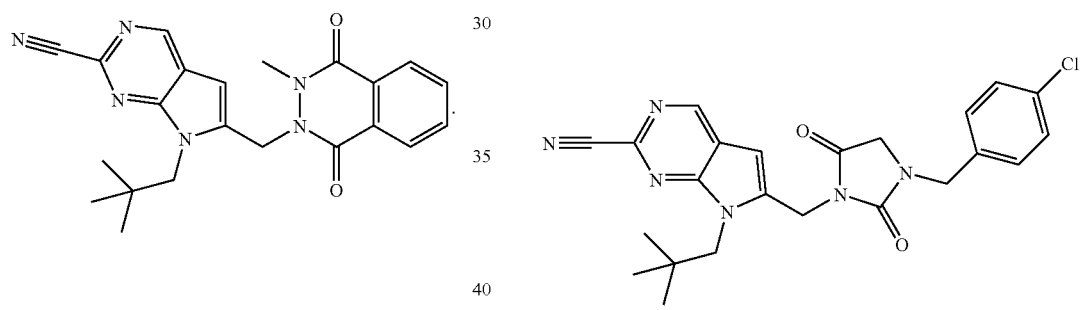

To a solution of 338 mg (1.3 mmoles) of phthalhydrazide in 20 ml of DMF, 252 mg (1.83 mmoles) of K$_2$CO$_3$ and 400 mg (1.30 mmoles) of 6-Bromomethyl-7-(2,2-dimethyl-propyl)-7H-pyrrolo[2,3-d]pyrimidine-2-carbonitrile are added successively and the mixture is stirred for 18 hours at ambient temperature. The reaction mixture is quenched with ice-water and extracted with AcOEt. The combined extracts are washed with H$_2$O, brine and dried over MgSO$_4$. Chromatography on silica gel (eluent: n-Hexane:AcOEt=1:2) give 412 mg of desired 7-(2,2-dimethyl-propyl)-6-(1,4-dioxo-3,4-dihydro-1H-phthalazin-2-ylmethyl)-7H-pyrrolo[2,3-d]pyrimidine-2-carbonitrile in 70% yield. The obtained product is treated with MeJ under the same condition to give N-methylated compound. To a solution of 295 mg (0.76 mmoles) of 7-(2,2-dimethyl-propyl)-6-(1,4-dioxo-3,4-dihydro-1H-phthalazin-2-ylmethyl)-7H-pyrrolo[2,3-d]pyrimidine-2-carbonitrile in 20 ml of DMF, 0.066 ml (1.06 mmoles) of MeJ and 168 mg (1.22 mmoles) of K$_2$CO$_3$ are added successively and the mixture is stirred for 18 hours at ambient temperature. The reaction mixture is quenched with ice-water and extracted with AcOEt. The combined extracts are washed with H$_2$O, brine and dried over MgSO$_4$. Chromatography on silica gel (eluent: n-Hexane:AcOEt=1:4) give 238 mg of 7-(2, To a solution of 200 mg (0.61 mmoles) of 7-(2,2-dimethyl-propyl)-6-(2,5-dioxo-imidazolidin-1-ylmethyl)-7H-pyrrolo[2,3-d]pyrimidine-2-carbonitrile in 10 ml of DMF, 136 mg (0.98 mmoles) of K$_2$CO$_3$, 138 mg (0.86 mmoles) of p-chlorobenzylchloride in 2 ml of DMF and 142 mg (0.86 mmoles) of KI are added successively at ambient temperature. After being stirred for 18 hours, the reaction mixture is quenched with ice water and extracted with AcOEt. The combined extracts are washed with H$_2$O, brine and dried over MgSO$_4$. Chromatography on silica gel (eluent: CH$_2$C$_2$:AcOEt=8:1) give 203 mg of desired 6-[3-(4-chloro-benzyl)-2,5-dioxo-imidazolidin-1-ylmethyl]-7-(2,2-dimethyl-propyl)-7H-pyrrolo[2,3-d]pyrimidine-2-carbonitrile in 73% yield.

$^1$H NMR(400 MHz, CDCl$_3$, δ): 1.03 (s, 9H), 3.78 (s, 2H), 4.37 (s, 2H), 4.53 (s, 2H), 4.96 (s, 2H), 6.74 (s, 1H), 7.18 (d, 2H), 7.34 (d, 2H), 8.92 (s, 1H) Rf=0.28 (n-Hexane:AcOEt=1:1)

By repeating the procedures described above using appropriate starting materials and conditions the following compounds of formula 9-2 are obtained as identified below in Table 9-2.

TABLE 9-2
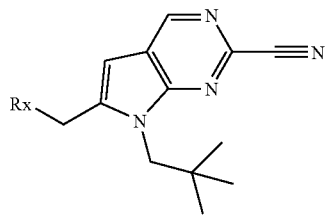
| Expl. No. | Rx | Rf(solvent) | $^1$H NMR(400 MHz, δ) |
|---|---|---|---|
| 9-29 | 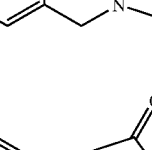 | 0.34 (n-Hexane:AcOEt = 1:1) | CDCl$_3$: 1.04(s, 9H), 3.80(m, 2H), 4.38(s, 2H), 4.54(s, 2H), 4.97(s, 2H), 6.75(s, 1H), 7.05–7.15(m, 1H), 7.22–7.35(m, 3H), 8.92(s, 1H) |
| 9-30 | 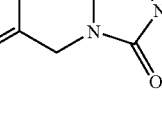 | 0.40 (n-Hexane:AcOEt = 1:1) | CDCl$_3$: 1.03(s, 9H), 3.84(s, 2H), 4.36(s, 2H), 4.71(s, 2H), 4.96(s, 2H), 6.74(s, 1H), 7.22–7.35(m, 3H), 7.37–7.45(m, 1H), 8.91(s, 1H) |
| 9-31 | 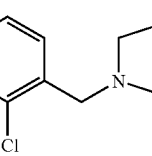 | 0.38 (n-Hexane:AcOEt = 1:1) | CDCl$_3$: 1.03(s, 9H), 3.85(s, 2H), 4.36(s, 2H), 4.67(s, 2H), 4.95(s, 2H), 6.73(s, 1H), 7.25–7.30(m, 2H), 7.44(d, 1H), 8.92(s, 1H) |
| 9-32 | 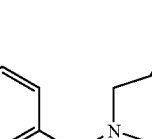 | 0.46(AcOEt) | CDCl$_3$: 1.04(s, 9H), 3.88(s, 2H), 4.38(s, 2H), 4.60(s, 2H), 4.99(s, 2H), 6.77(s, 1H), 6.81(brs, 1H), 7.07(d, 1H), 8.24(d, 1H), 8.93(d, 1H) |
| 9-33 | 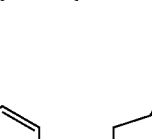 | 0.48(AcOEt) | CDCl$_3$: 1.03(s, 9H), 3.83(s, 2H), 4.37(s, 2H), 4.57(s, 2H), 4.96(s, 2H), 6.75(s, 1H), 6.95–7.00(m, 1H), 7.70–7.78(m, 1H), 8.15(dd, 1H), 8.92(d, 1H) |
| 9-34 | 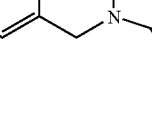 | 0.50(AcOEt) | CDCl$_3$: 1.04(s, 9H), 4.11(s, 2H), 4.33(s, 2H), 4.65(s, 2H), 4.97(s, 2H), 6.82(s, 1H), 6.89(dd, 1H), 7.15(dd, 1H), 7.75–7.85(m, 1H), 8.92(d, 1H) |
| 9-35 | 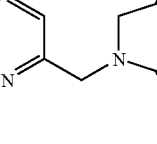 | 0.38 (n-Hexane:AcOEt = 1:1) | CDCl$_3$: 1.03(s, 9H), 3.86(s, 2H), 4.36(s, 2H), 4.63(s, 2H), 4.94(s, 2H), 6.73(s, 1H), 7.05–7.20(m, 2H), 7.30–7.40(m, 2H), 8.91(s, 1H) |

TABLE 9-2-continued 9-2

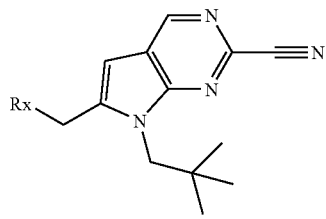

| Expl. No. | Rx | Rf(solvent) | $^1$H NMR(400 MHz, δ) |
|---|---|---|---|
| 9-36 | 6-fluoropyridin-2-ylmethyl-(3-methyl-2,4-dioxotetrahydropyrimidin-1-yl) | 0.46(AcOEt) | CDCl$_3$: 1.02(s, 9H), 2.85–2.95(m, 2H), 3.60–3.70(m, 2H), 4.30(s, 2H), 4.71(s, 2H), 5.22(s, 2H), 6.67(s, 1H), 6.85–6.90(m, 1H), 7.15–7.20(m, 1H), 7.75–7.85(m, 1H), 8.88(s, 1H) |
| 9-37 | 1-(2-pyrrolidin-1-ylethyl)-3-methyl-2,4-dioxoimidazolidin-1-ylmethyl | 0.38 (CH$_2$Cl$_2$:MeOH = 10:1) | CDCl$_3$: 1.03(s, 9H), 1.70–1.80(m, 4H), 2.40–2.80(m, 6H), 3.50–3.60(m, 2H), 4.07(s, 2H), 4.35(s, 2H), 4.93(s, 2H), 6.73(s, 1H), 8.90(s, 1H) |
| 9-38 | 6-fluoropyridin-3-ylmethyl-(3-methyl-2,4-dioxotetrahydropyrimidin-1-yl) | 0.38(AcOEt) | CDCl$_3$: 1.03(s, 9H), 2.75–2.85(m, 2H), 3.35–3.45(m, 2H), 4.36(s, 2H), 4.62(s, 2H), 5.22(s, 2H), 6.53(s, 1H), 6.90–7.00(m, 1H), 7.70–7.80(m, 1H), 8.17(d, 1H), 8.88(s, 1H) |
| 9-39 | 2,4-difluorobenzyl-(3-methyl-2,4-dioxoimidazolidin-1-yl) | 0.36 (n-Hexane:AcOEt = 1:1) | CDCl$_3$: 1.03(s, 9H), 3.86(s, 2H), 4.36(s, 2H), 4.58(s, 2H), 4.94(s, 2H), 6.73(s, 1H), 6.85–6.95(m, 2H), 7.26–7.38(m, 1H), 8.91(s, 1H) |
| 9-40 | 2,4-difluorobenzyl-(3-methyl-2,4-dioxotetrahydropyrimidin-1-yl) | 0.30 (n-Hexane:AcOEt = 1:1) | CDCl$_3$: 1.02(s, 9H), 2.70–2.80(m, 2H), 3.35–3.45(m, 2H), 4.34(s, 2H), 4.64(s, 2H), 5.20(s, 2H), 6.52(s, 1H), 6.80–6.92(m, 2H), 7.30–7.40(m, 1H), 8.86(s, 1H) |
| 9-41 | pyrazin-2-ylmethyl-(3-methyl-2,4-dioxoimidazolidin-1-yl) | 0.2(AcOEt) | CDCl$_3$: 1.03(s, 9H), 4.09(s, 2H), 4.36(s, 2H), 4.74(s, 2H), 4.97(s, 2H), 6.75(s, 1H), 8.50–8.60(m, 2H), 8.61(d, 1H), 8.92(s, 1H) |
| 9-42 | 4-chlorobenzyl-(3-methyl-2,4-dioxotetrahydropyrimidin-1-yl) | 0.22 (n-Hexane:AcOEt = 1:1) | (CDCl$_3$: 1.03(s, 9H), 2.70–2.80(m, 2H), 3.25–3.35(m, 2H), 4.36(s, 2H), 4.60(s, 2H), 5.23(s, 2H), 6.54(s, 1H), 7.20(d, 2H), 7.31(d, 2H), 8.88(s, 1H), |

TABLE 9-2-continued

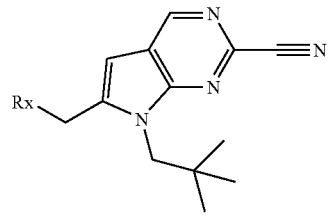

9-2

| Expl. No. | Rx | Rf(solvent) | $^1$H NMR(400 MHz, δ) |
|---|---|---|---|
| 9-43 | ![structure] | 0.28(AcOEt) | CDCl$_3$: 1.02(s, 9H), 2.77(t, 2H), 3.34(s, 3H), 3.50–3.58(m, 4H), 3.62(t, 2H), 4.34(s, 2H), 5.19(s, 2H), 6.53(s, 1H), 8.85(s, 1H) |
| 9-44 | ![structure] | 0.36(AcOEt) | CDCl$_3$: 1.03(s, 9H), 3.34(s, 3H), 3.50–3.60(m, 4H), 4.05(s, 2H), 4.37(s, 2H), 4.94(s, 2H), 6.74(s, 1H), 8.91(s, 1H) |

9-45

6-[(R)-3-(4-chloro-benzyl)-4-isopropyl-2,5-dioxo-imidazolidin-1-ylmethyl]-7-(2,2-dimethyl-propyl)-7H-pyrrolo[2,3-d]pyrimidine-2-carbonitrile

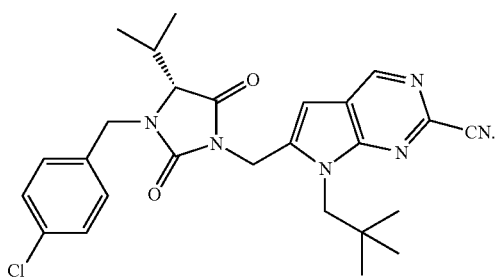

A) (R)-2-(4-Chloro-benzylamino)-3-methyl-butyric acid methyl ester

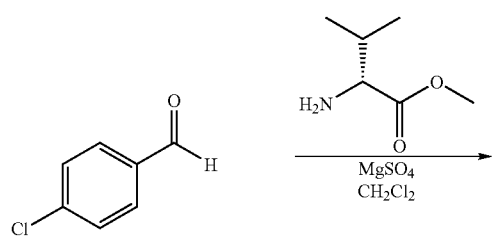

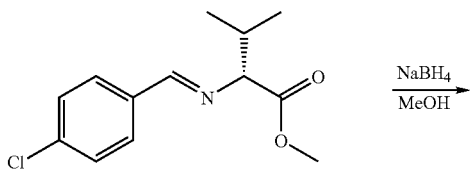

-continued

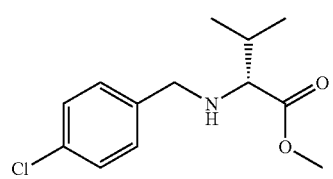

3 g (18 mmoles) of (R)-2-amino-3-methyl-butyric acid methyl ester hydrochloride, 2.1 g (15 mmoles) of 4-chloro-benzaldehyde and 2.94 ml (21 mmoles) of triethyl amine are dissolved in 100 ml of CH$_2$Cl$_2$ and excess of MgSO$_4$ is added at ambient temperature under N$_2$ atmosphere. After being stirred for 18 hours at ambient temperature, the reaction mixture is filtered off and washed with CH$_2$Cl$_2$. The filtrate is concentrated under reduced pressure. To the crude imine in 250 ml of MeOH, 2.04 g (54 mmoles) of NaBH$_4$ is added portionwise at 0° C. The reaction mixture is stirred at 0° C. for 2 hours and concentrated to ¼ of whole volume under reduced pressure. The mixture is extracted with AcOEt and the combined extracts are washed with sat. NaHCO$_3$ and brine, dried over Na$_2$SO$_4$ and concentrated under reduced pressure to give 3.72 g of desired (R)-2-(4-chloro-benzylamino)-3-methyl-butyric acid methyl ester in 97% yield.

¹H NMR (400 MHz, CDCl₃, δ): 0.92-0.95 (m, 6H), 1.75 (brs, 1H), 1.87-1.95 (m, 1H), 2.97 (d, 1H), 3.53 (d, 1H), 3.72 (s, 3H), 3.80 (d, 1H), 7.27 (s, 4H) Rf=0.76 (n-Hexane:AcOEt=1:1)

B) (R)-1-(4-Chloro-benzyl)-5-isopropyl-imidazolidine-2,4-dione

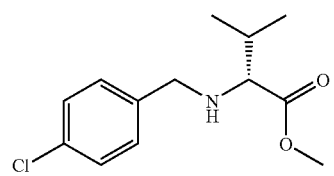

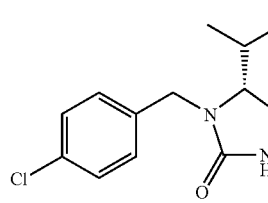

C) 6-[(R)-3-(4-Chloro-benzyl)-4-isopropyl-2,5-dioxo-imidazolidin-1-ylmethyl]-7-(2,2-dimethyl-propyl)-7H-pyrrolo[2,3-d]pyrimidine-2-carbonitrile

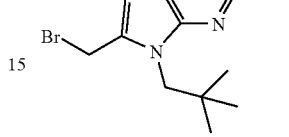 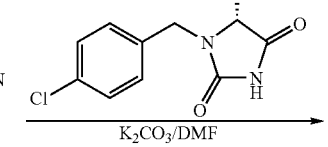

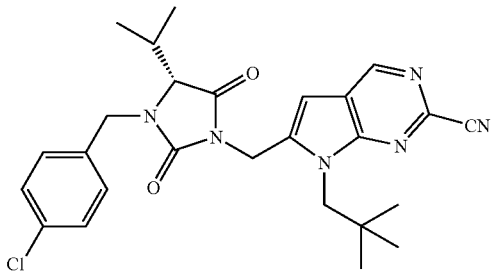

To a solution of 1.68 g (6.59 mmoles) of (R)-2-(4-chloro-benzylamino)-3-methyl-butyric acid methyl ester in 20 ml of acetic acid, 0.64 g (7.91 mmoles) of potassium cyanate is added at ambient temperature under N₂ atmosphere. The mixture is stirred for 15 hours at ambient temperature and heated for 3 hours at 100° C., and then the reaction mixture is concentrated under reduced pressure. The mixture is extracted with AcOEt, and the combined extracts are washed with sat. NaHCO₃ and brine, dried over MgSO₄ and then concentrated under reduced pressure. The residue is purified by silica gel column chromatography to give 1.57 g of desired (R)-1-(4-chloro-benzyl)-5-isopropyl-imidazolidine-2,4-dione in 77% yield.

¹H NMR (400 MHz, CDCl₃, δ): 0.92 (d, 3H), 1.12 (d, 3H), 2.14-2.22 (m, 1H), 3.70 (d, 1H), 4.06 (d, 1H), 4.98 (d, 1H), 7.20 (d, 2H), 7.34 (d, 2H), 8.21 (brs, 1H) Rf=0.38 (n-Hexane:AcOEt=1:1)

To a solution of 0.5 g (1.63 mmoles) of 6-bromomethyl-7-(2,2-dimethyl-propyl)-7H-pyrrolo[2,3-d]pyrimidine-2-carbonitrile in DMF (5 ml) are added 0.653 g of (2.45 mmoles) of (R)-1-(4-chloro-benzyl)-5-isopropyl-imidazolidine-2,4-dione and 0.293 g (2.12 mmoles) of K₂CO₃ at ambient temperature under N₂ atmosphere. The mixture is stirred at ambient temperature for 15 hours. The mixture is diluted with ethyl acetate, washed with water and brine, dried over MgSO₄ and concentrated. The crude product is purified by silica gel column chromatography to give 0.644 g of desired 6-[(R)-3-(4-chloro-benzyl)-4-isopropyl-2,5-dioxo-imidazolidin-1-ylmethyl]-7-(2,2-dimethyl-propyl)-7H-pyrrolo[2,3-d]pyrimidine-2-carbonitrile in 78% yield.

¹H NMR (400 MHz, CDCl₃, δ): 0.80 (d, 3H), 1.04 (s, 9H), 1.10 (d, 3H), 2.16-2.23 (m, 1H), 3.69 (d, 1H), 4.10 (d, 1H), 4.36 (s, 2H), 4.89-5.00 (m, 3H), 6.67 (s, 1H), 7.18 (d, 2H), 7.33 (d, 2H), 8.92 (s, 1H) Rf=0.41 (n-Hexane:AcOEt=1:1)

By repeating the procedures described above using appropriate starting materials and conditions the following compounds of formula 9-3 are obtained as identified below in Table 9-3.

TABLE 9-3

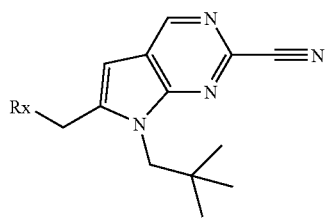

9-3

| Expl. No. | Rx | Rf(solvent) | ¹H NMR(400 MHz, δ) |
|---|---|---|---|
| 9-45 | (4-chlorobenzyl)-5-isopropyl-3-methylimidazolidine-2,4-dione | 0.41 (n-Hexane:AcOEt = 1:1) | CDCl₃: 0.80(d, 3H), 1.04(s, 9H), 1.10(d, 3H), 2.16–2.23(m, 1H), 3.69(d, 1H), 4.10(d, 1H), 4.36(s, 2H), 4.89–5.00(m, 3H), 6.67(s, 1H), 7.18 (d, 2H), 7.33(d, 2H), 8.92(s, 1H) |
| 9-46 | (4-chlorobenzyl)-3,5-dimethylimidazolidine-2,4-dione | 0.26 (n-Hexane:AcOEt = 1:1) | CDCl₃: 1.04(s, 9H), 1.38(d, 3H), 3.84(q, 1H), 4.18(d, 1H), 4.36(s, 2H), 4.88(d, 1H), 4.91–5.00(m, 2H), 6.69(s, 1H), 7.19(d, 2H), 7.33(d, 2H), 8.92(s, 1H) |
| 9-47 | (4-chlorobenzyl)-3,5-dimethylimidazolidine-2,4-dione | 0.26 (n-Hexane:AcOEt = 1:1) | CDCl₃: 1.04(s, 9H), 1.38(d, 3H), 3.84(q, 1H), 4.18(d, 1H), 4.36(s, 2H), 4.88(d, 1H), 4.91–5.00(m, 2H), 6.69(s, 1H), 7.19(d, 2H), 7.33(d, 2H), 8.92(s, 1H) |
| 9-48 | 1-(4-(4-methylpiperazin-1-yl)benzyl)-3-methylimidazolidine-2,4-dione | 0.44 (CH₂Cl₂:MeOH = 10:1) | CDCl₃: 1.03(s, 9H), 2.35(s, 3H), 2.55–2.65(m, 4H), 3.15–3.25(m, 4H), 3.75(s, 2H), 4.37(s, 2H), 4.46(s, 2H), 4.94(s, 2H), 6.73(s, 1H), 6.87(d, 2H), 7.11(d, 2H), 8.91(s, 1H) |
| 9-49 | 1-(4-(piperidin-1-yl)benzyl)-3-methylimidazolidine-2,4-dione | 0.32 (n-Hexane:AcOEt = 1:1) | CDCl₃: 1.09(s, 9H), 1.55–1.75(m, 6H), 3.10–3.20(m, 4H), 3.75(s, 2H), 4.37(s, 2H), 4.45(s, 2H), 4.94(s, 2H), 6.73(s, 1H), 6.87(d, 2H), 7.10(d, 2H), 8.91(s, 1H) |

9-50

7-(2,2-Dimethyl-propyl)-6-(2,4,8,8-tetraoxo-1-oxa-8λ⁶-thia-3-aza-spiro[4.5]dec-3-ylmethyl)-7H-pyrrolo[2,3-d]pyrimidine-2-carbonitrile

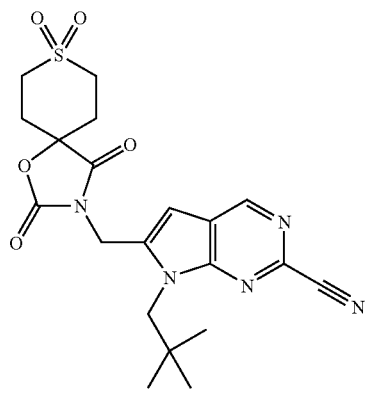

A) 1-Oxa-8-thia-3-aza-spiro[4.5]decane-2,4-dione

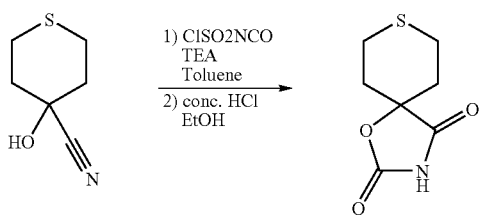

To a solution of 2.15 g (15 mmoles) of 4-hydroxy-tetrahydro-thiopyran-4-carbonitrile in 40 ml of toluene is added 1.30 ml (15 mmoles) of chlorosulfonyl isocyanate dropwise at ambient temperature. The mixture is stirred at ambient temperature for 1 hour, and 2.09 ml (15 mmoles) of triethylamine is added to the mixture. The mixture is stirred for 3 hours at 110° C., and then at ambient temperature for 15 hours and concentrated under reduced pressure. 16 ml of ethanol and 3.2 ml of conc. hydrochloric acid are added to the residue at ambient temperature. After being stirred for 5 hours at 110° C., the reaction mixture is diluted with CH₂Cl₂, washed with brine, dried over Na₂SO₄ and concentrated under reduced pressure. The residue is purified by silica gel column chromatography to give 1.14 g of disired 1-oxa-8-thia-3-aza-spiro[4.5]decane-2,4-dione in 41% yield.

¹H NMR (400 MHz, CDCl₃, δ); 2.10-2.15 (m, 2H), 2.22-2.29 (m, 2H), 2.66-2.71 (m, 2H), 2.95-3.02 (m, 2H), 8.47 (brs, 1H) Rf:=0.57 (AcOEt:n-Hexane=1:1)

B) 7-(2,2-Dimethyl-propyl)-6-(2,4-dioxo-1-oxa-8-thia-3-aza-spiro[4.5]dec-3-ylmethyl)-7H-pyrrolo[2,3-d]pyrimidine-2-carbonitrile

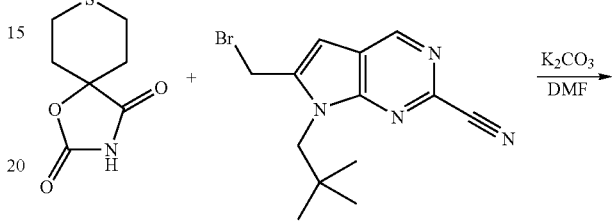

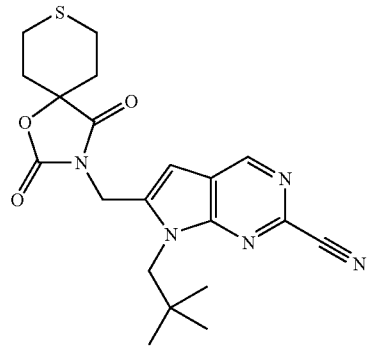

To a solution of 200 mg (0.52 mmoles) of 6-bromomethyl-7-(2,2-dimethyl-propyl)-7H-pyrrolo[2,3-d]pyrimidine-2-carbonitrile and 146 mg (0.78 mmoles) of 1-oxa-8-thia-3-aza-spiro[4.5]decane-2,4-dione in 5 ml of DMF, 117 mg (0.846 mmoles) of K₂CO₃ is added at ambient temperature. After being stirred for 18 hours, the reaction mixture is quenched with H₂O and extracted with AcOEt. The combined extracts are washed with brine, dried over MgSO₄ and concentrated under reduced pressure. The residue is purified by reverse-phase HPLC to give 85 mg of disired 7-(2,2-dimethyl-propyl)-6-(2,4-dioxo-1-oxa-8-thia-3-aza-spiro[4.5]dec-3-ylmethyl)-7H-pyrrolo[2,3-d]pyrimidine-2-carbonitrile (NVP-TAB516-NX) in 32% yield.

¹H NMR (400 MHz, CDCl₃, δ); 1.02 (s, 9H), 2.00-2.06 (m, 2H), 2.21-2.28 (m, 2H), 2.65-2.70 (m, 2H), 2.93-3.00 (m, 2H), 4.32 (s, 2H), 4.95 (s, 2H), 6.69 (s, 1H), 8.94 (s, 1H) Rf:=0.58 (AcOEt:n-Hexane=1:1)

C) 7-(2,2-Dimethyl-propyl)-6-(2,4,8,8-tetraoxo-1-oxa-8□⁶-thia-3-aza-spiro[4.5]dec-3-ylmethyl)-7H-pyrrolo[2,3-d]pyrimidine-2-carbonitrile

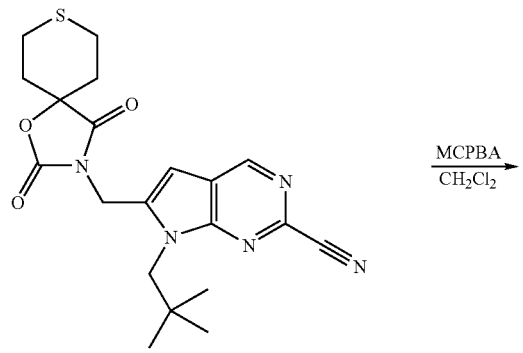

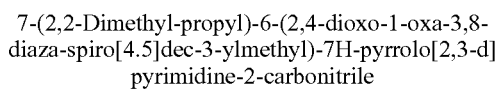

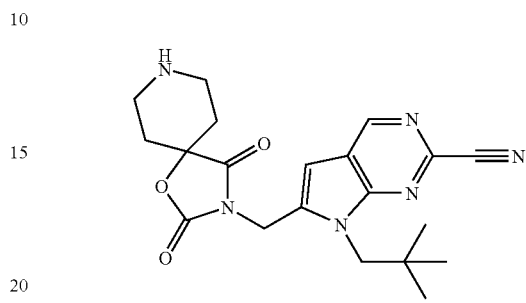

To a solution of 80 mg (0.193 mmoles) of 7-(2,2-dimethyl-propyl)-6-(2,4-dioxo-1-oxa-8-thia-3-aza-spiro[4.5]dec-3-ylmethyl)-7H-pyrrolo[2,3-d]pyrimidine-2-carbonitrile in 4 ml of $CH_2Cl_2$, 83 mg (0.484 mmoles) of 3-chloroperbenzoic acid is added at ambient temperature. After being stirred for 1 hour, the reaction mixture is diluted with $CH_2Cl_2$, and washed with saturated $NaHCO_3$ and brine, dried over $MgSO_4$ and concentrated under reduced pressure. The residue is purified by reverse-phase HPLC to give 54 mg of disired 7-(2,2-dimethyl-propyl)-6-(2,4,8,8-tetraoxo-1-oxa-8□⁶-thia-3-aza-spiro[4.5]dec-3-ylmethyl)-7H-pyrrolo[2,3-d]pyrimidine-2-carbonitrile in 62% yield.

¹H NMR (400 MHz, $CDCl_3$, δ); 1.03 (s, 9H), 2.28-2.32 (m, 2H), 2.71-2.78 (m, 2H), 3.19-3.23 (m, 2H), 3.29-3.36 (m, 2H), 4.35 (s, 2H), 5.01 (s, 2H), 6.78 (s, 1H), 9.01 (s, 1H) Rf:=0.23 (AcOEt:n-Hexane=1:1)

9-51

7-(2,2-Dimethyl-propyl)-6-(2,4-dioxo-1-oxa-3,8-diaza-spiro[4.5]dec-3-ylmethyl)-7H-pyrrolo[2,3-d]pyrimidine-2-carbonitrile

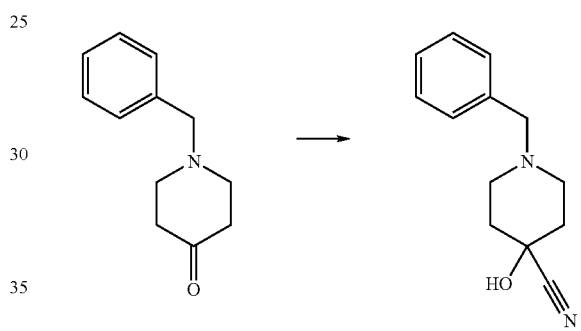

A). 1-Benzyl-4-hydroxy-piperidine-4-carbonitrile

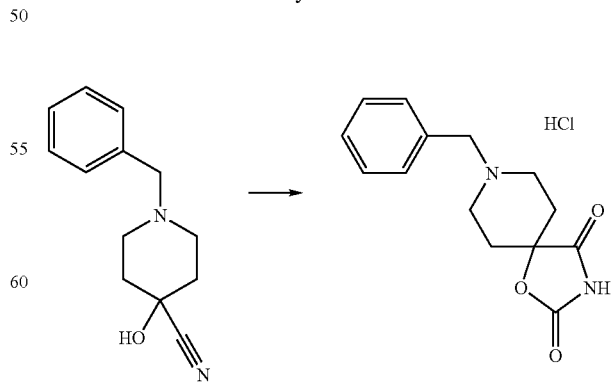

To a solution of 2 g (10.6 mmoles) of 1-benzyl-piperidin-4-one in 14 ml of ethanol are added 6.8 ml (74.5 mmoles) of 2-hydroxy-2-methyl-propionitrile and 0.41 g (3 mmoles) of $K_2CO_3$ at 0° C. The mixture is stirred at 0° C. for 5 hours and diluted with diethyl ether. The organic layer is washed with water, dried over $Na_2SO_4$ and concentrated. Chromatography on silica gel ($CH_2Cl_2$:MeOH=9:1) gives 1.94 g of desired 1-benzyl-4-hydroxy-piperidine-4-carbonitrile in 85% yield.
Rf=0.38 ($CH_2Cl_2$:MeOH=9:1)

8-Benzyl-1-oxa-3,8-diaza-spiro[4.5]decane-2,4-dione hydrochloride

To a solution of 1.94 g (9 mmoles) of 1-benzyl-4-hydroxy-piperidine-4-carbonitrile in 30 ml of toluene is added 0.78 ml (9 mmoles) of chlorosulfonyl isocyanate dropwise at ambient temperature. The mixture is stirred at 110° C. for 3 hours, and then stirred for 18 hours at ambient temperature and concentrated. 5 ml of Ethanol and 6N HCl are added at ambient temperature and the mixture is stirred at 110° C. for 5 hours. H$_2$O and CH$_2$Cl$_2$ are added and the aqueous layer is concentrated. Methanol is added to the residue and precipitates are collected. The crude product is used for the next step.

C) 6-(8-Benzyl-2,4-dioxo-1-oxa-3,8-diaza-spiro[4.5]dec-3-ylmethyl)-7-(2,2-dimethyl-propyl)-7H-pyrrolo[2,3-d]pyrimidine-2-carbonitrile

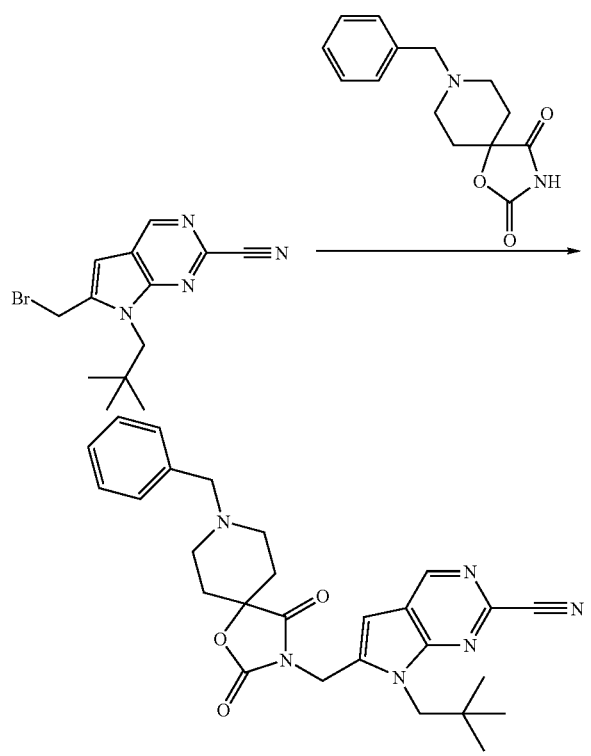

To a solution of 1.23 g (4 mmoles) of 6-bromomethyl-7-(2,2-dimethyl-propyl)-7H-pyrrolo[2,3-d]pyrimidine-2-carbonitrile in 20 ml of DMF are added 1.42 g (4.8 mmoles) of 8-benzyl-1-oxa-3,8-diaza-spiro[4.5]decane-2,4-dione hydrochloride(4.8 mmol) and 2.85 g (20.6 mmoles) of K$_2$CO$_3$. The mixture is stirred for 3 hours at 50° C. 0.67 ml (4.8 mmoles) of triethylamine is added and the reaction mixture is stirred for 18 hours at ambient temperature. The mixture is diluted with AcOEt, washed with water and brine, dried over Na$_2$SO$_4$ and concentrated under reduced pressure. The residue is purified by HPLC(n-Hexane/AcOEt) to give 0.59 g of desired 6-(8-benzyl-2,4-dioxo-1-oxa-3,8-diaza-spiro[4.5]dec-3-ylmethyl)-7-(2,2-dimethyl-propyl)-7-pyrrolo[2,3-d]pyrimidine-2-carbonitrile in 30% yield.

$^1$H NMR (400 MHz, CDCl$_3$, δ): 1.03 (s, 9H), 1.72-1.82 (m, 2H), 2.12-2.23 (m, 2H), 2.33-2.46 (m, 2H), 2.80-2.89 (m, 2H), 3.56 (s, 2H), 4.33 (s, 2H), 4.95 (s, 2H), 6.69 (s, 1H), 7.27-7.38 (m, 5H), 8.94 (s, 1H) Rf=0.38 (n-Hexane:AcOEt=1:1)

By repeating the procedures described above using appropriate starting materials and conditions the following compounds of formula 9-4 are obtained as identified below in Table 9-4.

TABLE 9-4

| Expl. No. | Rx | Rf(solvent) | $^1$H NMR(400 MHz, δ) |
|---|---|---|---|
| 9-52 | 4-Cl-C$_6$H$_4$-CH$_2$- | 0.36 (n-Hexane:AcOEt = 1:1) | CDCl$_3$: 1.03(s, 9H), 1.78(d, 2H), 2.17(dt, 2H), 2.37–2.43(m, 2H), 2.81–2.84(m, 2H), 3.52(s, 2H), 4.32(s, 2H), 4.95(s, 2H), 6.69(s, 1H), 7.24–7.28(m, 4H), 8.94(s, 1H) |

TABLE 9-4-continued

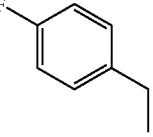

| Expl. No. | Rx | Rf(solvent) | ¹H NMR(400 MHz, δ) |
|---|---|---|---|
| 9-53 | ![F-phenyl-ethyl] | 0.38 (n-Hexane/AcOEt = 1/1) | $CDCl_3$: 1.05(s, 9H), 1.72–1.82(m, 2H), 2.1–2.25(m, 2H), 2.32–2.48(m, 2H), 2.80–2.89(m, 2H), 3.54(s, 2H), 4.34(s, 2H), 4.97(s, 2H), 6.71(s, 1H), 6.97–7.07(m, 2H), 7.2–7.35(m, 2H), 8.96(s, 1H) |

Example 9-54

3-[2-Cyano-7-(2,2-dimethyl-propyl)-7H-pyrrolo[2,3-d]pyrimidin-6-ylmethyl]-2,4-dioxo-1-oxa-3,8-diaza-spiro[4.5]decane-8-carboxylic acid 2,2,2-trichloro-ethyl ester

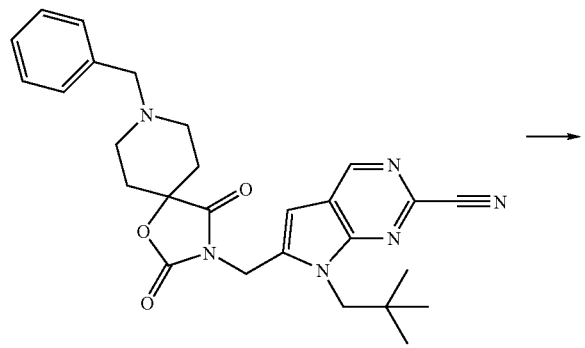

→

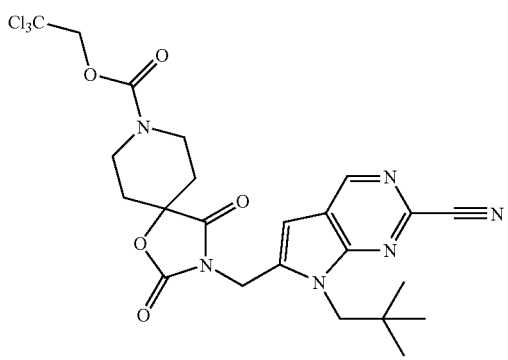

To a solution of 0.22 g (0.45 mmoles) of 6-(8-benzyl-2,4-dioxo-1-oxa-3,8-diaza-spiro[4.5]dec-3-ylmethyl)-7-(2,2-dimethyl-propyl)-7H-pyrrolo[2,3-d]pyrimidine-2-carbonitrile in 4 ml of $CH_3CN$ is added 2,2,2-trichloroethyl chloroformate(0.91 mmol) at ambient temperature and the mixture is stirred for 18 hours. Aqueous $NH_4Cl$ is added and the organic layer is extracted with AcOEt, washed with brine, dried over $Na_2SO_4$ and concentrated. The crude product is purified by silica gel column chromatography (n-Hexane:AcOEt=1:1) to give 0.25 g of 3-[2-cyano-7-(2,2-dimethyl-propyl)-7H-pyrrolo[2,3-d]pyrimidin-6-ylmethyl]-2,4-dioxo-1-oxa-3,8-diaza-spiro[4.5]decane-8-carboxylic acid 2,2,2-trichloro-ethyl ester in 96% yield.

Rf=0.56 (n-Hexane:AcOEt=1:1). ¹H NMR(400 MHz, $CDCl_3$) δ1.05(s, 9H), 1.78-1.88(m, 2H), 2.07-2.18(m, 2H), 3.38-3.5(m, 2H), 4.12-4.22(m, 2H), 4.26(s, 2H), 4.7-4.85(m, 2H), 4.98(s, 2H), 6.71(s, 1H), 8.95(s, 1H).

Example 9-55

7-(2,2-Dimethyl-propyl)-6-(2,4-dioxo-1-oxa-3,8-diaza-spiro[4.5]dec-3-ylmethyl)-7H-pyrrolo[2,3-d]pyrimidine-2-carbonitrile

9-56

7-(2,2-dimethyl-propyl)-6-(8-ethyl-2,4-dioxo-1-oxa-3,8-diaza-spiro[4.5]dec-3-ylmethyl)-7H-pyrrolo[2,3-d]pyrimidine-2-carbonitrile

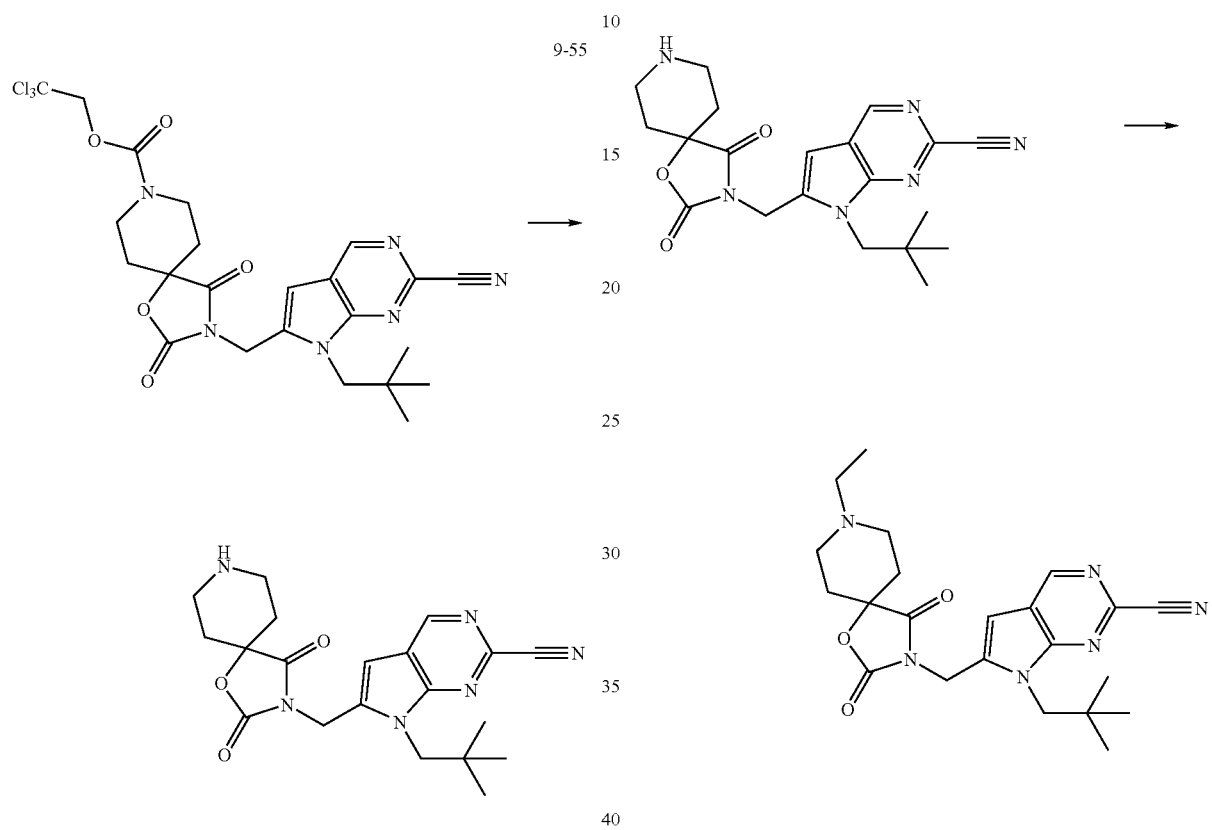

To a solution of 0.25 g (0.43 mmoles) of 3-[2cyano-7-(2,2-dimethyl-propyl)-7H-pyrrolo[2,3-d]pyrimidin-6-ylmethyl]-2,4-dioxo-1-oxa-3,8-diaza-spiro[4.5]decane-8-carboxylic acid 2,2,2-trichloro-ethyl ester in 7 ml of acetic acid is added 112 mg (1.7 mmoles) of zinc powder at ambient temperature and the mixture is stirred for 3 hours at ambient temperature. Additional 300 mg (4.6 mmoles) of zinc powder is added at ambient temperature and the mixture is stirred for 2 hours. After removal of zinc by filtration through celitec, aqueous NaHCO$_3$ is added and the mixture is extracted with CH$_2$Cl$_2$. The combined extracts are washed with brine, dried over Na$_2$SO$_4$ and concentrated under reduced pressure. The residue is purified by HPLC (H$_2$O—0.1% TFA/acetonitrile—0.1% TFA). Fractions are collected, basified with 5% aqueous NaHCO$_3$, extracted with AcOEt, washed with brine, dried over Na$_2$SO$_4$ and concentrated under reduced pressure to give 0.046 g of desired 7-(2,2ethyl-propyl)-6-(2,4-dioxo-1-oxa-3,8-diaza-spiro[4.5]dec-3-ylmethyl)-7H-pyrrolo[2,3-d]pyrimidine-2-carbonitrile in 28% yield.

$^1$H NMR (400 MHz, CDCl$_3$, δ): 1.03 (s, 9H), 1.68-1.78 (m, 2H), 1.98-2.12 (m, 2H), 2.94-3.15 (m, 4H), 4.33 (s, 2H), 4.96 (s, 2H), 6.70 (s, 1H), 8.94 (s, 1H) Rf=0.2 (CH$_2$Cl$_2$:MeOH=9:1)

To a solution of 7-(2,2-dimethyl-propyl)-6-(2,4-dioxo-1-oxa-3,8-diaza-spiro[4.5]dec-3-ylmethyl)-7H-pyrrolo[2,3-d]pyrimidine-2-carbonitrile (0.63 mmol) in DMF (2 ml) are added ethyl bromide (0.69 mmol), K$_2$CO$_3$ (0.76 mmol), and NaI (0.95 mmol). The mixture is allowed to stir at ambient temperature under nitrogen atmosphere for 18 hours. The reaction mixture is diluted with H$_2$O and extracted with AcOEt. The organic layer is washed with brine, dried over Na$_2$SO$_4$ and concentrated under reduced pressure. The residue is purified by HPLC(H$_2$O—0.1% TFA/acetonitrile—0.1% TFA). Fractions are collected, basified with 5% aqueous NaHCO$_3$, extracted with AcOEt, washed with brine, dried over Na$_2$SO$_4$ and concentrated under reduced pressure to give 7-(2,2-dimethyl-propyl)-6-(8-ethyl-2,4-dioxo-1-oxa-3,8-diaza-spiro[4.5]dec-3-ylmethyl)-7H-pyrrolo[2,3-d]pyrimidine-2-carbonitrile.

By repeating the procedures described above using appropriate starting materials and conditions the following compounds of formula 9-5 are obtained as identified below in Table 9-5.

TABLE 9-5
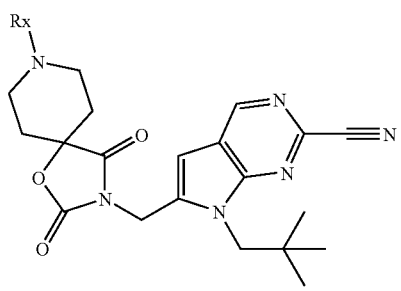
9-5
| Expl. No. | Rx | Rf(solvent) | $^1$H NMR(400 MHz, δ) |
|---|---|---|---|
| 9-56 | | 0.51 (CH$_2$Cl$_2$:MeOH = 10:1) | (CDCl$_3$): 1.05(s, 9H), 1.12(t, 3H), 1.82(d, 2H), 2.21(dt, 2H), 2.39(t, 2H), 2.51(q, 2H), 2.90–2.93(m, 2H), 4.35(s, 2H), 4.98(s, 2H), 6.72(s, 1H), 8.96(s, 1H) |
| 9-57 | | 0.56 (CH$_2$Cl$_2$:MeOH = 8:1) | (CDCl$_3$): 0.91(t, 3H), 1.03(,s 9H), 1.44–1.52(m, 2H), 1.78(d, 2H), 2.13–2.23(m, 2H), 2.32–2.41(m, 4H), 2.82–2.93(m, 2H), 4.33(s, 2H), 4.96(s, 2H), 7.00(s, 1H), 8.94(s, 1H) |
| 9-58 | | 0.30 (n-Hexane:AcOEt = 1:1) | (CDCl$_3$): 1.03(s, 9H), 1.79(d, 2H), 2.17(ddd, 2H), 2.27–2.34(m, 2H), 2.45(ddd, 2H), 2.67(dd, 2H), 2.85(d, 2H), 4.33(s, 2H), 4.96(s, 2H), 6.70(s, 1H), 8.95(s, 1H) |
| 9-59 | | 0.33 (n-Hexane:AcOEt = 1:1) | (CDCl$_3$): 0.89(d, 6H), 1.03(s, 9H), 1.74–1.81(m, 3H), 2.13(d, 2H), 2.19–2.20(m, 2H), 2.33(t, 2H), 2.80(d, 2H), 4.33(s, 2H), 4.95(s, 2H), 6.69(s, 1H), 8.94(s, 1H) |
| 9-60 | | 0.42 (CH$_2$Cl$_2$:MeOH = 10:1) | (CDCl$_3$): 0.11(q, 2H), 0.54(q, 2H), 0.85–0.87(m, 1H), 1.03(s, 9H), 1.80(d, 2H), 2.21(dt, 2H), 2.32(d, 2H), 2.43(t, 2H), 2.99–3.02(m, 2H), 4.33(s, 2H), 4.96(s, 2H), 6.70(s, 1H), 8.94(s, 1H) |
| 9-61 | | 0.31 (n-Hexane:AcOEt = 1:5) | (CDCl$_3$): 0.92(t, 3H), 1.03(s, 9H), 1.20–1.55(m, 4H), 1.70–1.82(m, 2H), 2.10–2.48(m, 6H), 2.78–2.95(m, 2H), 4.33(s, 2H), 4.96(s, 2H), 6.70(s, 1H), 8.94(s, 1H) |

9-62

7-(2,2-dimethyl-propyl)-6-(8-methanesulfonyl-2,4-dioxo-1-oxa-3,8-diaza-spiro[4.5]dec-3-ylmethyl)-7H-pyrrolo[2,3-d]pyrimidine-2-carbonitrile

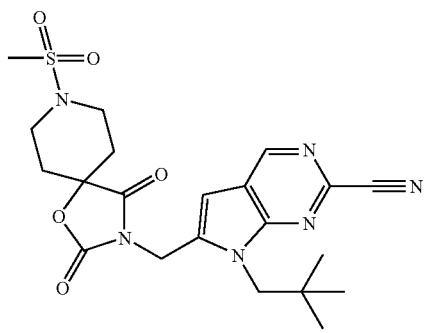

To a solution of 0.2 g (0.5 mmoles) of 7-(2,2-dimethyl-propyl)-6-(2,4-dioxo-1-oxa-3,8-diaza-spiro[4.5]dec-3-ylmethyl)-7H-pyrrolo[2,3-d]pyrimidine-2-carbonitrile in 5 ml of $CH_2Cl_2$ are added 0.05 ml (0.65 mmoles) of methanesulfonyl chloride and 0.08 ml (0.57 mmoles) of triethylamine. The mixture is stirred for 18 hours at ambient temperature and purified by HPLC(n-hexane/AcOEt) to give the product in 48% yield.

Rf=0.21(n-hexane:AcOEt=1:1) $^1$H NMR(400 MHz, DMSO-$d_6$) δ1.03(s, 9H), 1.85-1.95(m, 2H), 2,2-2.3(m, 2H), 2.84(s, 3H), 3.1-3.2(m, 2H), 3.75-3.85(m, 2H), 4.33(s, 2H), 4.98(s, 2H), 6.72(s, 1H), 8.95(s, 1H).

By repeating the procedures described above using appropriate starting materials and conditions the following compounds of formula 9-6 are obtained as identified below in Table 9-6.

9-65

7-(2,2-Dimethyl-propyl)-6-(1-methyl-2,4-dioxo-1,3,8-triaza-spiro[4.5]dec-3-ylmethyl)-7H-pyrrolo[2,3-d]pyrimidine-2-carbonitrile

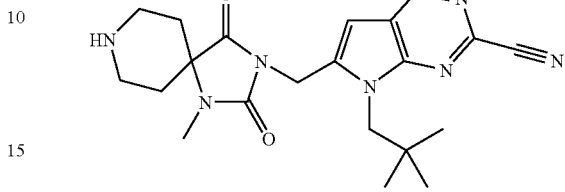

A) 3-[2-Cyano-7-(2,2-dimethyl-propyl)-7H-pyrrolo[2,3-d]pyrimidin-6-ylmethyl]-1-methyl-2,4-dioxo-1,3,8-triaza-spiro[4.5]decane-8-carboxylic acid .tert.-butyl ester 6.45 g (0.02 moles) of 1,3,8-triaza-spiro[4.5]decane-2,4-dione in 65 ml of DMF is added 3.32 g (0.024 moles) of $K_2CO_3$ and 7.35 g (0.027 moles) of 6-bromomethyl-7-(2,2-dimethyl-propyl)-7.H.-pyrrolo[2,3-.d.]pyrimidine-2-carbonitrile at ambient temperature. After being stirred for 5 hours, the reaction mixture is filtered to remove $K_2CO_3$. The filtrate is diluted with AcOEt and $H_2O$, and then extracted with AcOEt. The combined extracts are washed with water and brine, dried over $MgSO_4$ and concentrated under reduced pressure. The residue is purified by silica gel column chromatography to give 9.43 g of desired 3-[2-cyano-7-(2,2-dimethyl-propyl)-7H-pyrrolo[2,3-d]pyrimidin-6-ylmethyl]-1-methyl-2,4-dioxo-1,3,8-triaza-spiro[4.5]decane-8-carboxylic acid .tert.-butyl ester in 90% yield.

TABLE 9-6

9-6

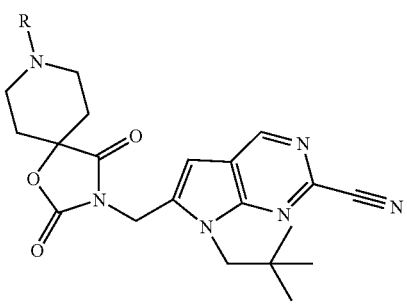

| Expl. No. | R | Rf(solvent) | $^1$H NMR(400 MHz, δ) |
|---|---|---|---|
| 9-63 | ![acetyl] | 0.43 ($CH_2Cl_2$:MeOH = 9:1) | ($CDCl_3$) 1.03(s, 9H), 1.75–1.87(m, 2H), 2.0–2.1(m, 2H), 2.13(s, 3H), 3.11–3.22(m, 1H), 3.45–3.55(m, 1H), 3.8–3.9(m, 1H), 4.33(s, 2H), 4.33–4.45(m, 1H), 4.98(s, 2H), 6.71(s, 1H), 8.95(s, 1H) |
| 9-64 | ![mesyl] | 0.21 (n-hexane:AcOEt = 1:1) | ($CDCl_3$) 1.03(s, 9H), 1.85–1.95(m, 2H), 2.2–2.3(m, 2H), 2.84(s, 3H), 3.1–3.2(m, 2H), 3.75–3.85(m, 2H), 4.33(s, 2H), 4.98(s, 2H), 6.72(s, 1H), 8.95(s, 1H) |

¹H NMR (400 MHz,CDCl₃, δ): 1.03 (s, 9H), 1.47 (s, 9H), 1.58-1.65 (m, 2H), 1.95-2.07 (m, 2H), 3.15-3.27 (m, 2H), 3.91-4.05 (m, 2H), 4.33 (s, 2H), 4.92 (s, 2H), 5.74 (brs, 1H), 6.71 (s, 1H), 8.92(s, 1H) Rf=0.25 (n-Hexane:AcOEt=1:1)

B) 3-[2-Cyano-7-(2,2-dimethyl-propyl)-7H-pyrrolo[2,3-d]pyrimidin-6-ylmethyl]-1-methyl-2,4-dioxo-1,3,8-triaza-spiro[4.5]decane-8-carboxylic acid .tert.-butyl ester

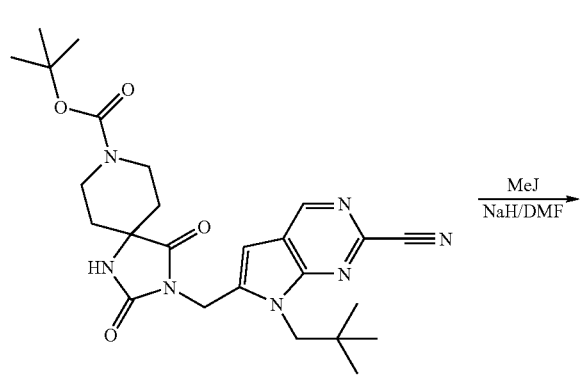

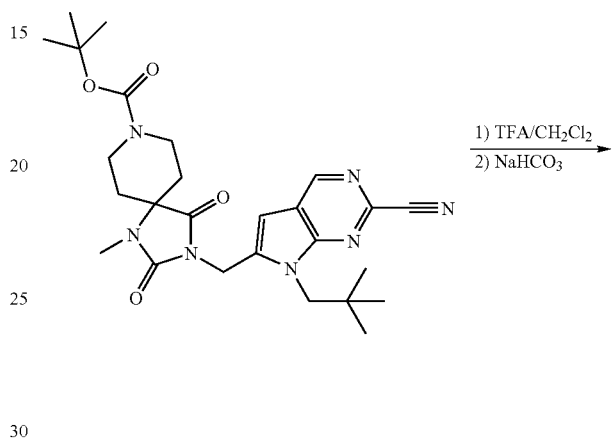

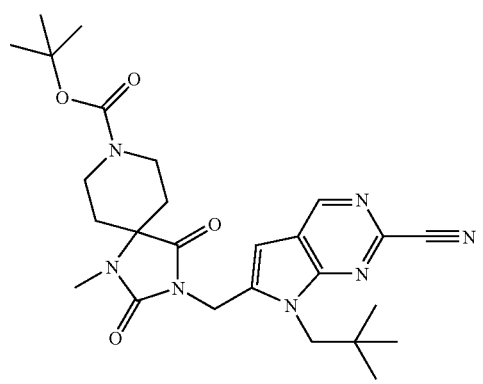

To a suspension of 0.9 g (0.024 moles) of NaH in 90 ml of DMF, is added 9.34 g (0.019 moles) of 3-[2-Cyano-7-(2,2-dimethyl-propyl)-7.H.-pyrrolo[2,3-.d.]pyrimidin-6-ylmethyl]-1-methyl-2,4-dioxo-1,3,8-triaza-spiro[4.5]decane-8-carboxylic acid .tert.-butyl ester at ambient temperature. After being stirred for 10 minutes, 1.6 ml (0.026 moles) of iodo methane is added slowly at 0° C. After being stirred for 5 hours at ambient temperature, the reaction mixture is quenched with cold H₂O and the mixture is extracted with AcOEt. The combined extracts are washed with brine, dried over MgSO₄ and concentrated under reduced pressure. The residue is purified by silica gel column chromatography to give 1.54 g of desired 3-[2-cyano-7-(2,2-dimethyl-propyl)-7H-pyrrolo[2,3-d]pyrimidin-6-ylmethyl]-1-methyl-2,4-dioxo-1,3,8-triaza-spiro[4.5]decane-8-carboxylic acid tert-butyl ester in 92% yield.

¹H NMR (400 MHz, CDCl₃., δ); 1.03 (s, 9H), 1.47 (s, 9H), 1.55-1.64 (m, 2H), 1.82-1.94 (m, 2H), 2.85 (s, 3H), 3.38-3.52 (m, 2H), 4.00-4.22 (m, 2H), 4.35 (s, 2H), 4.92 (s, 2H), 6.64 (s, 1H), 8.91 (s, 1H) Rf=0.20 (CH₂Cl₂:AcOEt=9:1)

C) 7-(2,2-Dimethyl-propyl)-6-(1-methyl-2,4-dioxo-1,3,8-triaza-spiro[4.5]dec-3-ylmethyl)-7H-pyrrolo[2,3-d]pyrimidine-2-carbonitrile To a solution of 7.62 g (0.015 moles) of 3-[2-cyano-7-(2,2-dimethyl-propyl)-7H-pyrrolo[2,3-d]pyrimidin-6-ylmethyl]-1-methyl-2,4-dioxo-1,3,8-triaza-spiro[4.5]decane-8-carboxylic acid .tert.-butyl ester in 30 ml of CH₂Cl₂, 30 ml (389 mmoles) of TFA is added at 0° C. After bing stirred for 1 hour at ambient temperature, sat. NaHCO₃ is added at 0° C. to the reaction mixture and the mixture is extracted with CH₂Cl₂. The combined extracts are dried over MgSO₄ and concentrated under reduced pressure to give desired 7-(2,2-dimethyl-propyl)-6-(1-methyl-2,4-dioxo-1,3,8-triaza-spiro[4.5]dec-3-ylmethyl)-7H-pyrrolo[2,3-d]pyrimidine-2-carbonitrile in quantitative yield. The crude product is used for the next step without purification.

¹H NMR (400 MHz, CDCl₃., δ): 1.03 (s, 9H), 1.58-1.67 (m, 2H), 1.87-1.98 (m, 2H), 2.89 (s, 3H), 3.03-3.11 (m, 2H), 3.31-3.40 (m, 2H), 4.35 (s, 2H), 4.92 (s, 2H), 6.64 (s, 1H), 8.91 (s, 1H) Rf=0.25 (CH₂Cl₂:MeOH=9:1)

9-66

7-(2,2-Dimethyl-propyl)-6-(1-methyl-2,4-dioxo-8-propyl-1,3,8-triaza-spiro[4.5]dec-3-ylmethyl)-7H-pyrrolo[2,3-d]pyrimidine-2-carbonitrile

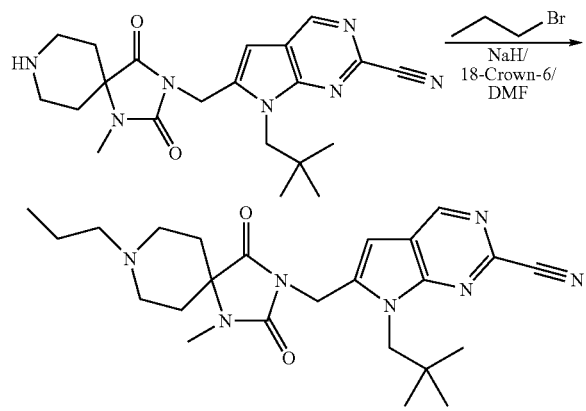

To a suspension of 27.4 mg (0.685 mmoles) of NaH and 6.5 mg (0.025 mmoles) of 18-crown-6 in 2.0 ml of DMF, 200 mg (0.488 mmoles) of 7-(2,2-Dimethyl-propyl)-6-(1-methyl-2,4-dioxo-1,3,8-triaza-spiro[4.5]dec-3-ylmethyl)-7H-pyrrolo[2,3-d]pyrimidine-2-carbonitrile is added at ambient temperature. After being stirred for 10 minutes, 75□l (0.823 mmoles) of 1-bromo propane is added at 0° C. and the reaction mixture is stirred for 5 hours at ambient temperature. The reaction mixture is quenched with cold H₂O and extracted with AcOEt. The combined extracts are washed with brine, dried over MgSO₄ and concentrated reduced pressure. The residue is purified by silica gel column chromatography to give 90.5 mg of desired 7-(2,2-dimethyl-propyl)-6-(1-methyl-2,4-dioxo-8-propyl-1,3,8-triaza-spiro[4.5]dec-3-ylmethyl)-7H-pyrrolo[2,3-d]pyrimidine-2-carbonitrile in 41% yield.

¹H NMR (400 MHz, CDCl₃., δ); 0.91 (t, 3H), 1.03 (s, 9H), 1.48-1.60 (m, 2H), 1.60-1.67 (m, 2H), 2.00-2.13 (m, 2H), 2.42 (t, 2H), 2.68-2.80 (m, 2H), 2.82-2.91 (m, 2H), 2.88 (s, 3H), 4.35 (s, 2H), 4.91 (s, 2H), 6.64 (s, 1H), 8.90 (s, 1H) Rf=0.15 (AcOEt:MeOH=4:1)

By repeating the procedures described above using starting material (ex.9-1) and appropriate bromide or chloride, the following compounds of formula 9-7 are obtained as identified below in Table 9-7.

TABLE 9-7

9-7

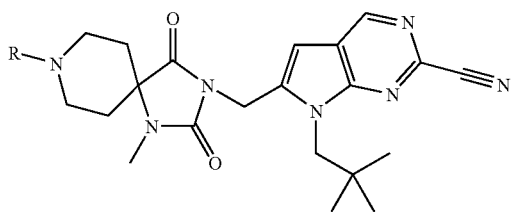

| Expl. No. | R | Rf(solvent) | ¹H NMR(400 MHz, δ) |
|---|---|---|---|
| 9-67 | cyclopropylmethyl | 0.13 (AcOEt:MeOH = 4:1) | CDCl₃: 0.10–0.17(m, 2H), 0.51–0.59(m, 2H), 0.83–0.98(m, 2H), 1.03(s, 9H), 1.61–1.69(m, 2H), 2.07–2.28(m, 2H), 2.34–2.42 (m, 2H), 2.70–2.80(m, 2H), 2.89(s, 3H), 2.97–3.08(m, 2H), 3.36(s, 2H), 4.34(s, 2H), 4.91(s, 2H), 6.64(s, 1H), 8.90(s, 1H) |
| 9-68 | cyclobutylmethyl | 0.25 (AcOEt:MeOH = 4:1) | CDCl₃: 1.03(s, 9H), 1.61–1.69(m, 2H), 2.07–2.28(m, 2H), 2.34–2.42(m, 2H), 2.70–2.80(m, 2H), 2.87(s, 3H), 2.97–3.08(m, 2H), 3.36(brs, 2H), 4.34(s, 2H), 4.90(s, 2H), 6.63(s, 1H), 8.90(s, 1H) |
| 9-69 | cyclohexylethyl | 0.49 (AcOEt:MeOH = 4:1) | CDCl₃: 0.81–0.98(m, 2H), 1.03(s, 9H), 1.14–1.26(m, 3H), 1.57–1.64(m, 2H), 1.65–1.81(m, 4H), 1.98–2.01(m, 2H), 2.22(d, 2H), 2.62–2.72(m, 2H), 2.73–2.80(m, 2H), 2.86(d, 2H), 2.88(s, 3H), 4.34(s, 2H), 4.90(s, 2H), 6.64(s, 1H), 8.90(s, 1H) |
| 9-70 | propargyl | 0.43 (AcOEt:MeOH = 4:1) | CDCl₃: 1.03(s, 9H), 1.62–1.70(m, 2H), 2.05–2.17(m, 2H), 2.30(brs, 1H), 2.88(s, 3H), 2.89–3.02(m, 4H), 3.36(brs, 2H), 4.34(s, 2H), 4.91(s, 2H), 6.64(s, 1H), 8.90(s, 1H) |
| 9-71 | 4-fluorobenzyl | 0.50 (AcOEt:MeOH = 4:1) | CDCl₃: 1.03(s, 9H), 1.58–1.66(m, 2H), 2.00–2.12(m, 2H), 2.70–2.83(m, 4H), 2.88 (s, 3H), 3.56(s, 2H), 4.34(s, 2H), 4.91(s, 2H), 6.63(s, 1H), 7.00(t, 2H), 7.26–7.30(m, 2□), 8.89(s, 1H) |

TABLE 9-7-continued 9-7

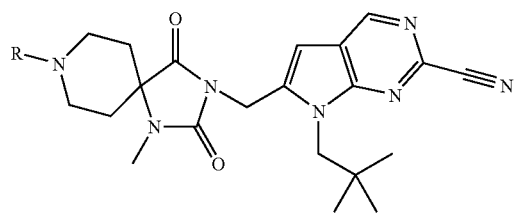

| Expl. No. | R | Rf(solvent) | $^1$H NMR(400 MHz, δ) |
|---|---|---|---|
| 9-72 | ⟋⟍⟋ (allyl) | 0.26 (AcOEt:MeOH = 4:1) | CDCl$_3$: 1.03(s, 9H), 1.59–1.66(m, 2H), 2.02–2.13(m, 2H), 2.68–2.77(m, 2H), 2.83–2.93(m, 2H), 2.88(s, 3H), 3.11(d, 2H), 4.35(s, 2H), 4.91(s, 2H), 5.14–5.25(m, 2H), 5.81–5.93(m, 1H), 6.64(s, 1H), 8.90(s, 1H) |
| 9-73 | 4-Cl-C$_6$H$_4$-CH$_2$- | 0.70 (AcOEt:MeOH = 4:1) | CDCl$_3$: 1.03(s, 9H), 1.57–1.64(m, 2H), 2.00–2.10(m, 2H), 2.72–2.84(m, 4H), 3.49 (s, 3H), 3.56(s, 2H), 4.34(s, 2H), 4.91(s, 2H), 6.63(s, 1H), 7.23–7.32(m, 4H), 8.90(s, 1H) |
| 9-74 | 2,4-F$_2$-C$_6$H$_3$-CH$_2$- | 0.78 (AcOEt:MeOH = 4:1) | CDCl$_3$: 1.03(s, 9H), 1.58–1.66(m, 2H), 2.00–2.12(m, 2H), 2.70–2.83(m, 4H), 2.88 (s, 3H), 3.56(s, 2H), 4.34(s, 2H), 4.91(s, 2H), 6.63(s, 1H), 7.00(t, 2H), 7.26–7.30(m, 2H), 8.89(s, 1H) |
| 9-75 | EtO-CH$_2$CH$_2$- | 0.23 (AcOEt:MeOH = 4:1) | CDCl$_3$: 1.03(s, 9H), 1.20(t, 3H), 1.58–1.64(m, 2H), 2.04–2.16(m, 2H), 2.69(t, 2H), 2.78–2.87(m, 2H), 2.88(s, 3H), 2.88–2.95(m, 2H), 3.51(q, 2H), 3.56(t, 2H), 4.34(s, 2H), 4.91(s, 2H), 6.63(s, 1H), 8.90(s, 1H) |
| 9-76 | EtO-CH$_2$-O-CH$_2$- | 0.40 (AcOEt:MeOH = 4:1) | CDCl$_3$: 1.03(s, 9H), 1.20(t, 3H), 1.56–1.64(m, 2H), 2.08–2.18(m, 2H), 2.70(t, 2H), 2.77–2.96(m, 2H), 2.88(s, 3H), 3.52 (q, 2H), 3.57–3.68(m, 6H), 4.34(s, 2H), 4.90(s, 2H), 6.63(s, 1H), 8.90(s, 1H) |
| 9-77 | MeO-CH$_2$CH$_2$- | 0.11 (AcOEt:MeOH = 4:1) | CDCl$_3$: 1.03(s, 9H), 1.58–1.66(m, 2H), 2.08–2.20(m, 2H), 2.66–2.71(m, 2H), 2.73–2.84(m, 2H), 2.87(s, 3H), 2.86–2.95 (m, 2H), 3.36(s, 3H), 3.47–3.55(m, 2H), 4.34(s, 2H), 4.91(s, 2H), 6.63(s, 1H), 8.90(s, 1H) |
| 9-78 | MeO-CH$_2$CH$_2$-O-CH$_2$CH$_2$- | 0.14 (AcOEt:MeOH = 4:1) | CDCl$_3$: 1.03(s, 9H), 2.04–2.16(m, 2H), 2.71(t, 2H), 2.77–2.95(m, 4H), 2.88(s, 3H), 2.38(s, 3H), 3.53–3.58(m, 2H), 3.59–3.67(m, 4H), 4.35(s, 2H), 4.90(s, 2H), 6.63(s, 1H), 8.90(s, 1H) |
| 9-79 | n-Pr-CH$_2$-S(O)$_2$-Me | 0.34 (n-hexane:AcOEt = 1:1) | CDCl$_3$: 0.96(t, 3H), 1.03(s, 9H), 1.42–1.54(m, 2H), 1.65–1.73(m, 2H), 1.75–1.85 (m, 2H), 2.06–2.18(m, 2H), 2.88(s, 3H), 2.97(t, 2H), 3.47–3.56(m, 2H), 3.80–3.87(m, 2H), 4.35(s, 2H), 4.92(s, 2H), 6.64(s, 1H), 8.92(s, 1H) |
| 9-80 | n-Pr-CH$_2$-C(O)- | 0.71 (AcOEt:MeOH = 4:1) | CDCl$_3$: 0.94(t, 3H), 1.03(s, 9H), 1.38(q, 2H), 1.49–1.73(m, 4H), 1.89–1.95(m, 2H), 2.35(dd, 2H), 2.84(s, 3H), 3.23–3.33(m, 1H), 3.74–3.90(m, 2H), 4.36(s, 2H), 4.62–4.71(m, 1H), 4.93(s, 2H), 6.65(s, 1H), 8.92(s, 1H) |

9-81

7-(2,2-Dimethyl-propyl)-6-(2,4-dioxo-1,3,8-triaza-spiro[4.5]dec-3-ylmethyl)-7H-pyrrolo[2,3-d]pyrimidine-2-carbonitrile

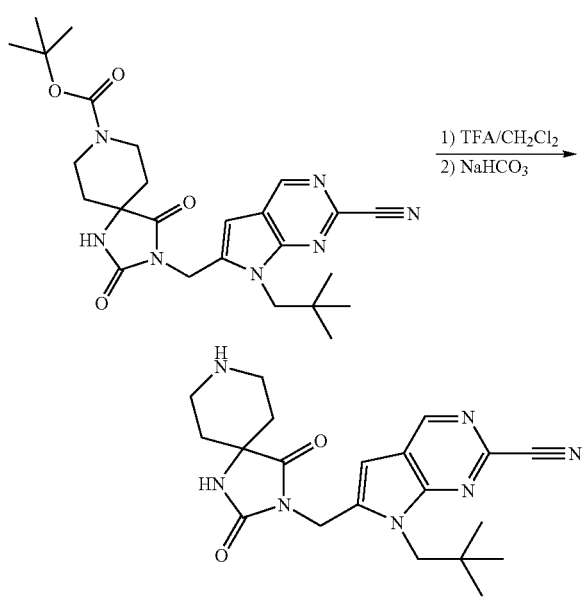

To a solution of 147.2 mg (0.297 mmoles) of 3-[2-cyano-7-(2,2-dimethyl-propyl)-7H-pyrrolo[2,3-d]pyrimidin-6-yl-methyl]-1-methyl-2,4-dioxo-1,3,8-triaza-spiro[4.5]decane-8-carboxylic acid tert-butyl in 2.0 ml of $CH_2Cl_2$, 2 ml (25.96 mmoles) of TFA is added at 0° C. The reaction mixture is stirred for 3 hours at ambient temperature and then sat. $NaHCO_3$ is added at 0° C. The mixture is extracted with $CH_2Cl_2$, dried over $MgSO_4$ and concentrated under reduced pressure. The residue is purified by silica gel column chromatography to give 26.3 mg of desired 7-(2,2-dimethyl-propyl)-6-(2,4-dioxo-1,3,8-triaza-spiro[4.5]dec-3-ylmethyl)-7H-pyrrolo[2,3-d]pyrimidine-2-carbonitrile in 22% yield.

$^1$H NMR (400 MHz, $CDCl_3$., δ): 1.03 (s, 2H), 1.54-1.72 (m, 2H), 2.00-2.10 (m, 2H), 2.78-2.89 (m, 2H), 3.21-3.30 (m, 2H), 4.33 (s, 2H), 4.92 (s, 2H), 6.15 (brs, 1H), 6.64 (s, 1H), 8.91 (s, 1H) Rf=0.10 ($CH_2Cl_2$:MeOH=9:1)

9-82

7-(2,2-Dimethyl-propyl)-6-(2,4-dioxo-8-propyl-1,3,8-triaza-spiro[4.5]dec-3-ylmethyl)-7H-pyrrolo[2,3-d]pyrimidine-2-carbonitrile

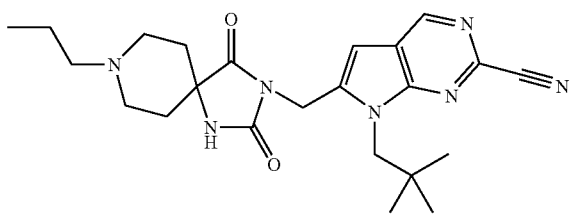

A) 8-Propyl-piperidin-4-one

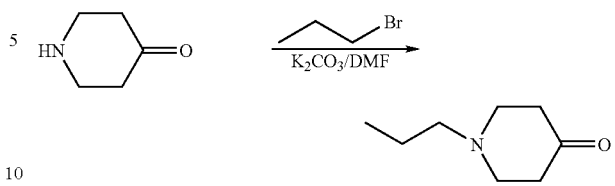

To a solution of 20 g (0.130 moles) of 4-piperidone hydrochloride monohydrate in 200 ml of DMF, 23.4 g (0.170 moles) of $K_2CO_3$ and 25 ml (0.274 moles) of 1-bromopropane are added at 0° C. The reaction mixture is stirred for 18 hours at ambient temperature and filtered to remove $K_2CO_3$. The filtrate is extracted with AcOEt and combined extracts are washed with water and brine, dried over $MgSO_4$ and concentrated to give 17.11 g of desired 8-propyl-piperidin-4-one in 93%. The crude product is used for the next step without purification.

$^1$H NMR (400 MHz, $CDCl_3$, δ): 0.94 (t, 3H), 1.55 (dd, 2H), 2.39-2.48 (m, 6H), 2.74 (t, 4H) Rf=0.30 (AcOEt)

B) 8-Propyl-1,3,8-triaza-spiro[4.5]decane-2,4-dione

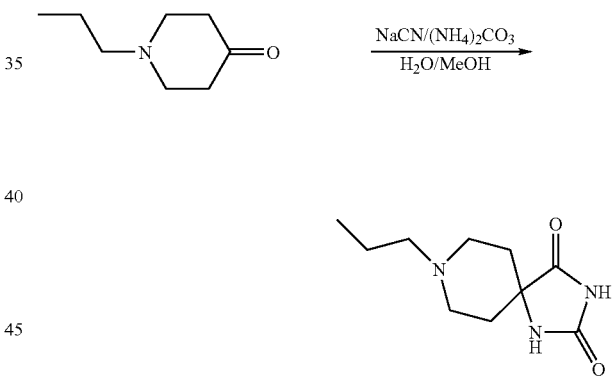

12.6 g (0.257 moles) of NaCN in 35 ml of $H_2O$ is added dropwise over 5 min to a solution of 17.1 g (0.121 moles) of 1-propyl-piperidin-4-one and 25.4 g (0.264 moles) of $(NH_4)_2CO_3$ in 65 ml of $H_2O$ and 75 ml of MeOH. The reaction mixture is stirred for 2 days at ambient temperature. An appered precipitate is removed by filtration, and the filtrate is concentrated under reduced pressure and dissolved in EtOH. After removal of insoluble material, the filtrate is concentrated again under reduced pressure. The resultant material is isolated by filtration and washed with ether to give 17.11 g of desired 8-propyl-1,3,8-triaza-spiro[4.5]decane-2,4-dione in 40% yield. The crude product is used for the next step without purification.

$^1$H NMR (400 MHz, DMSO-d6, δ): 0.84 (t, 3H), 1.37-1.49 (m, 4H), 1.72-1.83 (m, 2H), 2.02-2.27 (m, 2H), 2.24 (t, 2H), 2.66-2.75 (m, 2H), 8.03 (brs, 1H) Rf=0.10 (AcOEt)

C) 7-(2,2-Dimethyl-propyl)-6-(2,4-dioxo-8-propyl-1,3,8-triaza-spiro[4.5]dec-3-ylmethyl)-7H-pyrrolo[2,3-d]pyrimidine-2-carbonitrile

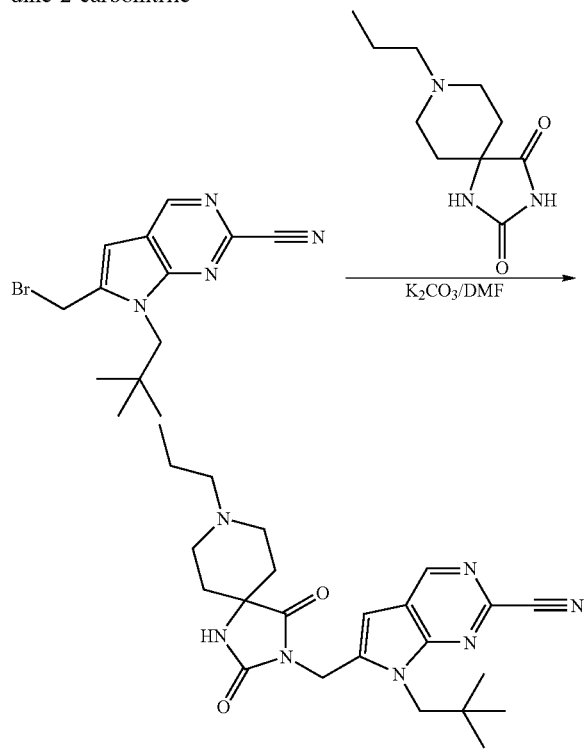

To a solution of 7.73 g (0.037 moles) of 8-propyl-1,3,8-triaza-spiro[4.5]decane-2,4-dione in 70 ml of DMF, 4.39 g (0.032 moles) of $K_2CO_3$ and 7.50 g (0.024 moles) of 6- are added at ambient temperature. The reaction mixture is stirred for 5 hours at ambient temperature and $K_2CO_3$ is filtered off. The filtrate is diluted with AcOEt, $H_2O$ and extracted with AcOEt. The combined extracts are washed with water and brine, dried over $MgSO_4$ and concentrated under reduced pressure. The residue is purified by silica gel column chromatography to give 5.87 g of desired 7-(2,2-dimethyl-propyl)-6-(2,4-dioxo-8-propyl-1,3,8-triaza-spiro[4.5]dec-3-ylmethyl)-7H-pyrrolo[2,3-d]pyrimidine-2-carbonitrile in 55% yield.

$^1$H NMR (400 MHz, $CDCl_3$., δ); 0.91 (t, 3H), 1.03 (s, 9H), 1.44-1.56 (m, 2H), 1.62-1.70 (m, 2H), 2.09-2.22 (m, 4H), 2.34 (t, 2H), 2.89-2.98 (m, 2H), 4.33 (s, 2H), 4.92 (s, 2H), 5.77 (brs, 1H), 6.64 (s, 1H), 8.91 (s, 1H) Rf=0.26 (AcOEt:MeOH=4:1)

By repeating the procedures described above using appropriate starting materials and conditions the following compounds of formula 9-8 are obtained as identified below in Table 9-8

TABLE 9-8

9-8

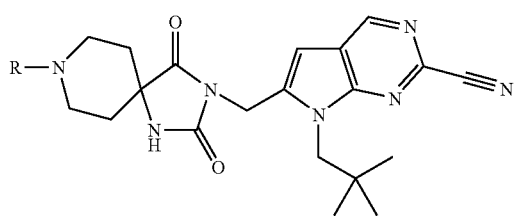

| Expl. No. | R | Rf(solvent) | $^1$H NMR(400 MHz, δ) |
|---|---|---|---|
| 9-83 | F-C₆H₄-CH₂- | 0.60 (AcOEt:MeOH = 4:1) | $CDCl_3$: 1.03(s, 9H), 1.60–1.72(m, 2H), 2.11–2.18(m, 4H), 2.87–2.93(m, 2H), 3.51(s, 2H), 4.33(s, 2H), 4.91(s, 2H), 5.78(brs, 1H), 6.63(s, 1H), 7.24–7.31(m, 2H), 7.24–7.30(□, 2H), 8.90(s, 1H) |
| 9-84 | n-butyl | 0.38 (AcOEt:MeOH = 4:1) | $CDCl_3$: 0.96(t, 3H), 1.03(s, 9H), 1.28–1.37(m, 2H), 1.41–1.50(m, 2H), 1.61–1.69(m, 2H), 2.05–2.20(m, 4H), 2.37(t, 2H), 2.89–2.97(m, 2H), 4.33(s, 2H), 4.92(s, 2H), 5.71(brs, 1H), 6.64(s, 1H), 8.91(s, 1H) |
| 9-85 | CF₂-CH₂CH₂F | 0.58 (AcOEt) | ($CDCl_3$): 1.05(s, 9H), 1.65–1.75(m, 2H), 2.11–2.22(m, 2H), 2.23–2.42(m, 4H), 2.65–2.69(m, 2H), 2.90–3.00(m, 2H), 4.35(s, 2H), 4.94(s, 2H), 6.00 (brs, 1H), 6.66(s, 1H), 8.93(s, 1H) |

TABLE 9-8-continued

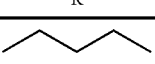

9-8

| Expl. No. | R | Rf(solvent) | ¹H NMR(400 MHz, δ) |
|---|---|---|---|
| 9-86 |  | 0.5 (AcOEt) | (CDCl₃): 0.95(s, 3H), 1.05(s, 9H), 1.39(dd, 2H), 1.62–1.68(m, 2H), 1.68–1.77(m, 2H), 1.98–2.13(m, 2H), 2.30–2.42(m, 2H), 3.39–3.57(m, 2H), 3.85–3.97(m, 1H), 4.10–4.21(m, 1H), 4.36(s, 2H), 4.95(s, 2H), 5.96(brs, 1H), 6.67(s, 1H), 8.943(s, 1H) |
| 9-87 | 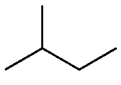 | 0.17 (AcOEt) | (CDCl₃): 0.92(t, 3H), 1.05(s, 9H), 1.25–1.41(m, 4H), 1.43–1.58(m, 2H), 1.62–1.73(m, 2H), 2.08–2.24(m, 2H), 2.35–2.43(t, 2H), 2.91–3.05(m, 2H), 4.35(s, 2H), 4.94(s, 2H), 5.77(brs, 1H), 6.66(s, 1H), 8.93(s, 1H) |
| 9-88 | 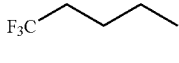 | 0.35 (AcOEt) | (CDCl₃): 0.91(s, 3H), 0.92(s, 3H), 1.03(s, 9H), 1.60–1.68(m, 2H), 1.72–1.85(m, 2H), 2.03–2.22(m, 2H), 2.86–2.95(m, 2H), 4.35(s, 2H), 4.94(s, 2H), 5.76(bs, 1H), 6.66(s, 1H), 8.93(s, 1H) |
| 9-89 | F₃C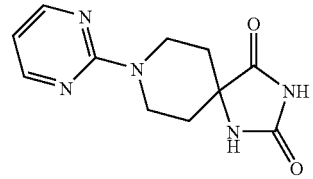 | 0.58 (MeOH:CH₂Cl₂ = 1:9) | (CDCl₃)□1.03(s, 9H), 1.48–1.57(m, 4H), 1.62–1.79(m, 4H), 2.07–2.22(m, 6H), 2.44(t, 2H), 2.85–2.93(m, 2H), 4.33(s, 2H), 4.92(s, 2H), 6.64(s, 1H), 7.19(brs, 1H), 8.91(s, 1H) |

9-90

7-(2,2-Dimethyl-propyl)-6-(2,4-dioxo-8-pyrimidin-2-yl-1,3,8-triaza-spiro[4.5]dec-3-ylmethyl)-7H-pyrrolo[2,3-d]pyrimidine-2-carbonitrile

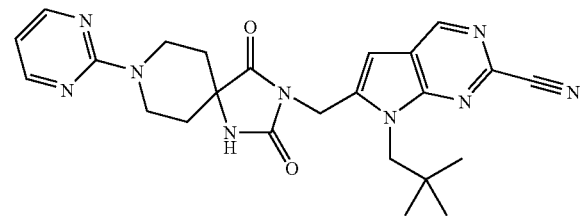

A) 8-pyrimidin-2-yl-1,3,8-triaza-spiro[4.5]decane-2,4-dione

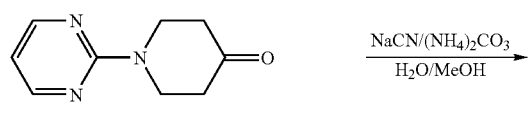 $\xrightarrow{\text{NaCN/(NH}_4)_2\text{CO}_3}{\text{H}_2\text{O/MeOH}}$ -continued 182.2 mg (3.718 mmoles) of NaCN in 0.5 ml of H₂O is added dropwise over 5 min to a solution of 300.0 mg (1.693 mmoles) of 1-pyrimidin-2-yl-piperidin-4-one and 341.0 mg (3.549 mmoles) of (NH₄)₂CO₃ in 0.9 ml of H₂O and 1.1 ml of MeOH. The reaction mixture is stirred for 2 days at ambient temperature. Precipitates are removed by filtration, the filtrate is extracted with CH₂Cl₂. The combined extracts are washed with water and brine, dried over MgSO₄ and concentrated to give 180 mg of desired 8-pyrimidin-2-yl-1,3,8-triaza-spiro[4.5]decane-2,4-dione in 43% yield, which is used for the next step without purification.

¹H NMR (400 MHz, DMSO, δ): 1.55-1.62 (m, 2H), 1.70-1.80 (m, 2H), 3.33-3.44 (m, 2H), 4.40-4.48 (m, 2H), 6.64 (t, 1H), 8.37 (d, 2H), 8.59 (brs, 1H), 10.7 (brs, 1H) Rf=0.3 (AcOEt)

B) 7-(2,2-Dimethyl-propyl)-6-(2,4-dioxo-8-pyrimidin-2-yl-1,3,8-triaza-spiro[4.5]dec-3-ylmethyl)-7H-pyrrolo[2,3-d]pyrimidine-2-carbonitrile

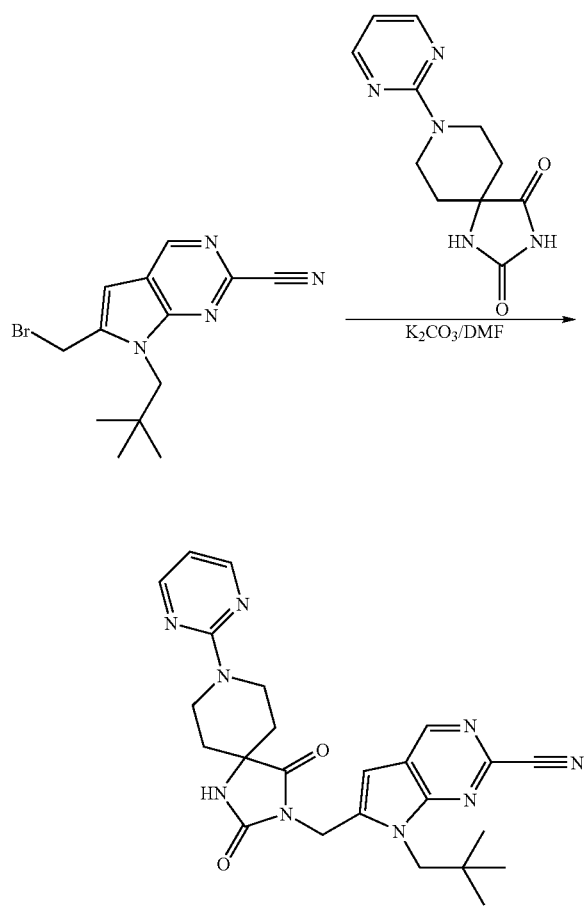

To a solution of 180.0 mg (0.728 mmoles) of 8-pyrimidin-2-yl-1,3,8-triaza-spiro[4.5]decane-2,4-dione in 2.0 ml of DMF, 99.4 mg (0.719 mmoles) of K$_2$CO$_3$ and 170.0 mg (0.553 mmoles) of 6-bromomethyl-7-(2,2-dimethyl-propyl)-7H-pyrrolo[2,3-d]pyrimidine-2-carbonitrile are added at ambient temperature. The mixture is stirred for 5 hours at ambient temperature and filtered. The mixture is diluted with AcOEt and H$_2$O, and then extracted with AcOEt. The combined extracts are washed with water and brine, dried over MgSO$_4$ and concentrated under reduced pressure. The residue is purified by silica gel column chromatography to give 151.5 mg of desired 7-(2,2-dimethyl-propyl)-6-(2,4-dioxo-8-pyrimidin-2-yl-1,3,8-triaza-spiro[4.5]dec-3-ylmethyl)-7H-pyrrolo[2,3-d]pyrimidine-2-carbonitrile in 58% yield.

$^1$H NMR (400 MHz, CDCl$_3$., δ): 1.01 (s, 9H), 1.67-1.77 (m, 2H), 2.05-2.15 (m, 2H), 3.45-3.54 (m, 2H), 4.32 (s, 2H), 4.51-4.60 (m, 2H), 4.93 (s, 2H), 6.55 (t, 1H), 6.65 (brs, 1H), 6.66 (s, 1H), 8.33 (d, 2H), 8.92 (s, 1H) Rf=0.44 (AcOEt)

9-91

4-[2-Cyano-7-(2,2-dimethyl-propyl)-7H-pyrrolo[2,3-d]pyrimidin-6-ylmethyl]-3,5-dioxo-piperazine-1-carboxylic acid tert-butyl ester

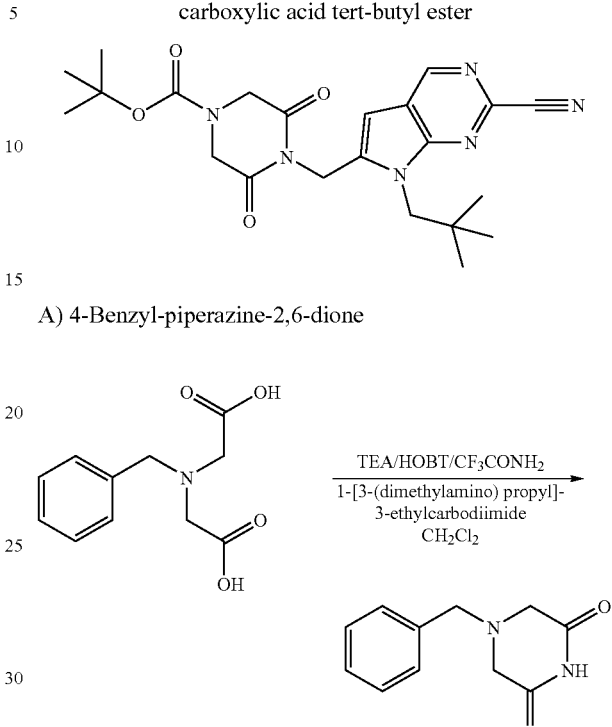

A) 4-Benzyl-piperazine-2,6-dione

To a suspensiopn of 15 g (67 mmoles) of benzyliminodiacetic acid in 300 ml of CH$_2$Cl$_2$, 28 ml (201 mmoles) of triethylamine, 21.77 g (161 mmoles) of 1H-hydroxybenztriazole and 10.6 g (94 mmoles) of trifluoroacetamide are successively added and then 28.34 g (147.8 mmoles) of 1-[3 (dimethylamino)propyl]-3-ethylcarbodiimide hydrochloride is added at 0° C. The reaction mixture is allowed to warm to ambient temperature and stirred for 18 hours. The reaction mixture is quenched with cold H$_2$O and extracted with CH$_2$Cl$_2$. The combined extracts are washed with H$_2$O brine, dried over MgSO$_4$ and concentrated under reduced pressure. The residue is purified by silica gel column chromatography (eluent: n-Hexane:AcOEt=2:1) to give 10 g of desired 4-benzyl-piperazine-2,6-dione in 73% yield.

$^1$H NMR (400 MHz, CDCl$_3$., δ); 3.37 (s, 4H), 3.67 (s, 2H), 7.25-7.40 (m, 5H), 8.35 (brs, 1 H) Rf=0.30 (n-Hexane:AcOEt=1:1)

B) Piperazine-2,6-dione

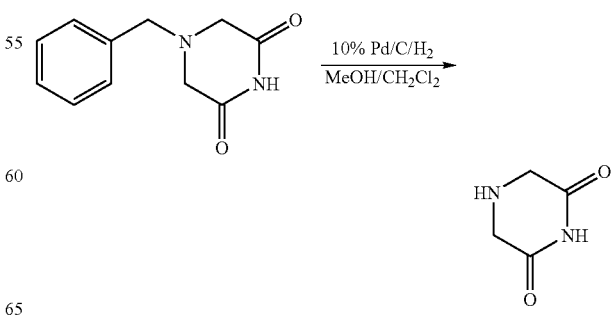

The mixture of 10 g (49 mmoles) of 4-benzyl-piperazine-2,6-dione and cat.amount of 10% Pd/C in 200 ml of MeOH and 50 ml of $CH_2Cl_2$ is stirred for 18 hours at ambient temperature. The reaction mixture is filtered off through celite, and the filtrate is concentrated under reduced pressure to give powder, which is washed with AcOEt to give 5.47 g of desired piperazine-2,6-dione in 98% yield.

$^1$H NMR (400 MHz, $CDCl_3$, δ): 3.15 (m, 4H), 3.35 (s, 4H), 10.80 (brs, 1H) Rf=0.27 ($CH_2Cl_2$:MeOH=10:1)

C) 3,5 Dioxo-piperazine-1-carboxylic acid tert-butyl ester

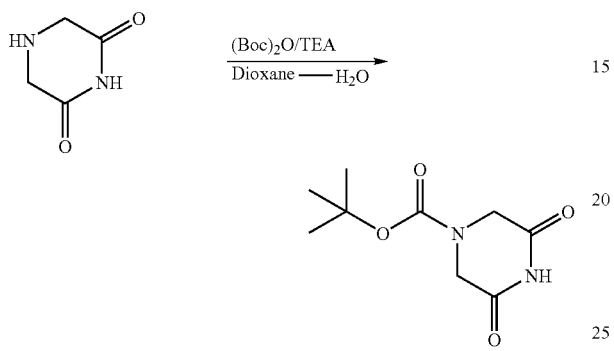

To a solution of 0.8 g (7 mmoles) of piperazine-2,6-dione in 10 ml of dioxane and 10 ml of $H_2O$, 1.46 ml (10.5 mmoles) of triethylamine and 1.99 g (9.1 mmoles) of $(Boc)_2O$ in 5 ml of dioxane are successively added at 0° C. The reaction mixture is allowed to warm to ambient temperature and stirred for 18 hours. The reaction mixture is diluted with AcOEt and then extracted with AcOEt. The combined extracts are washed with brine, dried over $MgSO_4$ and concentrated under reduced pressure to give 1.2 g of desired 3,5 dioxo-piperazine-1-carboxylic acid tert-butyl ester in 80% yield.

$^1$H NMR (400 MHz, $CDCl_3$, δ): 1.49 (s, 9H), 4.30 (s, 4H), 8.53 (s, 1H) Rf=0.68 ($CH_2Cl_2$:MeOH=10:1)

D) 4-[2-Cyano-7-(2,2-dimethyl-propyl)-7H-pyrrolo[2,3-d]pyrimidin-6-ylmethyl]-3,5-dioxo-piperazine-1-carboxylic acid tert-butyl ester To a solution of 6 g (28 mmoles) of 3,5-dioxo-piperazine-1-carboxylic acid tert.-butyl ester in 70 ml of DMF, 4.64 g (32.3 mmoles) of $K_2CO_3$ and 6.89 g (22.4 mmoles) of 6-bromomethyl-7-(2,2-dimethyl-propyl)-7H-pyrrolo[2,3-d]pyrimidine-2-carbonitrile are added at 0° C. and the reaction mixture is allowed to warm to ambient temperature and stirred for 1 hour. The reaction mixture is quenched with $H_2O$ and extracted with AcOEt. The combined extracts are washed with $H_2O$, brine, dried over $MgSO_4$ and concentrated under reduced pressure. The residue is purified by silica gel column chromatography (eluent: n-Hexane:AcOEt=3:1) to give 10.5 g of desired of 4-[2-cyano-7-(2,2-dimethyl-propyl)-7H-pyrrolo[2,3-d]pyrimidin-6-ylmethyl]-3,5-dioxo-piperazine-1-carboxylic acid .tert.-butyl ester in 85% yield.

$^1$H NMR (400 MHz, $CDCl_3$, δ): 1.02 (s, 9H), 4.36 (s, 2H), 4.39 (s, 4H), 5.19 (s, 2H), 6.53 (s, 1H), 8.88 (s, 1H) Rf=0.48 (n-Hexane:AcOEt=1:1)

9-92

7-(2,2-Dimethyl-propyl)-6-(2,6-dioxo-4-phenylsulfanyl-piperazin-1-ylmethyl)-7H-pyrrolo[2,3-d]pyrimidine-2-carbonitrile

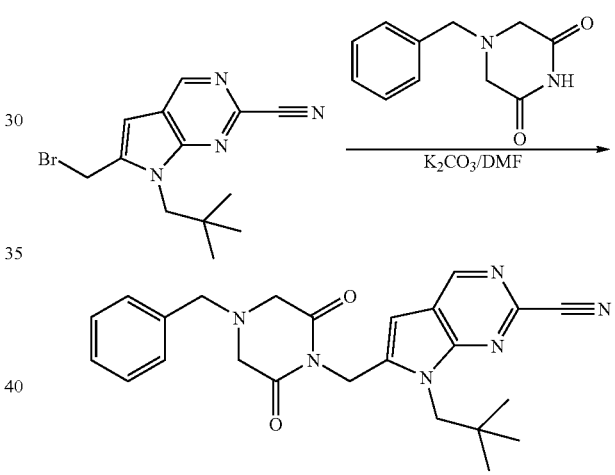

To a solution of 4.65 g (22.8 mmoles) of 4-benzyl-piperazine-2,6-dione in 50 ml of DMF, 3.40 g (24.6 mmoles) of $K_2CO_3$ and 5 g (16.2 mmoles) of 6-bromomethyl-7-(2,2-dimethyl-propyl)-7H-pyrrolo[2,3-d]pyrimidine-2-carbonitrile are added at 0° C. and the reaction mixture is allowed to warm to ambient temperature and stirred for 3 hour. The reaction mixture is quenched with $H_2O$ and extracted with AcOEt. The combined extracts are washed with $H_2O$ and brine, dried over $MgSO_4$ and then concentrated under reduced pressure. The residue is purified by silica gel column chromatography (eluent: n-Hexane:AcOEt=2:1) to give 5.75 g of desired 7-(2,2-dimethyl-propyl)-6-(2,6-dioxo-4-phenylsulfanyl-piperazin-1-ylmethyl)-7H-pyrrolo[2,3-d]pyrimidine-2-carbonitrile in 82% yield.

$^1$H NMR (400 MHz, $CDCl_3$, δ): 1.02 (s, 9H), 3.46 (s, 4H), 3.56 (s, 2H), 4.34 (s, 2H), 5.15 (s, 2H), 6.53 (s, 1H), 7.25-7.40 (m, 5H), 8.88 (s, 1H) Rf=0.48 (n-Hexane:AcOEt=1:1)

By repeating the procedures described above using appropriate starting materials and conditions the following compounds of formula 9-9 are obtained as identified below in Table 9-9.

TABLE 9-9

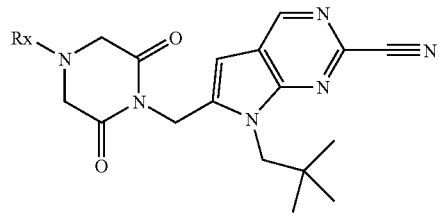

9-9

| Expl. No. | RX | Rf | ¹H NMR(400 MHz, δ) |
|---|---|---|---|
| 9-93 | F-C₆H₄-CH₂- | 0.40 (n-Hexane:AcOEt = 1:1) | CDCl₃: 1.02(s, 9H), 3.45(s, 4H), 3.62(s, 2H), 4.34(s, 2H), 5.15(s, 2H), 6.53(s, 1H), 7.00–7.10(m, 2H), 7.20–7.30(□, 2H), 8.88(s, 1H) |
| 9-94 | CH₃CH₂-O-CH₂CH₂- | 0.48 (AcOEt) | CDCl₃: 1.02(s, 9H), 1.20(t, 3H), 2.70–2.78(m, 2H), 3.47(q, 2H), 3.52–3.57(m, 2H), 3.59(s, 4H), 4.35(s, 2H), 5.16(s, 2H), 6.55(s, 1H), 8.87(s, 1H) |
| 9-95 | CH₃-O-CH₂CH₂- | 0.40 (AcOEt) | CDCl₃: 1.02(s, 9H), 2.72(t, 3H), 3.34(s, 3H), 3.53(t, 2H), 3.57(s, 4H), 4.35(s, 2H), 5.16(s, 2H), 6.55 (s, 1H), 8.87(s, 1H) |
| 9-96 | HC≡C-CH₂CH₂- | 0.30 (n-Hexane:AcOEt = 1:1) | CDCl₃: 1.02(s, 9H), 2.40(t, 1H), 3.50(d, 2H), 3.55(s, 4H), 4.34(s, 2H), 4.35(s, 2H), 5.17(s, 2H), 6.53 (s, 1H), 8.87(s, 1H) |

9-97

7-(2,2-Dimethyl-propyl)-6-(2,6-dioxo-piperazin-1-ylmethyl)-7H-pyrrolo[2,3-d]pyrimidine-2-carbonitrile

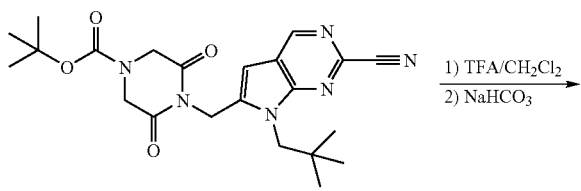

To a solution of 10.5 g (23.9 mmoles) of 4-[2-cyano-7-(2,2-dimethyl-propyl)-7H-pyrrolo[2,3-d]pyrimidin-6-ylmethyl]-3,5-dioxo-piperazine-1-carboxylic acid .tert.-butyl ester in 300 ml of CH₂Cl₂, 52 ml (675 mmoles) of TFA is added at 0° C. The reaction mixture is allowed to warm to ambient temperature and stirred for 6 hours. The reaction mixture is concentrated under reduced pressure, neutralized with sat.NaHCO₃ and extracted with CH₂Cl₂. The combined extracts are washed with brine, dried over MgSO₄ and concentrated under reduced pressure. The residue is purified by silica gel column chromatography (eluent: CH₂CO₂: AcOEt=1:3) give 7.18 g of desired 7-(2,2-dimethyl-propyl)-6-(2,6-dioxo-piperazin-1-ylmethyl)-7H-pyrrolo[2,3-d]pyrimidine-2-carbonitrile in 88.5% yield.

¹H NMR (400 MHz, CDCl₃, δ): 1.02 (s, 9H), 1.57 (brs, 1H), 3.78 (s, 4H), 4.36 (s, 2H), 5.19 (s, 2H), 6.56 (s, 1H), 8.86 (s, 1H) Rf=0.20 (AcOEt)

9-98

6-[4-(Butane-1-sulfonyl)-2,6-dioxo-piperazin-1-ylmethyl]-7-(2,2-dimethyl-propyl)-7H-pyrrolo[2,3-d]pyrimidine-2-carbonitrile

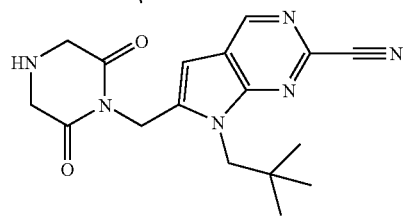 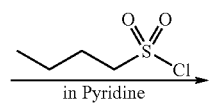

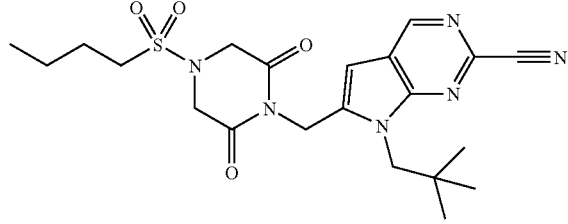

To a solution of 200 mg (0.59 mmoles) of 7-(2,2-dimethyl-propyl)-6-(2,6-dioxo-piperazin-1-ylmethyl)-7H-pyrrolo[2, 3-d]pyrimidine-2-carbonitrile in 4 ml of pyridine, 184 mg (1.2 mmoles) of 1-butanesulfonylchloride is added at 0° C. The reaction mixture is allowed to warm to ambient temperature and stirred for 2 hours and the mixture is concentrated under reduced pressure. The obtained crude powder is dissolved in $CH_2Cl_2$, and the $CH_7Cl_2$ layer is washed with 1N aqueous HCl, brine, and then dried over $MgSO_4$. The $CH_2Cl_2$ layer is concentrated under reduced pressure to give colorless powder, which is washed with ether to give 195 mg of desred 6-[4-(Butane-1-sulfonyl)-2,6-dioxo-piperazin-1-ylmethyl]-7-(2,2-dimethyl-propyl)-7H-pyrrolo[2,3-d]pyrimidine-2-carbonitrile in 72% yield.

$^1$H NMR (400 MHz, $CDCl_3$, δ): 0.93 (t, 3H), 1.02 (s, 9H), 1.35-1.50 (m, 2H), 1.70-1.82 (m, 2H), 3.00-3.10 (m, 2H), 4.28 (s, 4H), 4.32 (s, 2H), 5.20 (s, 2H), 6.58 (s, 1H), 8.87 (s, 1H) Rf=0.26 (n-Hexane:AcOEt=1:1)

By repeating the procedures described above using appropriate starting materials and conditions the following compounds of formula 9-10 are obtained as identified below in Table 9-10

A) (4-Fluoro-phenylamino)-acetic acid methyl ester

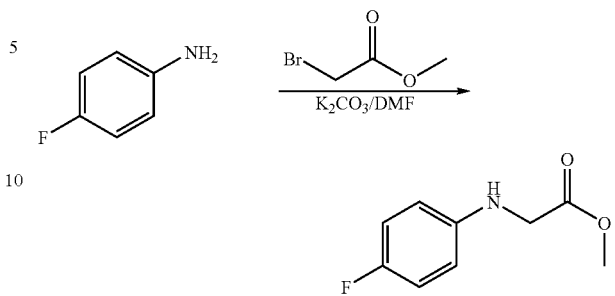

To a solution of 25 g (225 mmoles) of p-fluoroaniline in 250 ml of DMF, 25.56 ml of methyl bromoacetate and 46.6 g of $K_2CO_3$ are added successively at ambient temperature. After being stirred for 18 hours at ambient temperature, the reaction mixture is quenched with $H_2O$ and extracted with AcOEt. The combined extracts are washed with $H_2O$, brine, dried over $MgSO_4$ and concentrated under reduced pressure. The residue is purified by silica gel column chromatography (eluent: n-Hexane:AcOEt=3:1) to give 34.3 g of desired 4-fluoro-phenylamino)-acetic acid methyl ester in 83.2% yield.

$^1$H NMR (400 MHz, $CDCl_3$, δ): 3.78 (s, 3H), 3.88 (s, 2H), 4.16 (brs, 1H), 6.50-6.60 (m, 2H), 6.85-6.95 (s, 2H) Rf=0.45 (n-Hexane:AcOEt=1:1)

B) [tert.-Butoxycarbonylmethyl-(4-fluoro-phenyl)-amino]-acetic acid methyl ester

TABLE 9-10

9-10

| Expl. No. | R | Rf(solvent) | $^1$H NMR(400 MHz, δ) |
|---|---|---|---|
| 9-99 | 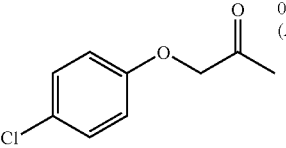 | 0.44 (AcOEt) | $CDCl_3$: 1.02(s, 9H), 2.97(s, 3H), 4.27(s, 4H), 4.33(s, 2H), 5.21(s, 3H), 6.57(s, 1H), 8.89 (s, 1H) |
| 9-100 | 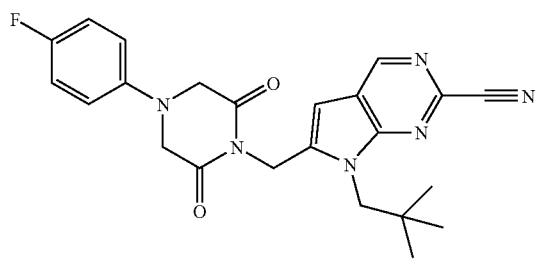 | 0.56 (AcOEt) | $CDCl_3$: 1.01(s, 9H), 4.32(s, 2H), 4.60(brs, 4H), 4.75(s, 2H), 5.14(s, 2H), 6.35(s, 1H), 6.85 (d, 2H), 7.24(d, 2H), 8.85(s, 1H) |

9-101

7-(2,2-Dimethyl-propyl)-6-[4-(4-fluoro-phenyl)-2,6-dioxo-piperazin-1-ylmethyl]-7H-pyrrolo[2,3-d]pyrimidine-2-carbonitrile

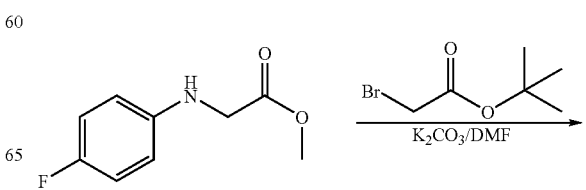

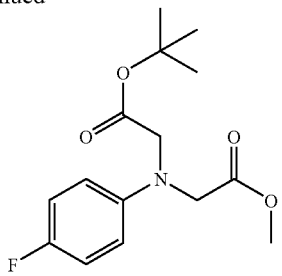

To a solution of 15 g of 4-fluoro-phenylamino)-acetic acid methyl ester in 70 ml of DMF, 15.7 ml of bromo-acetic acid tert.-butyl ester and 15.84 g of $K_2CO_3$ are added successively at ambient temperature. After being stirred for 18 hours at 65° C., the reaction mixture is quenched with $H_2O$ and extracted with AcOEt. The combined extracts are washed with $H_2O$, brine, dried over $MgSO_4$ and concentrated under reduced pressure. The residue is purified by silica gel column chromatography (eluent: n-Hexane:AcOEt=2:1) to give 20 g of desired tert.-butoxycarbonylmethyl-(4-fluoro-phenyl)-amino]-acetic acid methyl ester in 82% yield.

$^1$H NMR (400 MHz, CDCl$_3$, δ): 1.45 (s, 9H), 3.785 (s, 3H), 3.99 (s, 2H), 4.11 (s, 1H), 6.50-6.60 (m, 2H), 6.87-6.97 (s, 2H) Rf=0.55 (n-Hexane:AcOEt=1:1)

C) 4-(4-Fluoro-phenyl)-piperazine-2,6-dione

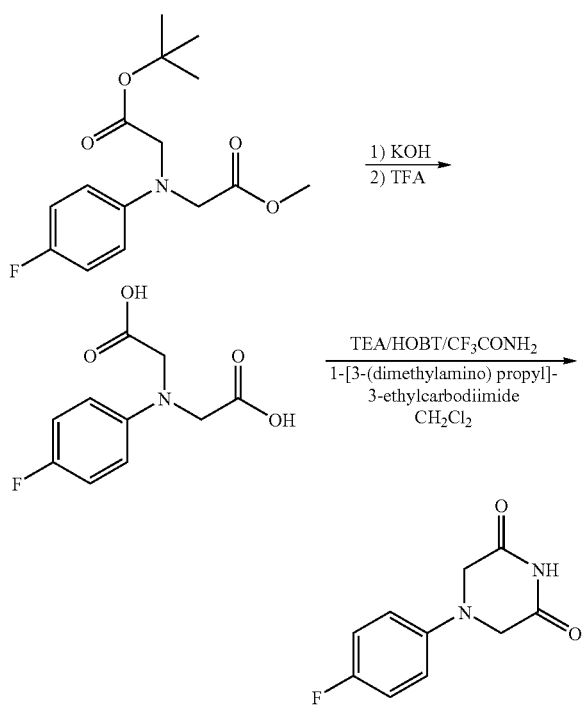

To a solution of 5 g (16.8 mmoles) of tert.-butoxycarbonylmethyl-(4-fluoro-phenyl)-amino]-acetic acid methyl ester in 100 ml of MeOH, 33.7 ml of 1 mole aqueous KOH is added at 0° C. The reaction mixture is stirred for 4 hours and acidified with 1 mole aueous HCl. The mixture is extracted with $CH_2Cl_2$ several times and the combined extracts are washed with brine, dried over $MgSO_4$ and concentrated under reduced pressure to give 4.08 g of desired crude mono acid in 85% yield. The crude acid in 200 ml of $CH_2Cl_2$ is treated with 31 ml of TFA. After being stirred for 18 hours at ambient temperature, the reaction mixture is concentrated under reduced pressure to give 4.92 g of desied [carboxymethyl-(4-fluoro-phenyl)-amino]-acetic acid in 100% yield as trifluoroacetic acid salt. To a solution of 4.92 g (14.4 mmoles) of [carboxymethyl-(4-fluoro-phenyl)-amino]-acetic acid in 300 ml of $CH_2Cl_2$, 9.63 ml (69.2 mmoles) of triethylamine, 4.67 g (34.6 mmoles) of 1H-hydroxybenztriazole and 2.45 g (21.7 mmoles) of trifluoroacetamide are successively added and then 6.64 g (34.6 mmoles) of 1-[3(dimethylamino)propyl]-3-ethylcarbodiimide hydrochloride is added at 0° C. The reaction mixture is allowed to warm to ambient temperature and stirred for 18 hours. The reaction mixture is quenched with cold $H_2O$ and extracted with $CH_2Cl_2$. The combined extracts are washed with $H_2O$, brine, dried over $MgSO_4$ and concentrated under reduced pressure. The residue is purified by silica gel column chromatography (eluent: n-Hexane:AcOEt=1:1) to give 1.15 g of desired 4-(4-fluoro-phenyl)-piperazine-2,6-dione in 38% yield.

$^1$H NMR (400 MHz, CDCl$_3$, δ): 4.03 (s, 4H), 6.85-6.95 (m, 2H), 7.00-7.10 (s, 2H), 8.21 (brs, 1 H) Rf=0.30 (n-Hexane:AcOEt=1:1)

D) 7-(2,2-Dimethyl-propyl)-6-[4-(4-fluoro-phenyl)-2,6-dioxo-piperazin-1-ylmethyl]-7H-pyrrolo[2,3-d]pyrimidine-2-carbonitrile

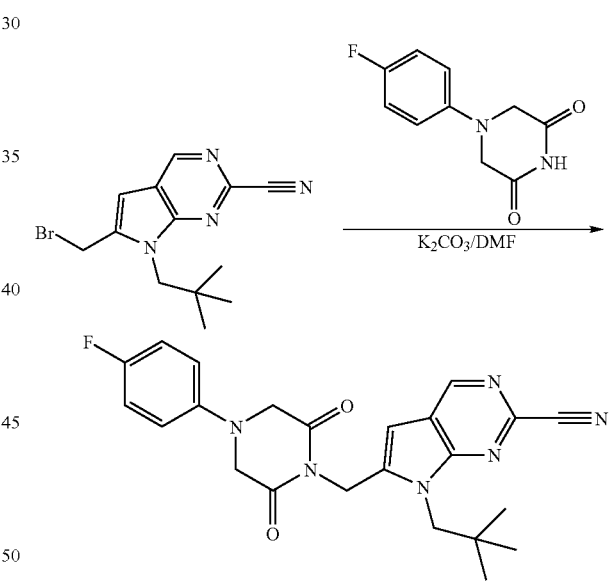

To a solution of 176 mg (0.8 mmoles) of 4-(4-fluorophenyl)-piperazine-2,6-dione In 5 ml of DMF, 176 mg (0.8 mmoles) of 6-bromomethyl-7-(2,2-dimethyl-propyl)-7.H.-pyrrolo[2,3-.d.]pyrimidine-2-carbonitrile and 0.126 g (0.9 mmoles) of $K_2CO_3$ are added at ambient temperature and the reaction mixture is stirred for 2 hour. The reaction mixture is quenched with $H_2O$ and extracted with AcOEt. The combined extracts are washed with $H_2O$, brine, dried over $MgSO_4$ and concentrated under reduced pressure. The residue is purified by silica gel column chromatography (eluent: n-Hexane:Acetone=3:1) to give 169 mg g of desired 7-(2,2-dimethyl-propyl)-6-[4-(4-fluoro-phenyl)-2,6-dioxo-piperazin-1-ylmethyl]-7H-pyrrolo[2,3-d]pyrimidine-2-carbonitrile in 59.8% yield.

¹H NMR (400 MHz, CDCl₃, δ): 1.02 (s, 9H), 4.14 (s, 4H), 4.33 (s, 2H), 5.20 (s, 2H), 6.37 (s, 1H), 6.85-6.95 (m, 2H), 7.00-7.10 (s, 2H), 8.83 (brs, 1H) Rf=0.40 (n-Hexane: AcOEt=1:1)

Example 10

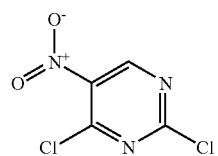 + 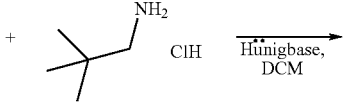

To a solution of 5 g of 2,4-dichloro-5-nitro-pyrimidine in 150 ml of dichloromethan 3.1 g of neopentylamine and 10.5 ml of diisopropylethylamine were added in succession at 0° C. After 2 hours the mixture was washed with saturated NaHCO₃ solution, dried over sodium sulfate and evaporated to dryness yielding (2-Chloro-5-nitro-pyrimidin-4-yl)-(2,2-dimethyl-propyl)-amine as yellow cristals.

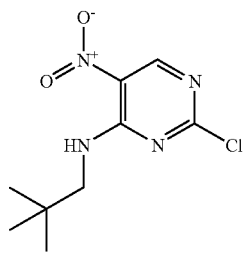

1.95 g of (2-Chloro-5-nitro-pyrimidin-4-yl)-(2,2-dimethyl-propyl)-amine and 1.69 g of iron filings were heated under reflux in 10 ml of methanol/HCl conc=1:1. After cooling and diluting with water 2-chloro-N4-(2,2-dimethyl-propyl)-pyrimidine-4,5-diamine precipitated as pale yellow

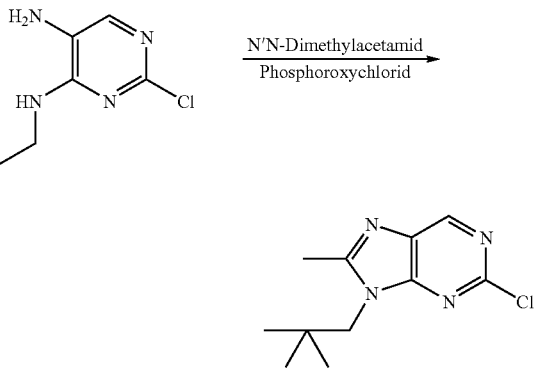

To a solution of 4.2 g of 2-chloro-N4-(2,2-dimethyl-propyl)-pyrimidine-4,5-diamine in 40 ml of DMA was added 1.6 ml of POCl₃. The solution was stirred at 100° C. for 2 hours, cooled and extracted with ethyl acetate and saturated NaHCO₃ solution. The organic phases were dried over sodium sulfate and evaporated to dryness yielding 2-chloro-9-(2,2-dimethyl-propyl)-8-methyl-9H-purine as a brown oil.

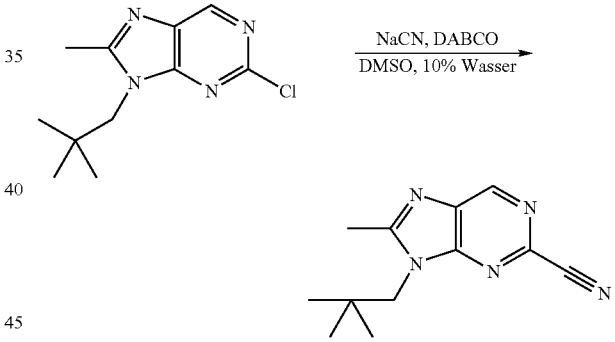

6.1 g of 2-chloro-9-(2,2-dimethyl-propyl)-8-methyl-9H-purine, 1.25 g of NaCN and 0.57 g of DABCO were heated for 6 hours to 80° C. in 60 ml DMSO/H₂O=90:10. The crude mixture was extracted with ethyl acetate and saturated NaHCO₃ solution and the organic phases were dried over sodium sulfate and evaporated to dryness. After chromatography on silicagel with ethyl acetate/hexanes=1:1 9-(2,2-dimethyl-propyl)-8-methyl-9H-purine-2-carbonitrile was isolated as a pale brown powder.

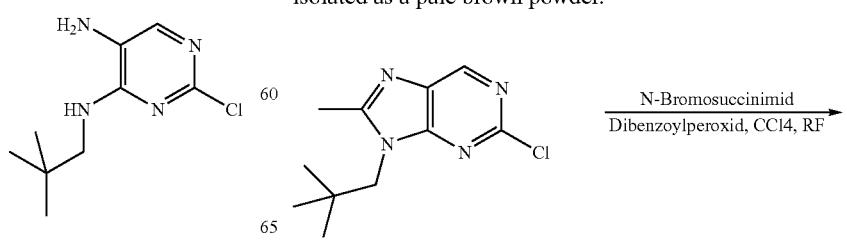

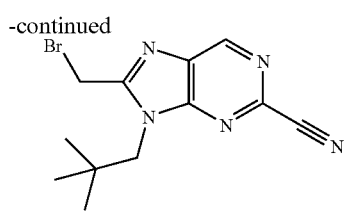

A mixture of 1.1 g 9-(2,2-dimethyl-propyl)-8-methyl-9H-purine-2-carbonitrile, 1.7 g of N-bromosuccinimide and 116 mg dibenzoylperoxide was heated for 18 hours under reflux in 5 ml of $CCl_4$. The mixture was evaporated and the residue was chromatographed on silicagel using hexanes/ethylacetate yielding 8-bromomethyl-9-(2,2-dimethyl-propyl)-9H-purine-2-carbonitrile as pale yellow wax.

By repeating the procedures described above using appropriate starting materials and conditions the following compounds of formula 10-1 are obtained as identified below in Table 10-1

TABLE 10-1

10-1

| | Rx | Name | NMR / MS |
|---|---|---|---|
| 10-1 | H | 9-(2,2-Dimethyl-propyl)-8-methyl-9H-purine-2-carbonitrile | $CDCl_3$, 300 MHz: 1.05(s, 9H), 2.75 (s, 3H), 4.08(s, 2H), 9.00(s, 1H). $MH^+$: 230. |
| 10-2 | benzyl | 8-Benzyl-9-(2,2-dimethyl-propyl)-9H-purine-2-carbonitrile | $CDCl_3$, 300 MHz: 1.08(s, 9H), 4.13 (s, 2H), 4.43(s, 2H), 7.15–7.4(m, 5H), 9.16(s, 1H). $MH^+$: 306. |
| 10-3 | 3-methoxyphenyl-piperazinyl | 9-(2,2-Dimethyl-propyl)-8-[4-(3-methoxy-phenyl)-piperazin-1-ylmethyl]-9H-purine-2-carbonitrile | $CDCl_3$, 300 MHz: 1.05(s, 9H), 2.71 (m, 4H), 3.21(m, 4H), 3.78(s, 3H), 4.03(s, 2H), 4.40(s, 2H), 6.4–6.55 (m, 3H), 7.16(t, 1H), 9.08(s, 1H), $MH^+$: 420. |
| 10-4 | 4-ethoxyphenyl-piperazinyl | 9-(2,2-Dimethyl-propyl)-8-[4-(4-ethoxy-phenyl)-piperazin-1-ylmethyl]-9H-purine-2-carbonitrile | $CDCl_3$, 300 MHz: 1.06(s, 9H), 1.40 (t, 3H), 2.73(m, 4H), 3.13(m, 4H), 3.97(q, 2H), 4.04(s, 2H), 4.41(s, 2H), 6.84(m,4H), 9.90(s, 1H). $MH^+$: 434. |
| 10-5 | 2,4-dimethoxyphenyl-piperazinyl | 8-[4-(2,4-Dimethoxy-phenyl)-piperazin-1-ylmethyl]-9-(2,2-dimethyl-propyl)-9H-purine-2-carbonitrile | $CDCl_3$, 300 MHz: 1.05(s, 9H), 2.76 (m, 4H), 3.04(m, 4H), 3.77(s, 3H), 3.84(s, 3H), 4.05(s, 2H), 4.41(s, 2H), 6.41(m,1H), 6.47(d, 1H), 6.86(d, 1H), 9.07(s, 1H). $MH^+$: 450. |
| 10-6 | 4-(2-hydroxyethoxy)phenyl-piperazinyl | 9-(2,2-Dimethyl-propyl)-8-{4-[4-(2-hydroxy-ethoxy)-phenyl]-piperazin-1-ylmethyl}-9H-purine-2-carbonitrile | $CDCl_3$, 300 MHz: 1.05(s, 9H), 2.22 (bs, 1H), 2.72(m, 4H), 3.13(m, 4H), 3.93(m, 2H), 4.03(m, 4H), 4.40(s, 2H),6.86(m, 4H), 9.08(s, 1H). $MH^+$: 450. |

TABLE 10-1-continued

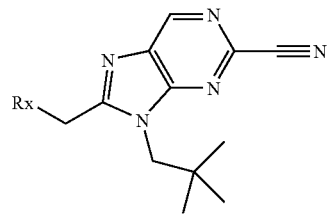

10-1

| | | | |
|---|---|---|---|
| 10-7 | 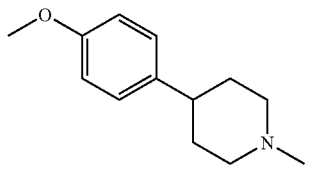 | 9-(2,2-Dimethyl-propyl)-8-[4-(4-methoxy-phenyl)-piperidin-1-ylmethyl]-9H-purine-2-carbonitrile | CDCl$_3$, 300 MHz: 1.06(s, 9H), 1.82 (m, 4H), 2.34(m, 2H), 2.50(m, 1H), 2.96(m, 2H), 3.78(s, 3H), 4.02(s, 2H), 4.43(s, 2H), 6.84(d, 2H), 7.12 (d, 2H), (9.06s,1H). MH$^+$: 419. |
| 10-8 | 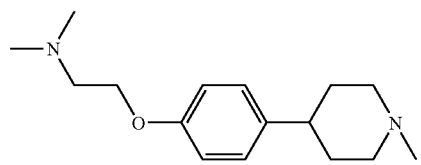 | 8-{4-[4-(2-Dimethylamino-ethoxy)-phenyl]-piperidin-1-ylmethyl}-9-(2,2-dimethyl-propyl)-9H-purine-2-carbonitrile | CDCl$_3$, 300 MHz: 1.05(s, 9H), 1.6–1.9(m, 4H), 2.28(m, 2H), 2.35(s, 6H), 2.46(m, 1H), 2.75(t, 2H), 2.92 (m, 2H), 3.99(s, 2H), 4.05(t, 2H), 4.44(s, 2H), 6.86(d,2H), 7.12(d, 2H), 9.06(s, 1H). MH$^+$: 476. |
| 10-9 | 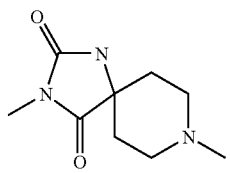 | 9-(2,2-Dimethyl-propyl)-8-(3-methyl-2,4-dioxo-1,3,8-triaza-spiro[4.5]dec-8-ylmethyl)-9H-purine-2-carbonitrile | CDCl$_3$, 300 MHz: 1.06(s, 9H), 1.79 (m, 2H), 2.16(m, 2H), 2.52(m, 2H), 3.00(m, 2H), 3.03(s, 3H), 4.08(m, 2H), 4.36(s, 2H), 6.08(s, 1H), 9.10 (s. 1H). MH$^+$: 411. |

By repeating the procedures described above using appropriate starting materials and conditions the following compounds of formula 10-2 are obtained as identified below in Table 10-2

TABLE 10-2

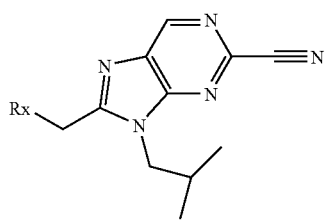

10-2

| | | | |
|---|---|---|---|
| 10-10 | H | 9-Isobutyl-8-methyl-9H-purine-2-carbonitrile | CDCl$_3$, 300 MHz: 0.97(d, 6H), 2.30(m, 1H), 2.73(s, 3H), 4.07(d, 2H), 9.00(s, 1H). MH$^+$: 216. |
| 10-11 | 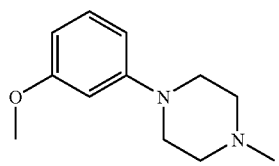 | 9-Isobutyl-8-[4-(3-methoxy-phenyl)-piperazin-1-ylmethyl]-9H-purine-2-carbonitrile | CDCl$_3$, 300 MHz: 0.98(d, 6H), 2.44(m, 1H), 2.74(m, 4H), 3.22 (m, 4H), 3.79(s, 3H), 3.95(s, 2H), 4.28(d, 2H), 6.4–6.6(m, 3H), 7.16 (t, 1H), 9.07(s, 1H). MH$^+$: 406. |

TABLE 10-2-continued 10-2

| | | | |
|---|---|---|---|
| 10-12 | HO-[2-hydroxyethoxy-phenyl-piperazinyl structure] | 8-{4-[4-(2-Hydroxy-eth-oxy)-phenyl]-piperazin-1-yl-methyl}-9-isobutyl-9H-purine-2-carbonitrile | CD$_3$OD, 300 MHz: 0.99(d, 6H), 2.54(m, 1H), (2.76m, 4H), 3.09 (m, 4H), 3.84(m, 2H), 3.95–4.05 (m, 4H), 4.34(d, 2H), 6.90(m, 4H), 9.10(s, 1H). MH$^+$: 436 |
| 10-13 | [2,4-dimethoxyphenyl-piperazinyl structure] | 8-[4-(2,4-Dimethoxy-phe-nyl)-piperazin-1-yl-methyl]-9-isobutyl-9H-purine-2-carbonitrile | CDCl$_3$, 300 MHz: 0.98(d, 6H), 2.44(m, 1H), 2.77(m, 4H), 3.03 (m, 4H), 3.77(s, 3H), 3.83(s, 3H), 3.96(s, 2H), 4.30(d, 2H), 6.41(m, 1H), 6.47(d, 1H), 6.85(m, 1H), 9.05(s, 1H). MH$^+$: 436. |
| 10-14 | [3-methyl-2,4-dioxo-1,3,8-triaza-spiro[4.5]dec-8-yl structure] | 9-Isobutyl-8-(3-methyl-2,4-di-oxo-1,3,8-triaza-spir-o[4.5]dec-8-yl-methyl)-9H-pur-ine-2-carbonitrile | CD$_3$OD, 300 MHz: 1.00(d, 6H), 1.66(m, 2H), 2.05(m, 2H), 2.53 (m, 3H), 2.95(m, 5H), 4.01(s, 2H), 4.33(d, 2H), 9.10(s, 1H). MH$^+$: 397 |

40

By repeating the procedures described above using appropriate starting materials and conditions the following compounds of formula 10-3 are obtained as identified below in Table 10-3

TABLE 10-3

10-3

| | | | |
|---|---|---|---|
| 10-15 | H | 8-Methyl-9-phenyl-9H-pur-ine-2-carbonitrile | CDCl$_3$, 300 MHz: 2.66(s, 3H), 7.39(d, 2H), 7.65(m, 3H), 9.1(s, 1H). MH$^+$: 236. |

TABLE 10-3-continued 10-3

| | | | |
|---|---|---|---|
| 10-16 | (structure) | 8-[4-(4-Ethoxy-phenyl)-piperazin-1-ylmethyl]-9-phenyl-9H-purine-2-carbonitrile | CD$_3$OD, 300 MHz: 1.36(t, 3H), 2.79(m, 4H), 3.04(m, 4H), 3.96 (q, 2H), 4.00(s, 2H), 6.82(d, 2H), 6.94(d, 2H), 7.64(m, 5H), 9.20(s, 1H). MH$^+$: 440. |
| 10-17 | (structure) | 8-[4-(2,4-Dimethoxy-phenyl)-piperazin-1-ylmethyl]-9-phenyl-9H-purine-2-carbonitrile | CD$_3$OD, 300 MHz: 2.74(m, 4H), 2.95(m, 4H), 3.75(s, 3H), 3.95(s, 3H), 3.95(m, 2H), 6.45(m, 1H), 6.54(s, 1H), 6.91(m, 1H), 7.64(m, 5H), 9.20(s, 1H). MH$^+$: 456. |
| 10-18 | (structure) | 8-{4-[4-(2-Hydroxy-ethoxy)-phenyl]-piperazin-1-ylmethyl}-9-phenyl-9H-purine-2-carbonitrile | CDCl$_3$, 300 MHz: 1.60(bs, 1H), 2.72(m, 4H), 3.05(m, 4H), 3.81(s, 2H), 3.94(m, 2H), 4.03(m, 2H), 6.85(m, 4H), 7.53(m, 2H), 7.61 (m, 3H), 9.18(s, 1H). MH$^+$: 456. |
| 10-19 | (structure) | 8-(3-Methyl-2,4-dioxo-1,3,8-tri-aza-spiro[4.5]dec-8-yl-methyl)-9-phenyl-9H-purine-2-carbonitrile | CDCl$_3$, 300 MHz: 1.64(m, 2H), 2.05(m, 2H), 2.45(m, 2H), 2.96 (m, 2H), 3.01(s, 3H), 3.82(m, 2H), 6.18(bs, 1H), 7.52(m, 2H), 7.63(m, 3H), 9.19(s, 1H). MH$^+$: 417. |

By repeating the procedures described above using appropriate starting materials and conditions the following compounds of formula 10-4 are obtained as identified below in Table 10-4

TABLE 10-4

10-4

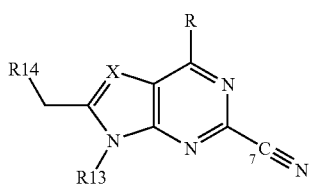

| | Rx | Name | NMR |
|---|---|---|---|
| 10-20 | H | 9-Cyclohexylmethyl-8-methyl-9H-purine-2-carbonitrile | CDCl$_3$, 300 MHz: 1.0–1.3(m, 5H), 1.56(m, 2H), 1.72(m, 3H), 1.92(m, 1H), 2.72(s, 3H), 4.07(d, 2H), 9.00 (s, 1H). MH$^+$: 256 |
| 10-21 | HO~~~O~~~(phenyl)-N(piperazine)N-Me | 9-Cyclohexylmethyl-8-{4-[4-(2-hydroxy-ethoxy)-phenyl]-piperazin-1-ylmethyl}-9H-purine-2-carbonitrile | DMSO-d6, 300 MHz: 1.0–1.3(m, 5H), 1.45–1.75(m, 5H), 2.16(m, 1H), 2.66(m, 4H), 3.00(m, 4H), 3.67(m, 2H), 3.88(m, 2H), 3.98(s, 2H), 4.25(d, 2H), 4.81(t, 1H), 6.83 (m, 4H), 9.15(s, 1H). MH$^+$: 476 |
| 10-22 | ~~~O~~~(phenyl)-N(piperazine)N-Me | 9-Cyclohexylmethyl-8-[4-(4-ethoxy-phenyl)-piperazin-1-ylmethyl]-9H-purine-2-carbonitrile | CD$_3$OD, 300 MHz: 1.1–1.4(m, 6H), 1.35(t, 3H), 1.55–1.9(m, 4H), 2.20 (m, 1H), 2.86(m, 4H), 3.14(m, 4H), 3.87(q, 2H), 4.08(m, 2H), 4.33(d, 2H), 6.89(m, 4H), 9.10(s, 1H). MH$^+$: 460 |
| 10-23 | (2,4-dimethoxyphenyl)-N(piperazine)N-Me | 9-Cyclohexylmethyl-8-[4-(2,4-dimethoxy-phenyl)-piperazin-1-ylmethyl]-9H-purine-2-carbonitrile | CD$_3$OD, 300 MHz: 1.1–1.4(m, 6H), 1.55–1.85(m, 4H), 2.22(m, 1H), 2.84(m, 4H), 3.18(m, 4H), 3.76(s, 3H), 3.85(s, 3H), 4.07(m, 2H), 4.24 (d, 2H), 6.46(m, 1H), 6.56(m, 1H), 6.94(m, 1H), 9.10(s, 1H). MH$^+$: 476. |

The invention claimed is:

1. A compound of formula I, or a pharmaceutically acceptable salt thereof

I wherein

R is H, —R2, —OR2 or NR1R2, wherein R1 is H, lower alkyl or $C_3$ to $C_{10}$ cycloalkyl, and R2 is lower alkyl or $C_3$ to $C_{10}$ $C_{10}$ cycloalkyl, and wherein R1 and R2 are independently, optionally substituted by halo, hydroxy, lower alkoxy, CN, NO$_2$, or optionally mono- or di-lower alkyl substituted amino;

X is =C(Z)-, wherein Z is H, —C(O)—NR3R4, —NH—C(O)—R3, —CH$_2$—NH—C(O)—R3, —C(O)—R3, —S(O)—R3, —S(O)$_2$—R3, —CH$_2$—C(O)—R3, —CH$_2$—NR3R4, —R4, —C≡C—CH$_2$—R5, N-heterocyclyl, N-heterocyclyl-carbonyl, or —C(P)=C(Q)-R4 wherein

P and Q independently are H, lower alkyl or aryl,

R3 is aryl, aryl-lower alkyl, $C_3$—$C_{10}$cycloalkyl, $C_3$—$C_{10}$cycloalkyl-lower alkyl, heterocyclyl or heterocyclyl-lower alkyl, R4 is H, aryl, aryl-lower alkyl, aryl-lower-alkenyl, $C_3$—$C_{10}$cycloalkyl, $C_3$—$C_{10}$cycloalkyl-lower alkyl, heterocyclyl or heterocyclyl-lower alkyl, or wherein R3 and R4 together with the nitrogen atom to which they are joined form an N-heterocyclyl group, wherein N-heterocyclyl denotes a saturated, partially unsaturated or aromatic nitrogen containing heterocyclic moiety attached via a nitrogen atom thereof having from 3 to 8 ring atoms optionally containing further 1, 2 or 3 heteroatoms selected from N, NR6, O, S, S(O) or S(O)$_2$ and wherein the N-heterocyclyl is optionally fused in a bicyclic structure and wherein the N-heterocyclyl is optionally linked in a spiro structure with a 3 to 8 membered cycloalkyl or heterocyclic ring wherein the heterocyclic ring has from 3 to 10 ring members and contains from 1 to 3 heteroatoms selected from N, NR6, O, S, S(O) or S(O)$_2$ R6 is hydrogen, optionally substituted lower alkyl, optionally substituted carboxy, formyl, optionally substituted acetyl, optionally substituted propionyl, optionally substituted benzoyl, optionally substituted amido, or optionally substituted aryl;

wherein R3 and R4 are independently, optionally substituted by 1-3 groups, selected from halo, hydroxy, oxo, lower alkoxy, CN or NO$_2$, amino, or optionally substituted mono- or di-lower alkyl amino, optionally substituted aryl, optionally substituted aryl-lower alkyl, optionally substituted N-heterocyclyl or optionally substituted N-heterocyclyl-lower alkyl (wherein the optional substitution comprises from 1 to 3 substituents selected from halo, hydroxy, lower alkoxy, CN, NO$_2$, or optionally mono- or di- lower alkyl substituted amino, and wherein R5 is aryl, aryl-lower alkyl, aryloxy, aroyl or N-heterocyclyl as defined above, and wherein R5 is optionally substituted by R7 which represents from 1 to 5 substitutents selected from halo, hydroxy, ON, NO$_2$ or oxo, or optionally substituted lower-alkoxy, optionally substituted lower-alkyl, optionally substituted aryl, optionally substituted aryloxy, optionally substituted aroyl, optionally substituted lower-alkylsulphonyl, optionally substituted arylsulphonyl, amino optionally substituted mono- or di-lower alkyl amino, or optionally substituted N-heterocyclyl, or optionally substituted N-heterocyclyl-lower alkyl wherein N-heterocyclyl is as defined above, and wherein R7 is optionally substituted by from 1 to 3 substitutents selected from halo, hydroxy, optionally mono- or di- lower-alkyl substituted amino, lower-alkyl carbonyl, lower-alkoxy or lower-alkylamido;

R13 is lower alkyl, $C_3$ to $C_{10}$ cycloalkyl or $C_3$—$C_{10}$cycloalkyl-lower alkyl, all of which are independently optionally substituted by halo, hydroxy, CN, NO$_2$ or optionally mono- or di- alkyl-substituted amino; and R14 is H or optionally substituted aryl, optionally substituted aryl-W—, optionally substituted aryl-lower alkyl-W—, optionally substituted $C_3$ to $C_{10}$ cycloalkyl, optionally substituted $C_3$ to $C_{10}$ cycloalkyl-W—, optionally substituted N-heterocyclyl or optionally substituted N-heterocyclyl-W— wherein N-heterocyclyl is as defined above, optionally substituted phthalimide, optionally substituted hydantoin, optionally substituted oxazolidinone, or optionally substituted 2,6-dioxo-piperazine, wherein —W— is —O—, —C(O)—, —N(R6)—, —N(R6)—C(O)—, —N(R6)—C(O)—O—, —S(O)—, —S(O)$_2$— or —S—, wherein R14 is optionally substituted by R18 which represents from 1 to 10 substitutents selected from halo, hydroxy, ON, NO$_2$, oxo, amido, carbonyl, sulphonamido, lower-alkyldioxymethylene, or optionally substituted (-lower-alkoxy, optionally substituted lower-alkyl, optionally substituted lower-alkenyl, optionally substituted lower alkynyl, optionally substituted lower alkoxy carbonyl, amino, optionally substituted mono- or di- lower alkyl amino, optionally substituted aryl, aryl-lower alkyl, aryl-lower alkenyl, aryloxy, aroyl, lower-alkylsulphonyl, arylsulphonyl, N-heterocyclyl, N-heterocyclyl-lower alkyl wherein N-heterocyclyl is as defined above, heterocyclyl or R14 comprising aryl has an aryl fused with a hetero-atom containing ring, and wherein R18 is optionally substituted by R19 which represents from 1 to 4 substitutents selected from halo, hydroxy, CN, NO$_2$ or oxo, or optionally substituted lower-alkoxy, optionally substituted lower-alkyl, optionally substituted lower-alkoxy-lower-alkyl, optionally substituted $C_3$—$C_{10}$cycloalkyl, optionally substituted lower-alkoxy carbonyl, optionally substituted halo-lower alkyl, amino, optionally substituted mono- or di-lower alkyl amino, optionally substituted aryl, optionally substituted aryloxy, optionally substituted aroyl optionally substituted lower-alkyl carbonyl, optionally substituted lower-alkylsulphonyl, optionally substituted arylsulphonyl, optionally substituted N-heterocyclyl, or optionally substituted N-heterocyclyl-lower alkyl wherein N-heterocyclyl is as defined above, wherein R19 is optionally substituted by from 1 to 4 substitutents selected from halo, hydroxy, CN, NO$_2$, oxo, optionally mono- or di-lower alkyl substituted amino, lower-alkyl, or lower-alkoxy.

2. A compound according to claim 1 of formula I or a pharmaceutically acceptable salt or ester thereof

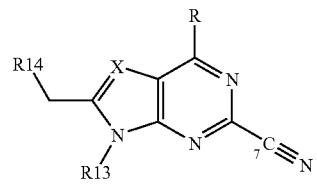

wherein R is hydrogen.

3. A pharmaceutical composition comprising a compound according to claim 1 and a pharmaceutically acceptable carrier.

4. A process for the preparation of a compound of claim 1 of formula I or a salt thereof which comprises

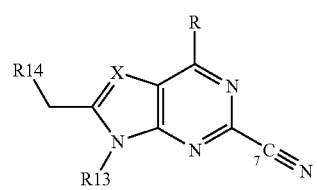

i) coupling of halo precursor of formula XI, wherein R13 and R14 are as defined in claim 1, except that R14 is not optionally substituted for carbocyclic aryl,

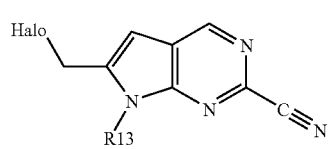

and wherein halo is bromo, with a corresponding R14 nucleophile, or ii) the preparation of compounds of formula I or pharmaceutically acceptable salts thereof

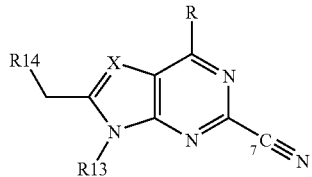

wherein R13 is as defined in claim 1 and R14 is optionally substituted carbocyclic aryl or optionally substituted azole, cyclizinq a corresponding carbocyclic aryl-1-prop-2-yne, or azole-1-prop-2-yne of formula XII with a 5-halo-pyrimidine-2-carbonitrile precursor of formula XIII

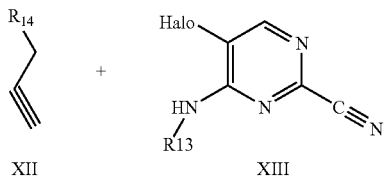

wherein halo is bromo, and thereafter, if desired, converting the product obtained into a further compound of formula I, or into a salt thereof.

5. A compound of formula

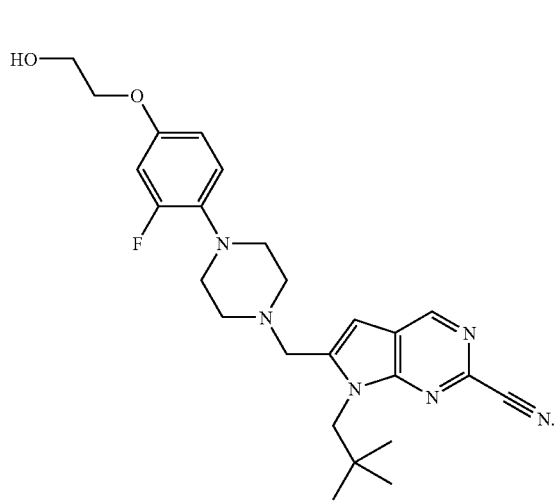

6. A pharmaceutical composition comprising the compound of claim 5 and a pharmaceutically acceptable carrier.

7. A method of treating atherosclerosis comprising administering the pharmaceutical composition of claim 6 to a patient in need thereof.

* * * * *